(12) United States Patent
Gravestock

(10) Patent No.: US 6,617,339 B1
(45) Date of Patent: Sep. 9, 2003

(54) OXAZOLIDINONE DERIVATIVES, PROCESS FOR THEIR PREPARATION AND PHARMACEUTICAL COMPOSITIONS CONTAINING THEM

(75) Inventor: Michael Barry Gravestock, Holliston, MA (US)

(73) Assignee: Syngenta Limited, London (GB)

( * ) Notice: Subject to any disclaimer, the term of this patent is extended or adjusted under 35 U.S.C. 154(b) by 0 days.

(21) Appl. No.: 09/719,012

(22) PCT Filed: Jun. 3, 1999

(86) PCT No.: PCT/GB99/01753
§ 371 (c)(1),
(2), (4) Date: Dec. 5, 2000

(87) PCT Pub. No.: WO99/64417
PCT Pub. Date: Dec. 16, 1999

(30) Foreign Application Priority Data

| Jun. 5, 1998 | (GB) | 9812021 |
| Sep. 17, 1998 | (GB) | 9820164 |
| Nov. 28, 1998 | (GB) | 9826066 |

(51) Int. Cl.⁷ .................. A61K 31/443; A61K 31/4439; A61K 31/421; A61K 31/422; C07D 413/14; C07D 413/12; C07D 417/14; C07D 451/02; A61P 31/04

(52) U.S. Cl. ............... 514/340; 514/210.2; 514/254.04; 514/376; 514/278; 514/326; 514/362; 514/249; 514/304; 514/369; 514/323; 514/253.1; 514/236.8; 514/252.04; 544/124; 544/235; 544/238; 544/364; 544/369; 546/19; 546/22; 546/125; 546/256; 546/209; 546/271.4; 546/269.1; 546/341; 548/110; 548/182; 548/187; 548/135; 548/232

(58) Field of Search ............................. 546/19.22, 125, 546/256, 209, 271.4, 269.1, 341; 544/124, 235, 238, 364, 369; 548/110, 182, 187, 135, 232; 514/340, 210.2, 254.04, 376, 278, 326, 362, 249, 304, 369, 333, 253.1, 236.8, 252.04

(56) References Cited

U.S. PATENT DOCUMENTS

| 4,150,029 A | 4/1979 | Dosert et al. |
| 4,287,351 A | 9/1981 | Bourgery et al. |
| 4,348,393 A | 9/1982 | Bourgery et al. |
| 4,372,967 A | 2/1983 | Langlois et al. |
| 4,413,001 A | 11/1983 | Bourgery et al. |
| 4,435,415 A | 3/1984 | Bourgery et al. |
| 4,476,136 A | 10/1984 | Dostert et al. |
| 4,526,786 A | 7/1985 | Bourgery et al. |
| 4,705,799 A | 11/1987 | Gregory |
| 4,942,183 A | 7/1990 | Gregory et al. |
| 4,948,801 A | 8/1990 | Carlson et al. |
| 4,977,173 A | 12/1990 | Brittelli et al. |
| 5,043,443 A | 8/1991 | Carlson et al. |
| 5,130,316 A | 7/1992 | Carlson et al. |
| 5,164,510 A | 11/1992 | Brickner |
| 5,182,403 A | 1/1993 | Brickner |
| 5,225,565 A | 7/1993 | Brickner |

(List continued on next page.)

FOREIGN PATENT DOCUMENTS

| EP | 0 645 376 A | 3/1995 |
| EP | 0 710 657 A | 5/1996 |
| EP | 741133 | 11/1996 |
| EP | 0789026 | 8/1997 |
| EP | 623615 | 6/1999 |
| FR | 2458547 | 6/1978 |
| JP | 7-309850 | 12/1997 |
| WO | WO 93 22298 A | 11/1993 |
| WO | WO 93 23384 A | 11/1993 |
| WO | WO 94/01110 | 1/1994 |

(List continued on next page.)

OTHER PUBLICATIONS

Chemical Abstract; vol. 122; 55826, No. 5.
Chemical Abstract; vol. 124; 342951, No. 25.
Society of Toxicologists Annual Meeting, 1996, Abstract No. 564.
M. R. Barcachyn et al, Bioorganic & Med. Chem. Letters, 1996, vol. 6, No. 9, pp. 1009–1014.
D.L. Shinabarger et al., Antimicrobial Agents Chemother., 1997, vol. 41, No. 10, pp. 2132–2136.
D.C. Eustice, J. Antimocrob. Chemother., 1988, vol. 32, No. 8, pp. 1218–1222.
J.S. Daly et al., J. Antimicrob. Chemother., 1988, vol. 21, No. 6, pp. 721–730.
Interscience Congress of Antimicrobial Agents and Chemotherapy conference abstracts: Sep. 17–20, 1995.
Interscience Congress of Antimicrobial Agents and Chemotherapy conference abstracts: Sep. 15–18, 1996.
Interscience Congress of Antimicrobial Agents and Chemotherapy conference abstracts: Sep. 28–Oct. 1, 1997.

(List continued on next page.)

Primary Examiner—Evelyn Mei Huang
(74) Attorney, Agent, or Firm—Ropes & Gray

(57) ABSTRACT

Compounds of formula (I) as defined herein, or a pharmaceutically acceptable salt, or an in-vivo-hydrolysable ester thereof, are useful as antibacterial agents. Processes for their manufacture and pharmaceutical compositions containing them are described.

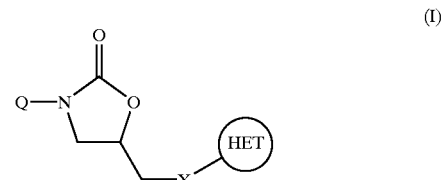

(I)

12 Claims, No Drawings

U.S. PATENT DOCUMENTS

| | | | |
|---|---|---|---|
| 5,231,188 A | 7/1993 | Brickner | |
| 5,247,090 A | 9/1993 | Brickner | |
| 5,254,577 A | 10/1993 | Carlson et al. | |
| 5,523,403 A | 6/1996 | Barbachyn | |
| 5,529,998 A | 6/1996 | Habich et al. | |
| 5,561,148 A | * 10/1996 | Gante | 514/376 |
| 5,565,571 A | 10/1996 | Barbachyn et al. | |
| 5,574,055 A | 11/1996 | Borgulya et al. | |
| 5,627,181 A | 5/1997 | Riedl et al. | |
| 5,652,238 A | 7/1997 | Brickner et al. | |
| 5,654,428 A | 8/1997 | Barbachyn et al. | |
| 5,654,435 A | 8/1997 | Barbachyn et al. | |
| 5,668,286 A | 9/1997 | Yamada et al. | |
| 5,684,023 A | 11/1997 | Riedl et al. | |
| 5,688,792 A | 11/1997 | Barbachyn et al. | |
| 5,698,574 A | 12/1997 | Riedl et al. | |
| 5,708,169 A | 1/1998 | Hester, Jr. et al. | |
| 5,719,154 A | 2/1998 | Tucker et al. | |
| 5,736,545 A | 4/1998 | Gadwood et al. | |
| 5,756,732 A | 5/1998 | Barbachyn et al. | |
| 5,792,765 A | 8/1998 | Riedl et al. | |
| 5,801,246 A | 9/1998 | Barbachyn et al. | |
| 5,827,857 A | 10/1998 | Riedl et al. | |
| 5,837,870 A | 11/1998 | Pearlman et al. | |
| 5,843,967 A | 12/1998 | Riedl et al. | |
| 5,861,413 A | 1/1999 | Habich et al. | |
| 5,869,659 A | 2/1999 | Stolle et al. | |
| 5,880,118 A | 3/1999 | Barbachyn et al. | |
| 5,910,504 A | 6/1999 | Hutchinson | |
| 5,952,324 A | 9/1999 | Barbachyn et al. | |
| 5,955,460 A | 9/1999 | Thomas | |
| 5,981,528 A | * 11/1999 | Gravestock | 514/252 |
| 6,124,334 A | 9/2000 | Hutchison | |

FOREIGN PATENT DOCUMENTS

| | | |
|---|---|---|
| WO | WO 94 22857 A | 10/1994 |
| WO | WO 96/13502 | 5/1996 |
| WO | WO 96/23788 | 8/1996 |
| WO | WO 96/35691 | 11/1996 |
| WO | WO 97 06791 A | 2/1997 |
| WO | WO 97 09328 A | 3/1997 |
| WO | WO 97/10223 | 3/1997 |
| WO | WO 98/07708 | 2/1998 |
| WO | WO 98/54161 | 12/1998 |
| WO | WO 99/02525 | 1/1999 |
| WO | WO 99-03846 | 1/1999 |
| WO | WO 99-12914 | 3/1999 |
| WO | WO 99/24393 | 5/1999 |
| WO | WO 99/24428 | 5/1999 |
| WO | WO 99/25344 | 5/1999 |
| WO | WO 99/29688 | 6/1999 |
| WO | WO 99-37652 | 7/1999 |
| WO | WO 99/41244 | 9/1999 |
| WO | WO 99/43671 | 9/1999 |

OTHER PUBLICATIONS

G. Ranaldi et al., Antimicrob.Agents Chemother.(1996), 40(3), 652–8.
G. W. Katz, Antimicrob.Agents Chemother.(1996), 40(3), 799–801.
R.N. Jones, Antimicrob.Agents Chemother.(1996), 40(3), 720–6.
S.K. Spangler, Antimicrob.Agents Chemother.(1996), 40(2), 481–4.
P.Seneci et al, J.Chem.Soc.Perkin Trans.1 (1994), 16, 2345–51.
C.L.J.Wang et al, Tetrahedron (1989), 45(5), 1323–6.
W.A.Gregory et al., J.Med.Chem.(1989), 32(8), 1673–81.
R.B.Silverman et al., Biochem.Biophys.Res.Commun.(1993), 195(2), 1077–80.
D.R.Ashtekar, Diagn.Microbiol.Infect.Dis(1991), 14(6), 465–71.
D.C.Eustice, Drugs Exp.Clin.Res. (1990), 16(4), 149–55.
W.Brumfitt et al, J.Antimicrob.Chemother. (1989), 24(3), 465–7.
S.J. Brickner et al, Journal of Medicinal Chemistry, vol. 39, No. 3, Feb. 1996, pp. 673–679.
M.R.Barbachyn et al, Journal of Medicinal Chemistry, vol. 39, No. 3, Feb. 1996, pp. 680–685.
A.M. Slee et al, Antimicrobial Agents & Chemotherapy, vol. 31, No. 11, Nov. 1987, pp. 1791–1797.
S.K. Spangler et al, Antimicrobial Agents & Chemotherapy, vol. 40, No. 2, Feb. 1996, pp. 481–484.
Zurenko et al, Exp.Opin.Invest.Drugs, vol. 6, No. 2, Feb. 1997, pp. 151–158.
Zurenko et al, Bioorganic & Med.Chem.Letters (1994), vol. 4, No. 16(4), 1925–1930.
A.D.Borthwick et al, Medicinal Chemistry Research, vol. 6, No. 1, Jan. 1996, pp. 22–27.
K.C.Grega et al., J.Org.Chem.(1995), 60(16), 5255–61.
M.R. Barachyn et al., Bioorganic & Med.Chem.Letter (1996), 6(9), 1003–1008.
P. Dostert et al., Int.Congr.Ser.—Excerpta Med. (1982), 564, 197–208.
W. Brumfitt et al., Diag.Microbiol.Infect.Dis. (1992), 15(7), 621–5.
S. J. Brickner, Current Pharmaceutical Design (1996), 2, 175–194.
J. H. Jorgensen et al., Antimicrob.Agents Chemother.(1997), 41(2), 465–467.
Drugs Future (1996), 21(11), 1116–1123.
S. E. Schaus et al., Tetrahedron Lett.(1996), 37(44), 7937–7940.
L. Mulazimoghu et al., Antimicrob.Agents Chemother.(1996), 41(10), 2428–2430.
G. M. Eliopoulus et al., Antimicrob.Agents Chemother.(1996), 40(7), 1745–1747.
S. Worth et al., Diagn.Microbiol.Infect.Dis.(1996), 24(2), 87–91.
C. W. Ford et al., Antimicrob.Agents Chemother.(1996), 40(6), 1580–1513.
E. O. Mason et al., Antimicrob.Agents Chemother.(1996), 40(4), 1039–40.
G. E. Zurenko et al., Antimicrob.Agents Chemother.(1996), 40(4), 839–45.
E. Mini et al., Eur.J.Clin.Microbiol.Infect.Dis. (1989), 8(3), 256–60.
P. A. Maple, J. Antimicrob.Chemother. (1989), 23(4), 517–25.
W. Brumfitt et al., J.Antimicrob.Chemother. (1988), 21(6), 711–20.
H. C. Neu et al., Antimicrob.Agents Chemother.(1988), 32(4), 580–3.
D. C. Eustice et al., Biochem.Biophys.Res.Commun.(1988), 150(3), 965–71.
A. L. Barry, Antimicrob.Agents Chemother.(1988), 32(1), 150–152.
A. H. Lin et al., Antimicrob.Agents Chemother.(1997), 41(10), 2127–2131.
R. D. Schaadt et al., Diagn.Microbiol.Infect.Dis. (1997), 28(4), 201–204.

J. E. Lund et al., Toxicol.Pathol.(1997), 25(4), 339–343.

J. P. Scholl et al., J.Chromatogr.,B:Biomed.Sci.Appl.(1997), 695(1), 147–156.

B. Reidel & R. Endermann, Expert Opinion on Therapeutic Patents, 1999, 9(5), 625–633.

Annual Report Med.Chem., 2000, 35, 135–144.

D. J. Diekema & R. N. Jones, Drugs (2000), 59(1), 7–16.

D. Clemett & A. Markham, Drugs (2000), 59(4), 815–827.

Chung–Ho Park et al.: "Antibacterials, Synthesis and Structure–Activity Studies of 3–Aryl–2–Oxooxazolidines, 4 Multiply–Substitued Aryl Derivatives" *Journal of Medicinal chemistry*, US, American Chemical Society, Washington, vol. 35, No. 6, 1992, pp. 1156–1165.

W A Gregory et al.: "Antibacterials, Synthesis and Structure–Activity Studies of 3–Aryl–2–oxooxazolidines. 2. The A Group" *Journal of Medicinal chemistry*, US, American Chemical Society, Washington, vol. 33, 1990, pp. 2569–2578.

* cited by examiner

OXAZOLIDINONE DERIVATIVES, PROCESS FOR THEIR PREPARATION AND PHARMACEUTICAL COMPOSITIONS CONTAINING THEM

This application is the 371 of PCT/GB 99/01753, filed on Jun. 6, 1999.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant Streptococcus pneumoniae and multiply resistant Enterococcus faecium.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

Certain antibacterial compounds containing an oxazolidinone ring have been described in the art (for example, Walter A. Gregory et al in J.Med.Chem. 1990, 33, 2569–2578 and Chung-Ho Park et al in J.Med.Chem. 1992, 35, 1156–1165). Such antibacterial oxazolidinone compounds with a 5-methylacetamide sidechain may be subject to mammalian peptidase metabolism. Furthermore, bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore. Therefore, there remains an ongoing need to find new antibacterial agents with a favourable pharmacological profile, in particular for compounds containing new pharmacophores.

We have discovered a class of antibiotic compounds containing a new class of substituted oxazolidinone ring which has useful activity against Gram-positive pathogens including MRSA and MRCNS and, in particular, against various strains exhibiting resistance to vancomycin and against E. faecium strains resistant to both aminoglycosides and clinically used β-lactams.

Accordingly the present invention provides a compound of the formula (I), or a pharmaceutically-acceptable salt, or an in-vivo-hydrolysable ester thereof,

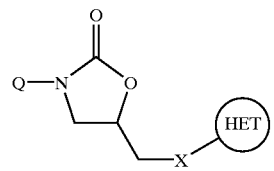

wherein X is —O—, —S—, —SO— or —SO$_2$—;

HET is a C-linked 5-membered heteroaryl ring containing 2 to 4 heteroatoms independently selected from N, O and S, which ring is optionally substituted on an available carbon atom by 1 or 2 substituents independently selected from (1–4C)alkyl, amino, (1–4C) alkylamino, (1–4C)alkoxy and halogen, and/or on an available nitrogen atom (provided that the ring is not thereby quaternised) by (1–4C)alkyl;

Q is selected from Q1 to Q9:

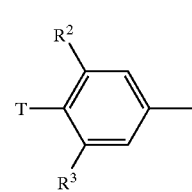

Q1

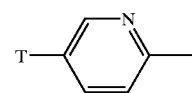

Q2

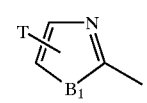

Q3

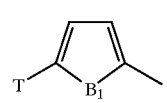

Q4

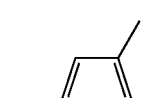

Q5

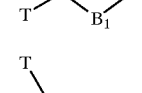

Q6

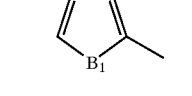

Q7

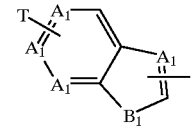

Q8

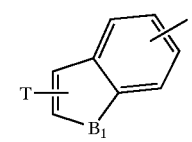

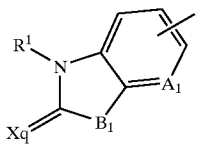

Q9 wherein R² and R³ are independently hydrogen or fluoro;

wherein $A_1$ is carbon or nitrogen; $B_1$ is O or S (or, in Q9 only, NH); $X_q$ is O, S or N—R¹ (wherein R¹ is hydrogen, (1–4C)alkyl or hydroxy-(1–4C)alkyl); and wherein in Q7 each $A_1$ is independently selected from carbon or nitrogen, with a maximum of 2 nitrogen heteroatoms in the 6-membered ring, and Q7 is linked to T via any of the $A_1$ atoms (when $A_1$ is carbon), and linked in the 5-membered ring via the specified carbon atom, or via $A_1$ when $A_1$ is carbon; Q8 is linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TD) below (wherein AR1, AR2, AR2a, AR2b, AR3, AR3a, AR3b, AR4, AR4a, CY1 and CY2 are defined hereinbelow);

(TA) T is selected from the following groups:
  (TAa) AR1, AR1-(1–4C)alkyl-, AR2(carbon linked), AR3;
  (TAb) AR1-CH(OH), AR2-CH(OH)—, AR3-CH(OH)—;
  (TAc) AR1-CO—, AR2-CO—, AR3-CO—, AR4-CO—;
  (TAd) AR1-O—, AR2-CO—, AR3-O—;
  (TAe) AR1-S(O)$_q$—, AR²-S(O)$_q$—, AR3-S(O)$_q$— (q is 0.1 or 2);
  (TAf) an optionally substituted N-linked (fully unsaturated) 5-membered heteroaryl ring system containing 1, 2 or 3 nitrogen atoms;
  (TAg) a carbon linked tropol-3-one or tropol-4-one, optionally substituted in a position not adjacent to the linking position; or (TB) T is selected from the following groups:
  (TBa) halo or (1–4C)alkyl
    {optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N—(1–4C)alkyl-N—(1–6C)alkanoylamino, (1–4C)alkylS(O)$_q$— (q is 0, 1 or 2), CY1, CY2 or AR1};
  (TBb) —NRv¹Rw¹;
  (TBc) ethenyl, 2-(1–4C)alkylethenyl, 2-cyanoethenyl, 2-cyano-2-(1–4C)alkyl)ethenyl, 2-nitroethenyl, 2-nitro-2-(1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;
  (TBd) R¹⁰CO—, R¹⁰S(O)$_q$— (q is 0, 1 or 2) or R¹⁰CS—
  wherein R¹⁰ is selected from the following groups:
    (TBda) CY1 or CY2;
    (TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-(1–4C)alkylaminocarbonyl)ethenyl, 2-((1–4C)alkoxycarbonyl)ethenyl, 2-(AR1)ethenyl or 2-(AR2)ethenyl; or
    (TBdc) (1–4C)alkyl {optionally substituted as defined in (TBa) above, or by (1–4C)alkylS(O)$_p$NH— or (1–4C)alkylS(O)$_p$—((1–4C)alkyl)N— (p is 1 or 2)};
  wherein Rv is hydrogen or (1–4C)alkyl; Rw is hydrogen or (1–4C)alkyl; Rv¹ is hydrogen, (1–4C)alkyl or (3–8C)cycloalkyl; Rw¹ is hydrogen, (1–4C)alkyl, (3–8C)cycloalkyl, (1–4C)alkyl-CO— or (1–4C)alkylS(O)$_q$— (q is 1 or 2); or (TC) T is selected from the following groups:
  (TCa) an optionally substituted, fully saturated 4-membered monocyclic ring containing 1 heteroatom selected from O, N and S (optionally oxidised), and linked via a ring nitrogen or sp³ carbon atom;
  (TCb) an optionally substituted 5-membered monocyclic ring containing 1 heteroatom selected from O, N and S (optionally oxidised), and linked via a ring nitrogen atom or a ring sp³ or sp² carbon atom, which monocyclic ring is fully saturated other than (where appropriate) at a linking sp² carbon atom;
  (TCc) an optionally substituted 6- or 7-membered monocyclic ring containing 1 or 2 heteroatoms independently selected from O, N and S (optionally oxidised), and linked via a ring nitrogen atom or a ring sp³ or sp² carbon atom, which monocyclic ring is fully saturated other than (where appropriate) at a linking sp² carbon atom; or (TD) T is selected from the following groups:
  (TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp³ or sp2 carbon atom) substituted (but not adjacent to the linking position) by a 3-, 4- or 5-membered spiro-carbon-linked ring; which bicyclic ring system is
    (i) fully saturated other than (where appropriate) at a linking sp² carbon atom;
    (ii) contains one —N(Rc)— group in the ring system (at least two carbon atoms away from the linking position when the link is via a nitrogen atom or an sp² carbon atom) or one —N(Rc)— group in an optional substituent (not adjacent to the linking position) and is
    (iii) optionally further substituted on an available ring carbon atom; or
  (TDb) a 7-, 8- or 9-membered bicyclic ring system (linked via a ring nitrogen atom or a ring sp³ or sp² carbon atom) containing 0, 1 or 2 ring nitrogen atoms (and optionally a further O or S ring heteroatom), the structure containing a bridge of 1, 2 or 3 carbon atoms; which bicyclic ring system is
    (i) fully saturated other than (where appropriate) at a linking sp² carbon atom;
    (ii) contains one O or S heteroatom, or one —N(Rc)— group in the ring (at least two carbon atoms away from the linking position when the link is via a nitrogen atom or an s carbon atom) or one —N(Rc)— group in an optional substituent (not adjacent to the linking position) and is
(iii) optionally further substituted on an available ring carbon atom;
wherein Rc is selected from groups (Rc1) to (Rc5):
(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N—(1–4C)alkyl-N—(1–6C)alkanoylamino, (1–4C)alkylS(O)$_p$NH— or (1–4C)alkylS(O)$_p$—((1–4C)alkyl)N— (p is 1 or 2)};
(Rc2) R$^{13}$CO—, R$^{13}$SO$_2$— or R$^{13}$CS—
wherein R$^{13}$ is selected from (Rc2a) to (Rc2e):
(Rc2a) AR1, AR2, AR2a, AR2b, AR3, AR3a, AR3b, AR4, AR4a, CY1, CY2;
(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(1–4C)alkylethenyl, 2-cyanoethenyl, 2-cyano-2-(1–4C)alkyl)ethenyl, 2-nitroethenyl, 2-nitro-2-(1–4C)alkyl)ethenyl, 2-((1–4C)alkylaminocarbonyl)ethenyl, 2-(1–4C)alkoxycarbonyl)ethenyl, 2-(AR1)ethenyl, 2-(AR2)ethenyl, 2-(AR2a)ethenyl;
(Rc2c) (1–10C)alkyl {optionally substituted by one or more groups (including geminal disubstitution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O)(OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C)alkoxycarbonyl, 1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N—(1–4C)alkyl-N—(1–6C)alkanoylamino, (1–4C)alkylaminocarbonyl, di((1–4C)alkyl)aminocarbonyl, (1–4C)alkylS(O)$_p$—((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};
(Rc2d) R$^{14}$C(O)O(1–6C)alkyl wherein R$^{14}$ is AR1, AR2, (1–4C)alkylamino, benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;
(Rc3) hydrogen, cyano, 2-cyanoethenyl, 2-cyano-2-(1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

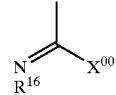

(Rc3a)

wherein X$^{00}$ is —OR$^{17}$, —SR$^{17}$, —NHR$^{17}$ and —N(R$^{17}$)$_2$;
wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;
(Rc4) trityl, AR1, AR2, AR2a, AR2b, AR3, AR3a, AR3b;
(Rc5) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;
wherein
AR1 is an optionally substituted phenyl or optionally substituted naphthyl;
AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;
AR2a is a partially hydrogenated version of AR2 (i.e. AR2 systems retaining some, but not the full, degree of unsaturation), linked via a ring carbon atom or linked via a ring nitrogen atom if the ring is not thereby quaternised;
AR2b is a fully hydrogenated version of AR2 (i.e. AR2 systems having no unsaturation), linked via a ring carbon atom or linked via a ring nitrogen atom;
AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

In this specification, where it is stated that a ring may be linked via an sp² carbon atom, which ring is fully saturated other than (where appropriate) at a linking sp² carbon atom, it is to be understood that the ring is linked via a C=C double bond.

In another embodiment, (Rc1) is as defined above other than the optional phenyl substituent on (1–6C)alkyl is optionally substituted as for AR1 defined hereinafter; and (Rc2c), is as defined above and further includes carboxy as an optional substituent on R¹³ as (1–10C)alkyl.

(TAf) When T is an optionally substituted N-linked (fully unsaturated) 5-membered heteroaryl ring system containing 1, 2 or 3 nitrogen atoms, it is preferably selected from a group of formula (TAf1) to (TAf6) below (particularly (TAf1), (TA2), (TAf4) and (TAf5), and especially (TAf1) and/or (TAf2)). The above preferred values of (TAf) are particularly preferred when present in Q1 or Q2, especially Q1, and when X is —O—.

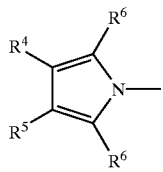

(TAf1)

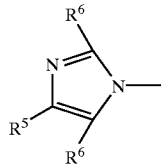

(TAf2)

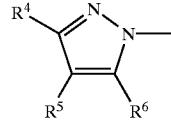

(TAf3)

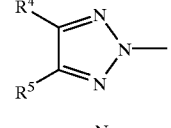

(TAf4)

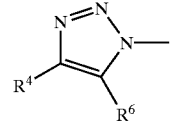

(TAf5)

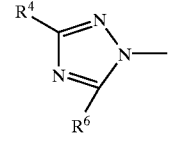

(TAf6)

wherein:

R⁶ is selected (independently where appropriate) from hydrogen, (1–4C)alkyl, (1–4C)alkoxycarbonyl, (1–4C)alkanoyl, carbamoyl and cyano;

R⁴ and R⁵ are independently selected from hydrogen, halo, trifluoromethyl, cyano, nitro, (1–4C)alkoxy, (1–4C)alkylS(O)$_q$— (q is 0, 1 or 2), (1–4C)alkanoyl, (1–4C)alkoxycarbonyl, (2–4C)alkanoyloxy-(1–4C)alkyl, benzoxy-(1–4C)alkyl, (2–4C)alkanoylamino, —CONRvRw, —NRvRw and (1–4C)alkyl {optionally substituted by hydroxy, trifluoromethyl, cyano, nitro, (1–4C)alkoxy, (1–4C)alkylS(O)$_q$— (q is 0, 1 or 2), (1–4C)alkoxycarbonyl, (1–4C)alkanoylamino, —CONRvRw, —NRvRw; wherein RvRw is hydrogen or (1–4C)alkyl; Rw is hydrogen or (1–4C)alkyl};

or R⁴ is selected from one of the groups in (TAfa) to (TAfc) below, or (where appropriate) one of R⁴ and R⁵ is selected from the above list of R⁴ and R⁵ values, and the other is selected from one of the groups in (TAfa) to (TAfc) below:

(TAfa) a group of the formula (TAfa1)

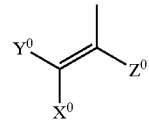

(TAfa1)

wherein Z⁰ is hydrogen or (1–4C)alkyl;

X⁰ and Y⁰ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO₂—, trifluoromethyl, pentafluoroethyl, (1–4C)alkanoyl and —CONRvRw [wherein Rv is hydrogen or (1–4C)alkyl; Rw is hydrogen or (1–4C)alkyl); or one of X⁰ and Y⁰ is selected from the above list of X⁰ and Y⁰ values, and the other is selected from phenyl, phenylcarbonyl, —S(O)$_q$-phenyl (q is 0, 1 or 2), N-(phenyl)carbamoyl, phenylaminosulfonyl, AR2, (AR2)-CO—, (AR2)-S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAfb) an acetylene of the formula —≡—H or —≡—(1–4C)alkyl;

(TAfc) —$X^1$—$Y^1$—AR2, —$X^1$—$Y^1$—AR2a, —$X^1$—$Y^1$—AR2b, —$X^1$—$Y^1$—AR3, —$X^1$—$Y^1$—AR3a or —$X^1$—$Y^1$—AR3b;

wherein $X^1$ is a direct bond or —CH(OH)— and $Y^1$ is —$(CH_2)_m$—, —$(CH_2)_n$—NH—$(CH_2)_m$—, —CO—$(CH_2)_m$—, —CONH—$(CH_2)_m$—, —C(=S)NH—$(CH_2)_m$— or —C(=O)O—$(CH_2)_m$—;

or wherein $X^1$ is —$(CH_2)_n$— or —CH(Me)—$(CH_2)_m$— and $Y^1$ is —$(CH_2)_m$—NH—$(CH_2)_m$—, —CO—$(CH_2)_m$—, —CONH—$(CH_2)_m$—, —C(=S)NH—$(CH_2)_m$—, —C(=O)O—$(CH_2)_m$— or —S(O)$_q$—$(CH_2)_m$—;

or wherein $X^1$ is —$CH_2O$—, —$CH_2NH$— or —$CH_2N$((1–4C)alkyl)— and $Y^1$ is —CO—$(CH_2)_m$, —CONH—$(CH_2)_m$— or —C(=S)NH—$(CH_2)_m$—; and additionally $Y^1$ is —$SO_2$— when $X^1$ is —$CH_2NH$— or —$CH_2N$((1–4C)alkyl)—, and $Y^1$ is —$(CH_2)_m$— when $X^1$ is —$CH_2O$— or —$CH_2N$((1–4C)alkyl)—; wherein n is 1, 2 or 3; m is 0, 1, 2 or 3 and q is 0, 1 or 2; and when $Y^1$ is —$(CH_2)_m$—NH—$(CH_2)_m$— each m is independently selected from 0, 1, 2 or 3.

It is to be understood that when a value for —$X^1$— is a two-atom link and is written, for example, as —$CH_2NH$— it is the left hand part (—$CH_2$— here) which is bonded to the group of formula (TAf1) to (TAf6) and the right hand part (—NH— here) which is bonded to —$Y^1$— in the definition in (TAfc). Similarly, when —$Y^1$— is a two-atom link and is written, for example, as —CONH— it is the left hand part of —$Y^1$—(—CO— here) which is bonded to the right hand part of —$X^1$—, and the right hand part of —$Y^1$—(—NH— here) which is bonded to the AR2, AR2a, AR2b, AR3, AR3a or AR3b moiety in the definition in (TAfc).

Preferably $R^6$ is hydrogen or (1–4C)alkyl, and $R^4$ and $R^5$ are independently selected from hydrogen, (1–4C)alkyl or one of $R^4$ and $R^5$ is selected from group (TAfa). Other preferable substituents on the (TAf1) to (TAf6) are illustrated in the accompanying Examples.

(TAg) When T is a carbon linked tropol-3-one or tropol-4-one, optionally substituted in a position not adjacent to the linking position (TAg), it is preferably selected from a group of formula (TAg1), (TAg2) or (TAg3). The above preferred values of (TAg) are particularly preferred when present in Q1 or Q2, especially Q1, and when X is —O—.

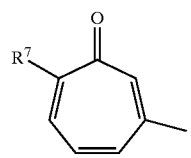

(TAg1)

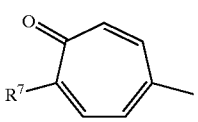

(TAg2)

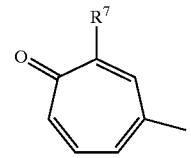

(TAg3)

wherein $R^7$ is selected from (TAga) hydrogen, (1–4C)alkyl {optionally substituted by one or two substituents (excluding geminal disubstitution) independently selected from fluoro, hydroxy, (1–4C)alkoxy and —NRvRw]}; or (TAgb) $R^8$—O—, $R^8$—S—, $R^8$—NH— or $R^8R^8$—N—;

wherein $R^8$ is selected (independently where appropriate) from hydrogen, (1–4C)alkyl or (3–8C)cycloalkyl {both optionally substituted by one or two substituents (excluding geminal disubstitution) independently selected from hydroxy, (1–4C)alkoxy, (1–4C)alkoxycarbonyl and —NRvRw}, (2–4C)alkenyl {optionally substituted by one or two —NRvRw substituents}, (1–4C)alkanoyl {optionally substituted by one or two substituents independently selected from —NRvRw and hydroxy}, phenyl-(1–4C)alkyl or pyridyl-(1–4C)alkyl {the phenyl and pyridyl (preferably pyridin-4-yl) rings being optionally substituted by one or two —NRvRw substituents}; or (TAgc) morpholino, thiomorpholino, pyrrolidino {optionally independently substituted in the 3- and/or 4-positions by (1–4C)alkyl}, piperidino substituted in the 4-position by $R^9$—, $R^9$—O—, $R^9$—S—, $R^9$—NH— or $R^9R^9$—N—; wherein $R^9$ is selected (independently where appropriate) from hydrogen, (1–4C)alkyl {optionally substituted by one or two (excluding geminal disubstitution) hydroxy, (1–4C)alkoxy, (1–4C)alkoxycarbonyl or —NRvRw} and piperazino {optionally substituted in the 4-position by (1–4C)alkyl, (3–8C)cycloalkyl, (1–4C)alkanoyl, (1–4C)alkoxycarbonyl or (1–4C)alkylsulfonyl, and optionally independently substituted in the 3- and/or 5-positions by (1–4C)alkyl}; wherein Rv is hydrogen or (1–4C)alkyl; Rw is hydrogen or (1–4C)alkyl.

(TC) Preferred values for the optional substituents and groups defined in (TCa) to (TCc) are defined by formulae (TC1) to (TC4):

(TC1)

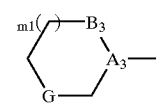

(TC2)

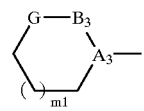

(TC3)

-continued

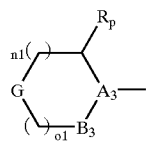
(TC4)

wherein in (TC1): >A₃—B₃— is >C(Rq)—CH(Rr)— and G is —O—, —S—, —SO—, —SO₂— or >N(Rc);

wherein in (TC2): m1 is 0, 1 or 2; >A₃—B₃— is >C=C(Rr)— or >C(Rq)—CH(Rr)— and G is —O—, —S—, —SO—, —SO₂— or >N(Rc);

wherein in (TC3) m1 is 0, 1 or 2; >A₃—B₃— is >C(Rq)—CH(Rr)— (other than when Rq and Rr are both together hydrogen) and G is —O—, —S—, —SO—, —SO₂— or >N(Rc);

wherein in (TC4): n1 is 1 or 2; o1 is 1 or 2 and n1+o1=2 or 3; >A₃—B₃— is >C=C(Rr)— or >C(Rq)—CH(Rr)— or >N—CH₂— and G is —O—, —S—, —SO—, —SO₂— or >N(Rc); Rp is hydrogen, (1–4C)alkyl (other than when such substitution is defined by >A₃—B₃—), hydroxy, (1–4C)alkoxy or (1–4C)alkanoyloxy;

wherein in (TC1), (TC2) and (TC4); m1, n1 and o1 are as defined hereinbefore: >A₃—B₃— is >N—CH₂— and G is >C(R¹¹)(R¹²), >C=O, >C—OH, >C—(1–4C)alkoxy, >C=N—OH, >C=N—(1–4C)alkoxy, >C=N—NH—(1–4C)alkyl, >C=N—N(1–4C)alkyl)₂ (the last two (1–4C)alkyl groups above in G being optionally substituted by hydroxy) or >C=N—N—CO—(1–4C)alkoxy; wherein > represents two single bonds;

Rq is hydrogen, hydroxy, halo, (1–4C)alkyl or (1–4C)alkanoyloxy;

Rr is (independently where appropriate) hydrogen or (1–4C)alkyl;

R¹¹ is hydrogen, (1–4C)alkyl, fluoro(1–4C)alkyl, (1–4C)alkyl-thio-(1–4C)alkyl or hydroxy-(1–4C)alkyl and R¹² is —[C(Rr)(Rr)]ₘ₂—N(Rr)(Rc) wherein m2 is 0, 1 or 2;

and, other than the ring substitution defined by G, >A₃—B₃— and Rp, each ring system may be optionally further substituted on a carbon atom not adjacent to the link at >A₃— by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR-oxymethyl, AR-thiomethyl, oxo (=O) (other than when G is >N—Rc and Rc is group (Rc2) defined hereinbefore) or independently selected from Rc; and also hydroxy or halo (the last two optional substituents only when G is —O— or —S—);

wherein AR is as defined for formula (IP) hereinafter; Rc is selected from groups (Rc1) to (Rc5) defined hereinbefore.

For the avoidance of doubt, ( )ₘ₁, ( )ₙ₁ and ( )ₒ₁ indicate (—CH₂—)ₘ₁, (—CH₂—)ₙ₁ and (—CH₂—)ₒ₁ respectively (optionally substituted as described above).

In the above definition of (TC1) to (TC4) and of the further optional substituents, AR is preferably AR2, and the further optional substituents are preferably not selected from the values listed for Rc. A preferred value for G is >N(Rc) or >C(R¹¹)(R¹²).

Particularly preferred values for the optional substituents and groups defined in (TCa) to (TCc), and (TC1) to (TC4) are contained in the following definitions (TC5) to (TC11):

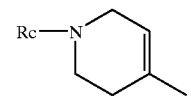
(TC5)

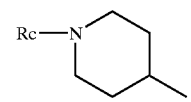
(TC6)

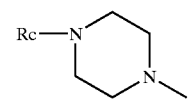
(TC7)

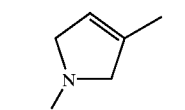
(TC8)

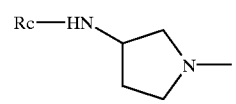
(TC9)

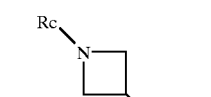
(TC10)

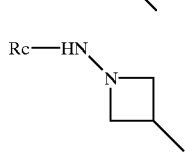
(TC11)

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially R¹³CO— with the preferable R¹³ values given hereinafter). In (TC5) Rc is preferably selected from the group (Rc2), especially R¹³CO— with the preferable R¹³ values given hereinafter. In (TC7) Rc is preferably selected from group (Rc3) or (Rc4).

The above preferred values of (TCa) to (TCc) are particularly preferred when present in Q1 or Q2, especially Q1, and when X is —O— (especially when HET is isoxazole).

(TDa) When T is a bicyclic spiro-ring system as defined in (TDa), it is preferably selected from a group of formula (TDa1) to (TDa9). The above preferred values of(TDa) are particularly preferred when present in Q1 or Q2, especially Q1, and when X is —O—.

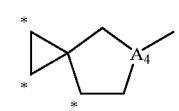
(TDa1)

-continued (TDa2) 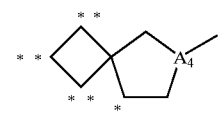

(TDa3) 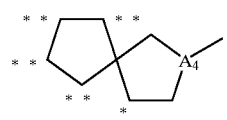

(TDa4) 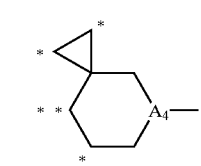

(TDa5) 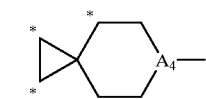

(TDa6) 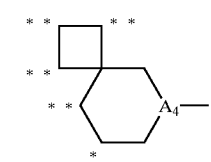

(TDa7) 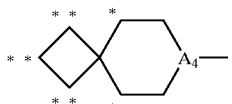

(TDa8) 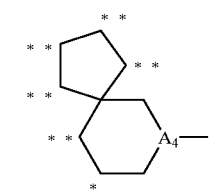

(TDa9) 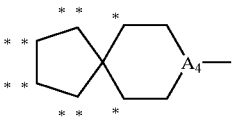

wherein;
(i) the $A_4$ linking group is a nitrogen atom or an sp³ or sp² carbon atom (with the double bond, where appropriate, orientated in either direction); and
(ii) one of the ring carbon atoms at positions marked * and ** is replaced by one of the following groups: —NRc—, >CH—NHRc, >CH—NRc—(1–4C)alkyl, >CH—CH₂—NHRc, >CH—CH₂—NRc—(1–4C)alkyl [wherein a central —CH₂— chain link is optionally mono- or di-substituted by (1–4C)alkyl]; with the provisos that positions marked * are not replaced by —NH— in the ring containing the $A_4$ link when $A_4$ is a nitrogen atom or an sp² carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR2-oxymethyl, AR2-thiomethyl, oxo (=O) (other than when the ring contains an >N—Rc and Rc is group (Rc2)) and also hydroxy or halo;

wherein Rc has any of the values listed hereinbefore or hereinafter.

(TDb) When T is a 7-, 8- or 9-membered bicyclic ring system containing a bridge of 1, 2 or 3 carbon atoms as defined in (TDb), it is preferably selected from a group defined by the ring skeletons shown in formulae (TDb1) to (TDb14):

7-membered ring skeletons (TDb1) 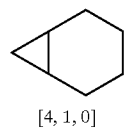

[4, 1, 0]

(TDb2) 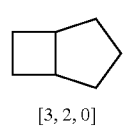

[3, 2, 0]

(TDb3) 

[3, 1, 1]

(TDb4) 

[2, 2, 1]

8-membered ring skeletons (TDb5) 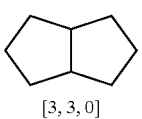

[3, 3, 0]

(TDb6) 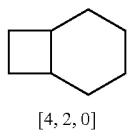

[4, 2, 0]

(TDb7) 

[4, 1, 1]

-continued

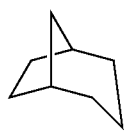

[3, 2, 1]

[2, 2, 2]

9-membered ring skeletons

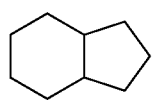

[4, 3, 0]

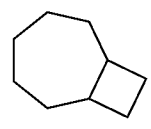

[5, 2, 0]

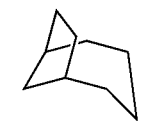

[4, 2, 1]

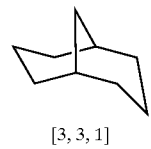

[3, 3, 1]

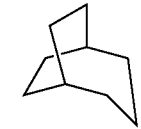

[3, 2, 2]

wherein;
(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);
(ii) the ring system is linked via a ring nitrogen atom or a ring $sp^3$ or $sp^2$ carbon atom (with the double bond, where appropriate, orientated in either direction) from any position in either ring [other than from a bridgehead position or from an $sp^2$ carbon atom in the 4-membered ring in (TDb2), (TDb6) and (TDb11)];
(iii) one of the ring carbon atoms at a position not adjacent to the linking position, is replaced (other than when the ring contains an O or S heteroatom) by one of the following groups —NRc— [not at a bridgehead position], >C(H)—NHRc, >C(H)—NRc—(1–4C) alkyl, >C(H)—CH$_2$—NHRc, >C(H)—CH$_2$—NRc—(1–4C)alkyl [wherein the hydrogen atom shown in (TDb8)

(TDb9)

(TDb10)

(TDb11)

(TDb12)

(TDb13)

(TDb14)

brackets is not present when the replacement is made at a bridgehead position and wherein a central —CH$_2$— chain link is optionally mono- or di-substituted by (1–4C)alkyl]; with the proviso that when the ring system is linked via a ring nitrogen atom or an $sp^2$ carbon atom any replacement of a ring carbon atom by —NRc—, O or S is at least two carbon atoms away from the linking position; and
(iv) the ring system is optionally (further) substituted on an available ring carbon atom as for the bicyclic spiro-ring systems described in (TDa); wherein Rc has any of the values listed hereinbefore or hereinafter.

It will be appreciated that unstable anti-Bredt compounds are not contemplated in this definition (i.e. compounds wraith structures (TDb3), (TDb4), (TDb7), (TDb8), (TDb9), (TDb12), (TDb13) and (TDb14) in which an $sp^2$ carbon atom is directed towards a bridgehead position).

Particularly preferred values of (TDb) are the following structures of formula (TDb4), (TDb8) and/or (TDb9); wherein Rc has any of the values listed hereinbefore or hereinafter. The above preferred values of (TDb) are particularly preferred when present in Q1 or Q2, especially Q1, and when X is —O—.

(TDb4a & b)

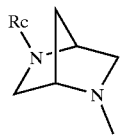

[2, 2, 1]

(TDb8)

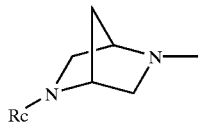

[3, 2, 1]

(TDb9)

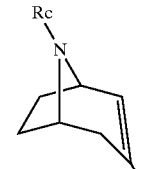

[2, 2, 2]

In another embodiment there is provided a compound of the formula (I) which is defined by the formula (IP) below, or a pharmaceutically-acceptable salt or an in-vivo hydrolysable ester thereof, wherein X is —O—, —S—, —SO— or —SO$_2$—;
HET is a C-linked 5-membered heteroaryl ring containing 2 or 3 heteroatoms independently selected from N, O and S (with the proviso that there are no O—O, O—S or S—S bonds), which ring is optionally substituted on any available C atom (provided that when a N atom is adjacent to the X-link, there is no substitution on any C atom that is adjacent to this N atom) by 1 or 2 substituents independently selected from (1–4C)alkyl, amino, (1–4C)alkylamino, (1–4C)alkoxy and halogen, and/or on an available N atom (provided that the ring is not thereby quaternised), by (1–4C)alkyl;

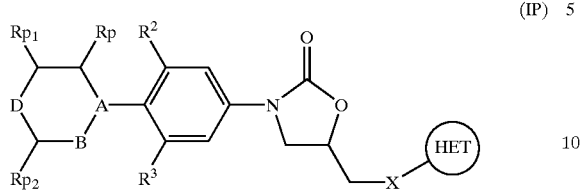

(IP)

wherein: $R^2$ and $R^3$ are independently hydrogen or fluoro;
Rp is hydrogen, (1–4C)alkyl, hydroxy, (1–4C)alkoxy or (2–4C)alkanoyloxy;
>A—B— is of the formula >C=C(Rr)—, >CHCHRr—, >C(OH)CHRr— or >N—CH$_2$— (>represents two single bonds) wherein Rr is hydrogen or (1–4C)alkyl;
D is —O—, —S—, —SO—, —SO$_2$— or >NRcp;
Rp1 and Rp2 are independently oxo (=O) [but not when Rcp is group (PC) below], (1–4C)alkyl, (1–4C)alkanoylamino-(1–4C)alkyl, hydroxy-(1–4C)alkyl, carboxy, (1–4C)alkoxycarbonyl, AR-oxymethyl, AR-thiomethyl (wherein AR is as defined hereinbelow) or independently as defined for Rcp hereinbelow with the proviso that Rp1 and Rp2 are not phenyl, benzyl, AR (as defined hereinbelow), a tetrazole ring system, cyclopentyl or cyclohexyl; and when D is —O— or —S—, Rp1 and Rp2 are additionally independently hydroxy or bromo;
wherein Rcp is selected from (PA) to (PE) below:
  (PA) hydrogen, cyano, 2-((1–4C)alkoxycarbonyl) ethenyl, 2-cyanoethenyl, 2-cyano-2-((1–4C)alkyl) ethenyl, 2-((1–4C)alkylaminocarbonyl)ethenyl;
  (PB) phenyl, benzyl, AR (as defined hereinbelow) or a tetrazole ring system [optionally mono-substituted in the 1- or 2-position of the tetrazole ring by (1–4C) alkyl, (2–4C)alkenyl, (2–4C)alkynyl or (1–4C) alkanoyl] wherein the tetrazole ring system is joined to the nitrogen in >NRcp by a ring carbon atom;
  (PC) $R^{13p}$CO—, $R^{13p}$SO$_2$— or $R^{13p}$CS— wherein $R^{13p}$ is selected from (PCa) to (PCf):
    (PCa) AR (as defined hereinbelow);
    (PCb) cyclopentyl or cyclohexyl, 1,3-dioxolan-4-yl, 1,3-dioxan-4-yl or 1,4-dioxan-2-yl [optionally mono- or di-substituted by substituents independently selected from (1–4C)alkyl (including geminal disubstitution), hydroxy (but excluding 1,3-dioxolan-4-yl, 1,3-dioxan-4-yl or 1,4-dioxan-2-yl substituted by hydroxy), (1–4C)alkoxy, (1–4C) alkylthio, acetamido, (1–4C)alkanoyl, cyano and trifluoromethyl];
    (PCc) hydrogen, (1–4C)alkoxycarbonyl, trifluoromethyl, amino, (1–4C)alkylamino, di((1–4C)alkyl)amino, 2-(5- or 6-membered heteroaryl)ethenyl, 2-(5- or 6-membered (partially) hydrogenated heteroaryl)ethenyl, 2-phenylethenyl [wherein the heteroaryl or phenyl substituent is optionally substituted on an available carbon atom by up to three substituents independently selected from (1–4C)alkoxy, halo, cyano and (for the phenyl substituent only) (1–4C) alkylsulfonyl];
    (PCd) (1–10C)alkyl [optionally substituted by one or more groups (including geminal disubstitution) each independently selected from hydroxy and amino, or optionally monosubstituted by cyano, halo, (1–10C)alkoxy, trifluoromethyl, (1–4C) alkoxy-(1–4C)alkoxy, (1–4C)alkoxy-(1–4C) alkoxy-(1–4C)alkoxy, (1–4C)alkanoyl, (1–4C) alkoxycarbonyl, (1–4C)alkylamino, di((1–4C) alkyl)amino, (1–6C)alkanoylamino, (1–4C) alkoxycarbonylamino, N—(1–4C)alkyl-N—(2–6C)alkanoylamino, (1–4C)alkylS(O)$_p$NH—, (1–4C)alkylS(O)$_p$—((1–4C)alkyl)N—, fluoro (1–4C)alkylS(O)$_p$NH—, fluoro(1–4C)alkylS(O)$_p$ ((1–4C)alkyl)N—, phosphono, (1–4C)alkoxy (hydroxy)phosphoryl, di-(1–4C) alkoxyphosphoryl, (1–4C)alkylS(O)$_q$—, phenyl, naphthyl, phenoxy, naphthoxy, phenylamino, naphthylamino, phenylS(O)$_q$—, naphthylS(O)$_q$— [wherein said phenyl and naphthyl groups are optionally substituted by up to three substituents independently selected from (1–4C)alkoxy, halo and cyano], or CY (as defined hereinbelow), wherein p is 1 or 2 and q is 0, 1 or 2];
    (PCe) $R^{14p}$C(O)O(1–6C)alkyl wherein $R^{14p}$ is an optionally substituted 5- or 6-membered heteroaryl, optionally substituted phenyl, (1–4C) alkylamino, benzyloxy-(1–4C)alkyl or optionally substituted (1–10C)alkyl;
    (PCf) $R^{15p}$O— wherein $R^{15p}$ is benzyl or optionally substituted (1–6C)alkyl;
  (PD) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C) alkyl, or Rd and Re together form a (3–4C)alkylene chain; Rf is hydrogen, (1–6C)alkyl, hydroxy(1–6C) alkyl, (1–6C)alkoxy(1–6C)alkyl, amino, (1–4C) alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy, di-(1–4C)alkylamino (2–6C)alkoxy; Rg is (1–6C)alkyl, hydroxy or (1–6C) alkoxy; Rh is hydrogen or (1–6C)alkyl; Ri is hydrogen, (1–6C)alkyl, optionally substituted phenyl or an optionally substituted 5- or 6-membered heteroaryl [and (partially) hydrogenated versions thereof] and Rj is hydrogen or (1–6C)alkyl;
  (PE) $R^{16p}$CH($R^{17p}$)(CH$_2$)$_{mp}$— wherein mp is 0 or 1; $R^{17p}$ is fluoro, cyano, (1–4C)alkoxy, (1–4C)alkylsulfonyl, (1–4C)alkoxycarbonyl or hydroxy, (provided that when mp is 0, $R^{17p}$ is not fluoro or hydroxy) and $R^{16p}$ is hydrogen or (1–4C)alkyl;
    wherein AR is optionally substituted phenyl, optionally substituted phenyl(1–4C)alkyl, optionally substituted naphthyl, optionally substituted 5- or 6-membered heteroaryl;
    wherein AR is also an optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated;
    wherein CY is selected from:
      (i) cyclobutyl, cyclopentyl, cyclohexyl, cyclopentenyl or cyclohexenyl ring;
      (ii) 5- or 6-membered heteroaryl, 5- or 6-membered heteroaryloxy, 5- or 6-membered heteroaryl-S(O)$_q$—, 5- or 6-membered heteroarylamino [and (partially) hydrogenated versions thereof] and (iii) 5/6 or 6/6 bicyclic heteroaryl, 5/6 or 6/6 bicyclic heteroaryloxy, 5/6 or 6/6 bicyclic heteroaryl-S(O)$_q$—, 5/6 or 6/6 bicyclic heteroarylamino [and (partially) hydrogenated versions thereof]; wherein q is 0, 1 or 2 and any of the afore-mentioned ring systems in CY may be optionally substituted by up to three substituents independently selected from halo, (1–4C)alkyl [including geminal disubstitution when CY is a cycloalkyl or cycloalkenyl ring in (i)], acyl, oxo and nitro-(1–4C)alkyl.

For the avoidance of doubt, phosphono is —P(O)(OH)$_2$; (1–4C)alkoxy(hydroxy)-phosphoryl is a mono-(1–4C)alkoxy derivative of —O—P(O)(OH)$_2$; and di-(1–4C)alkoxyphosphoryl is a di-(1–4C)alkoxy derivative of —O—P(O)(OH)$_2$.

In this embodiment of formula (IP) a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

Particular examples of 5-membered heteroaryl rings containing 2 or 3 heteroatoms independently selected from N, O and S (with the proviso that there are no O—O, O—S or S—S bonds; and in an alternative embodiment, also no N—S bonds) are pyrazole, imidazole, 1,2,3-triazole, 1,2,4-triazole, oxazole, isoxazole, thiazole, 1,2,3-oxadiazole, 1,2,4-oxadiazole, 1,2,5-oxadiazole, 1,3,4-oxadiazole; and also in an alternative embodiment, isothiazole, 1,2,5-thiadiazole, 1,2,4-thiadiazole or 1,2,3-thiadiazole.

In this embodiment of formula (IP) a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

Particular optional substituents for alkyl, phenyl (and phenyl containing moieties) and naphthyl groups and ring carbon atoms in heteroaryl (mono or bicyclic) rings in $R^{14p}$, $R^{15p}$, Ri and AR include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkyl S(O)$_q$— (q is 0, 1 or 2), carboxy, (1–4C)alkoxycarbonyl, (2–4C)alkenyl, (2–4C)alkynyl, (1–4C)alkanoyl, (1–4C)alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1–4C)alkyl, cyano(1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{14p}$, Ri and AR may be mono- or di-substituted on ring carbon atoms with substituents independently selected from the above list of particular optional substituents.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

There follow particular and suitable values for certain substituents and groups referred to in this specification. These values may be used where appropriate with any of the definitions and embodiments disclosed hereinbefore, or hereinafter.

Examples of (1–4C)alkyl and (1–5C)alkyl include methyl, ethyl, and propyl and isopropyl; examples of (1–6C)alkyl include methyl, ethyl, propyl, isopropyl, pentyl and hexyl; examples of (1–10C)alkyl include methyl, ethyl, propyl, isopropyl, pentyl, hexyl, heptyl, octyl and nonyl; examples of (1–4C)alkanoylamino-1–4C)alkyl include formamidomethyl, acetamidomethyl and acetamidoethyl; examples of hydroxy(1–4C)alkyl and hydroxy(1–6C)alkyl include hydroxymethyl, 1-hydroxyethyl, 2-hydroxyethyl and 3-hydroxypropyl; examples of (1–4C)alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C)alkyl)ethenyl include 2-cyano-2-methylethenyl and 2-cyano-2-ethylethenyl; examples of 2-nitro-2-(1–4C)alkyl)ethenyl include 2-nitro-2-methylethenyl and 2-nitro-2-ethylethenyl; examples of 2-((1–4C)alkylaminocarbonyl)ethenyl include 2-(methylaminocarbonyl)ethenyl and 2-(ethylaminocarbonyl)ethenyl; examples of (2–4C)alkenyl include allyl and vinyl; examples of (2–4C)alkynyl include ethynyl and 2-propynyl; examples of (1–4C)alkanoyl include formyl, acetyl and propionyl; examples of (1–4C)alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of (1–4C)alkoxy-1–4C)alkoxy and (1–6C)alkoxy-(1–6C)alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy; examples of (1–4C)alkylS(O)$_2$amino include methylsulfonylamino and ethylsulfonylamino; examples of(1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N—(1–4C)alkyl-N—(1–6C)alkanoylamino include N-methylacetamido, N-ethylacetamido and N-methylpropionamido; examples of (1–4C)alkyl S(O)$_p$NH— wherein p is 1 or 2 include methylsulfinylamino, methylsulfonylamino, ethylsulfinylamino and ethylsulfonylamino; examples of (1–4C)alkylS(O)$_p$((1–4C)alkyl)N— wherein p is 1 or 2 include methylsulfinylmethylamino, methylsulfonylmethylamino, 2-(ethylsulfinyl)ethylamino and 2-(ethylsulfonyl) ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$((1–4C)alkyl)NH— wherein p is 1 or 2 include trifluoromethylsulfinylmethylamino and trifluoromethylsulfonylmethlylamino examples of (1–4C)alkoxy(hydroxy)phosphoryl include methoxy(hydroxy)phosphoryl and ethoxy(hydroxy)phosphoryl; examples of di-(1–4C)alkoxyphosphoryl include di-methoxyphosphoryl, di-ethoxyphosphoryl and ethoxy(methoxy)phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C)alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl; examples of di((1–4C)alkyl)carbamoyl include di(methyl)carbamoyl and di(ethyl)carbamoyl; examples of hydroxyimino(1–4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C) alkanesulfonamido include methanesulfonamido and ethanesulfonamido; examples of (1–4C)alkylaminosulfonyl include methylaminosulfonyl and ethylaminosulfonyl; and examples of di-1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C)alkylaminocarbonyl include methylaminocarbonyl and ethylaminocarbonyl; examples of di((1–4C)alkyl)aminocarbonyl include dimethylaminocarbonyl and diethylaminocarbonyl; examples of (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of di(N-(1–4C)alkyl)aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazinc and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazole[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5-bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid- 7-yl, (3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen), W. L. Mosby (Intercsience Publishers Inc., New York), 1961, Parts 1 and 2.

Where optional substituents are listed such substitution is preferably not geminal disubstitution unless stated otherwise. If not stated elsewhere suitable optional substituents for a particular group are those as stated for similar groups herein.

Suitable substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by (preferably one) substituents selected independently from hydroxy, trifluoromethyl, (1–4C)alkyl S(O)$_q$— (q is 0, 1 or 2) (this last substituent preferably on AR1 only), 1–4C) alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N—(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo(=O), thioxo(=S), (1–4C)alkanoylamino {the (1–4C) alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C)alkyl].

Further suitable substituents on AR1, AR2, AR2a, AR2b, AR3, AR3a, AR3b, AR4, AR4a, CY1 and CY2 are (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, 1–4C)alkanesulfonamido, —SO$_2$NRvRw [wherein Rv is hydrogen or 1–4C)alkyl; Rw is hydrogen or (1–4C)alkyl].

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or 1–4C)alkyl; Rw is hydrogen or 1–4C)alkyl]}, (2–4C)alkenyl, (2–4C)alkynyl, (1–4C) alkoxycarbonyl or oxo (to form an N-oxide).

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C) cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N—(di-(1–4C)alkylaminoethyl)-N—(1–4C)alkylcarbamoyl (to give carbamates), di-(1–4C)alkylaminoacetyl and carboxyacetyl. Examples of substituents on benzoyl include chloromethyl or aminomethyl, 1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification, for example esters described by the definition (Rc2d), and some groups within (Rc2c). Suitable in-vivo hydrolysable esters of a compound of the formula (I) are described as follows. For example, a 1,2-diol may be cyclised to form a cyclic ester of formula (PD1) or a pyrophosphate of formula (PD2):

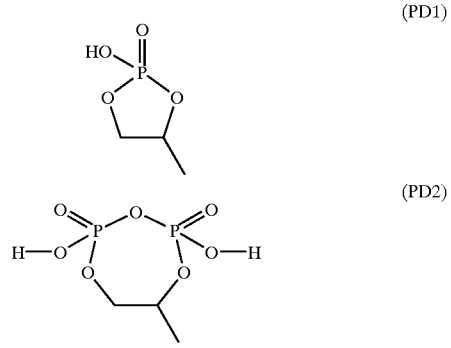

(PD1)

(PD2)

Particularly interesting are such cyclised pro-drugs when the 1,2-diol is on a (1–4C)alkyl chain linked to a carbonyl group in a substituent of formula Rc borne by a nitrogen atom in (TC4). Esters of compounds of formula (I) wherein the HO— function/s in (PD1) and (PD2) are protected by (1–4C)alkyl, phenyl or benzyl are useful intermediates for the preparation of such pro-drugs.

Further in-vivo hydrolysable esters include phosporamidic esters, and also compounds of formula (I) in which any free hydroxy group independently forms a phosphoryl (npd is 1) or phosphiryl (npd is 0) ester of the formula (PD3):

(PD3)

Useful intermediates for the preparation of such esters include compounds containing a group/s of formula (PD3) in which either or both of the —OH groups in (PD3) is independently protected by (1–4C)alkyl (such compounds also being interesting compounds in their own night), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs contain in groups such as (PD1), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection.

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1-6C)alkyl-CO—$ (wherein $R^{14}$ is for example, benzyloxy-(1–4C)alkyl, or phenyl). Suitable substituents on a phenyl group in such esters include, for example, 4-(1–4C) piperazino-(1–4C)alkyl, piperazino-(1–4C)alkyl and morpholino-(1–4C)alkyl.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the oxazolidinone ring. The pharmaceutically active enantiomer is of the formula (IA):

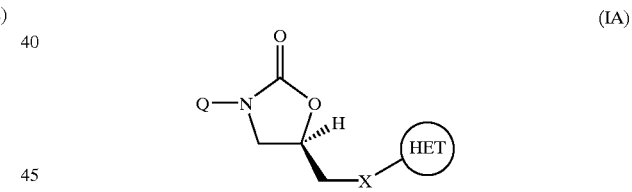

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above is the 5R enantiomer.

Furthermore, some compounds of the formula (I) may have other chiral centres. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics. Physical and/or pharmacokinetic properties, for example increased stability to mammalian peptidase metabolism and a favourable toxicological profile are important features. The following compounds possess particularly favourable physical and/or pharmacokinetic properties and are preferred.

Particularly preferred compounds of the invention comprise a compound of formula (I) or of formula (IP), or a pharmaceutically-acceptable salt or an in-vivo hydrolysable ester thereof, wherein the substituents Q, X, HET, T and other substituents mentioned above have values disclosed hereinbefore, or any of the following values (which may be used where appropriate with any of the definitions and embodiments disclosed hereinbefore or hereinafter):

Preferably Q is selected from Q1, Q2, Q4, Q6 and Q9; especially Q1, Q2 and Q9; more particularly Q1 and Q2; and most preferably Q is Q1.

Preferably T is selected from (TAf), (TDb) or (TC); especially groups (TCb) and (TCc); more particularly (TC2), (TC3) and (TC4); and most preferably (TC5), (TC7) or (TC9), and most particularly (TC5). Especially preferred is each of these values of T when present in Q1 and Q2, particularly in Q1.

Preferable values for other substituents (which may be used where appropriate with any of the definitions and embodiments disclosed hereinbefore or hereinafter) are:

(a) Preferably X is —O—;
 (a1) In another aspect X is —S—;
(b) Preferably HET is pyrazole, imidazole, oxazoic, isoxazole, 1,2,4-oxadiazole, 1,2,5-oxadiazole, 1,3,4-oxadiazole, isothiazole or 1,2,5-thiadiazole. Yet more preferably HET is pyrazol-3-yl, imidazol-2-yl, oxazol-2-yl, isoxazol-3-yl, 1,2,4-oxadiazol-3-yl, 1,3,4-oxadiazol-2-yl, isothiazol-3-yl or 1,2,5-thiadiazol-3-yl;
 (b1) Especially preferred is HET as isoxazole (optionally substituted as disclosed hereinbefore), particularly isoxazol-3-yl;
 (b2) In another embodiment HET is as defined hereinbefore or hereinafter, but excluding thiazole and thiadiazole; and in another embodiment HET is as defined hereinbefore or hereinafter, but excluding isothiazole and thiadiazole;
 (b3) Preferably HET is unsubstituted;
(c) Preferably Rp is hydrogen;
(d) Preferably Rp1 and Rp2 are independently selected from hydrogen, (1–4C)alkyl, carboxy, (1–4C)alkoxycarbonyl, hydroxymethyl, (1–4C)alkoxymethyl or carbamoyl;
(e) Most preferably Rp1 and Rp2 are hydrogen;
(f) Preferably one of $R^2$ and $R^3$ is hydrogen and the other fluoro;
(g) In another aspect both $R^2$ and $R^3$ are fluoro;
(h) Preferably >A—B— is of the formula >C=CH— (i.e. Rr is preferably hydrogen) or >N—CH$_2$—;
(i) Preferably D is —O— or >NRcp;
(j) Preferably Rcp is AR, $R^{13P}CO$—, $R^{13P}SO_2$—, $R^{13P}CS$—;
(k) More preferably Rcp is AR (most preferably benzyl, pyrimidyl, pyridinyl, pyridazinyl or pyrazinyl) or $R^{13P}CO$— (especially $R^{13P}CO$—);
(l) Preferably AR is 5- or 6-membered heteroaryl; more preferably AR is 6-membered heteroaryl, such as pyridinyl;
(m) Preferred substituents for phenyl and carbon atoms in heteroaryl (mono- and bicyclic) ring systems in AR, $R^{14P}$ and Ri include halo, (1–4C)alkyl, hydroxy, nitro, amino, cyano, (1–4C)alkylS(O)$_p$— and (1–4C)alkoxy;
(n) Preferably the optionally substituted ring systems in AR, $R^{14P}$ and Ri are unsubstituted;
 (n1) In another embodiment in the definition of $R^{13P}$ in (PC) of embodiment (IP), 1,3-dioxolan-4-yl and 1,4-dioxan-2-yl are excluded.
(o) Preferably $R^{13P}$ is 1–4C)alkoxycarbonyl, hydroxy(1–4C)alkyl, 1–4C)alkyl (optionally substituted by one or two hydroxy groups, or by an (1–4C)alkanoyl group), (1–4C)alkylamino, dimethylamino(1–4C)alkyl, (1–4C)alkoxymethyl, (1–4C)alkanoylmethyl, (1–4C)alkanoyloxy(1–4C)alkyl, 1–5C)alkoxy or 2-cyanoethyl;
(p) More preferably $R^{13P}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl;
 (p1) Yet more preferably $R^{13P}$ is 1,2-dihydroxyethyl, 1,3-dihydroxyprop-2-yl or 1,2,3-trihydroxyprop-1-yl;
(q) Preferred optional substituents for (1–10C)alkyl in $R^{14P}$ are hydroxy, cyano, amino, (1–4C)alkylamino, di((1–4C)alkyl)amino, 1–4C)alkylS(O)$_p$— (wherein p is 1 or 2), carboxy, (1–4C)alkoxycarbonyl, (1–4C) alkoxy, piperazino or morpholino;
(r) Preferred optional substituents for (1–6C)alkyl in $R^{15P}$ are hydroxy, (1–4C)alkoxy, cyano, amino, (1–4C) alkylamino, di((1–2C)alkyl)amino, (1–4C)alkyl S(O)$_p$— (wherein p is 1 or 2);
(s) Preferably 5- or 6-membered heteroaryl in $R^{14P}$ is pyridinyl or imidazol-1-yl;
(t) Preferably $R^{15P}$ is (1–6C)alkyl; most preferably $R^{15P}$ is tert-butyl or methyl;
(u) Preferably $R^{17P}$ is cyano or fluoro;
(v) Preferably $R^{16P}$ is hydrogen;
(w) Preferably CY is naphthoxy, especially naphth-1-oxy or naphth-2-oxy.

Where preferable values are given for substituents in a compound of formula (IP), the corresponding substituents in a compound of formula (I) have the same preferable values (thus, for example, $R^{13}$ and Rc in formula (I) correspond with Rcp and $R^{13P}$ in formula (IP), and similarly for groups D and G). For compounds of formula (I) preferred values for Rc are those in group (Rc2). The preferred values for $R^{13P}$ listed above for compounds of formula (IP) are also preferred values for $R^{13}$ in compounds of formula (I). In the definition of (Rc2c) the AR2a, AR2b, AR3a and AR3b versions of AR2 and AR3 containing groups are preferably excluded.

In another aspect, HET is a C-linked 5-membered heteroaryl ring containing 2 or 3 heteroatoms independently selected from N, O and S (with the proviso that there are no O—O, O—S, S—S or N—S bonds), which ring is optionally substituted on any available C atom (provided that when a N atom is adjacent to the X-link, there is no substitution on any C atom that is adjacent to this N atom) by 1 or 2 substituents independently selected from (1–4C)alkyl, amino, (1–4C)alkylamino, (1–4C)alkoxy and halogen, and/ or on an available N atom (provided that the ring is not thereby quaternised), by (1–4C)alkyl.

In another aspect, HET is selected from the formulae (HET1) to (HET3) below:

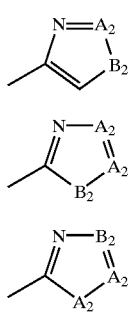

(HET1)

(HET2)

(HET3)

wherein $A_2$ is carbon or nitrogen and $B_2$ is O, S or N (with a maximum of 3 hetero atoms per ring), with carbon or nitrogen ring atoms being optionally substituted as described for HET hereinbefore (preferably with no substitution on any carbon atom that is adjacent to the specified N atom).

In another embodiment HET is as defined herein and also optionally substituted on an available suitable C atom by (1–4C)alkoxycarbonyl.

The above HET definitions are especially preferred in embodiment (IP), and with preferable value (n1) of $R^{13P}$.

Especially preferred compounds of the present invention are of the formula (IB):

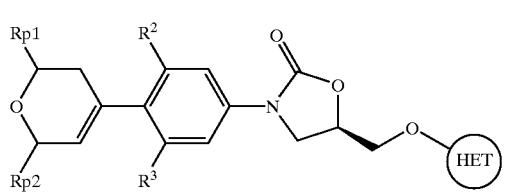

(IB)

wherein HET is isoxazol-3-yl, 1,2,4-oxadiazol-3-yl, isothiazol-3-yl or 1,2,5-thiadiazol-3-yl; $R^2$ and $R^3$ are independently hydrogen or fluoro; and Rp1 and Rp2 are independently hydrogen, hydroxy, bromo, (1–4C)alkyl, carboxy, (1–4C)alkoxycarbonyl, hydroxymethyl, (1–4C) alkoxymethyl or carbamoyl; or pharmaceutically-acceptable salts thereof.

Further especially preferred compounds of the invention are of the formula (IB) wherein HET is isoxazol-3-yl, 1,2,4-oxadiazol-3-yl, isothiazol-3-yl or 1,2,5-thiadiazol-3-yl; $R^2$ and $R^3$ are independently hydrogen or fluoro; and Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene); or pharmaceutically-acceptable salts thereof.

Of the above especially preferred compounds of the invention of the formula (IB), particularly preferred compounds are those wherein Rp1 and Rp2 are hydrogen are particularly preferred.

Further, especially preferred compounds of the invention are of the formula (IC):

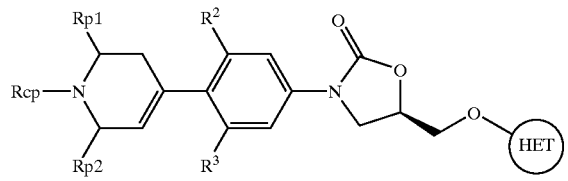

(IC)

wherein HET is isoxazol-3-yl, 1,2,4-oxadiazol-3-yl, isothiazol-3-yl or 1,2,5-thiadiazol-3-yl; $R^2$ and $R^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{13P}CO—$, $R^{13P}SO_2—$ or $R^{13P}CS—$ (wherein $R^{13P}$ is hydrogen, (1–5C) alkyl [optionally substituted by one or more groups each independently selected from hydroxy and amino, or optionally monosubstituted by (1–4C)alkoxy, (1–4C)alkyl $S(O)_q—$, (1–4C)alkylamino, (1–4C)alkanoyl, naphthoxy, (2–6C)alkanoylamino or (1–4C)alkylS(O)$_p$NH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or $R^{13P}$ is of the formula $R^{14P}C(O)O(1–6C)$alkyl wherein $R^{14P}$ is (1–6C)alkyl), or Rcp is of the formula $RfC(=O)C(=O)—$ wherein Rf is (1–6C)alkoxy; or pharmaceutically-acceptable salts thereof.

Of the above especially preferred compounds of the invention of the formula (IC), those wherein HET is isoxazol-3-yl, 1,2,4-oxadiazol-3-yl, isothiazol-3-yl or 1,2,5-thiadiazol-3-yl; $R^2$ and $R^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{13P}CO—$, $R^{13P}SO_2—$ or $R^{13P}CS—$ (wherein $R^{13P}$ is hydrogen, 1–5C) alkyl [optionally substituted by one or more groups each independently selected from hydroxy and amino, or optionally monosubstituted by (1–4C)alkoxy, (1–4C)alkylS(O)$_q$, (1–4C)alkylamino, (1–4C)alkanoyl, (2–6C)alkanoylamino or (1–4C)alkylS(O)$_p$NH— wherein p is 1 or 2 and q is 0, 1 or 2], pyridine, or $R^{13P}$ is of the formula $R^{14P}C(O)O(1–6C)$ alkyl wherein $R^{14P}$ is (1–6C)alkyl), or Rcp is of the formula $RfC(=O)C(=O)—$ wherein Rf is (1–6C)alkoxy; or pharmaceutically-acceptable salts thereof are further preferred.

Of the above especially preferred compounds of the invention of the formula (IC), particularly preferred compounds are those wherein HET is isoxazol-3-yl, 1,2,4-oxadiazol-3-yl, isothiazol-3-yl or 1,2,5-thiadiazol-3-yl; $R^2$ and $R^3$ are independently hydrogen or fluoro; Rp1 and Rp2 are hydrogen, and Rcp is pyridin-2-yl (optionally substituted with cyano) or Rcp is of the formula $R^{13p}CO$— (wherein $R^{13p}$ is hydrogen, 1,3-dioxolan-4-yl (optionally disubstituted with (1–4C)alkyl) or (1–5C)alkyl [optionally substituted by one or more hydroxy groups] or $R^{13p}$ is of the formula $R^{14p}C(O)O(1–6C)$alkyl wherein $R^{14p}$ is (1–6C) alkyl)); or pharmaceutically-acceptable salts thereof.

Of the above especially preferred compounds of the invention of the formula (IC), particularly preferred compounds are those wherein Rcp is of the formula $R^{13p}CO$— (wherein $R^{13p}$ is hydrogen, 1,3-dioxolan-4-yl (optionally disubstituted with (1–4C)alkyl) or (1–5C)alkyl [substituted by two hydroxy groups]; or pharmaceutically-acceptable salts thereof.

In another aspect of the invention all of the compounds of formula (IB) or (IC) described above are further preferred when HET is isoxazol-3-yl, isothiazol-3-yl or 1,2,5-thiadiazol-3-yl.

In yet another aspect the invention relates to all of the compounds of formula (IB) or (IC) described above wherein HET is isoxazol-3-yl or 1,2,4-oxadiazol-3yl.

In yet another aspect the invention relates to all of the compounds of formula (IB) or (IC) described above wherein HET is isoxazol-3-yl.

In another aspect of the invention there are provided preferred compounds of the formula (IP) wherein —X—HET is isoxazol-3-yloxy, 1,2,4-oxadiazol-3-yloxy, isothiazol-3-yloxy, 1,2,5-thiadiazol-3-yloxy; >A—B— is >N—CH$_2$— and D is NRcp wherein Rcp is a 6-membered heteroaryl ring containing 1, 2 or 3 ring nitrogen atoms as the only ring heteroatoms, linked via a ring carbon atom and optionally substituted on a ring carbon atom by one, two or three substituents independently selected from (1–4C)alkyl, halo, trifluoromethyl, (1–4C)alkyl S(O)$_q$— (wherein q is 0, 1 or 2), 1–4C)alkylS(O)$_2$amino, (1–4C)alkanoylamino, carboxy, hydroxy, amino, (1–4C)alkylamino, di-(1–4C) alkylamino, (1–4C)alkoxycarbonyl, carbamoyl, N—(1–4C) alkylcarbamoyl, di-(N—(1–4C)alkyl)carbamoyl, (1–4C) alkoxy, cyano or nitro, or pharmaceutically-acceptable salts thereof.

In all of the above aspects and preferred compounds of formula (IB) or (IC), in-vivo hydrolysable esters are preferred, especially phosphoryl esters (as defined by formula (PD3) with npd as 1).

In all of the above definitions the preferred compounds are as shown in formula (IA), i.e. the pharmaceutically active (5(R)) enantiomer.

Particular compounds of the present invention include the following (and the individual isomers where a mixture of isomers is possible):

5(R)-Isoxazol-3-yloxymethyl-3-(3-fluoro-4-(3,6-dihydro-(2H)-pyran-4-yl)phenyl)oxazolidin-2-one;

5(R)-(5-Methylisoxazol-3-yloxymethyl)-3-(3-fluoro-4-(3,6-dihydro-(2H)-pyran-4-yl)phenyl)oxazolidin-2-one;

5(R)-Isoxazol-3-yloxymethyl-3-(4-(1-(2,2-dimethyl-1,3-dioxolan-4(R,S)-ylcarbonyl)-5,6-tetrahydropyrid-4-yl)-3,5-difluorophenyl)oxazolidin-2-one;

5(R)-Isoxazol-3-yloxymethyl-3-(4-(1-(2(R,S),3-dihydroxypropanoyl)-1,2,5,6-tetrahydropyrid-4-yl)-3,5-difluorophenyl)-oxazolidin-2-one;

5(R)-Isoxazol-3-yloxymethyl-3-(4-(1-formyl-1,2,5,6-tetrahydropyrid-4-yl)-3,5-difluorophenyl)oxazolidin-2-one;

5(R)-Isoxazol-3-yloxymethyl-3-(4-(1-acetoxyacetyl-1,2,5,6-tetrahydropyrid-4-yl)-3,5-difluorophenyl)oxazolidin-2-one;

5(R)-Isoxazol-3-yloxymethyl-3-(4-(1-hydroxyacetyl-1,2,5,6-tetrahydropyrid-4-yl)-3,5-difluorophenyl)oxazolidin-2-one;

5(R)-Isoxazol-3-yloxymethyl-3-(4-(4-(5-cyanopyrid-2-yl)piperazin-1-yl)-3-fluorophenyl)oxazolidin-2-one;

5(R)-Isothiazol-3-yloxymethyl-3-(3-fluoro-4-(3,6-dihydro-(2H)-pyran-4-yl)phenyl)oxazolidin-2-one;

5(R)-(1,2,5-Thiadiazol-3-yloxymethyl)-3-(3-fluoro-4-(3,6-dihydro-(2H)-pyran-4-yl)phenyl)oxazolidin-2-one;

or pharmaceutically-acceptable salts thereof.

Of the above compounds, especially preferred is (and the individual isomers thereof):

5(R)-Isoxazol-3-yloxymethyl-3-(4-(1-(2(R,S),3-dihydroxypropanoyl)-1,2,5,6-tetrahydropyrid-4-yl)-3,5-difluorophenyl)-oxazolidin-2-one; or pharmaceutically-acceptable salts or in-vivo hydrolysable esters thereof.

Also preferred are the 3-fluorophenyl analogues of the particular 3,5-difluoro compounds mentioned above.

Other preferred Examples if not already specifically mentioned are Example Nos. 1, 2, 7, 14, 48, 148, 151 and 23.

Also preferred is the compound (and the individual isomers thereof):

5(R)-Isothiazol-3-yloxymethyl-3-(4-(1-(2(R,S),3-dihydroxypropanoyl)-1,2,5,6-tetrahydropyrid-4-yl)-3-fluorophenyl)-oxazolidin-2-one; or pharmaceutically-acceptable salts or in-vivo hydrolysable esters thereof.

Most particularly preferred Examples are Example Nos. 12, 18, 19, 20, 21 and 22 or pharmaceutically-acceptable salts. In-vivo hydrolysable esters of Examples 12 and 18 are preferred, especially phosphoryl esters.

Thus, preferred are the compounds, or pharmaceutically-acceptable salts thereof:

5(R)-Isoxazol-3-yloxymethyl-3-(4-(1-(2(S),3-diphosphoryl-propanoyl )-1,2,5,6-tetrahydropyrid-4-yl)-3-fluorophenyl)oxazolidin-2-one;

5(R)-Isoxazol-3-yloxymethyl-3-(4-(1-(2(S),3-diphosphoryl-propanoyl)-1,2,5,6-tetrahydropyrid-4-yl)-3,5-difluorophenyl)oxazolidin-2-one.

Also preferred are the compounds, or pharmaceutically-acceptable salts thereof:

5(R)-Isoxazol-3-yloxymethyl-3-(4-(1-(2(S)-hydroxy-3-phosphoryl-propanoyl)-1,2,5,6-tetrahydropyrid-4-yl)-3-fluorophenyl)oxazolidin-2-one;

5(R)-Isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one.

Also preferred are the compounds, or pharmaceutically-acceptable salts thereof:

5(R)-Isoxazol-3-yloxymethyl-3-(4-(1-(3-hydroxy-2(S)-phosphoryl-propanoyl)-1,2,5,6-tetrahydropyrid-4-yl)-3-fluorophenyl)oxazolidin-2-one;

5(R)-Isoxazol-3-yloxymethyl-3-(4-(1-(3-hydroxy-2(S)-phosphoryl-propanoyl)-1,2,5,6-tetrahydropyrid-4-yl)-3,5-difluorophenyl)oxazolidin-2-one.

Suitable pharmaceutically-acceptable salts of the last two named compounds and of Example Nos. 19, 20, 21 and 22 are the mono- and di-salts of the mono-phosphoryl ester compounds and the mono-, di-, tri- and tetra-salts of the di-phosphoryl ester compounds (Examples 19 and 21). Particularly preferred salts are the sodium salts.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Examples of the use of resins as a protecting group are illustrated in Examples 135 & 136 herein.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference:

WO99/02525; WO98/54161; WO97/37980; WO97/30981 (& U.S. Pat. No. 5,736,545); WO97/21708 (& U.S. Pat. No. 5,719,154); WO97/10223; WO97/09328; WO96/35691; WO96/23788; WO96/15130; WO96/13502; WO95/25106 (& U.S. Pat. No. 5,668,286); WO95/14684 (& U.S. Pat. No. 5,652,238); WO95/07271 (& U.S. Pat. No. 5,688,792); WO94/13649; WO94/01110; WO93/23384 (& U.S. Pat. No. 5,547,950 & U.S. Pat. No. 5,700,799); WO93/09103 (& U.S. Pat. No. 5,565,571, U.S. Pat. No. 5,654,428, U.S. Pat. No. 5,654,435, U.S. Pat. No. 5,756,732 & U.S. Pat. No. 5,801,246); U.S. Pat. No. 5,231,188; U.S. Pat. No. 5,247,090; U.S. Pat. No. 5,523,403; WO97/27188; WO97/30995; WO97/31917; WO98/01447; WO98/01446; WO99/10342; WO99/10343; WO99/11642; European Patent Application Nos. 0,359,418 and 0,609,905; 0,693,491 A1 (& U.S. Pat. No. 5,698,574); 0,694,543 A1 (& AU 24985/95); 0,694,544 A1 (& CA 2,154,024); 0,697,412 A1 (& U.S. Pat. No. 5,529,998); 0,738,726 A1 (& AU 50735/96); 0,785,201 A1 (& AU 10123/97); German Patent Application Nos. DE 195 14 313 A1 (& U.S. Pat. No. 5,529,998); DE 196 01 264 A1 (& AU 10098/97); DE 196 01 265 A1 (& AU 10097/97); DE 196 04 223 A1 (& AU 12516/97); DE 196 49 095 A1 (& AU 12517/97).

The following Patent and Application Publications may also provide useful information and the contents of the relevant process sections are hereby incorporated herein by reference:

FR 2458547; FR 2500450(& GB 2094299, GB 2141716 & U.S. Pat. No. 4,476,136); DE 2923295 (& GB 2028306, GB 2054575, U.S. Pat. No. 4,287,351, U.S. Pat. No. 4,348,393, U.S. Pat. No. 4,413,001, U.S. Pat. No. 4,435,415 & U.S. Pat. No. 4,526,786), DE 3017499 (& GB 2053196, U.S. Pat. No. 4,346,102 & U.S. Pat. No. 4,372,967); U.S. Pat. No. 4,705,799; European Patent Application Nos. 0,312,000; 0,127, 902; 0,184,170; 0,352,781; 0,316,594;

The skilled organic chemist will be able to use and adapt the information contained and referenced within the above references to obtain necessary starting materials.

Thus, the present invention also provides that the compounds of the formulae (I) and pharmaceutically-acceptable salts and in vivo hydrolysable esters thereof, can be prepared by a process (a) to (i) as follows (wherein the variables are as defined above unless otherwise stated):

(a) by modifying a substituent in or introducing a substituent into another compound of formula (I);
(b) by reaction of a compound of formula (II)

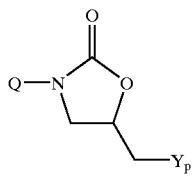

(II)

wherein Yp is hydroxy with a compound of the formula (b1) HET—OH or (b2) HET—Lg, wherein Lg is a suitable leaving group;
(c) by reaction of a compound of formula (II) wherein Yp is a leaving group, for example halogen, mesylate or tosylate, with a metal alkoxide compound of the formula HET—OM where M is an alkali metal, or another metal, such as silver, known to promote O-alkylation;
(d) by reaction of a compound of the formula Q—Zp wherein Zp is an isocyanate or amine group with an epoxide of the formula $CH_2(O)CH$—$CH_2O$—HET;
(e) when X is —S— by a process analogous to process (c) wherein (e1) a metal thioxide compound of the formula HET—SM where M is an alkali metal, or another metal, such as silver, known to promote S-alkylation; or
(e2) alternatively by a process analogous to process (c) using HET—SH and a compound of formula (II) in which Yp is a suitable leaving group;
(f) when X is —SO— or —$SO_2$— by oxidation of a compound wherein X is —S—;
(g) by conversion to a non-quaternary compound of a compound of formula (I) in which the ring HET bears a quaternary nitrogen;
(h) when HET is an isoxazole ring by reaction of a compound of the formula (II) in which Yp is —O—CH=N—OH with an acetylene;
(i) by reaction of a urethane compound of formula (III) with a compound of formula (IV)

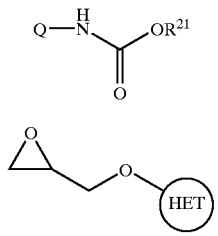

wherein $R^{21}$ is (1–6C)alkyl or benzyl; and thereafter if necessary
(i) removing any protecting groups; (ii) forming a pharmaceutically-acceptable salt; (iii) forming an in vivo hydrolysable ester.

General guidance on reaction conditions and reagents may be obtained in Advanced Organic Chemistry, $4^{th}$ Edition, Jerry March (publisher: J. Wiley & Sons), 1992. Necessary starting materials may be obtained by standard procedures of organic chemistry, such as described in this process section, in the Examples section or by analogous procedures within the ordinary skill of an organic chemist. Certain references are also provided (see above) which describe the preparation of certain suitable starting materials, for particular example see International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the art. For example an alkylthio group may be oxidised to an alkylsulfinyl or alkylsulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet.Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I).

One compound of formula (I) may be converted into another compound of formula (I) by reacting a compound of formula (I) in which T is halo with a suitable compound to form another value of T. Thus, for example, T as halo may be displaced by suitable vinyl, aromatic, tropolone and nitrogen-linked systems as T by reaction using known Pd(0) coupling techniques.

Further examples of converting substituents into other substituents are contained in the accompanying non-limiting Examples.

(b1) When HET—OH is used reaction (b1) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

(b2) When HET—Lg is used reaction (b2) is performed using a suitably reactive HET and under basic conditions (using a base such as 1,8-diazabicyclo[5,4,0]undec-7-ene) which are sufficiently mild not to destroy the oxazolidinone ring structure. The skilled organic chemist will appreciate which suitable leaving group Lg (such as chloro or bromo) and reaction conditions to use.

Compounds of the formula (II) wherein Yp is hydroxy may be obtained by reacting a compound of the formula (III) with a compound of formula (V):

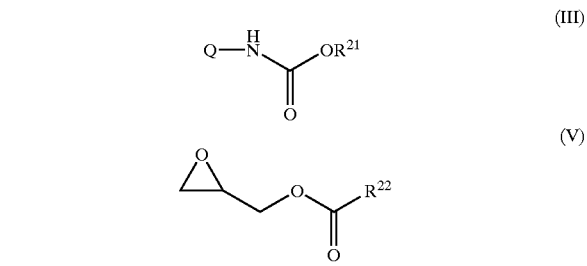

wherein $R^{21}$ is (1–6C)alkyl or benzyl and $R^{22}$ is (1–4C)alkyl or $S(O)_q$(1–4C)alkyl where q is 0, 1 or 2. Preferably $R^{22}$ is (1–4C)alkyl.

Compounds of the formula (II), (III) and (V) may be prepared by the skilled chemist, for example as described in International Patent Application Publication Nos. WO95/07271, WO97/27188, WO 97/30995, WO 98/01446 and WO 98/01446, the contents of which are hereby incorporated by reference, and by analogous processes.

If not commercially available, compounds of the formula HET—OH and HET—Lg may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt.I (1993), 45–225, B. J. Wakefield (for isoxazoles) and E8c, Pt.I (1994) 409–525, U. Kraatz (for 1,2,4-oxadiazoles). Also, for example, 3-hydroxyisoxazole may be prepared by cyclisation of CH≡C—CO—NHOH (prepared from CH≡C—CO—O—(-4C)alkyl) as described in Chem.Pharm.Bull.Japan, 14, 92, (1966).

(c) & (e) Reactions (c) and (e) are performed conveniently at a temperature in the range 25–60° C. in a solvent such as MAP or DMF.

A compound of the formula (II) wherein Yp is fluoro may be prepared by reacting a compound of the formula (II) wherein Yp is hydroxy (hiydroxy compound) with a fluorinating agent such as diethylaminosulfur trifluoride in an organic solvent such as dichloromethane in the temperature range of 0° C. to ambient temperature.

When Yp is chloro, the compound of the formula (II) may be formed by reacting the hydroxy compound with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Yp is chloro or iodo may also be prepared from a compound of the formula (II) wherein Yp is mesyl ate or tosylate, by reacting the latter compound with lithium chloride or lithium iodide and crown ether, in a suitable organic solvent such as THF, in a temperature range of ambient temperature to reflux When Yp is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

Compounds of the formula HET—OM and HET—SM may be prepared by the skilled chemist from the corresponding HET—OH or HET—SH compound, using a suitable base, such as sodium hydride, silver carbonate, sodium carbonate or an alkoxide.

When X is —S— and a process is used that is analogous to process (c) but using HET—SH and a compound of formula (II) in which Yp is a suitable leaving group, a suitable leaving group is, for example, mesylate and a suitable base for the reaction is a base such as 1,8-diazabicyclo[5,4,0]undec-7-ene (see for example, Example 153).

(d) Reaction (d) is performed under conditions analogous to those described in the following references which disclose how suitable and analogous starting materials may be obtained.

Compounds of the formula Q—Zp wherein Zp is an isocyanate may be prepared by the skilled chemist, for example by analogous processes to those described in Walter A. Gregory et al in J.Med.Chem. 1990, 33, 2569–2578 and Chung-Ho Park et al in J.Med.Chem. 1992, 35, 1156–1165.

Compounds of the formula Q—Zp wherein Zp is a urethane (see process (i)) may be prepared by the skilled chemist, for example by analogous processes to those described in International Patent Application Publication Nos. WO 97/30995 and WO 97/37980.

A similar reaction to reaction (d) may be performed in which Q—Zp wherein Zp is a amine group is reacted with the epoxide (optionally in the presence of an organic base), and the product is reacted with, for example, phosgene to form the oxazolidinone ring. Such reactions and the preparation of starting materials in within the skill of the ordinary chemist with reference to the above-cited documents disclosing analogous reactions and preparations.

Epoxides of the formula CH$_2$(O)CH—CH$_2$O—HET may be prepared from the corresponding CH$_2$=CH—CH$_2$—O—HET compound. Certain such epoxide and alkene intermediates are novel and are provided as a further feature of the invention. For example, when HET is isoxazol-3-yl, 3-(2,3-oxiranepropyloxy)isoxazole may be prepared from 3-allyloxyisoxazole. Asymmetric epoxidation may be used to give the desired optical isomer.

(f) When X is —SO— or —SO$_2$— the oxidation of a compound wherein X is —S— may be achieved by oxidising with standard reagents known in the art for the oxidation of a thio group to a sulfinyl or sulfonyl group. For example, a thio group may be oxidised to a sulfinyl group with a peracid such as m-chloroperoxybenzoic acid and oxidising agents such as potassium permanganate can be used to convert a thio group to a sulfonyl group.

(g) The conversion to a non-quaternary compound of a compound of formula (I) in which the ring HET bears a quaternary nitrogen may be achieved under thermal conditions suitable to achieve elimination of the quaternary group (for example, a methyl group will be eliminated as a methyl halide).

A compound of formula (I) in which the ring HET bears a quaternary nitrogen may be prepared in a similar manner to the conditions described for reaction (c), although a suitably quaternised HET compound, substituted in the alpha position next to nitrogen by a leaving group (such as halogen), and a compound of the formula (II) in which Yp is —OH or —SH, is used. Such starting materials are readily prepared by the ordinary organic chemist.

A compound of formula (I) in which the ring HET bears a quaternary nitrogen may also be prepared in a similar manner to the conditions described in Chem.Pharm.Bull.Japan, 27, 2415–2423, (1979), by reaction of an N-alkylated HET—OH or HET—SH compound in the keto-form (with the keto (oxo or thioxo) group in the alpha position next to nitrogen) with a compound of formula (II) in which Yp is a leaving group such as mesylate.

(h) When the HET ring is isoxazole it may be built up as a final step from a compound of the formula (II) in which Yp is —O—CH=N—OH by reaction under standard conditions with an acetylene (see for example, Acta Chem. Scand 47, 1004, 1993).

(i) A compound of formula (III) is reacted with a compound of formula (IV) using similar conditions to those for reaction of a compound of the formula (III) with a compound of formula (V) described above. If not commercially available, the preparation of suitable starting materials of formulae (III) and (IV) is as described above, or by using analogous processes.

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 $mgkg^{-1}$ to 20 $mgkg^{-1}$ of a compound of this invention, the composition being administered 1 to 4 times per day. In another embodiment a daily dose of 5 $mgkg^{-1}$ to 20 $mgkg^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S.aureus* and coagulase negative staphylococci. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 µg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

| Organism | MIC (µg/ml) | | | |
|---|---|---|---|---|
| | Example 4 | Example 12 | Example 18 | Example 151 |
| *Staphylococcus aureus;* | | | | |
| Oxford | 0.25 | 0.25 | 0.25 | 0.13 |
| Novb. Res | 0.50 | 0.5 | 0.25 | 0.25 |
| MRQR | 0.50 | 0.5 | 0.5 | 0.25 |
| Coagulase Negative Staphylococci | | | | |
| MS | 0.13 | 0.13 | 0.13 | 0.13 |
| MR | 0.50 | 0.5 | 0.5 | 0.25 |
| *Streptococcus pyogenes* | | | | |
| C203 | 0.50 | 0.5 | 0.25 | 0.25 |
| *Enterococcus faecalis* | 1.00 | 1.00 | 0.5 | 0.25 |
| *Bacillus subtilis* | 0.25 | 0.25 | 0.25 | 0.13 |

Novb. Res = Novobiocin resistant
MRQR = methicillin resistant quinolone resistant
MR = methicillin resistant
MS = methicillin sensitive Certain Reference Examples described hereinafter (for example, Reference Examples 9, 10, 11, 30, 38 & 39) may also possess useful activity.

The invention is now illustrated but not limited by the following Examples in which unless otherwise stated:

i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the formula (I) were generally confirmed by NMR and mass spectral techniques [proton magnetic resonance spectra were generally determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; t, triplet; m, multiplet; fast-atom bombardment (FAB) mass spectral data were generally obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:
® is a Trademark; DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; THF is tetrahydrofuran; TFA is trifluoroacetic acid; NMP is N-methylpyrrolidone; HOBT is 1-hydroxy-benzotriazole; EtOAc is ethyl acetate; MeOH is methanol; phosphoryl is $(HO)_2$—P(O)—O—; phosphiryl is $(HO)_2$—P—O—; EDC is 1-(3-dimethylaminopropyl)-3-ethylcarbodiimide (hydrochloride); PTSA is para-toluenesulfonic acid.

EXAMPLE 1

5(R)-Isoxazol-3-yloxymethyl-3-(3-fluoro-4-(3,6-dihydro-(2H)-pyran-4-yl)phenyl)oxazolidin-2-one Diisopropylazodicarboxylate (248 mg, 1.22 mmol) was added dropwise, at ambient temperature, to a stirred solution of 5(R)-hydroxymethyl-3-(3-fluoro-4-(3,6-dihydro-(2H)-pyran-4-yl)phenyl)oxazolidin-2-one (International Patent Application Publication WO 97/09328) (300 mg, 1.02 mmol), 3-hydroxyisoxazole (104 mg, 1.22 mmol) and triphenylphosphine (340 mg, 1.30 mmol) in THF (8.0 ml). The resulting solution was stirred at ambient temperature for 30 minutes before evaporating the solvent to give an oil which was purified by flash chromatography (Merck 9385 silica, EtOAc/iso-hexane (7:3) eluant) to give the title product (219 mg, 59%) as a crystalline solid.

$^1$H-NMR (300 MHz, $CDCl_3$): δ=2.45–2.55 (m, 2H), 3.88–4.00 (m, 3H), 4.17 (t, 1H), 4.33 (m, 2H), 4.50 (dd, 1H), 4.58 (dd, 1H), 5.04 (m, 1H), 6.01 (d, 1H), 6.06 (m, 1H), 7.22–7.32 (m, 2H), 7.42 (d, 1H), 8.15 (d, 1H). MS: $ESP^+$ $(M+H)^+$=361.

EXAMPLE 2

5(R)-(5-Methylisoxazol-3-yloxymethyl)-3-(3-fluoro-4-(3,6-dihydro-(2H)-pyran-4-yl)phenyl)oxazolidin-2-one 5(R)-hydroxymethyl-3-(3-fluoro-4-(3,6-dihydro-(2H)-pyran-4-yl)phenyl)oxazolidin-2-one (300 mg, 1.02 mmol), 3-hydroxy-5-methylisoxazole (120 mg, 1.21 mmol), triphenylphosphine (270 mg, 1.03 mmol) and diisopropylazodicarboxylate (204 mg, 1.01 mmol) were reacted in THF (8.0 ml) using the general method of Example 1. The resultant product was purified by flash chromatography (Merck 9385 silica, EtOAc/isohexane (7:3) eluant) to give the title product (176 mg, 46%) as a crystalline solid.

$^1$H-NMR (300 MHz, $CDCl_3$): δ=2.34 (s, 3H), 2.45–2.55 (m, 2H), 3.86–4.00 (m, 3H), 4.14 (t, 1H), 4.32 (m, 2H), 4.46 (dd, 1H), 4.54 (dd, 1H), 5.02 (m, 1H), 5.65 (s, 1H), 6.05 (m, 1H), 7.20–7.32 (m, 2H), 7.42 (d, 1H). MS: $ESP^+$ $(M+H)^+$=375.

REFERENCE EXAMPLE 1

3,5-Difluoro-4-(1-benzyl-4-hydroxyhexahydropyrid-4-yl)aniline nBuLi (1.32M in hexanes, 350 ml, 0.462 mol) was added dropwise over 20 minutes to a solution of N,N-(1,2-bis (dimethylsilyl)ethane)-3,5-difluoroaniline, (108.4 g, 0.40 mol, J. Org. Chem., 60, 5255–5261 (1995)) in 800 ml dry THF at −70° C. under argon. After stirring for a further 4 hours at −70° C., N-benzyl-4-piperidone (87.8 g, 0.46 mol) in 270 ml dry THF was added dropwise over 40 minutes at the same temperature and the reaction allowed to stir to ambient temperature overnight. Solvent was removed in vacuo and the resultant product treated with ice and conc.HCl and extracted with ether. The aqueous acidic phase was then treated with 40% NaOH with cooling, extracted with ether (and worked up by washing with water, with brine and drying with an anhydrous drying agent such as magnesium sulfate or sodium sulfate before evaporation—this work up procedure is referred to as work up in the usual manner hereinafter) to give 144.7 g of a sludge. Analysis by TLC using 10% MeOH/dichloromethane on silica indicated that the desired alcohol was present as approximately 90% of the product, and the crude product was used without further purification. MS: ESP+ (M+H)=319.

REFERENCE EXAMPLE 2

3,5-Difluoro-4-(1-benzyl-1,2,5,6-tetrahydropyrid-4-yl)aniline

The crude product from Reference Example 1 (144.7 g) was suspended in 400 ml conc.HCl and heated at reflux with stirring for 18 hours. TLC showed all starting material had reacted and after cooling in ice the reaction mixture was taken to pH 11 with conc. $NH_3$ (aq) and extracted three times with dichloromethane. Usual work-up gave 119.5 g of a viscous oil. TLC indicated a purity of ca. 80% and the crude product was used without further purification. MS: ESP+ (M+H)=301.

REFERENCE EXAMPLE 3

N-Benzyloxycarbonyl-3,5-difluoro-4-(1-benzyl-1,2,5,6-tetrahydropyrid-4-yl)aniline The crude aniline from Reference Example 2 (3.2 g, 10.7 mmol) in 10 ml of acetone was added in one portion to a stirred solution of sodium dihydrogen phosphate (3.0 g) in 30 ml water. The resulting mixture was cooled to 5–10° C. and a solution of benzylchloroformate (2.18 g, 1.8 ml, 12.8 mmol) in 10 ml of acetone was added dropwise. The mixture was stirred for a further hour at ice-bath temperature and then at ambient temperature for 2 hours. The mixture was diluted with 80 ml water, basified with conc.$NH_3$(aq) and extracted with EtOAc. Usual work-up gave a viscous oil which was purified by flash chromatography (Merck 9385 silica, EtOAc/isohexane (3:7 eluant) and triturated with isohexane to give a solid (1.53 g 33%). MS: ESP+ (M+H)=434.

REFERENCE EXAMPLE 4

5(R)-Hydroxymethyl-3-(4-(1-benzyl-1,2,5,6-tetrahydropyrid-4-yl)-3,5-difluorophenyl)oxazolidin-2-one The benzylurethane from Reference Example 3 (5.54 g, 12.76 mmol) in 50 ml dry THF was cooled to −70° C. under nitrogen and 8.80 ml of 1.6M nBuLi in hexanes (14.08 mmol) added dropwise at the same temperature. After 20 minutes at the same temperature a solution of (R)-glycidyl butyrate (2.00 g, 13.88 mmol in 5 ml THF) was added dropwise and the mixture stirred for 30 minutes at −70° C., and then stirred to ambient temperature overnight. After quenching with 100 ml 10% ammonium chloride, the mixture was extracted with EtOAc and usual work-up to give an oily solid, which was purified by flash chromatography (Merck C60 silica, 5% MeOH/dichloromethane eluant) to give a crystalline solid (4.40 g, 86%). MS: ESP+ (M+H)=401.

$^1$H-NMR (250 MHz, DMSO-d6): δ=2.32 (m, 2H), 2.63 (t, 2H), 3.05 (m, 2H), 3.50–3.72 (m, 4H), 3.82 (dd, 1H), 4.06 (t, 1H), 4.73 (m, 1H), 5.18 (t, 1H), 5.78 (m, 1H).

REFERENCE EXAMPLE 5

5(R)-Isoxazol-3-yloxymethyl-3-(4-(1-benzyl-1,2,5,6-tetrahydropyrid-4-yl)-3,5-difluorophenyl)oxazolidin-2-one Reference Example 4 (2.6 g, 6.5 mmol), 3-hydroxyisoxazole (0.60 g, 7.06 mmol), triphenylphosphine (1.96 g, 7.48 mmol) and diisopropylazodicarboxylate (1.44 g, 7.13 mmol) in THF (40 ml) were reacted using the general method of Example 1. The resultant product was purified by flash chromatograpy (Merck 9385 silica, EtOAc/isohexane (3:2) eluant initially, then repeated using methyl tert-butylether eluant) to give the title product (2.6 g, 86%) as a gum, MS: ESP$^+$ (M+H)$^+$=468.

REFERENCE EXAMPLE 6

5(R)-Isoxazol-3-yloxymethyl-3-(4-(1,2,5,6-tetrahydropyrid-4-yl)-3,5-difluorophenyl)oxazolidin-2-one Reference Example 5 (2.6 g, 5.57 mmol) in dichloromethane (40 ml) was cooled, under an atmosphere of nitrogen, in an ice-water bath then 1-chloroethyl chloroformate (0.80 g, 5.59 mmol) added dropwise via syringe. The resulting solution was stirred at ice temperature for 1 hour before isolating the intermediate product (carbamate) by flash chromatograhy (Merck 9385 silica, EtOAc/isohexane (1:1) eluant). The resulting gum was taken up in MeOH (40 ml) and refluxed for 1 hour. Evaporation of the solvent after this time gave the title product (1.46 g, 64%) as a crystalline solid.

$^1$H-NMR (300 MHz, DMSO-d6): δ=2.54 (m, 2H), 3.27 (m, 2H), 3.72 (m, 2H), 3.92 (dd, 1H), 4.20 (t, 1H), 4.38–4.52 (m, 2H), 5.10 (m, 1H), 5.88 (m, 1H), 6.38 (d, 1H), 7.37 (m, 2H), 8.68 (d, 1H), 9.39 (s(broad), 2H). MS: ESP$^+$ (M+H)$^+$=378.

EXAMPLE 3

5(R)-Isoxazol-3-yloxymethyl-3-(4-(1-(2,2-dimethyl-1,3-dioxolan-4(R,S)-ylcarbonyl)-1,2,5,6-tetrahydropyrid-4-yl)-3,5-difluorophenyl)oxazolidin-2-one 1-(3-Dimethylaminopropyl)-3-ethylcarbodiimide hydrochloride (160 mg, 0.84 mmol) was added portionwise at ambient temperature to a stirred mixture of Reference Example 6 (300 mg, 0.72 mmol), (R/S)-2,3-O-isopropylideneglyceric acid (122 mg, 0.84 mmol) and triethylamine (73 mg, 0.72 mmol) in dichloromethane (6 ml). The resulting mixture was stirred for 3 hours then left to stand overnight before washing with water. The dichloromethane solution was purified by flash chromatography (Merck 9385 silica. EtOAc/isohexane (3:1) eluant) to give the title product (143 mg, 39%) as a crystalline solid. MS: ESP$^+$ (M+H)$^+$=506.

$^1$H-NMR (300 MHz, CDCl$_3$): δ=1.41 (s, 6H), 2.35–2.65 (m, 2H), 3.65–3.80 (m, 1H), 3.92–4.00 (m, 2H), 4.10–4.22

(m, 3H), 4.22–4.45 (m, 1H), 4.45–4.62 (m, 3H), 4.75 (t, 1H), 5.05 (m, 1H), 5.80–5.91 (m, 1H), 6.01 (d, 1H), 7.18 (m, 2H), 8.16 (d, 1H).

EXAMPLE 4

5(R)-Isoxazol-3-yloxymethyl-3-(4-(1-(2(R,S),3-dihydroxypropanoyl)-1,2,5,6-tetrahydropyrid-4-yl)-3,5-difluorophenyl)-oxazolidin-2-one Example 3 (194 mg, 0.38 mmol ) in a mixture of THF (3 ml) and 1N hydrochloric acid (1 ml) was left to stand at ambient temperature for 4 days. The solvent was then evaporated to give an oil which was purified by flash chromatography (Merck 9385 silica, 10% MeOH/dichloromethane eluant) to give the title product (144 mg, 80%) as a crystalline solid. MS: ESP$^+$ (M+H)$^+$=466.

$^1$H-NMR (300 MHz, DMSO-d6): δ=2.20–2.46 (m, 2H), 3.40–3.63 (m, 2H), 3.63–3.85 (m, 2H), 3.92 (dd, 1H), 4.10 (m, 1H), 4.18 (t, 1H), 4.26–4.52 (m, 4H), 4.68 (m, 1H), 4.96 (m, 1H), 5.10 (m, 1H), 5.86 (m, 1H), 6.37 (d, 1H), 7.34 (m, 2H), 8.68 (d, 2H).

EXAMPLE 5

5(R)-Isoxazol-3-yloxymethyl-3-(4-(1-formyl-1,2,5,6-tetrahydropyrid-4-yl)-3,5-difluorophenyl)oxazolidin-2-one Reference Example 6 (300 mg, 0.72 mmol ) and triethylamine (102 mg, 1.01 mmol ) in ethyl formate (10 ml) were refluxed for 12 hours, and then evaporated to give an oil which was purified by flash chromatoraphy (Merck 9385 silica, 4% MeOH/dichloromethane eluant) to give the title product (261 mg, 89%) as a crystalline solid.

$^1$H-NMR (300 MHz, CDCl$_3$): δ=2.18 & 2.37 (2s, 2H), 3.20–3.40 (m (partially obscured), 2H), 3.57–3.66 (m, 2H), 3.92 (m, 1H), 4.05 & 4.10 (2m, 2H), 4.20 (t, 1H), 4.38–4.54 (m, 2H), 5.10 (m, 1H), 5.86 & 5.90 (2m, 1H), 6.37 (d, 1H), 7.32 (m, 2H), 8.10 & 8.18 (2s, 1H), 8.68 (d, 1H). MS: ESP$^+$ (M+H)$^+$=406.

EXAMPLE 6

5(R)-Isoxazol-3-yloxymethyl-3-(4-(1-acetoxyacetyl-1,2,5,6-tetrahydropyrid-4-yl)-3,5-difluorophenyl)oxazolidin-2-one Reference Example 6 (400 mg, 0.97 mmol ), triethylamine (205 mg, 2.03 mmol ) and 4-(dimethylamino)pyridine (30 mg) in dichloromethane (10 ml) were cooled in an ice-water bath then acetoxyacetyl chloride (145 mg, 1.06 mmol ) was added dropwise via syringe. The mixture was stirred at ice temperature for 2 hours then purified by flash chromatography (Merck 9385 silica, 2.5% MeOH/dichloromethane eluant) to give the title product (430 mg, 93%) as a crystalline solid.

$^1$H-NMR (300 MHz, CDCl$_3$): δ=2.20 (s, 3H), 2.40–2.56 (m, 2H), 3.59 (t, 1H), 3.82 (t, 1H), 3.95 (dd, 1H), 4.08 & 4.25 (2m 2H), 4.12 (t, 1H), 4.50 (dd, 1H), 4.58 (dd, 1H), 4.74 & 4.78 (2s, 2H), 5.05 (m, 1H), 5.80 & 5.88 (2m, 1H), 6.00 (d, 1H), 7.19 (m, 2H), 8.17 (d, 1H). MS: ESP$^+$ (M+H)$^+$=478.

EXAMPLE 7

5(R)-Isoxazol-3-yloxymethyl-3-(4-(1-hydroxyacetyl-1,2,5,6-tetrahydropyrid-4-yl)-3,5-difluorophenyl)oxazolidin-2-one Example 6 (280 mg, 0.59 mmol ) and potassium carbonate (150 mg, 1.09 mmol ) in MeOH (6 ml) were stirred at ambient temperature for 4 hours. Water (30 ml) was added to give a crystalline solid, which was filtered, washed with water and dried to give the title product (215 mg, 84%). MS: ESP$^+$ (M+H)$^+$=436.

$^1$H-NMR (300 MHz, DMSO d-6): δ=2.22–2.42 (m, 2H), 3.52 (m, 1H), 3.68 (m, 1H), 3.92 (dd, 1H), 4.00–4.24 (m, 5H), 4.40–4.52 (m, 2H), 4.52–4.76 (m, 1H), 5.10 (m, 1H), 5.86 (m, 1H), 6.36 (d, 1H), 7.35 (m, 2H), 8.68 (d, 2H).

REFERENCE EXAMPLE 7

5(R)-Hydroxymethyl-3-(4-(4-(5-cyanopyrid-2-yl)piperazin-1-yl)-3-fluorophenyl)oxazolidin-2-one 5(R)-hydroxymethyl-3-(3-fluoro-4-(4-t-butoxycarbonylpiperazin-1-yl)phenyl)oxazolidin-2-one (International Patent Application Publication WO 93/23384. 43.1 g, 0.11 M) was suspended by stirring in ethanol (1000 ml) under nitrogen. An ethanol solution of hydrogen chloride (3.8 M, 400 ml) was added slowly, and the mixture was stirred at ambient temperature for 18 hours. The resulting precipitate was filtered, washed with diethyl ether (3×250 ml), and dried, to give 5(R)-hydroxymethyl-3-(3-fluoro-4-(piperazin-1-yl)phenyl)oxazolidin-2-one hydrochloride. A further crop was obtained by evaporation of the mother liquors to give a total yield of 38.7 g.

$^1$H-NMR (300 MHz, DMSO-D6) δ: 3.17 (m, 8H); 3.53 (dd, 1H); 3.64 (dd, 1H); 3.79 (dd, 1H) 4.03 (t, 1H); 4.66 (m, 1H); 7.10 (t, 1H); 7.21 (dd, 1H); 7.52 (dd, 1H) 9.39 (br s, 2H). MS: ESP+ (M+H)$^+$=296.

5(R)-hydroxymethyl-3-(3-fluoro-4-(piperazin-1-yl)phenyl)oxazolidin-2-one hydrochloride (25 g, 75.4 mmol ) was suspended by stirring in acetonitrile (700 ml) under nitrogen, and triethylamine (16.8 g, 166 mmol ) added, The mixture was stirred for 10 minutes and then 2-chloro-5-cyanopyridine (10.3 g, 75.4 mmol ) added, and the mixture heated under reflux for 18 hours. After cooling, the resultant solid was filtered, washed with water (3×500 ml) and diethyl ether (2×500 ml) to give 5(R)-hydroxymethyl-3-(4-(4-(5-cyanopyrid-2-yl)piperazin-1-yl)-3-fluorophenyl)-oxazolidin-2-one. A further crop was obtained by evaporation of the mother liquors to give a total yield of 23.2 g. MS: ESP+ (M+H)$^+$=398.

$^1$H-NMR (300 MHz, DMSO-D6)δ: 3.03 (t, 4H); 3.54 (m, 1H); 3.63(m, 1H); 3.78 (t overlapping m, 5H); 4.03 (t, 1H); 4.66 (m, 1H); 5.18 (t, 1H); 6.97 (d, 1H); 7.07 (t, 1H); 7.20 (dd, 1H); 7.53 (dd, 1H); 7.85 (dd, 1H); 8.49 (d, 1H).

EXAMPLE 8

5(R)-Isoxazol-3-yloxymethyl-3-(4-(4-(5-cyanopyrid-2-yl)piperazin-1-yl)-3-fluorophenyl)oxazolidin-2-one Reference Example 7 (397 mg, 1 mmol ), 3-hydroxyisoxazole (85 mg, 1.1 mmol ) and polymer bound triphenylphosphine (3 mmol /g, 416 mg, 1.25 mmol ) were suspended with stirring in 10 ml dry THF and diisopropylazodicarboxylate (242 mg, 1.2 mmol) added dropwise by syringe, and the mixture stirred at ambient temperature for 1 hour. The mixture was filtered, evaporated to dryness, and dissolved in EtOAc and purified by chromatography (on a 10 g silica Mega Bond Elut® column, eluting with a gradient increasing in polarity from 80 to 100% EtOAc in isohexane) to give the title product (93 mg). MS: ESP+: (M+H)$^+$=465.

$^1$H-NMR (300 MHz, DMSO-D6) δ: 3.06 (t, 4H); 3.80 (t, 4H); 3.87 (dd, 1H); 4.16 (t, 1H); 4.42 (dd, 1H); 4.48 (dd, 1H); 5.04 (m, 1H); 6.37 (d, 1H); 6.97 (d, 1H); 7.08 (t, 1H); 7.20 (dd, 1H); 7.51 (dd, 1H); 7.86 (dd, 1H); 8.49 (d, 1H); 8.67 (d, 1H).

EXAMPLE 9

5(R)-Isothiazol-3-yloxymethyl-3-(3-fluoro-4-(3,6-dihydro-(2H)-Pyran-4-yl)phenyl)oxazolidin-2-one Diisopropylazodicarboxylate (227 mg, 1.12 mmol) was added dropwise, at ambient temperature, to a stirred solution of 5(R)-hydroxymethyl-3-(3-fluoro-4-(3,6-dihydro-(2H)-pyran-4-yl)phenyl)oxazolidin-2-one (300 mg, 1.02 mmol ; see Example 1), 3-hydroxyisothiazole (114 mg, 1.13 mmol) and triphenylphosphine (304 mg, 1.16 mmol) in THF (8.0 ml). The resulting solution was stirred at room temperature for 30 minutes before evaporating the solvent to give an orange oil. It was purified by flash chromatography (Merck 9385 silica, EtOAc/isohexane (3:2)) to give the title product (257 mg, 67%) as a colourless crystalline solid. MS: ESP$^+$ (M+H)$^+$=377.

$^1$H-NMR (300 MHz, CDCl$_3$): δ=2.45–2.55 (m, 2H), 3.94 (t, 2H), 3.98 (dd, 1H), 4.14 (t, 1H), 4.32 (m, 2H), 4.61–4.72 (m, 2H), 5.04 (m, 1H), 6.07 (m, 1H), 6.62 (d, 1h), 7.22–7.30 (m, 2H), 7.42 (dd, 1H), 8.48 (d, 1H).

EXAMPLE 10

5(B)-(1,2,5-Thiadiazol-3-yloxymethyl)-3-(3-fluoro-4-(3,6-dihydro-(2H)-pyran-4-yl)phenyl)oxazolidin-2-one A solution of 5(R)-hydroxymethyl-3-(3-fluoro-4-(3,6-dihydro-(2H)-pyran-4-yl)phenyl)oxazolidin-2-one (0.275 g, 0.93 mmol ; see Example 1), 3-hydroxy-1,2,5-thiadiazole (Weinstock et al, J.Org. Chem, 32, 2823 (1967)) (0.112 g, 1.1 mmol), and triphenylphosphine (0.288 g, 1.1 mmol) was stirred in dry THF (7 ml) at ambient temperature and diisopropylazodicarboxylate (0.22 g. 1.1 mmol) in dry THF (1.0 ml) added dropwise over ten minutes. After 1.5 hours, tlc (70% EtOAc/isohexane) showed essentially complete reaction. The reaction mixture was evaporated in vacuo and purified by chromatography (Merck 9385 silica, 50% EtOAc/isohexane eluant) to give the title product (256 mg, 73%) as a colourless solid mp, 46–8 C.

$^1$H-NMR (300 MHz, DMSO-d6): δ=2.40 (m, 1H), 3.78 (m, 3H), 3.96 (dd, 1H), 4.20 (m, 3H), 4.64 (m, 2H), 5.10 (m, 1H), 6.08 (s, 1H), 7.35 (m, 2H), 7.50 (d, 1H), 8.41 (s, 1H). MS: ESP$^+$ (M+H)$^+$=377.

REFERENCE EXAMPLE 8

5(R)-(1,2,5-Thiadiazol-3-yloxymethyl)-3-phenyloxazolidin-2-one

Diisopropylazodicarboxylate (4.45 g, 22 mmol) was added dropwise to a stirred solution of 5(R)-hydroxymethyl-3-phenyloxazolidin-2-one (Gregory et al. J. Med, Chem, 32, 1673 (1989); 4.25 g,22 mmol), triphenyl phosphine (5.76 g, 22 mmol) and 3-hydroxy-1,2,5-thiadiazole (Weinstock et al, J.Org. Chem, 32, 2823 (1967)) (2.04 g, 20 mmol) in 30 ml THF, in an ice-bath. After stirring at ambient temperature for two hours and evaporating in vacuo, the resulting oil was purified by chromatography (Merck 9385 silica. Gradient elution from isohexane to ca. 50% EtOAc/isohexane to give a white solid. Further purification by flash chromatography on silica using 1% MeOH/dichloromethane was necessary to remove remaining diisopropylcarboxyhydrazine yielding the title product as a white crystalline solid (4.7 g, 83%). MS: ESP$^+$ (M+H)$^+$=278.

$^1$H-NMR (300 MHz,CDCl$_3$): δ=4.0 (dd, 1H), 4.21 (t, 1H), 4.6–4.77 (m, 2H), 5.04 (m, 1H), 7.17 (t, 1H), 7.39 (m, 2H), 7.56 (d, 2H), 8.0 (s, 1H).

REFERENCE EXAMPLE 9

5(R)-(1,2,5-Thiadiazol-3-yloxymethyl)-3-(4-iodophenyl)oxazolidin-2-one

Silver trifluoroacetate (0.727 g, 3.29 mmol) was added to a stirred solution of the compound of Reference Example 8 (0.70 g, 2.53 mmol) in chloroform/acetonitrile (6 ml/4 ml) at ambient temperature. Iodine (0.67 g, 2.64 mmol) was then added in portions. The resulting brown mixture was then stirred for 65 h with protection from light. A yellow solid was filtered off, washing with chloroform, The filtrate and washings were evaporated in vacuo, the residue redissolved in EtOAc and washed with dilute ammonium hydroxide, water and brine. Dried over sodium sulfate and evaporated in vacuo to give a pale yellow solid on standing. Trituration with ether gave the title product as an off-white solid (0.749 g, 73%).

$^1$H-NMR (300 MHz, DMSO-d$_6$): δ=3.95 (dd, 1H), 4.19 (t, 1H), 4.67 (m, 2H), 5.1 (m, 1H), 7.37 (d, 2H), 7.69 (d, 2H), 8.4 (s, 1H). MS: ESP+ (M+H)$^+$=404.

REFERENCE EXAMPLE 10

5(R)-Isoxazol-3-yloxymethyl-3-(4-(1-benzyl-1,2,5,6-tetrahydropyrid-4-yl)-3-fluorophenyl)oxazolidin-2-one Prepared by the general method of Example 1 using as starting material 5(R)-hydroxymethyl-3-(4-(1-benzyl-1,2,5,6-tetrahydropyrid-4-yl)-3-fluorophenyl)oxazolidin-2-one (WO97/30995; 4.0 g, 10.5 mmol), 3-hydroxyisoxazole (1.0 g, 11.8 mmol), triphenylphosphine (3.24 g, 12.4 mmol) and diisopropylazodicarboxylate (2.36 g, 11.7 mmol) in tetrahydrofuran (60 ml). Purified by flash chromatography (Merck 9385 silica; tert-butyl methyl ether/EtOAc/MeOH (70:30:0.5) eluant) to give the product (3.0 g, 64%) as a colourless crystalline solid. MS: ESP$^{30}$ (M+H)$^+$=450.

REFERENCE EXAMPLE 11

5(R)-Isoxazol-3-yloxymethyl-3-(4-(1,2,5,6-tetrahydropyrid-4-yl)-3-fluorophenyl)oxazolidin-2-one Prepared by the general method of Reference Example 6 using Reference Example 10 (7.09 g, 15.8 mmol) and 1-chloroethyl chloroformate (2.26 g, 15.8 mmol) in dichloromethane (120 ml) to give the product (3.71 g, 59%) as a pale yellow crystalline solid. MS: ESP$^+$ (M+H)$^+$=360.

$^1$H-NMR (300 MHz, DMSO-d6): d=2.64 (m, 2H), 3.22–3.30 (m, 2H), 3.72 (m, 2H), 3.92 (dd, 1H), 4.21 (t, 1H), 4.40–4.55 (m, 2H), 5.10 (m, 1H), 6.02 (m, 1H), 6.38 (d, 1H), 7.32–7.44 (m, 2H), 7.52 (d, 1H), 8.68 (d, 1H), 9.30 (s(br), 2H).

EXAMPLE 11

5(R)-Isoxazol-3-yloxymethyl-3-(4-(1-(2,2-dimethyl-1,3-dioxolan-4(S)-ylcarbonyl)-1,2,5,6-tetrahydropyrid-4-yl)-3-fluorophenyl)oxazolidin-2-one 1,3 Dicyclohexylcarbodiimide (550 mg, 2.67 mmol) was added in one go at ambient temperature to a stirred solution of (S)-2,3-O-isopropylidineglyceric acid (390 mg, 2.67 mmol) and 1-hydroxybenzotriazole (410 mg, 2.58 mmol) in dichloromethane (10 ml). The resulting suspension was stirred for 1 hr then a further 10 ml dichloromethane was added, followed by Reference Example 11 (1.0 g, 2.53 mmol) and N,N-diisopropylethylamine (326 mg, 2.53 mmol). The reaction was stirred at ambient temperature for 18 hr then filtered, The filtrate was washed with water (2X) and brine then purified by flash chromatography (Merck 9385 silica; 2% MeOH in dichloromethane eluant) to give the product (754 mg, 61%) as a colourless crystalline solid. MS: ESP$^+$ (M+H)$^+$=488.

$^1$H-NMR (300 MHz, CDCl$_3$): d=1.44 (s, 6H), 2.45–2.72 (m, 2H), 3.62–3.76 (m, 1H), 3.89–4.05 (m, 2H), 4.10–4.20 (m, 3H), 4.24–4.38 (m, 1H), 4.44–4.62 (m, 3H), 4.75 (m, 1H), 5.04 (m, 1H), 5.97 (m, 1H), 6.00 (d, 1H), 7.25 (m, 2H), 7.45 (d, 1H), 8.15 d, 1H).

EXAMPLE 12

5(R)-Isoxazol-3-yloxymethyl-3-(4-(1-(2(S),3-dihydroxypropanoyl)-1,2,5,6-tetrahydropyrid-4-yl)-3-fluorophenyl)oxazolidin-2-one Prepared by the general method of Example 4 using Example 11 (754 mg, 1.55 mmol) in a mixture of THF (15 ml) and 1N hydrochloric acid (5 ml). Purified by flash chromatography (Merck 9385 silica; 10% MeOH in dichloromethane eluant) to give the product (486 mg, 70%) as a colourless crystalline solid, mp 140–143° C.

$^1$H-NMR (300 MHz, DMSO-d6): d=2.42 (m, 2H), 3.40–3.60 (m, 2H), 3.62–3.85 (m, 2H), 3.92 (dd 1H), 4.10–4.30 (m, 3H), 4.30–4.56 (m, 3H), 4.79 (m, 1H), 4.94 (m, 1H), 5.09 (m, 1H), 6.00 (m, 1H), 6.37 (d, 1H), 7.28–7.44 (m, 2H), 7.50 (d, 1H), 8.66 (d, 1H). MS: ESP$^+$ (M+H)$^+$=448. HPLC: Chiralpak AD (250 mm×4.6 mm i.d,), 100% MeOH eluant, 1 ml/min. flow rate: ret. time=42.5 min.

EXAMPLE 13

5(R)-Isoxazol-3-yloxymethyl-3-(4-(1-(2,2-dimethyl-1,3-dioxolan-4(R)-ylcarbonyl)-1,2,5,6-tetrahydropyrid-4-yl)-3-fluorophenyl)oxazolidin-2-one Prepared by the general method of Example 11 using (R)-2,3-O-isopropylidineglyceric acid (390 mg, 2.67 mmol), 1-hydroxybenzotriazole (410 mg, 2.58 mmol), dicyclohexylcarbodiimide (550 mg, 2.67 mmol), Reference Example 11 (1.0 g, 2.53 mmol) and N,N-diisopropylethylamine (326 mg, 2.53 mmol) in dichloromethane (20 ml). Purified by flash chromatography (Merck 9385 silica; 2% MeOH in dichloromethane eluant) to give the product (682 mg, 55%) as a colourless crystalline solid. MS: ESP$^+$ (M+H)$^+$=488.

$^1$H-NMR (300 MHz, CDCl$_3$): d=1.44 (s, 6H), 2.45–2.72 (m, 2H), 3.62–3.76 (m, 1H), 3.89–4.05 (m, 2H), 4.10–4.20 (m, 3H), 4.24–4.38 (m, 1H), 4.44–4.62 (m, 3H), 4.75 (m, 1H), 5.04 (m, 1H), 5.97 (m, 1H), 6.00 (d, 1H), 7.25 (m, 2H), 7.45 (d, 1H), 8.15 d, 1H).

EXAMPLE 14

5(R)-Isoxazol-3-yloxymethyl-3-(4-(1-(2(R),3-dihydroxypropanoyl)-1,2,5,6-tetrahydropyrid-4-yl)-3-fluorophenyl)oxazolidin-2-one Prepared by the general method of Example 12 using Example 13 (682 mg, 1.40 mmol) in a mixture of THF (15 ml) and 1N hydrochloric acid (5 ml). Purified by flash chromatography (Merck 9385 silica; 10% MeOH in dichloromethane eluant) to give the product (466 mg, 74%) as a colourless crystalline solid: mp 136–140° C.

$^1$H-NMR (300 MHz, DMSO-d6): d=2.42 (m, 2H), 3.40–3.60 (m, 2H), 3.62–3.85 (m, 2H), 3.92 (dd, 1H), 4.10–4.30 (m, 3H), 4.30–4.56 (m, 3H), 4.79 (m, 1H), 4.94 (m, 1H), 5.09 (m, 1H), 6.00 (m, 1H), 6.37 (d, 1H), 7.28–7.44 (m, 2H), 7.50 (d, 1H), 8.66 (d, 1H). MS: ESP$^+$ (M+H)$^+$=448. HPLC: Chiralpak AD (250 mm×4.6 mm i.d,), 100% MeOH eluant. 1 ml/min. flow rate: ret. time=18.5 min.

EXAMPLE 15

5(R)-Isoxazol-3-yloxymethyl-3-(4-(1-(2,2-dimethyl-1,3-dioxolan-4(R)-ylcarbonyl)-1,2,5,6-tetrahydropyrid-4-yl)-3,5-difluorophenyl)oxazolidin-2-one 1,3 Dicyclohexylcarbodiimide (315 mg, 1.53 mmol) was added in one go at ambient temperature to a stirred mixture of Reference Example 6 (660 mg, 1.45 mmol), (R)-2,3-O-isopropylidineglyceric acid (240 mg, 1.64 mmol) and pyridine (115 mg, 1.45 mmol) in dichloromethane (15 ml). The resulting mixture was stirred at ambient temperature for 18 hr then purified by flash chromatography (Merck 9385 silica; EtOAc/isohexane (3:1) eluant) to give the product (315 mg, 43%) as a colourless crystalline solid.

EXAMPLE 16

5(R)-Isoxazol-3-yloxymethyl-3-(4-(1-(2(R),3-dihydroxypropanoyl)-1,2,5,6-tetrahydropyrid-4-yl)-3,5-difluorophenyl)oxazolidin-2-one Prepared by the general method of Example 14 using Example 15 (315 mg, 0.62 mmol) in a mixture of THF (6 ml) and 1N hydrochloric acid (2 ml). Purified by flash chromatography (Merck 9385 silica; 10% MeOH in dichloromethane eluant) to give the product (208 mg, 72%) as a colourless crystalline solid: mp 128–134 ° C.

$^1$NMR (300 MHz, DMSO-d$_6$): d 2.20–2.46 (m, 2H), 3.40–3.63 (m, 2H), 3.63–3.85 (m, 2H), 3.92 (dd, 1H), 4.10 (m, 1H), 4.18 (t, 1H), 4.26–4.52 (m, 1H), 4.68 (m, 1H), 4.96 (m, 1H), 5.10 (m, 1H), 5.86 (m, 1H), 6.37 (d, 1H), 7.34 (m, 2H), 8.68 (d, 2H). MS: ESP$^+$ (M+H)$^+$=466. HPLC: Chiralpak AD (250 mm×4.6 mm i.d,), 100% MeOH eluant. 1 ml/min. flow rate: ret. time=11.2 min.

EXAMPLE 17

5(R)-Isoxazol-3-yloxymethyl-3-(4-(1-(2,2-dimethyl-1,3-dioxolan-4(S)-ylcarbonyl)-1,2,5,6-tetrahydropyrid-4-yl)-3,5-difluorophenyl)oxazolidin-2-one Prepared by the general method of Example 15 using 1,3 dicyclohexylcarbodiimide (315 mg, 1.53 mmol). Reference Example 6 (660 mg, 1.45 mmol), (S)-2,3-O-isopropylidineglyceric acid (240 mg, 1.64 mmol) and pyridine (115 mg, 1.45 mmol) in dichloromethane (15 ml). Purified by flash chromatography (Merck 9385 silica; EtOAc/isohexane (3:1) eluant) to give the product (282 mg, 38%) as a colourless crystalline solid. MS: ESP$^+$ (M+H)$^+$= 506.

$^1$H-NMR (300 MHz, DMSO-d6): δ=1.32 (s, 3H), 1.34 (s, 3H), 2.25–2.50 (m, 2H), 3.63–3.87 (m, 2H), 3.95 (dd, 1H), 4.02–4.32 (m, 4H), 4.43–4.55 (m, 2H), 4.92 (m, 1H), 5.12 (m, 1H), 5.89 (m, 1H), 6.37 (d, 1H), 7.35 (d, 2H), 8.68 (d, 1H).

EXAMPLE 18

5(R)-Isoxazol-3-yloxymethyl-3-(4-(1-(2(S),3-dihydroxypropanoyl)-1,2,5,6-tetrahydropyrid-4-yl)-3,5-difluorophenyl)oxazolidin-2-one Prepared by the general method of Example 16 using Example 17 (282 mg, 0.56 mmol) in a mixture of THF (6 ml)

and 1N hydrochloric acid (2 ml). Purified by flash chromatography (Merck 9385 silica; 10% MeOH in dichloromethane eluant) to give the product (183 mg, 70%) as a colourless crystalline solid: mp 136–142° C.

$^1$NMR (300 MHz, DMSO-$d_6$): d 2.20–2.46 (m, 2H), 3.40–3.63 (m, 2H), 3.63–3.85 (m, 2H), 3.92 (dd, 1H), 4.10 (m, 1H), 4.18 (t, 1H), 4.26–4.52 (m, 1H), 4.68 (m, 1H), 4.96 (m, 1H), 5.10 (m, 1H), (m, 1H), 6.37 (d, 1H), 7.34 (m, 2H) 8.68 (d, 2H). MS: ESP$^+$ (M+H)$^+$=466. HPLC: Chiralpak AD (250 mm×4.6 mm i.d,), 100% MeOH eluant, 1 ml/min. flow rate: ret. time=38.4 min.

REFERENCE EXAMPLE 12

5(R)-Isoxazol-3-yloxymethyl-3-(4-(1-(2(S),3-di-(di-t-butoxyphosphoryl)propanoyl)-1,2,5,6-tetrahydropyrid-4-yl)-3-fluorophenyl)oxazolidin-2-one Di-tert-butyl N,N diethylphosphoramidite (1.67 g, 6.24 mmol) was added dropwise at room temperature, under an atmosphere of nitrogen, to a stirred suspension of Example 12 (1.0 g, 2.24 mmol) and 1H-tetrazole (1.4 g, 20.0 mmol) in tetrahydrofuran (40 ml). The resulting mixture was stirred for 2 hr, then cooled to −40° C. and treated portionwise with 3-chloroperoxybenzoic acid (1.9 g 60% strength, 6.6 mmol). The reaction was stirred at −40 to −20° C. for 1 hr, then diluted with EtOAc (150 ml), washed succesively with 10% aqueous sodium bisulfite solution, sat. sodium bicarbonate solution and water, dried over magnesium sulfate and evaporated to give a colourless oil.Purified by flash chromatography (Merck 9385 silica, 20–30% acetonitrile/EtOAc) to give the product (625 mg, 34%) as a colourless foam.

$^1$H-NMR (300 MHz, CDCl$_3$): δ=1.48 (m, 36H), 2.45–2.70 (m, 2H), 3.58–3.71 & 3.73–3.86 (m, 1H), 3.92–4.10 (m, 2H), 4.10–4.38 (m, 5H), 4.47–4.62 (m, 2H), 4.97–5.08 (m, 1H), 5.22–5.32 (m, 1H), 5.88 (m, 1H), 6.02 (d, 1H), 7.18–7.28 (m, 2H), 7.43 (d, 1H), 8.16 (d, 1H). MS: ESP$^+$ (M+H)$^+$=832.

EXAMPLE 19

5(R)-Isoxazol-3-yloxymethyl-3-(4-(1-(2(S),3-diphosphoryl-propanoyl)-1,2,5,6-tetrahydropyrid-4-yl)-3-fluorophenyl)oxazolidin-2-one

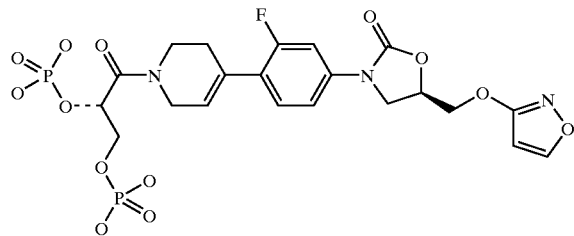

A 4M solution of HCl in dioxane (6 ml) was added in one go at room temperature to a stirred solution of Reference Example 12 (600 mg, 0.72 mmol) in dioxane (6 ml). The resulting yellow mixture was stirred 1 hr, then concentrated under reduced pressure. Trituration with diethyl ether gave a yellow solid which was filtered, washed with ether, dried and then dissolved in water and lyophilized to a pale yellow solid (435 mg).

$^1$H-NMR (300 MHz, DMSO-d6+CD$_3$COOD): δ=2.35–2.50 (m, 2H), 3.52–3.68 & 3.70–3.85 (m, 2H), 3.90 (dd, 1H), 4.05–4.35 (m, 5H), 4.35–4.53 (m, 2H), 5.05 (m, 1H), 5.10–5.25 (m, 1H), 5.98 (m, 1H), 6.25 (d, 1H), 7.25–7.40 (m, 2H), 7.45 (dd, 1H), 8.54 (d, 1H). MS: ESP$^+$ (M+H)$^+$=608.

REFERENCE EXAMPLE 13

5(R)-Isoxazol-3-yloxymethyl-3-(4-(1-(2(S)-hydroxy-3-(di-t-butoxyphosphoryl)propanoyl)-1,2,5,6-tetrahydropyrid-4-yl)-3-fluorophenyl)oxazolidin-2one To a stirred solution of the starting material Example 12 (600 mg, 1.34 mmol) and 1H-tetrazole (310 mg, 4.43 mmol) in THF (30 ml) under nitrogen was added di-tert-butyl N,N diethylphosphoramidite (368 mg, 1.48 mmol) over a few minutes. After stirring for 90 minutes the solution was cooled to −40° C. and 3-chloroperoxybenzoic acid (425 mg 60% strength, 1.48 mmol) added in portions. The reaction mixture was allowed to warm to ambient temperature and stirred for 30 minutes. EtOAc was added, the solution washed with sodium metabisulfite, sodium bicarbonate and brine solutions, the organic phase dried over anhydrous magnesium sulfate and evaporated in vacuo. The crude product was purified by flash chromatography (Merck 9385 silica, 10–20% acetonitrile/EtOAc) to give the title compound (165 mg, 19%) as a colourless gum.

$^1$H-NMR (300 MHz, CDCl$_3$): δ=1.48 (s, 9H), 1,50 (s, 9H), 2.45–2.80 (m, 2H), 3.61–3.86 (m, 2H), 3.96 (dd, 1H), 4.02–4.12 (m, 3H), 4.16 (t, 1H), 4.22–4.30 (m, 2H), 4.47–4.61 (m, 2H), 4.64–4.77 (m, 1H), 5.03 (m, 1H), 6.00 (m, 1H), 6.03 (d, 1H), 7.20–7.30 (m, 2H), 7.46 (d, 1H), 8.16 (d, 1H). MS: ESP$^+$ (M+H)$^+$=640.

EXAMPLE 20

5(R)-Isoxazol-3-yloxymethyl-3-(4-(1-(2(S)-hydroxy-3-phosphoryl-propanoyl)-1,2,5,6-tetrahydropyrid-4-yl)-3-fluorophenyl)oxazolidin-2-one

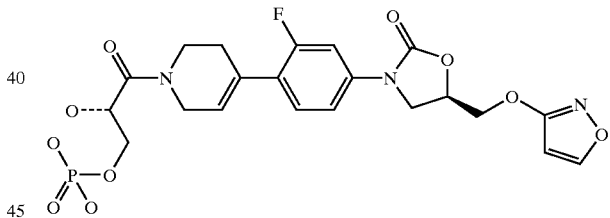

TFA (2 ml) was added dropwise at room temperature to a stirred solution of Reference Example 13 (165 mg, 0.26 mmol) in dichloromethane (8 ml). The resulting yellow solution was stirred 30 min. then evaporated under reduced pressure to a yellow foam, Trituration with diethyl ether gave the title compound (120 mg) as a yellow solid.

$^1$H-NMR (300 MHz, DMSOd6+CD$_3$COOD): δ=2.30–2.50 (m, 2H), 3.50–3.65 & 3.65–3.82 (m, 2H), 3.92 (dd, 1H), 3.97–4.40 (m, 5H), 4.40–4.62 (m, 3H), 5.05 (m, 1H), 6.00 (m, 1H), 6.28 (d, 1H), 7.25–7.43 (m, 2H), 7.48 (d, 1H), 7.57 (d, 1H). MS: ESP$^+$ (M+H)$^+$=528.

REFERENCE EXAMPLE 14

5(R)-Isoxazol-3-yloxymethyl-3-(4-(1-(2(S),3-di-(di-t-butylphosphoryl)propanoyl)-1,2,5,6-tetrahydropyrid-4-yl)-3,5-difluorophenyl)oxazolidin-2-one The title compound was prepared, with only non-critical variations, by the method for Reference Example 12 on a 4.3 mM scale, using as starting material Example 18.

Yield=1.86 g (51%). NMR (300 Mz, DMSO-d6): δ 1.42 (s, 36H), 2.5 (m, partially obscured), 3.3–3.9 (m, 4H), 3.94 (d of d, 1H), 4.1 (s, 2H) 4.21 (t, 1H), 4.48 (m, 2H), 5.14 (m, 2H), 5.90 (s, 1H), 6.38 (s, 1H), 7.37 (d, 2H), 8.70 (s, 1H). MS: ESP+ (M+H)=850.

EXAMPLE 21

5(R)-Isoxazol-3-yloxymethyl-3-(4-(1-(2(S),3-diphosphoryl-propanoyl)-1,2,5,6-tetrahydropyrid-4-yl)-3,5-difluorophenyl)oxazolidin-2-one

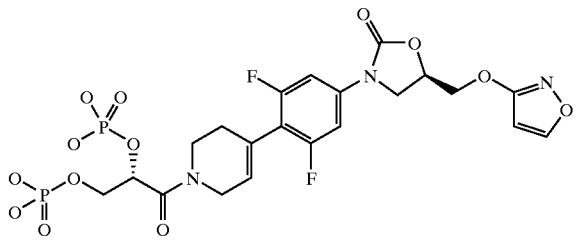

The title compound was prepared, with only non-critical variations, by the method for Example 19 on a 1.4 mM scale, using as starting material Reference Example 14.

Yield=735 mg (98%). NMR (300 Mz, DMSO-d6): δ=2.5 (m, partially obscured), 3.57 & 3.77 (2m, 2H), 3.91 (d of d, 1H), 4.0–4.4 (m, 4H), 4.18 (t, 1H), 4.58 (m, 2H), 5.1 (m, 2H), 5.85 (s, 1H), 6.36 (s, 1H), 7.35 (d, 2H), 8.78 (s, 1H). MS: ESP+ (M+H)=626.

REFERENCE EXAMPLE 15

5(R)-Isoxazol-3-yloxymethyl-3-(4-(1-(2(S)-hydroxy-3-(di-t-butylphosphoryl)propanoyl)-1,2,5,6-tetrahydropyrid-4-yl)-3,5-difluorophenyl)oxazolidin-2-one To a stirred solution of the starting material Example 18 (1.02 g, 2.2 mmol) and tetrazole (462 mg, 6.6 mg) in THF (30 ml) at ambient temperature under nitrogen, was added di-tert-butyl N,N diethylphosphoramidite (575 mg, 2.31 mmol) over ~2 minutes. After stirring for 90 minutes the solution was cooled to −40° C. and m-chloroperbenzoic acid (2.5 mmol , 480 mg of 90% strength) was added in portions. The reaction mixture was allowed to warm to ambient temperature and stir for 30 minutes. EtOAc was added and the mixture was washed with aqueous sodium metabisulfite, saturated sodium bicarbonate and brine solutions. The organic phase was dried over anhydrous MgSO$_4$ and evaporated under reduced pressure. The title compound was isolated by MPLC (EtOAc) as a brittle glass (406 mg, 28%). MS: ESP+ (M+H)=658; ESP− (M−H)=656.

NMR (300 Mz, DMSO-d6): δ 1.42 (s, 18H), 2.5 (m, partially obscured), 3.55–3.95 (m, 4H), 3.95 (d of d, 1H), 4.0–4.15 (m, 2H), 4.25 (t, 1H), 4.50 (m, 2H), 4.63 (m, 1H), 5.14 (m, 1H), 5.54 (d, 1H), 5.91 (s, 1H), 6.40 (s, 1H), 7.37 (d, 2H), 8.70 (1H, s).

EXAMPLE 22

5(R)-Isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one

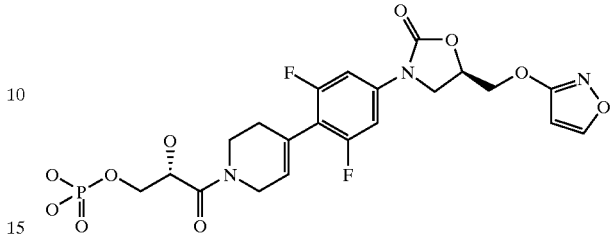

To a stirred solution of the starting material Reference Example 15 (100 mg, 0.15 mmol) in dioxan (1 ml) was added 4M HCl/dioxan (3 ml). The solution was stirred at ambient temperature for 30 mins. and then evaporated. The residue was triturated well with ether giving the title compound as a white powder (80 mg, 96%).

NMR (300 Mz, DMSO-d6): 2.43 (m, partially obscured), 3.6–4.35 (m, 8H), 4.35–4.60 (m, 3H), 5.09 (m, 1H), 5.85 (s, 1H), 6.30 (s, 1H), 7.31 (d, 2H), 8.60 (s, 1H). MS: ESP+ (M+H)=546.

EXAMPLE 23

5(R)-Isoxazol-3-yloxymethyl-3-(4-(1-(cyclo-2(S),3-diphosphoryl-propanoyl)-1,2,5,6-tetrahydropyrid-4-yl)-3,5-difluorophenyl)oxazolidin-2-one To a stirred partial solution of the starting material Example 21 (100 mg, 0.16 mmol) in THF (8 ml) was added dicyclohexyl carbodiimide (40 mg, 0.195 mmol). DMF(4 ml) was added to give a clear solution. After stirring for 18 hrs at ambient temperature, more DCCI (40 mg, 0.195 mmol) was added, The reaction was essentially complete by HPLC (Partisil SAX 10 μ column, 0.0M to 0.3M pH6.5 phosphate buffer gradient) after a further 3 hrs. The solvent was evaporated and the residue was taken into water and filtered, The filtrate was chromatographed by MPLC (0–25% acetonitrile/water gradient on Mitsubishi HP20SS polystyrene resin) and the title compound was obtained by freeze drying after partial evaporation to remove acetonitrile.

Yield=49 mg (50%). MS: ESP− (M−H)=606. NMR (300 Mz, DMSO-d6): δ=2.4 (m, partially obscured), 3.7–4.0 (m, 3H), 4.18 (m, 4H), 4.48 (m, 3H), 5.05 (m, 1H), 5.19 & 5.30 (2 m, 1H), 5.85 (s, 1H), 6.30 (s, 1H), 7.31 (d, 2H), 8.59 (s, 1H).

EXAMPLE 24

5(R)-Isoxazol-3-yloxymethyl-3-(4-(1-(4-hydroxybutanoyl)-1,2,5,6-tetrahydropyrid-4-yl)-3,5-difluorophenyl)oxazolidin-2-one To a stirred solution of Reference Example 6 (0.223 g, 0.54 mmol), 4-hydroxybutyric acid sodium salt (0.082 g, 0.65 mmol) and HOBT (0.087 g, 0.65 mmol) in DMF (5 ml) was added EDC (0.124 g, 0.65 mmol). The mixture was stirred for 4 days and then evaporated, The residue was purified by MPLC [5% MeOH/CH$_2$Cl$_2$ as eluant] to give after trituration with diethyl ether, as a white solid (0.141 g, 56%).

$^1$H-NMR (300 MHz, DMSO-d6): δ=1.63 (m, 2H), 2.29 (m, 1H), 2.38 (m, 2H), 3.25 (d, 1H), 3.40 (m, 2H), 3.62 (m, 2H), 3.91 (dd, 1H), 4.10 (d, 1H), 4.19 (t, 2H), 4.44 (m, 3H), 5.09 (m, 1H), 5.84 (s, 1H), 6.38 (d, 1H), 7.36 (d, 2H) and 8.70 (d, 1H). MS: ESP$^-$ (M+H)$^+$=464.

EXAMPLE 25

5(R)-Isoxazol-3-yloxymethyl-3-(4-(1-(4-methoxybutanoyl)-1,2,5,6-tetrahydropyrid-4-yl)-3,5-difluorophenyl)oxazolidin-2-one To a stirred solution of Reference Example 6 (0.285 g, 0.69 mmol), 2-(2-methoxyethoxy)acetic acid (0.111 g, 0.83 mmol), triethylamine (0.070 g, 0.096 ml, 0.69 mmol) and HOBT (0.112 g, 0.83 mmol) in dichloromethane (5 ml) was added EDC (0.159 g, 0.83 mmol). The mixture was stirred for 17 h and then the solution was washed with water (10 ml), dried and evaporated, The residue was purified by MPLC [3% MeOH/CH$_{2Cl2}$ as eluant] to give a colourless oil (0.201 g, 61%).

$^1$H-NMR (300 MHz, DMSO-d6): δ=2.36 (d, 2H), 3.25 (s, 3H), 3.45 (m, 2H), 3.59 (m, 4H), 3.92 (dd, 1H), 4.09 (m, 2H), 4.18 (m, 3H), 4.45 (m, 2H), 5.09 (m, 1H), 5.86 (s, 1H), 6.38 (d, 1H), 7.35 (d, 2H) and 8.69 (d, 1H).

REFERENCE EXAMPLE 16

6-Hydroxymethyl-2-phenyl-1,3-dioxane (D,L)-Malic acid (5.0 g, 37 mmol) in dry THF (25 ml) under nitrogen was treated with trimethyl borate (12.5 ml) and borane-dimethylsulfide (2.0 M in THF) (60 ml, 120 mmol) dropwise at 0° C. After the addition was complete stirring was continued at 0° C. for 5 min. During which time a white precipitate formed. The ice-bath was removed and stirring continued overnight. After 17 h the solution was slowly treated with MeOH (30 ml) and then evaporated, The residue was purified by MPLC [10% MeOH/CH$_2$Cl$_2$ as eluant] to give the triol (3.57 g). This was dissolved in benzaldehyde (150 ml) containing tosic acid (0.64 g, 3.37 mmol) and stirred for 60 h and then evaporated, The residue was dissolved in dichloromethane, washed with saturated aqueous sodium hydrogen carbonate, dried and evaporated, The residue was was purified by MPLC [20→45% EtOAc/hexanes eluant] to give the product as an oil (1.47 g, 22%). MS: ESP$^+$ (M+H)$^+$=195.

$^1$H-NMR (300 MHz, DMSO-d6): δ=1.50 (d, 1H), 1.62 (ddd, 1H), 3.38 (dd, 1H), 3.48 (dd, 1H), 3.90 (m, 2H), 4.14 (dd, 1H), 4.70 (t, 1H), 5.49 (s, 1H) and 7.38 (m, 5H).

REFERENCE EXAMPLE 17

6-Carboxy-2-phenyl-1,3-dioxane

To a stirred solution of the alcohol Reference Example 16 (1.47 g, 7.60 mmol) in aqueous sodium hydroxide (7.60 mmol, 0.304 g in 30 ml) at 0° C. was added potassium permanganate (1.80 g, 11.4 mmol) portionwise. After 3.5 h the mixture was filtered and acidified to pH 2. The solution was saturated with sodium chloride and extracted with EtOAc (4×50 ml), dried and evaporated to a residue. This white solid was dissolved in dichloromethane and extracted with ammonium hydroxide (2×15 ml). The basic extracts were acidified at 0° C. to pH 2 with conc. hydrochloric acid, and the acidic mixture extracted with dichloromethane (2×50 ml). The organics were dried and evaporated to give the acid as a gum (0.15 g, 10%). MS: ESP$^+$ (M+H)$^+$=209.

$^1$H-NMR (300 MHz, DMSO-d6): δ=1.82 (m, 2H), 3.96 (m, 1H), 4.18 (dd, 1H), 4.50 (dd, 1H), 5.58 (m, 1H), 7.40 (m, 5H) and 12.82 (s, 1H).

EXAMPLE 26

5(R)-Isoxazol-3-yloxymethyl-3-(4-(1-(2(R,S)-phenyl-1,3-dioxan-4(R,S)-ylcarbonyl)-1,2,5,6-tetrahydropyrid-4-yl)-3,5-difluorophenyl)oxazolidin-2-one To a stirred solution of Reference Example 6 (0.220 g, 0.53 mmol), Reference Example 17 (0.133 g, 0.64 mmol), triethylamine (0.054 g, 0.074 ml, 0.53 mmol) and HOBT (0.086 g, 0.64 mmol) in dichloromethane (6 ml) was added EDC (0.123 g, 0.64 mmol). The mixture was stirred for 60 h and then the solution was washed with 2N HCL (10 ml), brine (10 ml), dried and evaporated, The residue was purified by MPLC [4% MeOH/CH$_2$Cl$_2$ as eluant] to give an oil (0.246 g, 82%). MS: ESP$^+$ (M+H)$^+$=568.

$^1$H-NMR (300 MHz, DMSO-d6): δ=1.59 (d, 1H), 2.10 (m, 1H), 2.33 (m, 2H), 3.55 (m, 1H), 3.78 (m, 1H), 3.90 (dd, 1H), 4.07 (m, 2H), 4.15 (m, 3H), 4.45 (m, 2H), 4.90 (m, 1H), 5.10 (m, 1H), 5.71 (d, 1H), 5.88 (s, 1H), 6.38 (d, 1H), 7.38 (m, 7H) and 8.70 (d, 1H).

REFERENCE EXAMPLE 18

5(R)-Isoxazol-3-yloxymethyl-3-(4-(1-(3-t-butoxycarbonylamino-2(R,S)-hydroxy-propanoyl)-1,2,5,6-tetrahydropyrid-4-yl)-3,5-difluorophenyl)oxazolidin-2-one To a stirred solution of Reference Example 6 (0.091 g, 0.22 mmol), (D,L)-N-BOC-isoserine (0.054 g, 0.27 mmol), triethylamine (0.022 g, 0.031 ml, 0.22 mmol) and HOBT (0.036 g, 0.27 mmol) in dichloromethane (3 ml) was added EDC (0.052 g, 0.27 mmol). The mixture was stirred for 18 h and then the solution was washed with 2N HCL (10 ml), brine (10 ml), dried and evaporated. The residue was purified by MPLC [3% MeOH/CH$_2$Cl$_2$ as eluant] to give the product as a tan solid (0.047 g, 38%). MS: ESP$^+$ (M+H)$^+$=565.

EXAMPLE 27

5(R)-Isoxazol-3-yloxymethyl-3-(4-(1-(3-amino-2(R,S)-hydroxy-propanoyl)-1,2,5,6-tetrahydropyrid-4-yl)-3,5-difluorophenyl)oxazolidin-2-one Reference Example 18 (0.047 g, 0.083 mmol) was dissolved in EtOAc (3 ml) saturated with hydrogen chloride and stirred for 18 h. The solution was evaporated and triturated with EtOAc to give the product as an off-white solid (0.034 g, 88%).

$^1$H-NMR (300 MHz, DMSO-d6): δ=2.30 (d, 2H), 3.70 (m, 2H), 3.90 (dd, 1H), 45.19 (m, 4H), 4.44 (m, 2H), 4.60 (m, 1H), 5.10 (m, 1H), 5.90 (s, 1H), 6.37 (d, 1H), 7.30 (s, 1H), 7.38 (s, 1H), 7.89 (s, 3H) and 8.69 (d, 1H). MS: ESP$^+$ (M+H)$^+$=465.

EXAMPLE 28

5(R)-Isoxazol-3-yloxymethyl-3-(4-(1-(2(R,S)-phenyl-1,3-dioxan-5(R,S)-ylcarbonyl)-1,2,5,6-tetrahydropyrid-4-yl)-3,5-difluorophenyl)oxazolidin-2-one To a stirred solution of Reference Example 6 (0.344 g, 0.83 mmol), 5-carboxy-2-phenyl-1,3-dioxan (JOC, 1997, 62, 4029) (0.208 g, 1.00 mmol), triethylamine (0.084 g, 0.116 ml, 0.83 mmol) and HOBT (0.135 g, 0.1.00 mmol) in dichloromethane (10 ml), was added EDC (0.192 g, 1.00 mmol). The mixture was stirred for 24 h and then the solution was washed with 2N HCL (10 ml), brine (10 ml), dried and evaporated. The residue was purified by MPLC [2% MeOH/CH$_2$Cl$_2$ as eluant] to give the product as an oil (0.357 g, 76%).

$^1$H-NMR (300 MHz, DMSO-d6): δ=2.38 (d, 2H), 2.99 (s, 1H), 3.70 (d, 2H), 3.90–4.55 (m, 10H), 5.10 (m, 1H), 5.55 (s, 1H), 5.90(s, 1H), 6.37 (d, 1H), 7.40 (m, 7H) and 8.68 (d, 1H). MS: ESP$^+$ (M+H)$^+$=568.

EXAMPLE 29

5(R)-Isoxazol-3-yloxymethyl-3-(4-(1-(3-hydroxy-2-hydroxymethyl-propanoyl)-1,2,5,6-tetrahydropyrid-4-yl)-3,5-difluorophenyl)oxazolidin-2-one Example 28 (0.155 g, 0.27 mmol) in dichloromethane (4 ml) at 0° C. was treated with boron trichloride-dimethyl sulfide (2.0 M in CH$_2$Cl$_2$) (0.40 ml, 0.81 mmol) for 4.5 h. MeOH (1 ml) was added until all solids had dissolved. The solution was then evaporated and the residue purified by MPLC [6% MeOH/CH$_2$Cl$_2$] as eluant] to give after trituration with diethyl ether, a white solid (0.025 g, 19%). MS: ESP$^+$ (M+H)$^+$=480.

$^1$H-NMR (300 MHz, DMSO-d6): δ=2.40 (d, 2H), 3.15 (m, 1H), 3.40 (m, 6H), 3.79 (d, 2H), 3.98 (dd, 1H), 4.19 (s, 1H), 4.26 (dd, 1H), 4.34 (s, 1H), 4.51 (m 2H), 5.15 (m, 1H), 5.93 (m, 1H), 6.43 (d, 1H), 7.40 (s, 1H), 7.44 (s, 1H) and 8.74 (d, 1H).

EXAMPLE 30

5(R)-Isoxazol-3-yloxymethyl-3-(4-(1-(2,3-propenoyl)-1,2,5,6-tetrahydropyrid-4-yl)-3,5-difluorophenyl)oxazolidin-2-one Acryloyl chloride (0747 g, 0.67 ml, 8.25 mmol) in dichloromethane (5 ml) at 0° C. was treated with Reference Example 6 (0.682 g, 1.65 mmol) in dichloromethane (5 ml) containing DMAP (0.201 g, 1.65 mmol) and triethylamine (0.333 g, 0.46 ml, 3.39 mmol). The solution was stirred for 1.5 h. The solution was washed with 2N HCL (10 ml), saturated aqueous sodium hydrogen carbonate (10 ml), brine (10 ml), dried and evaporated. The residue was purified by MPLC [2% MeOH/CH$_2$Cl$_2$ as eluant] to give a white solid (0.471 g, 66%). MS: ESP$^+$ (M+H)$^+$=432.

$^1$H-NMR (300 MHz, DMSO-d6): δ=2.40 (d, 2H), 3.80 (d, 2H), 3.99 (dd, 1H), 4.25 (m, 3H), 4.54 (m, 2H), 5.16 (m, 1H), 5.75 (d, 1H), 5.93 (s, 1H), 6.20 (d, 1H), 6.45 (s, 1H), 6.88 (m, 1H), 7.42 (s, 1H), 7.48 (s, 1H) and 8.75 (d, 1H).

REFERENCE EXAMPLE 19

5(R)-Isoxazol-3-yloxymethyl-3-(4-(1-(2,3(R,S)-enoxypropanoyl)-1,2,5,6-tetrahydropyrid-4-yl)-3,5-difluorophenyl)oxazolidin-2-one n-Butyllithium (1.6M in hexanes) (0.65 ml, 1.04 mmol) was added to a solution of tert-butylhydroperoxide (5.5M in decane) (0.26 ml, 1.43 mmol) in THF (5 ml) at −78 ° C. The mixture was stirred for 5 min. A solution of the acrylamide. Example 30 (0.408 g, 0.95 mmol) in dry THF (2 ml) was added and stirring continued with the ice-bath removed until the temperature reached ca. 0° C. whereupon a water ice-bath was put in place. Solid sodium sulfite (0.080 g, 0.30 mmol) was added and stirring continued for 15 min. Dichloromethane (10 ml) was added and the mixture filtered through Celite and then evaporated. The residue was purified by MPLC [2% MeOH/CH$_2$Cl$_2$ as eluant] to give the product as a gum (0.378 g, 89%).

$^1$H-NMR (300 MHz, DMSO-d6): δ=2.46 (d, 2H), 2.87 (m, 1H), 3.00 (m, 1H), 3.67–4.04 (m, 4H), 4.17 (s, 1H), 4.27 (t, 1H), 4.40 (d, 1H), 4.52 (m, 2H), 5.16 (m, 1H), 5.95 (s, 1H), 6.43 (s, 1H), 7.40 (s, 1H), 7.45 (s, 1H) and 8.76 (d, 1H). MS: ESP$^+$ (M+H)$^+$=448.

EXAMPLE 31

5(R)-Isoxazol-3-yloxymethyl-3-(4-(1-(2(R,S)-hydroxy-3-morpholinopropanoyl)-1,2,5,6-tetrahydropyrid-4-yl)-3,5-difluorophenyl)oxazolidin-2-one Reference Example 19 (0.073 g, 0.16 mmol) and morpholine (0.014 g, 0.014 ml, 0.16 mmol) were refluxed in isopropanol (1 ml) for 1 h, and then heated at 50° C. for 2 h. The solution was allowed to cool to RT overnight and then evaporated. The residue was purified by MPLC [4% MeOH/CH$_2$Cl$_2$ as eluant] to give a white foam (0.056 g, 66%).

$^1$H-NMR (300 MHz, DMSO-d6): δ=2.41 (d, 2H), 2.60 (m, 6H), 3.60 (d, 4H), 3.78 (m, 2H), 4.00 (dd, 1H), 4.17 (s, 1H), 4.26 (dd, 1H), 4.34 (s, 1H), 4.56 (m, 3H), 5.04 (dd, 1H), 5.15 (m, 1H), 5.94 (s, 1H), 6.43 (d, 1H), 7.40 (s, 1H), 7.44 (s, 1H) and 8.74 (s, 1H). MS: ESP$^+$ (M+H)$^+$=535.

REFERENCE EXAMPLE 20

5(R)-Isoxazol-3-yloxymethyl-3-(4-(1-(2(R,S)-hydroxy-3-(2-tert-butyldimethylsilyloxypyrrolidin-1-yl)propanoyl)-1,2,5,6-tetrahydropyrid-4-yl)-3,5-difluorophenyl)oxazolidin-2-one Reference Example 19 (0.149 g, 0.333 mmol) and 2-tert-butyldimethylsilyloxy pyrrolidine (0.067 g, 0.333 mmol) in isopropanol (3 ml) were heated at 60 ° C. until TLC indicated completion. The solution was evaporated and the residue was purified by MPLC [3→10% MeOH/CH$_2$Cl$_2$ as eluant] to give a colourless gum (0.173 g, 80%). MS: ESP$^+$ (M+H)$^+$=649.

$^1$H-NMR (300 MHz, DMSO-d6): δ=0.00 (s, 6H), 0.82 (s, 9H), 1.50 (m, 1H), 1.98 (m, 1H), 2.23–2.95 (m, 8H), 3.71 (s, 2H), 3.90 (dd, 1H), 4.08 (s, 1H), 4.17 (t, 1H), 4.30 (s, 2H), 4.45 (m, 3H), 5.03 (m, 2H), 5.83 (s, 1H), 6.33 (d, 1H), 7.30 (s, 1H), 7.34 (s, 1H) and 8.64 (s, 1H).

EXAMPLE 32

5(R)-Isoxazol-3-yloxymethyl-3-(4-(1-(2(R,S)-hydroxy-3-(2-hydroxypyrrolidino)propanoyl)-1,2,5,6-tetrahydropyrid-4-yl)-3,5-difluorophenyl)oxazolidin-2-one The silyl ether Reference Example 20, (0.169 g, 0.26 mmol) in dry THF (5 ml) at 0° C. was treated with tetrabutylammonium flouride (1.0 M in THF) (0.52 ml, 0.52 mmol) and then stirred for 5 h. The solution was evaporated and the residue was purified by MPLC [3→6% MeOH/CH$_2$Cl$_2$ as eluant] to give a white solid(0.104 g, 75%).

$^1$H-NMR (300 MHz, DMSO-d6): δ=1.54 (s, 1H), 1.92 (m, 1H), 2.30 (m, 3H), 2.50–2.88 (m, 5H), 3.63 (m, 2H), 3.89 (dd, 1H), 4.13 (m, 4H), 4.45 (m, 3H), 4.65 (s, 1H), 5.05 (m, 2H), 5.86 (s, 1H), 6.35 (d, 1H), 7.34 (s, 1H), 7.38 (s, 1H) and 8.68 (d, 1H). MS: ESP$^+$ (M+H)$^+$=535.

REFERENCE EXAMPLE 21

5(R)-Isoxazol-3-yloxymethyl-3-(4-(1-(2(R,S)-phenyl-1,3-dioxan-5(R,S)-ylcarbonyl)-1,2,5,6-tetrahydropyrid-4-yl)-3-fluorophenyl)-oxazolidin-2-one To a stirred solution of Reference Example 11 (0.368 g, 0.93 mmol) the acid, 5-carboxy-2-phenyl-1,3-dioxan (JOC, 1997, 62, 4029) (0.232 g, 1.12 mmol), triethylanine (0.094 g, 0.129 ml, 0.93 mmol) and HOBT (0.151 g, 1.12 mmol) in dichloromethane (11 ml) was added EDC (0.215 g, 1.12 mmol). The mixture was stirred for 20 h and then the solution was washed with 2N HCL (10 ml), brine (10 ml), dried and evaporated. The residue was purified by MPLC [2% MeOH/CH$_2$Cl$_2$ as eluant] to give an oil (0.475 g, 93%).

$^1$H-NMR (300 MHz, DMSO-d6): δ=2.62 (m, 2H), 3.48 (m, 1H), 3.70 (m, 1H), 3.82 (m, 1H), 3.93–4.60 (m, 10H), 5.14 (m, 1H), 5.60 (s, 1H), 6.08 (s, 1H), 6.42 (d, 1H), 7.46 (m, 8H) and 8.76 (d, 1H). MS: ESP$^+$ (M+H)$^+$=550.

EXAMPLE 33

5(R)-Isoxazol-3-yloxymethyl-3-(4-(1-(3-hydroxy-2-hydroxymethyl-propanoyl)-1,2,5,6-tetrahydropyrid-4-yl)-3-fluorophenyl)oxazolidin-2-one Reference Example 21(0.475 g, 0.87 mmol) was stirred in 80% acetic acid/water (10 ml) for 24 h. The precipitate slowly dissolved. The solution was evaporated and purified by MPLC [5% MeOH/CH$_2$Cl$_2$ as eluant] to give after trituration with diethyl ether, a white powder (0.284 g, 71%). MS: ESP$^+$ (M+H)$^+$=462.

$^1$H-NMR (300 MHz, DMSO-d6): δ=2.51 (d, 2H), 3.15 (m, 1H)). 3.58 (m, 4H), 3.78 (m, 2H), 3.99 (dd, 1H), 4.26 (d, 2H), 4.28 (t, 1H), 4.54 (m, 2H), 4.65 (m, 2H), 5.15 (m, 1H), 6.06 (s, 1H), 6.43 (d, 1H), 7.35–7.63 (m, 3H) and 8.76 (d, 1H).

REFERENCE EXAMPLE 22

5(R,S)-Carboxymethyl-2,2-dimethyl-4-oxo-1,3-dioxolane (D,L)-Malic acid (12.41 g, 92.6 mmol) and PTSA (2.32 g, 9.26 mmol) in 2,2-dimethoxypropane (35 ml) were stirred for 5 days. The solution was evaporated and the residue was purified by MPLC [25% EtOAc/isohexane as eluant] to give a colurless gum (11.48 g, 71%).

$^1$H-NMR (300 MHz, DMSO-d6): =1.58 (s, 3H), 1.60 (s, 3H), 2.82 (m, 2H), 4.85 (t, 1H) and 12.64 (s, 1H).

EXAMPLE 34

5(R)-Isoxazol-3-yloxymethyl-3-(4-(1-(2,2-dimethyl-4-oxo-1,3-dioxolan-5(R,S)-ylacetyl-1,2,5,6-tetrahydropyrid-4-yl)-3-fluorophenyl)-oxazolidin-2-one To a stirred solution of Reference Example 11 (0.384 g, 0.97 mmol), the acid (Reference Example 22) (0.203 g, 1.17 mmol), triethylamine (0.098 g, 0.135 ml, 0.97 mmol) and HOBT (0.158 g, 1.17 mmol) in dichloromethane (11 ml) was added EDC (0.225 g, 1.17 mmol). The mixture was stirred for 60 h and then the solution was dried and evaporated. The residue was purified by MPLC [3% MeOH/CH$_2$Cl$_2$ as eluant] to give an oil (0.356 g, 71%). MS: ESP$^+$ (M+H)$^+$=516.

$^1$H-NMR (300 MHz, DMSO-d6): δ=1.57 (s, 3H), 1.60 (s, 3H), 2.53 (d, 2H), 3.02 (m, 2H), 3.70 (m, 2H), 4.00 (dd, 1H), 4.19 (d, 2H), 4.25 (t, 1H), 4.52 (m, 2H), 4.89 (t, 1H), 5.15 (m, 1H), 6.05 (s, 1H), 6.44 (d, 1H), 7.36–7.63 (m, 3H) and 8.75 (d, 1H).

EXAMPLE 35

5(R-Isoxazol-3-yloxymethyl-3-(4-(1-(3-carboxy-3(R,S)-hydroxypropanoyl)-1,2,5,6-tetrahydropyrid-4-yl)-3-fluorophenyl)oxazolidin-2-one Example 34 (0.345 g, 0.67 mmol) was stirred in 80% acetic acid/water (5 ml) for 20 h. The acetonide slowly dissolved and then the product slowly precipitated, Diethyl ether (10 ml) was added and the solid collected by filtration to give a white solid (0.300 g, 94%). MS: ESP$^+$ (M–H)$^+$=474.

$^1$H-NMR (300 MHz, DMSO-d6): δ=2.52 (d, 2H), 2.80 (m, 2H), 3.71 (s, 2H), 4.00 (dd, 1H), 4.20 (d, 2H), 4.28 (t, 1H), 4.41 (t, 1H), 4.55 (m, 2H), 5.15 (m, 1H), 6.08 (s, 1H), 6.46 (d, 1H), 7.35–7.62 (m, 3H) and 8.77 (d, 1H).

REFERENCE EXAMPLE 23

5(R,S)-Methylaminocarbonylmethyl-2,2-dimethyl-4-oxo-1,3-dioxolane

The acid Reference Example 22 (2.84 g, 16.32 mmol) was heated under reflux in thionyl chloride (25 ml) for 1.25 h under nitrogen. The solution was evaporated and azeotroped with toluene (2×). A portion of the crude acid chloride (5.44 mmol) was dissolved in dichloromethane (5 ml), treated with methylamine (2.0 M in THF) (5.44 ml, 10.88 mmol) and stirred for 1.5 h. The resultant suspension was diluted, washed with 2N HCL (10 ml), brine (10 ml), dried and evaporated. The residue was purified by MPLC [5% MeOH/CH$_2$Cl$_2$ as eluant] to give a pale tan solid (0.393 g, 39%).

$^1$H-NMR (300 MHz, DMSO-d6): δ=1.56 (s, 6H), 2.66 (m, 2H), 2.68 (s, 3H), 4.82 (t, 1H) and 7.95 (s, 1H). MS: ESP$^+$ (M+H)$^+$=188.

REFERENCE EXAMPLE 24

2(R,S)-hydroxy-3-methylaminocarbonylpropanoic Acid

The amide Reference Example 23 (0.392 g, 2.10 mmol) was stirred in MeOH (4 ml) containing PTSA (0.053 g, 0.21 mmol) for 5 days. The solution was evaporated and the residue was purified by MPLC [5% MeOH/CH$_2$Cl$_2$ as eluant] to give the methyl ester (0.284 g). This was dissolved in MeOH/water (3:1) (4 ml), treated with lithium hydroxide (0.370 g, 8.82 mmol) and stirred for 15 min. The mixture was diluted with water (20 ml), treated with Dowex 50W-X8(H), stirred for 5 min filtered and evaporated to in vacuo to give a gum (0.216 g, 83%).

$^1$H-NMR (300 MHz, DMSO-d6): δ=2.38 (dd, 1H), 2.49 (dd, 1H), 2.64 (s, 3H), 3.54 (br s, 1H), 4.34 (m, 1H), 7.87 (m, 1H) and 12.53 (br s, 1H). MS: ESP$^-$ (M–H)$^+$=146.

EXAMPLE 36

5(R)-Isoxazol-3-yloxymethyl-3-(4-(1-(2(R,S)-hydroxy-3-methylaminocarbonylpropanoyl)-1,2,5,6-tetrahydrolpyrid-4-yl)-3-fluorophenyl)oxazolidin-2-one To a stirred solution of Reference Example 11 (0.175 g, 0.44 mmol), the acid Reference Example 24 (0.078 g, 0.53 mmol), triethylamine (0.044 g, 0.061 ml, 0.44 mmol) and HOBT (0.072 g, 0.53 mmol) in dichloromethane (6 ml) was added EDC (0.102 g, 0.53 mmol). The mixture was stirred for 16 h. TLC indicated incomplete reaction and more acid (0.138 g, 0.94 mmol), HOBT (0.127 g, 0.94 mmol) and EDC (0.180 g, 0.94 mmol) was added, After 5 h the solution was evaporated. The residue was purified by MPLC [5→15% MeOH/CH$_2$Cl$_2$ as eluant] to give an oil (0.070 g, 33%). MS: ESP$^+$ (M+H)$^+$=489.

$^1$H-NMR (300 MHz, DMSO-d6): δ=2.44 (m, 4H), 2.63 (d, 3H), 3.66 (m, 1H), 3.77 (s, 1H), 4.00 (dd, 1H), 4.22 (m, 3H), 4.54 (m, 2H), 4.79 (m, 1H), 5.15 (m, 1H), 5.38 (d, 1H), 6.10 (s, 1H), 6.48 (d, 1H), 7.35–7.64 (m, 3H), 7.88 (s, 1H) and 8.79 (d, 1H).

EXAMPLE 37

5(R)-Isoxazol-3-yloxymethyl-3-(4-(1-(3(R,S)-hydroxy-3-methylaminocarbonylpropanoyl)-1,2,5,6-tetrahydropyrid-4-yl)-3-fluorophenyl)oxazolidin-2-one To a stirred solution of Example 35 (0.070 g, 0.15 mmol) and HOBT (0.020 g, 0.15 mmol) in dichloromethane (4 ml) was added EDC (0.028 g, 0.15 mmol) and then methylamine (2.0M in THF) (0.23 ml, 0.45 mmol). The mixture was stirred for 22 h and then purified by MPLC [5% MeOH/CH$_2$Cl$_2$ as eluant] to give after trituration with diethyl ether a white solid (0.01 g, 14%).

$^1$H-NMR (300 MHz, DMSO-d6): δ=2.48 (d, 2H), 2.65 (d, 3H), 2.69 (m, 2H), 3.69 (m, 2H), 3.94 (dd, 1H), 4.17 (m, 2H), 4.20 (t, 1H), 4.30 (m, 1H), 4.48 (m, 2H), 5.08 (m, 1H), 5.61 (m, 1H), 6.00 (s, 1H), 6.39 (d, 1H), 7.38 (m, 2H), 7.50 (d, 1H), 7.78 (m, 1H) and 8.70 (d, 1H). MS: ESP$^+$ (M+H)$^+$=489.

REFERENCE EXAMPLE 25

5(R,S)-(2-(2-Methoxyethoxy)ethoxy)carbonylmethyl-2,2-dimethyl-4-oxo-1,3-dioxolane The acid (Reference Example 22) (2.75 g, 15.80 mmol) in dichloromethane (15 ml) at 0° C. was treated with oxalyl chloride (2.99 g, 2.1 ml, 23.71 mmol) and stirred with a drop of DMF for 2 h. The solution was evaporated, A portion of the crude acid chloride (1.90 g, 9.84 mmol) in dichloromethane (20 ml) at 0° C. containing 4-DMAP (1.20 g, 9.84 mmol) was treated with 2-(2-methoxyethoxy)ethanol (4.72 g, 4.70 ml, 39.36 mmol) and stirred overnight. The solution was washed with 2N HCL (2×15 ml), brine (10 ml), dried and evaporated. The residue was purified by MPLC [3% MeOH/CH$_2$Cl$_2$ as eluant] to give an oil (0.785 g, 29%).

$^1$H-NMR (300 MHz, DMSO-d6): δ=1.54 (s, 6H), 2.89 (t, 2H), 3.27 (s, 3H), 3.43 (m, 2H), 3.53 (m, 2H), 3.60 (m, 2H), 4.19 (m, 2H) and 4.84 (t, 1H).

REFERENCE EXAMPLE 26

2(R,S)-Hydroxy-3-(2-(2-methoxyethoxy)ethoxy)carbonyl-propanoic Acid

Reference Example 25 (0.785 g, 2.84 mmol) was stirred in 80% acetic acid/water (5 ml) for 5 days. The solution was evaporated to give an orange oil (0.600 g, 89%).

$^1$H-NMR (300 MHz, DMSO-d6): δ=2.54 (dd, 1H), 2.72 (dd, 1H), 3.26 (s, 3H), 3.42 (m, 2H), 3.52 (m, 2H), 3.59 (m, 2H), 4.13 (m, 2H), 4.30 (m, 1H), 5.49 (s, 1H) and 12.58 (s, 1H). MS: ESP$^-$ (M−H)$^+$=235.

EXAMPLE 38

5(R)-Isoxazol-3-yloxymethyl-3-(4-(1-(2(R,S)-hydroxy-3-(2-(2-methoxyethoxy)ethoxy)carbonylpropanoyl)-1,2,5,6-tetrahydropyrid-4-yl)-3-fluorophenyl)oxazolidin-2-one To a stirred solution of Reference Example 11 (0.329 g, 0.79 mmol), the acid Reference Example 26 (0.225 g, 0.95 mmol), triethylamine (0.079 g, 0.110 ml, 0.79 mmol) and HOBT (0.129 g, 0.95 mmol) in dichloromethane (10 ml) was added EDC (0.183 g, 0.95 mmol). The mixture was stirred for 48 h and then the solution was dried and evaporated. The residue was purified by MPLC [5% MeOH/CH$_2$Cl$_2$ as eluant] to give a white solid (0.283 g, 62%).

$^1$H-NMR (300 MHz, DMSO-d6): δ=2.52 (d, 2H), 2.60 (dd, 1H), 2.85 (dd, 1H), 3.31 (s, 3H), 3.50 (m, 2H), 3.60 (m, 2H), 3.68 (m, 2H), 3.80 (m, 2H), 4.00 (dd, 1H), 4.10–4.40 (m, 5H), 4.54 (m, 2H), 4.76 (m, 1H), 5.15 (m, 1H), 5.64 (m, 1H), 6.09 (s, 1H), 6.43 (d, 1H), 7.43 (m, 2H), 7.58 (d, 1H) and 8.75 (d, 1H). MS: ESP$^+$ (M+H)$^+$=578.

EXAMPLE 39

5(R)-Isoxazol-3-yloxymethyl-3-(4-morpholino-3-fluoro-phenyl)oxazolidin-2-one

Prepared by the general method of Example 1 using as starting material 5(R)-hydroxymethyl-3-(4-morpholino-3-fluoro-phenyl)oxazolidin-2-one (WO95/07271; 300 mg, 1.01 mmol), 3-hydroxyisoxazole (95 mg, 1.12 mmol), diisopropylazodicarboxylate (225 mg, 1.11 mmol) and triphenylphosphine (305 mg, 1.16 mmol) in THF (5 ml). Purified by flash chromatography (Merck 9385 silica. EtOAc/isohexane (7/3)) to give the title compound (254 mg, 69%) as a colourless solid.

$^1$H-NMR (300 MHz, CDCl$_3$): δ=3.05 (m, 4H), 3.88 (m, 4H), 3.94 (dd, 1H), 4.14 (t, 1H), 4.47–4.62 (m, 2H), 5.01 (m, 4H), 6.00 (d, 1H), 6.94 (t, 1H), 7.15 (dd, 1H), 7.46 (d, 1H), 8.15 (d, 1H). MS: ESP$^+$ (M+H)$^+$=364.

REFERENCE EXAMPLE 27

5(R)-Hydroxymethyl-3-(4-iodophenyl)oxazolidin-2-one

3-Phenyl-oxazolidin-2-one (U.S. Pat. No. 4,705,799; 3.0 g, 15.5 mmol), silver trifluoroacetate (4.5 g, 20.4 mmol) and iodine (4.7 g, 18.5 mmol) in a mixture of acetonitrile (30 ml) and chloroform (30 ml) were stirred at room temperature for 72 hr then a further 1 g silver trifluoroacetate and 1 g iodine added and stirring continued for 18 hr. The mixture was then filtered and the filtrate evaporated to give an orange oil which was purified by flash chromatography (Merck 9385 silica, 5% MeOH/dichloromethane) followed by recrystallisation from EtOAc/isohexane to give the title compound (1.85 g, 38%) as a colourless solid. MS: ESP$^+$ (M+H)$^+$=320.

$^1$H-NMR (300 MHz, DMSO-d6): δ=3.53 (m, 1H), 3.47 (m, 1H), 3.78 (dd, 1H), 4.05 (t, 1H), 4.69 (m, 1H), 5.18 (t, 1H), 7.38 (d, 2H), 7.69 (d, 2H).

REFERENCE EXAMPLE 28

5(R)-Isoxazol-3-yloxymethyl-3-(4-iodophenyl)oxazolidin-2-one

Prepared by the general method of Example 1 using (1.85 g, 5.80 mmol), 3-hydroxyisoxazole (0.55 g, 6.47 mmol), diisopropylazodicarboxylate (1.29 g, 6.39 mmol) and triphenylphosphine (1.75 g, 6.68 mmol) in THF (30 ml). Purified by flash chromatography (Merck 9385 silica, EtOAc/isohexane (1/1)) to give the title compound (1.45 g, 64%) as a colourless solid. MS: ESP$^+$ (M+H)$^+$=387.

$^1$H-NMR (300 MHz, CDCl$_3$) δ=3.94 (dd, 1H), 4.13 (t, 1H), 4.46–4.61 (m, 2H), 5.03 (m, 1H), 6.00 (d, 1H), 7.34 (d, 2H), 7.69 (d, 2H), 8.15 (d, 1H).

REFERENCE EXAMPLE 29

5(R)-Isoxazol-3-yloxymethyl-3-(4-(1-tert-butoxycarbonyl-1,2,5,6-tetrahydrolpyrid-4-yl)phenyl)oxazolidin-2-one Lithium chloride (1.0 g, 23.6 mmol), triphenylarsine (0.95 g, 3.10 mmol) and tris(dibenzylideneacetone)dipalladium(0)

(0.7 g, 0.76 mmol) were added at room temperature, under an atmosphere of nitrogen, to a stirred solution of Reference Example 28 (3.0 g, 7.77 mmol) in DMF (50 ml, degassed). The resulting mixture was stirred for 15 min then N-tert-butoxycarbonyl-4-trimethylstannyl-1,2,5,6-tetrahydropyridine (3.0 g, 8.67 mmol ; prepared from N-tert-butoxycarbonyl-4-triflate-1,2,5,6-tetrahydropyridine (WO97/30995) reacted with hexamethyltin using a Pd(0) catalyst) in DMF (10 ml) added in one go. The reaction was stirred and heated at 50°–55° C. for 3 hr, cooled to room temperature then treated with a 2N aqueous solution of potassium fluoride (8 ml). After stirring for 30 min the solvent was evaporated (50°, high vac.) then the residue partitioned between dichloromethane and water, filtered and the dichloromethane layer separated, Washed with water (2X) and sat. brine, dried over magnesium sulfate and evaporated to an orange viscous oil. Purified by flash chromatography (Merck 9385 silica, EtOAc/isohexane (3/2)) to give the title compound as a pale yellow solid. MS: ESP$^+$ (M+H)$^+$=442.

REFERENCE EXAMPLE 30

5(R)-Isoxazol-3-yloxymethyl-3-(4-(1,2,5,6-tetrahydropyrid-4-yl)-phenyl)oxazolidin-2-one Reference Example 29 (2.1 g, 4.76 mmol) in MeOH (30 ml) (partial solution) was treated at room temperature with an approx. 4M solution of HCl in ethanol and the resulting mixture stirred 4 hr then left to stand 16 hr. Diethyl ether (50 ml) was then added and the resulting pale yellow solid filtered, washed with ether and dried: 1.71 g (95% yield)—title compound as the hydrochloride salt.

$^1$H-NMR (300 MHz, DMSO-d6): δ=2.66 (m, 2H), 3.30 (m, partially obscured by DMSO, 2H), 3.73 (m, 2H), 3.92 (dd, 1H), 4.20 (t, 1H), 4.41–4.53 (m, 2H), 5.08 (m, 1H), 6.16 (m, 1H), 6.35 (d, 1H), 7.49 (d, 2H), 7.57 (d, 2H), 8.68 (d, 1H), 9.30 (s(br), 2H). MS: ESP$^+$ (M+H)$^+$=342. Free base isolated by treating with aqueous sodium hydroxide solution and extraction with dichloromethane to give title compound as a yellow solid.

REFERENCE EXAMPLE 31

5(R)-Isoxazol-3-yloxymethyl-3-(4-(1-(2,2-dimethyl-1,3-dioxolan-4(R)-ylcarbonyl)-1,2,5,6-tetrahydropyrid-4-yl)phenyl)oxazolidin-2-one 1,3 Dicyclohexylcarbodiimide (298 mg, 1.45 mmol) was added in one go at room temperature to a stirred solution of (R)-2,3-O-isopropylideneglyceric acid (235 mg, 1.40 mmol 87% purity) and 1-hydroxybenzotriazole (218 mg, 1.42 mmol) in dichloromethane (15 ml). The resulting suspension was stirred 1 hr then a further 5 ml dichloromethane was added followed by Reference Example 30 (500 mg, 1.47 mmol), stirred 16 hr, filtered and the filtrate washed with water and sat. brine. Purified by flash chromatography (Merck 9385 silica, 2.5% MeOH/dichloromethane) to give the title compound (395 mg, 57%) as a colourless solid. MS: ESP$^+$ (M+H)$^+$=470.

REFERENCE EXAMPLE 32

5(R)-Isoxazol-3-yloxymethyl-3-(4-(1-(2,2-dimethyl-1,3-dioxolan-4(S)-ylcarbonyl)-1,2,5,6-tetrahydropyrid-4-yl)phenyl)oxazolidin-2-one Prepared by the general method of Reference Example 31, using Reference Example 30 (500 mg, 1.47 mmol), 1,3 dicyclohexylcarbodiimide (298 mg, 1.45 mmol), (S)-2,3-O-isopropylideneglyceric acid (235 mg, 1.40 mmol 87% purity) and 1-hydroxybenzotriazole (218 mg, 1.42 mmol) in dichloromethane (15 ml). Purified by flash chromatography (Merck 9385 silica, 2.5% MeOH/dichloromethane) to give the title compound (408 mg, 59%) as a colourless solid. MS: ESP$^+$ (M+H)$^+$=470.

EXAMPLE 40

5(R)-Isoxazol-3-yloxymethyl-3-(4-(1-(2(R),3-dihydroxypropanoyl)-1,2,5,6-tetrahydropyrid-4-yl) phenyl)oxazolidin-2-one Prepared by the general method of Example 4 using Reference Example 31 (395 mg, 0.84 mmol) in 1N hydrochloric acid (3 ml) and THF (9 ml). Purified by flash chromatography (Merck 9385 silica, 8% MeOH/dichloromethane) to give the title compound (203 mg, 56%) as a colourless solid, mp=138°–144° C.

$^1$H-NMR (300 MHz, DMSO-d6): δ=2.40–2.56 (m, partially obscured by DMSO, 2H), 3.40–3.63 and 3.63–3.88 (m, 4H), 3.92 (dd, 1H), 4.11 (m, 2H), 4.20 (t, 1H), 4.30–4.54 (m, 3H), 4.68 (m, 1H), 4.92 (m, 1H), 5.07 (m, 1H), 6.15 (m, 1H), 6.37 (d, 1H), 7.46 (d, 2H), 7.53 (d, 2H), 8.68 (d, 1H). MS: ESP$^+$ (M+H)$^+$=430.

EXAMPLE 41

5(R)-Isoxazol-3-yloxymethyl-3-(4-(1-(2(S),3-dihydroxypropanoyl)-1,2,5,6-tetrahydropyrid-4-yl) phenyl)oxazolidin-2-one Prepared by the general method of Example 4 using Reference Example 32 (408 mg, 0.87 mmol) in 1N hydrochloric acid (3 ml) and THF (9 ml). Purified by flash chromatography (Merck 9385 silica, 8% MeOH/dichloromethane) to give the title compound (124 mg, 33%) as a colourless solid, mp=200°–202° C.(dec).

$^1$H-NMR (300 MHz, DMSO-d6): δ=2.38–2.56 (2H), 3.20–3.40 (m, partially obscured by DMSO, 2H), 3.54 (m, 1H), 3.64–3.85 (m, 1H), 3.92 (dd, 1H), 4.12 (m, 2H), 4.20 (t, 1H), 4.30–4.55 (m, 3H), 5.07 (m, 1H), 6.15 (m, 1H), 6.37 (d, 1H), 7.46 (d, 2H), 7.53 (d, 2H), 8.66 (d, 1H). MS: ESP$^+$ (M+H)$^+$=430.

EXAMPLE 42

5(R)-Isoxazol-3-yloxymethyl-3-(4-methylthiophenyl)oxazolidin-2-one

Prepared by the general method of Example 1 using 5(R)-hydroxymethyl-3-(4-methylthiophenyl)oxazolidin-2-one (650 mg, 2.72 mmol ; prepared from the reaction of 4-methylthioaniline and (R)-glycidyl butyrate), 3-hydroxyisoxazole (243 mg, 2.86 mmol), diisopropylazodicarboxylate (577 mg, 2.86 mmol) and triphenylphosphine (770 mg, 2.94 mmol) in THF (10 ml). Purified by flash chromatography (Merck 9385 silica, EtOAc/isohexane (1/1)) to give the title compound 507 mg, 61%) as a colourless solid. MS: ESP$^+$ (M+H)$^+$=307.

$^1$H-NMR (300 MHz, CDCl$_3$): δ=2.47 (s, 3H), 3.97 (dd, 1H), 4.15 (t, 1H), 4.47–4.62 (m, 2H), 5.02 (m, 1H), 6.00 (d, 1H), 7.30 (d, 2H), 7.49 (d, 2H), 8.14 (d, 1H).

EXAMPLE 43

5(R)-Isoxazol-3-yloxymethyl-3-(4-methylsulfinylphenyl)oxazolidin-2-one and Example 44: 5(R)-Isoxazol-3-yloxymethyl-3-(4-methylsulfonylphenyl)oxazolidin-2-one 3-Chloroperoxybenzoic acid (282 mg,70% strength, 1.14 mmol) was added to a solution of Example 42 (340 mg, 1.11 mmol) in dichloromethane (10 ml) at −40° C. The reaction was stirred at −30° to −40° C. for 3 hr then diluted with more dichloromethane (10 ml), washed with aq. sodium bisulfite solution, sat. aq. sodium bicarbomate solution and water, dried over magnesium sulfate and evaporated to a colourless oil. Purified by flash chromatography (Merck 9385 silica, 5% MeOH/dichloromethane) to give Example 43 (275 mg, 77%) and Example 44 (31 mg), both as colourless solids.

Example 43: MS: ESP$^+$ (M+H)$^+$=323.

$^1$H-NMR (300 MHz, CDCl$_3$): δ=2.73 (s, 3H), 4.06 (dd, 1H), 4.22 (t, 1H), 4.50–4.65 (m, 2H), 5.08 (m, 1H), 6.00 (d, 1H), 7.69 (d, 2H), 7.77 (d, 2H), 8.15 (d, 1H).

Example 44: MS: ESP$^+$ (M+H)$^+$=339.

$^1$H-NMR (300 MHz, DMSO-d6) δ=3.14 (s, 3H), 3.98 (dd, 1H), 4.26 (t, 1H), 4.43–4.54 (m, 2H), 5.10 (m, 1H), 6.34 (d, 1H), 7.80 (d, 2H), 7.92 (d, 2H), 8.66 (d, 1H).

EXAMPLE 45

5(R)-Isoxazol-3-yloxymethyl-3-(4-(1-(2(R,S)-hydroxy-3-(1-imidazoyl)propanoyl)-1,2,5,6-tetrahydropyrid-4-yl)-3,5-difluorophenyl)-oxazolidin-2-one Reference Example 19 (200 mg, 0.45 mmol) and 1H-imidazole (34 mg, 0.50 mmol) in 2-propanol (2 ml) were refluxed for 8 hr then the resulting solution cooled to room temperature and purified by flash chromatography (Merck 9385 silica, 10% MeOH/dichloromethane) to give the title compound (83 mg, 36%) as a colourless solid.

$^1$H-NMR (300 MHz, DMSO-d6) δ=2.25–2.50 (m, 2H), 3.55–3.83 (m, 2H), 3.95 (dd, 1H), 4.00–4.40 (m, 5H), 4.44–4.56 (m, 2H), 4.56–4.68 (m, 1H), 5.11 (m, 1H), 5.65 (d) and 5.75 (d) (1H), 5.87 (m, 1H), 6.37 (d, 1H), 6.85 (m, 1H), 7.15 (m, 1H), 7.36 (d, 2H), 7.58 (m, 1H), 8.68 (d, 1H). MS: ESP$^+$ (M+H)$^+$=516.

EXAMPLE 46

5(R)-Isoxazol-3-yloxymethyl-3-(4-(1-(2(R,S)-hydroxy-3-(1,2,4-triazol-1-yl)propanoyl)-1,2,5,6-tetrahydropyrid-4-yl)-3,5-difluorophenyl)-oxazolidin-2-one Prepared by the general method of Example 45 using Reference Example 19 (200 mg, 0.45 mmol) and 1H-1,2,4-Triazole (35 mg, 0.50 mmol) in 2-propanol (2 ml). Purified by flash chromatography (Merck 9385 silica, 10% MeOH/dichloromethane) to give the title compound (84 mg, 36%) as a colourless solid. MS: ESP$^+$ (M+H)$^+$=517.

$^1$H-NMR (300 MHz, DMSO-d6): δ=2.25–2.50 (m, 2H), 3.55–3.85 (m, 2H), 3.95 (dd, 1H), 4.00–4.40 (m, 5H), 4.40–4.55 (m, 2H), 4.68–4.82 (m, 1H), 5.12 (m, 1H), 5.77 (d) and 5.81 (d) (1H), 5.90 (m, 1H), 6.77 (d, 1H), 7.35 (d, 2H), 7.95 (s, 1H), 8.44 (s, 1H), 8.68 (d, 1H).

EXAMPLE 47

5R)-Isoxazol-3-yloxymethyl-3-(4-(1-(2(S)-acetoxypropanoyl)-1,2,5,6-tetrahydropyrid-4-yl)-3-fluorophenyl)oxazolidin-2-one (S)-2-Acetoxypropionyl chloride (126 mg, 0.84 mmol) was added dropwise at room temperature to a stirred suspension of Reference Example 11 (300 mg, 0.76 mmol) and N,N diisopropyl ethylamine (210 mg, 1.63 mmol) in dichloromethane (10 ml). The reaction was stirred at room temperature for 2 hr then purified by flash chromatography (Merck 9385 silica, 2.5% MeOH/dichloromethane) to give the title compound (322 mg, 90%) as a colourless solid. MS: ESP$^+$ (M+H)$^+$=474.

$^1$H-NMR (300 MHz, CDCl$_3$): δ=1.48 (s) and 1.51 (s) (3H), 2.14 (s, 3H), 2.50–2.74 (m, 2H), 3.68 (m) and 3.96 (m) (3H), 4.05–4.36 (m, 3H), 4.47–4.62 (m, 2H), 5.04 (m, 1H), 5.35–5.55 (m, 1H), 5.97 (m, 1H), 6.00 (d, 1H), 7.20–7.30 (m, 2H), 7.45 (d, 1H), 8.15 (d, 1H).

EXAMPLE 48

5(R)-Isoxazol-3-yloxymethyl-3-(4-(1-(2(S)-hydroxypropanoyl)-1,2,5,6-tetrahydropyrid-4-yl)-3-fluorophenyl)oxazolidin-2-one Example 47 (200 mg, 0.42 mmol) in 10 ml of a saturated solution of ammonia in MeOH was stirred at room temperature for 18 hr then cooled in ice-water before filtering the resulting colourless solid. Washed with ice-cold MeOH and diethyl ether then dried to give the title compound (156 mg, 86%). MS: ESP$^+$ (M+H)$^+$=432.

$^1$H-NMR(300 MHz, DMSO-d6): δ=1.23 (s) and 1.25 (s) (3H), 2.33–2.50 (m, 2H), 3.52–3.85 (m, 2H), 3.93 (dd, 1H), 4.02–4.38 (m, 3H), 4.40–4.60 (m, 2H), 4.85–5.00 (m, 1H), 5.11 (m, 1H), 6.03 (m, 1H), 6.38 (d, 1H), 7.33 (dd, 1H), 7.41 (t, 1H), 7.52 (dd, 1H), 8.68 (d, 1H).

EXAMPLE 49

5(R)-Isoxazol-3-yloxymethyl-3-(4-(1-acetoxyacetyl-1,2,5,6-tetrahydropyrid-4-yl)-3-fluorophenyl) oxazolidin-2-one Prepared by the general method of Example 6 using Reference Example 11 (300 mg, 0.76 mmol), acetoxyacetyl chloride (114 mg, 0.83 mmol), triethylamine (88 mg, 0.87 mmol) and 4-(dimethylamino) pyridine (25 mg) in dichloromethane 10 ml). Purified by chromatography (bond elut (silica, 10 g), 1–2% MeOH/dichloromethane) to give the title compound (230 mg, 66%) as a colourless solid. MS: ESP$^+$ (M+H)$^+$=460.

$^1$H-NMR (300 MHz, CDCl$_3$): δ=2.20 (s, 3H), 2.50–2.66 (m, 2H), 3.60 (t) and 3.83 (t) (2H), 3.96 (dd, 1H), 4.10 (m) and 4.24 (m, 2H), 4.15 (t, 1H), 4.50–4.64 (m, 2H), 4.77 (s) and 4.81 (s) (2H), 5.04 (m, 1H), 5.90–6.00 (m, 1H), 6.00 (d, 1H), 7.21–7.30 (m, 2H), 7.45 (d, 1H), 8.15 (d, 1H).

EXAMPLE 50

5(R)-Isoxazol-3-yloxymethyl-3-(4-(1-hydroxyacetyl-1,2,5,6-tetrahydropyrid-4-yl)-3-fluorophenyl) oxazolidin-2-one Prepared by the general method of Example 48 using Example 49 (170 mg, 0.37 mmol) in 10 ml of a saturated solution of ammonia in MeOH to give the title compound (121 mg, 79%) as a colourless solid. MS: ESP$^+$ (M+H)$^+$=418.

$^1$H-NMR (300 MHz, CDCl$_3$): δ=2.52–2.62 (m, 2H), 3.48 (t) and 3.65 (t) (2H), 3.87 (t) and 3.95 (m) (3H), 4.16 (t, 1H), 4.22 (dd, 1H), 4.30 (m, 1H), 4.48–4.62 (m, 2H), 5.04 (m, 1H), 5.92 (m) and 6.00 (m) (d, 1H), 6.00 (d, 1H), 7.20–7.30 (m, 2H), 7.43 (d, 1H), 8.15 (d, 1H).

EXAMPLE 51

5(R)-Isoxazol-3-yloxymethyl-3-(4-(1-(2(S)-hydroxy-3-(3-pyridin-1-iummethyl-benzoyloxy)-propanoyl)-1,2,5,6-tetrahydropyrid-4-yl)-3-fluorophenyl) oxazolidin-2-one Chloride Example 12 (0.40 g, 0.89 mmol) was suspended in dichloromethane (20 ml), and pyridine (0.07 g, 0.89 mmol), 4-dimethylaminopyridine (0.2 g) was added, 3-chloromethylbenzoyl chloride was added dropwise and the reaction mixture was stirred at room temperature for 2 hr. The resulting solution was washed with water, dried (MgSO$_4$) and purified by chromatography (Merck 9385 silica, 5–10% MeOH in CH$_2$Cl$_2$) to give the title compound as a pale yellow solid (0.30 g, 42%) after trituration with diethyl ether.

$^1$H-NMR (300 MHz, DMSO-d6): δ=2.43 (partially obscured by DMSO, 2H), 3.64–4.52 (m, 10H), 4.74 (m, 1H), 5.08 (m, 1H), 5.98 (m, 3H), 6.37 (m, 1H), 7.35 (m, 2H), 7.46–7.63 (m, 2H), 7.81 (m, 1H), 8.00 (m, 1H), 8.16 (m, 2H), 8.54–8.65 (m, 2H), 8.68 (m, 1H), 9.26 (M, 2H). MS: ESP$^+$ (M)$^+$=643.

EXAMPLE 52

5(R)-Isoxazol-3-yloxymethyl-3-(4-(1-(2(S)-hydroxy-3-(3-chloromethylbenzoyloxy)-propanoyl)-1,2,5,6-tetrahydropyrid-4-yl)-3-fluorophenyl)oxazolidin-2-one Example 12 (0.50 g, 1.12M) was suspended in dichloromethane (20 ml), and triethylamine (0.11 g, 0.16 mmol) was added. 3-chloromethylbenzoyl chloride was added dropwise and the reaction mixture was stirred at room temperature for 2 hr. The resulting solution was washed with water, dried (MgSO$_4$) and purified by chromatography (Merck 9385 silica, 4–5% MeOH in CH$_2$Cl$_2$) to give the title compound as a yellow solid (0.46 g, 69%) after trituration with diethyl ether and isohexane, also containing some di-substituted derivative.

$^1$H-NMR (300 MHz, DMSO-d6): δ=2.45 (partially obscured by DMSO, 2H), 3.65–3.98 (m, 3H), 3.98–4.25 (m, 2H), 4.31–4.55 (m, 4H), 4.70–4.87 (m, 4H), 5.07 (m, 1H), 5.71 (m, 1H), 6.04 (m, 1H), 6.41 (m, 1H), 7.28–7.46 (m, 2H), 7.46–7.59 (m, 2H), 7.71 (m, 1H), 7.87–8.12 (m, 2H), 8.72 (m, 1H). MS: ESP$^+$ (M+H)$^+$=600.

EXAMPLE 53

5(R)-Isoxazol-3-yloxymethyl-3-(4-(1-(2(S)-hydroxy-3-(3-morpholinomethylbenzoyloxy)-propanoyl)-1,2,5,6-tetrahydropyrid-4-yl)-3-fluorophenyl)oxazolidin-2-one Example 52 (0.01 g, 0.17 mmol), was stirred in DMF (3 ml), sodium iodide (ca, 10 mg) and morpholine (0.07 g, 0.67 mmol) was added and the reaction mixture was heated at 50° C. for 5 hr. The DMF was removed by evaporation and the residue was taken up in dichloromethane, washed with water, dried (MgSO$_4$) and purified by chromatography (Merck 9385 silica, 5–10% MeOH in CH$_2$Cl$_2$) to give the title compound as an off white solid (65 mg, 60%), after trituration with isohexane and diethyl ether.

$^1$H-NMR (300 MHz, DMSO-d6): δ=2.27 (m, 4H), 2.41 (partially obscured by DMSO, 2H), 3.40–3.59 (m, 6H), 3.63–3.98 (m, 3H), 3.98–4.57 (m, 7H), 4.74 (m, 1H), 5.08 (m, 1H), 5.67 (m, 1H), 6.04 (m, 1H), 6.39 (m, 1H), 7.28–7.64 (m, 5H), 7.88 (m, 2H), 8.72 (m, 1H). MS: ESP$^+$ (M+H)$^+$=651.

EXAMPLE 54

5(R)-Isoxazol-3-yloxymethyl-3-(4-(1-(2(S)-hydroxy-3-(3-(4-methylpiperazinomethyl)benzoyloxy)propanoyl)-1,2,5,6-tetrahydropyrid-4-yl)-3-fluorophenyl)oxazolidin-2-one Prepared by the general method of Example 53, using Example 52 (0.10 g, 0.17 mmol), sodium iodide (ca, 10 mg) and N-methylpiperazine (0.07 g, 0.67 mmol). Purified by chromatography (Merck 9385 silica, 5–10% MeOH in CH$_2$Cl$_2$–10% MeOH+1% ammonia in CH$_2$Cl$_2$), to give the title compound as white solid (55 mg, 50%) after trituration with isohexane.

$^1$H-NMR (300 MHz, DMSO-d6): δ=2.44 (partially obscured by DMSO, 5H), 2.62 (m, 4H), 3.21–3.35 (partially obscured by water, 4H), 3.55 (m, 2H), 3.65–3.84 (m, 2H), 3.92 (dd, 1H), 4.08–4.25 (m, 2H), 4.34 (m, 1H), 4.45 (m, 4H), 4.75 (m, 1H), 5.08 (m, 1H), 5.62 (m, 1H), 6.02 (broad s, 1H), 6.36 (m, 1H), 7.28–7.60 (m, 5H), 7.88 (m, 2H), 8.68 (m, 1H). MS: ESP$^+$ (M+H)$^+$=664.

EXAMPLE 55

5(R)-Isoxazol-3-yloxymethyl-3-(4-(1-(2(S)-hydroxy-3-(3-di-n-butylaminomethylbenzoyloxy)propanoyl)-1,2,5,6-tetrahydropyrid-4-yl)-3-fluorophenyl)oxazolidin-2-one Prepared by the general method of Example 53, using Example 52 (0.10 g, 0.17 mmol), sodium iodide (ca, 10 mg) and di-N-butylamine (0.07 g, 0.67 mmol). Purified by chromatography Merck 9385 silica, 5–10% MeOH in CH$_2$Cl$_2$–10% MeOH+1% ammonia in CH$_2$Cl$_2$), to give the title compound as white solid (54 mg, 47%) after trituration with isohexane.

$^1$H-NMR (300 MHz, DMSO-d6): δ=0.71–0.89 (m, 6H), 1.13–1.43 (m, 8H), 2.31 (partially obscured by DMSO, 6H), 3.33 (partially obscured by water, 2H), 3.42–3.59 (m, 2H), 3.67–3.97 (m, 3H), 3.97–4.56 (m, 5H), 4.74 (m, 1H), 5.08 (m, 1H), 5.67 (m, 1H), 6.03 (broad s, 1H), 6.38 (m, 1H), 7.28–7.63 (m, 5H), 7.87 (m, 2H), 8.69 (m, 1H). MS: ESP$^+$ (M+H)$^+$=693.

EXAMPLE 56

5(R)-Isoxazol-3-yloxymethyl-3-(4-(1-n-propyl-1,2,5,6-tetrahydropyrid-4-yl)-3-fluorophenyl)oxazolidin-2-one Reference Example 11 (500 mg, 1.26 mmol) was stirred in MeOH (10 ml) and glacial acetic acid (~0.5 ml) was added to pH4. Propanal (80.7 mg, 1.39 mmol) was added dropwise, and the reaction was stirred for 40 minutes. To the stirred solution, sodium cyanoborohydride was added (83.4 mg, 1.33 mmol) portionwise. The reaction was stirred for a further 30 minutes at room temperature. The reaction was quenched with 10% NaOAc and extracted with dichloromethane and the combined organic phases were dried over MgSO$_4$ and evaporated under reduced pressure. The resulting brown oil was triturated with ether to yield the title compound as an orange solid (300.6 mg, 59%). MS: ESP+ (M+H)$^+$=402.

$^1$H-NMR (300 MHz, DMSO-d6): δ=0.85 (t, 3H), 1.46 (m, 2H), 2.32 (t, 2H), 2.40 (broad s, 2H), 2.57 (t, 2H), 3.04 (d, 2H), 3.93 (dd, 1H), 4.19 (t, 1H), 4.48 (m, 2H), 5.08 (m, 1H), 5.97 (broad s, 1H), 6.37 (d, 1H), 7.29–7.40 (m, 2H), 7.49 (dd, 1H), 8.70 (d, 1H).

EXAMPLE 57

5(R)-Isoxazol-3-yloxymethyl-3-(4-(1-(2-hydroxyethyl)-1,2,5,6-tetrahydropyrid-4-yl)-3-fluorophenyl)oxazolidin-2-one To a stirred partial solution of Reference Example 11 (318 mg, 0.80 mmol) and NaHCO$_3$ (169 mg, 2.01 mmol) in ethanol (5 ml) under an atmosphere of nitrogen, 2-bromoethanol (151 mg, 1.21 mmol) was added dropwise. The reaction was then refluxed for 20 hours. Water was added (200 ml) and the reaction extracted with EtOAc and the combined organic phases were washed with sat NaCl and then dried over $MgSO_4$ and evaporated under reduced pressure. The resulting yellow oil was triturated with ether to give the title compound as a yellow solid (163 mg, 50%).

$^1$H-NMR (300 MHz, DMSO-d6): δ=2.40 (broad s, 2H), 2.49(Obscured by DMSO, 2H), 2.63 (t, 2H), 3.09 (d, 2H), 3.52 (m, 2H), 3.91 (dd, 1H), 4.19 (t, 1H), 4.39 (m, 1H), 4.45 (m, 2H), 5.05 (m, 1H), 5.96 (broad s, 1H), 6.37 (d, 2H), 7.25–7.38 (m, 2H), 7.47 (dd, 1H), 8.68 (d, 2H). MS: ESP+ $(M+H)^+$=404.

EXAMPLE 58

5(R)-Isoxazol-3-yloxymethyl-3-(4-(1-(2-acetoxyethyl)-1,2,5,6-tetrahydropyrid-4-yl)-3-fluorophenyl)oxazolidin-2-one To a stirred solution of Example 57(103 mg, 0.26 mmol) and triethylamine (77.4 mg, 0.77 mmol) in dichloromethane (10 ml) at 0° C. and under an atmosphere of nitrogen, was added dropwise acetyl chloride (60.2 mg, 0.77 mmol). The reaction was then allowed to warm to ambient temperature and stir for 1 hour. Water was added and the organic phase separated, washed with sat NaCl and then dried over $MgSO_4$ and evaporated under reduced pressure. This yielded the title compound as a clear orange glass (110 mg, 97%). MS: ESP+ $(M+H)^+$=446.

$^1$H-NMR (300 MHz, DMSO-d6): 2.09 (s, 3H), 2.50 (broad s, 2H), 2.74 (m, 4H), 3.20 (broad s, 2H), 3.99 (m, 1H), 4.19–4.29 (m, 3H), 4.53 (m, 2H), 5.14 (m, 1H), 6.04 (broad s, 1H), 6.46 (d, 1H), 7.34–7.49 (m, 2H), 7.55 (dd, 1H), 8.75 (d, 1H).

EXAMPLE 59

5(R)-Isoxazol-3-yloxymethyl-3-(4-(1-(2,2-dimethyl-1,3-dioxan-5-yl)-1,2,5,6-tetrahydropyrid-4-yl)-3-fluorophenyl)oxazolidin-2-one To a stirred partial solution of Reference Example 11 (600 mg, 1.52 mmol) in MeOH (15 ml), at 0° C. was added dropwise 2,2-dimethyl-1,3-dioxan-5-one (218 mg, 1.67 mmol). The reaction was allowed to warm to ambient temperature and stirred for 40 minutes. Sodium cyanoborohydride (100.4 mg, 1.60 mmol) was then added portionwise and the reaction stirred for a further 48 hours. The reaction was quenched with 10% NaOAc and extracted with dichloromethane and the combined organic phases were dried over $MgSO_4$ and evaporated under reduced pressure. The reaction was then purified by MPLC (Merck 9385 silica, 5% MeOH in dichloromethane). The solvent was removed to yield an orange oil which was triturated with ether to give the title compound as an orange solid (295 mg, 41%). MS: ESP+$(M+H)^+$=474.

$^1$H-NMR (300 MHz, DMSO-d6): δ=1.29 (s, 3H), 1.35 (s, 3H), 2.39 (broad s, 2H), 2.58 (m, 1H), 2.74 (m, 2H), 3.22 (d, 2H), 3.78 (m, 2H), 3.92 (m, 3H), 4.20 (t, 1H), 4.45 (m, 2H), 5.05 (m, 1H), 5.95 (broad s, 1H), 6.38 (d, 1H), 7.29–7.40 (m, 2H), 7.48 (dd, 1H), 8.69 (d, 1H).

EXAMPLE 60

5(R)-Isoxazol-3-yloxymethyl-3-(4-(1-(1-(hydroxymethyl)-2-hydroxyethyl)-1,2,5,6-tetrahydropyrid-4-yl)-3-fluorophenyl)oxazolidin-2-one To a stirred solution of Example 59 (203 mg, 0.43 mmol) in THF (15 ml) was added 1N HCl (10 ml). The reaction was allowed to stir at ambient temperature for 18 hours. The reaction was basified with ammonia solution until aqueous layer was pH12. The reaction was extracted with EtOAc and the combined organic phases were washed with sat NaCl and then dried over $MgSO_4$ and evaporated under reduced pressure. The resulting yellow oil was triturated with ether to give the title compound as a pale yellow solid (167 mg, 90%). MS: ESP+ $(M+H)^+$=434.

$^1$H-NMR (300 MHz, DMSO-d6): δ=2.39 (broad s, 2H), 2.59 (m, 1H), 2.84 (m, 2H), 3.38 (d, 2H), 3.51 (m, 4H), 3.91 (dd, 1H), 4.20 (t, 1H), 4.30 (broad s, 2H), 4.48 (m, 2H), 5.08 (m, 1H), 5.96 (broad s, 1H), 6.37 (d, 1H), 7.27–7.38 (m, 2H), 7.48 (dd, 1H), 8.69 (d, 1H).

REFERENCE EXAMPLE 33

3,5-Difluoro-4-(1-methyl-4-hydroxyhexahydropyrid-4-yl)-aniline

To a stirred solution of 3,5-difluoroaniline (7.0 g, 54 mmol) in anhydrous THF (250 ml) under an atmosphere of nitrogen and cooled to –74° C. was added dropwise "BuLi (1.45M in hexanes, 78.6 ml, 0.114 mol) over a period of 10 minutes. The reaction was allowed to stir at –74° C. for 30 minutes. Chlorotrimethylsilane (12.4 g, 0.114 mol), in anhydrous THF (100 ml) was added dropwise over a period of 10 minutes. The solution was allowed to warm to ambient temperature and then stir for 40 minutes. The reaction was then cooled again to –74° C. and nBuLi (1.45M in hexanes, 43.0 ml, 62.4 mmol) was added dropwise over a period of 10 minutes. After stirring for a further 3.5 hours at –74° C., N-methyl-4-piperidone (7.90 g, 70.5 mmol) in anhydrous THF (50 ml) was added dropwise over a period of 10 minutes. The reaction was allowed to stir to ambient temperature over the weekend. The reaction was acidified with 10% HCl to pH<1 and extracted with diethyl ether. The aqueous phase was separated and treated with 40% NaOH to pH 12 then extracted with diethyl ether and the combined organic phases were washed with sat NaCl and then dried over $MgSO_4$ and evaporated under reduced pressure. The resulting brown oil was triturated with cyclohexane to give the title compound as a pale yellow solid (9.30 g, 71%).

$^1$H-NMR (300 MHz, DMSO-d6): δ=1.87–2.05 (m, 4H), 2.10 (s, 3H), 2.25–2.42 (m, 4H), 4.70 (s, 1H), 5.54 (s, 2H), 6.07 (dd, 2H). MS: ESP+ $(M+H)^+$=243; ESP– $(M+H)^+$=241.

REFERENCE EXAMPLE 34

3,5-Difluoro-4-(1-methyl-1,2,5,6-tetrahydropyrid-4-yl)-aniline

Prepared by the general method of Reference Example 2 using Reference Example 33 (9.0 g, 37 mmol) and conc. HCl (35 ml). Yield =8.20 g, 98%. MS: ESP+ $(M+H)^+$=225.

$^1$H-NMR (300 MHz, DMSO-d6): δ=2.25 (s, 5H), 2.50 (partially obscured by DMSO, 2H), 2.93 (m, 2H), 5.60 (broad s, 1H), 5.66 (s, 2H), 6.15 (dd, 2H).

REFERENCE EXAMPLE 35

N-Benzyloxycarbonyl-3,5-difluoro-4-(1-methyl-1,2,5,6-tetrahydropyrid-4-yl)aniline To a stirred solution of Reference Example 34 (8.20 g, 35.7 mmol) in dichloromethane (250 ml) and pyridine (4.00 ml, 49.4 mmol) under an atmosphere of nitrogen at –10° C. was added dropwise benzyl chloroformate (7.49 g, 43.9 mmol) in dichloromethane. The reaction was allowed to warm to ambient temperature and stir for 2 hours. Water and ice was added and the organic phase separated, washed with sat NaCl and then dried over MgSO$_4$ and evaporated under reduced pressure. The resulting brown oil was purified by MPLC (Merck 9385 silica, 4–8% MeOH in dichloromethane). The solvent was removed to yield a yellow oil which was triturated with cyclohexane to give the title compound as a pale yellow solid (7.60 g, 58%). MS:ESP+ (M+H)$^+$=359.

$^1$H-NMR (300 MHz, DMSO-d6): δ=2.29 (m, 5H), 2.54 (Partially obscured by DMSO, 2H), 2.90 (m, 2H), 5.15 (s, 2H), 5.73 (broad s, 1H), 7.15 (dd, 2H), 7.31–7.44 (m, 5H), 10.18 (s, 1H).

REFERENCE EXAMPLE 35A

5(R)-Hydroxymethyl-3-(4-(1-methyl-1,2,5,6-tetrahydropyrid-4-yl)-3,5-difluorophenyl)-oxazolidin-2-one To a stirred solution of Reference Example 35 (7.25 g, 20.3 mmol) in anhydrous THF (100 ml) under an atmosphere of nitrogen and cooled to −74° C. was added dropwise "BuLi (1.45M in hexanes, 14.9 ml, 21.7 mmol) over a period of 10 minutes. The reaction was allowed to stir at −74° C. for 30 minutes. R-glycidyl butyrate (3.18 g, 22.1 mmol) was added in one portion and the reaction was allowed to warm to ambient temperature and stir overnight. MeOH (10 ml) was added and the reaction allowed to stir for 10 minutes. Water was added (150 ml) and the reaction extracted with EtOAc and the combined organic phases were washed with sat NaCl and then dried over MgSO$_4$ and evaporated under reduced pressure. The resulting oil was triturated with ether to give the title compound as a pale yellow solid (4.51, 69%).

$^1$H-NMR (300 MHz, DMSO-d6): δ=2.25 (s, 3H), 2.31 (broad s, 2H), 2.53 (partially obscured by DMSO, 2H), 2.98 (m, 2H), 3.55 (m, 1H), 3.67 (m, 1H), 3.82 (dd, 1H), 4.06, (t, 1H), 4.71 (m, 1H), 5.21 (m, 1H), 5.78 (broad s, 1H), 7.32(dd, 2H). MS: ESP+ (M+H)$^+$=325.

There is no Example 61.

EXAMPLE 62

5(R)-Isoxazol-3-yloxymethyl-3-(4-(1-methyl-1,2,5,6-tetrahydropyrid-4-yl)-3,5-difluorophenyl)oxazolidin-2-one Reference Example 35A (1.0 g, 3.10 mmol), 3-hydroxyisoxazole (0.39, 4.59 mmol), triphenylphosphine (1.21 g, 4.63 mmol) and diisopropylazodicarboxylate (1.17 g, 4.64 mmol) in anhydrous THF (60 ml) were reacted using the general method of Example 1. The resultant product was purified by MPLC (Merck 9385 silica, 5% MeOH in dichloromethane). The solvent was removed to yield a clear orange glass (0.93 g, 77%). MS: ESP+ (M+H)$^+$=392.

$^1$H-NMR (300 MHz, DMSO-d6): δ=2.25 (s, 3H), 2.30 (broad s, 2H), 2.54 (Partially obscured by DMSO, 2H), 2.97 (m, 2H), 3.90 (dd, 1H), 4.19 (t, 1H), 4.46 (m, 2H), 5.09 (m, 1H), 5.78 (broad s, 1H), 6.37 (d, 1H), 7.31 (dd, 2H), 8.68 (d, 1H).

EXAMPLE 63

5(R)-Isoxazol-3-yloxymethyl-3-(4-(1-(2(S)-hydroxy-3-acetamidopropanoyl)-1,2,5,6-tetrahydropyrid-4-yl)-3-fluorophenyl)oxazolidin-2-one To a solution of Reference Example 11 (500 mg, 1.25 mmol) in anhydrous DMF (25 ml), stirred at room temperature, was added in sequence: N-methylmorpholine (220 μl, 2.0 mmol), N-acetyl-L-isoserine, 220 mg, 1.5 mmol), 1-hydroxybenzotriazole (213 mg, 1.5 mmol) and 1-(3-dimethylaminopropyl)-3-ethylcarbodiimide hydrochloride (287 mg, 1.5 mmol) and stirred for 18 h. The DMF was removed by hi-vac rotary evaporation and the residue purified by MPLC (Merck 9385 Silica, eluting with 5%MeOH/CH$_2$Cl$_2$) to give the title compound as a white solid (430 mg, 70%) upon trituration with diethyl ether. MS: ES$^+$. (M+H)$^+$=489.

NMR (300 MHz, DMSO-d$_6$) δ/ppm: 1.78(s, 3H), 2.21(m, 2H), 3.10(m, 1H), 3.30(m, 1H), 3.70(m, 2H), 3.92(dd, 1H), 4.08(dd, 2H), 4.21 (m, 2H), 4.43 (m, 2H), 5.08 (m, 1H), 5.18 (t, 1H), 6.00 (br s, 1H), 6.38 (d, 1H), 7.28–7.41(m, 2H), 7.50 (dd, 1H), 7.92 (m, 1H), 8.65 (d, 1H).

REFERENCE EXAMPLE 36

5(R)-Isoxazol-3-yloxymethyl-3-(4-(1-(2(S)-tert-butoxycarbonylamino-3-hydroxy-propanoyl)-1,2,5,6-tetrahydropyrid-4-yl)-3-fluorophenyl)oxazolidin-2-one Prepared using the method of Example 63 using the following quantities of reagents: Reference Example 11 (1.00 g, 2.5 mmol); DMF (50 ml); : N-methylmorpholine (440 μl, 4.0 mmol); N-BOC-L-serine(616 mg, 3.0 mmol); 1-hydroxybenzotriazole(425 mg, 3.0 mmol); 1-(3-dimethylaminopropyl)-3-ethylcarbodiimide hydrochloride (575 mg, 3.0 mmol). Yielding the title compound as a white foam (1.32 g, 96%).

NMR (300 MHz, DMSO-d$_6$) δ/ppm: (300 MHz, DMSO-d$_6$) δ/ppm:

1.37 (s, 9H), 2.40 (m, partly obscured, 2H), 3.46 (m,1H), 3.57 (m, 1H), 3.70 (m, 2H), 3.93 (dd, 1H), 4.06 (s, 1H), 4.20 (m, 2H), 4.46 (m, 3H), 4.81 (t, 1H), 5.08 (m, 1H), 6.02 (br s, 1H), 6.38 (d, 1H), 6.86 (dd, 1H), 7.35 (m, 2H), 7.50 (d, 1H), 8.69 (d, 1H). MS: ES$^+$. (M+H)$^+$=547.

REFERENCE EXAMPLE 37

5(R)-Isoxazol-3-yloxymethyl-3-(4-(1-(2(S)-amino-3-hydroxypropanoyl)-1,2,5,6-tetrahydropyrid-4-yl)-3-fluorophenyl)oxazolidin-2-one TFA (2.0 ml) was added to Reference Example 36 (250 mg, 0.46 mmol) with some gas evolution and stirred at room temperature for 5 minutes, producing a yellow solution. The excess TFA was removed by rotary evaporation and the title compound (230 mg, 89%) obtained as a pale yellow solid upon trituration with diethyl ether. MS: ES$^+$. (M+H)$^+$=447.

EXAMPLE 64

5(R)-Isoxazol-3-yloxymethyl-3-(4-(1-(2(S)-acetamido-3-hydroxypropanoyl)-1,2,5,6-tetrahydropyrid-4-yl)-3-fluorophenyl)oxazolidin-2-one To a stirred solution of Reference Example 37 (168 mg, 0.3 mmol) and sodium bicarbonate(totalling 202 mg, 2.4 mmol) in acetone/water (10 ml, 1:1), cooled at 0° C., under N$_2$ was added drop-wise, acetyl chloride (totalling 70.6 mg, 0.90 mmol) in acetone (1.0 ml) and stirred for 5 hours. The acetone was removed by rotary evaporation, water and 1N. HCl solution added to pH=5 and extracted with CH$_2$Cl$_2$ (3×), the organic phases were separated, and the title compound obtained as a white solid (30 mg, 20%) following MPLC (Merck 9385 silica, eluting with 10%MeOH/CH$_2$Cl$_2$) and trituration with diethyl ether. MS: (M+H)$^+$=489.

NMR (400 MHz, DMSO-d$_6$) δ/ppm: (300 MHz, DMSO-d$_6$) δ/ppm: 1.84 (s, 3H), 2.47 (d, partially obscured, 2H), 3.46 (m, 1H), 3.62 (m, 1H), 3.73 (m, 2H), 3.96 (t, 1H), 4.10–4.30 (m, 3H), 4.50 (m, 2H), 4.88 (m, 2H), 5.11 (m, 1H), 6.03 (br s, 1H), 6.40 (d, 1H), 7.35 (dd, 1H), 7.41 (m, 1H), 7.52 (dd, 1H), 8.07 (t, 1H), 8.70 (d, 1H).

EXAMPLE 65

3-(4-(3-Hydroxy-1-azetidinyl)-3-fluorophenyl)-5(R)-(isoxazol-3-yl-oxymethyl)oxazolidin-2-one 3-(4-(3-t-Butyldimethylsilyloxy-1-azetidinyl)-3-fluorophenyl)-5(R)-(isoxazol-3-yloxy methyl)oxazolidin-2-one (230 mg, 0.5 mmol) was dissolved in tetrahydrofuran (10 ml), and cooled under nitrogen to 0°. A solution of tetra-n-butylammonium fluoride (1 M, 1 ml, 1 mmol) was added and the mixture allowed to come to ambient temperature. Water (2 ml) was added, and the mixture evaporated to dryness. The residue was purified by chromatography on a 10 g silica Mega Bond Elut(D column, eluting with a gradient increasing in polarity from 0 to 2.5% MeOH in dichloromethane. Relevant fractions were combined and evaporated, then redissolved in EtOAc and the desired product (96 mg) precipitated by addition of isohexane.

MS (ESP): 350 (MH$^+$) for C$_{16}$H$_{16}$FN$_3$O$_5$

NMR (DMSO-d$_6$) δ: 3.52 (t, 2H); 3.83 (dd, 1H); 4.09 (overlapping m, 3H); 4.45 (m, 2H); 4.51 (quintet, 1H); 5.00 (m, 1H); 5.53 (d, 1H); 6.37 (d, 1H); 6.56 (t, 1H); 7.11 (dd, 1H); 7.37 (dd, 1H); 8.66 (d, 1H).

The intermediate for this compound was prepared as follows:

3-(4-(3-t-Butyldimethylsilyloxy-1-azetidinyl)-3-fluorophenyl)-5(R)-(isoxazol-3-yl-oxymethyl)oxazolidin-2-one 3-(4-(3-t-Butyldimethylsilyloxy-1-azetidinyl)-3-fluorophenyl)-5(R)-hydroxymethyloxazolidin-2-one (WO 96/13502; 2.47 g, 6.25 mmol), 3-hydroxyisoxazole (580 mg, 6.86 mmol), and tributylphosphine (1.58 g, 7.8 mmol) were dissolved by stirring in dry tetrahydrofuran (100 ml) under nitrogen. The mixture was cooled in an ice-bath, and 1,1'-(azodicarbonyl)dipiperidine (1.96 g, 7.8 mmol) added dropwise over 10 minutes. The solution was stirred 18 hours, allowing the temperature to rise to ambient. Reduced azo compound was filtered off, and the solution evaporated to dryness and the residue triturated with ether. The residue was purified by chromatography on a silica flash column, eluting with a gradient from 50 to 75% EtOAc in isohexane. Relevant fractions were combined and evaporated to the product as an oil (1.31 g).

NMR (DMSO-d$_6$) δ: 0.00 (s, 6H); 0.79 (s, 9H); 3.47 (t, 2H); 3.77 (dd, 1H); 4.07 (t, 1H); 4.11 (t, 2H); 4.39 (m, 2H); 4.65 (quintet, 1H); 4.95 (m, 1H); 6.30 (d, 1H); 6.53 (t, 1H); 7.06 (dd, 1H); 7.33 (dd, 1H); 8.61 (d, 1H).

EXAMPLE 66

3-(4-(3-Oxo-1-azetidinyl)-3-fluorophenyl)-5(R)-(isoxazol-3-yloxymethyl)oxazolidin-2-one 3-4-(3-Hydroxy-1-azetidinyl)-3-fluorophenyl)-5(R)-(isoxazol-3-yloxymethyl)oxazolidin-2-one (349 mg, 1 mmol) was dissolved in dry DMSO(5 ml) under nitrogen, and treated with pyridine sulfur trioxide complex (502 mg, 3.15 mmol) in dry DMSO(5 ml) over 10 minutes. The solution was stirred 3 hours, poured into water (100 ml), and extracted with EtOAc (3×50 ml). The organic extracts were washed with water (3×50 ml), saturated brine (50 ml), and dried (magnesium sulfate). The residue was purified by chromatography on a 10 g silica Mega Bond Elut® column, eluting with a gradient increasing in polarity from 0 to 5% MeOH in dichloromethane. Relevant fractions were combined, evaporated, and the residue triturated with diethyl ether to give the desired product (227 mg).

MS (ESP): 348 (MH$^+$) for C$_{16}$H$_{14}$FN$_3$O$_5$; 380 (MH$^+$+ MeOH) for C$_{17}$H$_{18}$FN$_3$O$_6$. NMR (DMSO-d$_6$) δ: 3.89 (dd, 1H); 4.16 (t, 1H); 4.47 (m, 2H), 4.76 (s, 4H); 5.04 (m, 1H); 6.38 (d, 1H); 6.77 (d, 1H); 7.21 (dd, 1H); 7.49 (dd, 1H); 8.67 (d, H1).

EXAMPLE 67

3-(4-(4-t-Butoxycarbonyl-piperazin-1-yl)-3-fluorophenyl)-5(R)-(isoxazol-3-yloxymethyl)oxazolidin-2-one 3-(4-(4-t-Butoxycarbonyl-piperazin-1-yl)-3-fluorophenyl)-5(R)-hydroxymethyloxazolidin-2-one (WO 93/23384; 10 g, 25.3 mmol), 3-hydroxyisoxazole (2.58 g, 30 mmol), and triphenylphosphine (9.95 g, 37.8 mmol) were dissolved in anhydrous tetrahydrofuran (300 ml), and cooled under nitrogen to 4°. Diisopropylazodicarboxylate (6.04 g, 30 mmol) was added dropwise over 10 minutes, and stirring was continued at the same temperature for 2 hours. The mixture was evaporated to dryness, and the residue purified by flash chromatography on silica, eluting with 50% EtOAc in isohexane. Relevant fractions were combined and evaporated to give the desired product (10.2 g).

MS (ESP): 463 (MH$^+$) for C$_{22}$H$_{27}$FN$_4$O$_6$ NMR (DMSO-d$_6$) δ: 1.39 (s, 9H); 2.91 (t, 4H); 3.45 (t, 4H); 3.87 (dd, 1H); 4.14 (t, 1H); 4.44 (m, 2H); 5.03 (m, 1H); 6.35 (d, 1H); 7.06 (t, 1H); 7.18 (dd, 1H); 7.36 (dd, 1H); 8.66 (d, 1H).

EXAMPLE 68

3-(4-(Piperazin-1-yl)-3-fluorophenyl)-5(R)-(isoxazol-3-yloxymethyl)-oxazolidin-2-one Dihydrochloride 3-(4-(4-t-Butoxycarbonyl-piperazin-1-yl)-3-fluorophenyl)-5(R)-(isoxazol-3-yloxymethyl)-oxazolidin-2-one (10.24 g, 22 mmol) was suspended in ethanol (150 ml), and a solution of hydrogen chloride in ethanol (5M, 75 ml) added at 0°. A complete solution occurred, and the solution was left to stir 18 hours at ambient temperature, as product precipitated. After dilution with anhydrous diethyl ether (200 ml), the product (8.91 g) was filtered off.

Microanalysis: Found: C, 46.9, H, 4.8, N, 12.2%; C$_{17}$H$_{19}$FN$_4$O$_4$.2HCl requires C, 46.9, H, 4.6, N, 12.9%. MS (ESP): 363 (MH$^+$) for C$_{17}$H$_{19}$FN$_4$O$_4$ NMR (DMSO-d$_6$) δ: 3.19 (s, 8H); 3.87 (dd, 1H); 4.16 (t, 1H); 4.45 (m, 2H); 5.03 (m, 1H); 6.36 (d, 1H); 7.11 (t, 1H); 7.22 (dd, 1H); 7.51 (dd, 1H); 8.68 (d, 1H); 9.47 (br, 2H).

EXAMPLE 69

3-(4-(4-(2(R),3-Dihydroxypropanoyl)piperazin-1-yl)-3-fluorophenyl)-5(R)-(isoxazol-3-yloxymethyl)oxazolidin-2-one A solution of 2,2-dimethyl-1,3-dioxolane-4(R)-carboxylic acid (162 mg, 1.1 mmol) in dichloromethane (20 ml) under nitrogen was cooled with stirring to 4°, and treated successively with dicyclohexylcarbodiimide (227 mg, 1.1 mmol) and 1-hydroxybenzotriazole (147 mg, 1.1 mmol), then stirred at the same temperature for 1 hour. N,N-Diisopropylethylamine (129 mg, 1 mmol) was added, followed by 3-(4-(piperazin-1-yl)-3-fluorophenyl)-5(R)-(isoxazol-3-yloxymethyl)oxazolidin-2-one dihydrochloride (399 mg, 0.92 mmol). The mixture was stirred for 2 hours, allowing the temperature to rise to ambient. Solid was filtered off, and the organic solution washed with water (2×20 ml), dried over magnesium sulfate and evaporated to dryness. The residue was purified by chromatography on a 10 g silica Mega Bond Elut® column, eluting with a gradient increasing in polarity from 0 to 10% MeOH in dichloromethane. Relevant fractions were combined and evaporated to give the desired product (82 mg).

MS (ESP): 451 (MH$^+$) for $C_{20}H_{23}FN_4O_7$ NMR (DMSO-$d_6$) δ: 2.93 (br m, 4H); 3.49 (m, 2H); 3.66 (br m, 4H); 3.88 (dd, 1H); 4.14 (t, 1H); 4.34 (m, 1H); 4.43 (m, 2H); 4.67 (m, 1H); 4.92 (d, 1H); 5.04 (m, 1H); 6.36 (d, 1H); 7.06 (t, 1H); 7.20 (dd, 1H); 7.51 (dd, 1H); 8.67 (d, 1H).

EXAMPLE 70

3-(4-(4-(2(S),3-Dihydroxypropanoyl)piperazin-1-yl)-3-fluorophenyl)-5(R)-(isoxazol-3-yloxymethyl) oxazolidin-2-one Using the same procedure and scale as Example 69, but starting from 2,2-dimethyl-1,3-dioxolane-4(S)-carboxylic acid, the title compound (75 mg) was obtained, MS (ESP): 451 (MH$^+$) for $C_{20}H_{23}FN_4O_7$ NMR (DMSO-$d_6$) δ: 2.93 (br m, 4H); 3.45 (m, 1H); 3.53 (m, 1H); 3.65 (br m, 4H); 3.87 (dd, 1H); 4.16 (t, 1H); 4.34 (dd, 1H); 4.45 (m, 2H); 4.67 (t, 1H); 4.92 (d, 1H); 5.04 (m, 1H); 6.37 (d, 1H); 7.07 (t, 1H); 7.20 (dd, 1H); 7.51 (dd, 1H); 8.67 (d, 1H).

EXAMPLE 71

3-(4-(4-(2-(2-Methoxyethoxy)ethoxy) acetylpiperazin-1-yl)-3-fluorophenyl)-5(R)-(isoxazol-3-yloxymethyl)oxazolidin-2-one To a solution of 3-(4-(piperazin-1-yl)-3-fluorophenyl)-5(R)-(isoxazol-3-yloxymethyl)-oxazolidin-2-one dihydrochloride (399 mg, 0.92 mmol) in pyridine (10 ml) was added triethylamine (0.31 ml, 2.2 mmol) and 2-(2-(2-methoxyethoxy)ethoxy)acetyl chloride (197 mg, 1 mmol). The mixture was stirred for 18 hours, evaporated to dryness, the residue dissolved in dichloromethane, and purified by chromatography on a 10 g silica Mega Bond Elut® column, eluting with a gradient increasing in polarity from 0 to 10% MeOH in dichloromethane. Relevant fractions were combined and evaporated to give the desired product (95 mg).

MS (ESP): 523 (MH$^+$) for $C_{24}H_{31}FN_4O_8$ NMR (DMSO-$d_6$) δ: 2.93 (br m, 4H); 3.21 (s, 3H); 3.41 (t, 2H); 3.47 (t, 2H); 3.54 (overlapping m, 8H); 3.87 (dd, 1H); 4.14 (t, 1H); 4.16 (s, 2H); 4.45 (m, 2H); 5.03 (m, 1H); 6.36 (d, 1H); 7.06 (t, 1H); 7.20 (dd, 1H); 7.51 (dd, 1H), 8.67 (d, 1H).

EXAMPLE 72

3-(4-(4-(3-Hydroxy-2-hydroxymethylpropanoyl) piperazin-1-yl)-3-fluorophenyl)-5(R)-(isoxazol-3-yloxymethyl)oxazolidin-2-one 3-(4-(4-(2-Phenyl-1,3-dioxan-5-ylcarbonyl)piperazin-1-yl)-3-fluorophenyl)-5(R)-(isoxazol-3-yloxymethyl) oxazolidin-2-one (450 mg, 0.82 mmol) was dissolved in a mixture of acetic acid and water (4:1, 10 ml) and stirred at ambient temperature for 18 hours. After evaporation to dryness, the residue was azeotroped with toluene (15 ml), and the residual gum purified by chromatography on a 20 g silica Mega Bond Elut® column, eluting with a gradient increasing in polarity from 5 to 10% MeOH in dichloromethane. Relevant fractions were combined and evaporated to give the desired product (237 mg).

MS (ESP): 465 (MH$^+$) for $C_{21}H_{25}FN_4O_7$ NMR (DMSO-$d_6$) δ: 2.94 (br d, 4H); 3.05 (quintet, 1H); 3.47 (m, 4H); 3.65 (br d, 4H); 3.87 (dd, 1H); 4.15 (t, 1H); 4.46 (m, 2H); 4.56 (t, 2H); 5.03 (m, 1H); 6.34 (d, 1H); 7.06 (t, 1H); 7.19 (dd, 1H); 7.50 (dd, 1H); 8.67 (d, 1H), The intermediate for this compound was prepared as follows:

3-(4-(4-(2-Phenyl-1,3-dioxan-5-ylcarbonyl)piperazin-1-yl)-3-fluorophenyl)-5(R)-(isoxazol-3-yloxymethyl)oxazolidin-2-one To a stirred solution of 2-phenyl-1,3-dioxan-5-ylcarboxylic acid (478 mg, 2.3 mmol) and N-hydroxysuccinimide (291 mg, 2.5 mmol) in anhydrous dichloromethane (25 ml) at 0° was added dicyclohexylcarbodiimide (522 mg, 2.5 mmol). After sitting 1 hour at 0°, N,N-diisopropylethylamine (623 mg, 4.8 mmol) was added, followed by 3-(4-(piperazin-1-yl)-3-fluorophenyl)-5(R)-(isoxazol-3-yloxymethyl)oxazolidin-2-one dihydrochloride (1 g, 2.3 mmol) in portions over 5 minutes. The temperature was allowed to rise to ambient, and stirring continued for 3 hours. Solid was filtered off, washed with dichloromethane (2×20 ml), and the combined organics evaporated to dryness. The residue was purified by chromatography on a 20 g silica Mega Bond Elut® column, eluting with a gradient increasing in polarity from 0 to 10% MeOH in dichloromethane. Relevant fractions were combined and evaporated to give the required product (890 mg) as a mixture of cis and trans isomers.

MS (ESP): 553 (MH$^+$) for $C_{28}H_{29}FN_4O_7$ NMR (DMSO-$d_6$) δ: 2.93 (br d, 4H); 3.58 (br, 4H); 3.87 (dd, 1H); 3.96–4.30 (overlapping m, 6H); 4.45 (m, 2H); 5.03 (m, 1H); 5.53 (2×s, 1H); 6.36 (d, 1H); 7.06 (t, 1H); 7.21 (dd, 1H); 7.34 (m, 5H): 7.51 (dd, 1H): 8.66 (d, 1H).

EXAMPLE 73

3-(4-(4-Acetoxyacetylpiperazin-1-yl)-3-fluorophenyl)-5(R)-(isoxazol-3-yl-oxymethyl) oxazolidin-2-one 3-(4-(piperazin-1-yl)-3-fluorophenyl)-5(R)-(isoxazol-3-yloxymethyl)oxazolidin-2-one dihydrochloride (1.29 g, 3 mmol) was suspended in dichloromethane (25 ml) under nitrogen at ambient temperature. Triethylamine (1.06 g, 10.5 mmol) was added, to give a solution after 15 minutes. The mixture was cooled to 4°, and acetoxyacetyl chloride (410 mg, 3 mmol) was added dropwise. The mixture was stirred for 18 hours at ambient temperature, washed with water (2×20 ml), saturated brine (20 ml), and dried (magnesium sulfate). The residue was purified by chromatography on a 20 g silica Mega Bond Elut® column, eluting with a gradient increasing in polarity from 0 to 5% MeOH in dichloromethane. Relevant fractions were combined and evaporated to give the desired product (1.16 g).

MS (ESP): 463 (MH$^+$) for $C_{21}H_{23}FN_4O_7$ NMR (DMSO-$d_6$) δ: 2.07 (s, 3H); 2.94 (br, 4H); 3.53 (br d, 4H); 3.87 (dd, 1H); 4.16 (t, 1H); 4.45 (m, 2H); 4.78 (s, 2H); 5.03 (m, 1H); 6.36 (d, 1H); 7.08 (t, 1H); 7.21 (dd, 1H); 7.48 (dd, 1H); 8.66 (d, 1H).

EXAMPLE 74

3-(4-(4-Hydroxyacetylpiperazin-1-yl)-3-fluorophenyl)-5(R)-(isoxazol-3-yloxymethyl) oxazolidin-2-one 3-(4-(4-(Acetoxyacetyl)piperazin-1-yl)-3-fluorophenyl)-5(R)-(isoxazol-3-yloxymethyl-oxazolidin-2-one (0.93 g, 2 mmol) and potassium carbonate (417 mg, 3 mmol) were stirred at ambient temperature under nitrogen in MeOH (20 ml) for 4 hours. The mixture was evaporated to dryness, dissolved in dichloromethane (80 ml), washed with water (2×30 ml), saturated brine (30 ml), and dried (magnesium sulfate). Filtration and evaporation gave the desired product (0.59 g).

MS (ESP): 421 (MH$^+$) for $C_{19}H_{21}FN_4O_6$; NMR (DMSO-$d_6$) δ: 2.93 (br, 4H); 3.48 (br s, 2H); 3.60 (br s, 2H); 3.86 (dd, 1H); 4.11 (d, 2H); 4.15 (t, 1H); 4.45 (m, 2H); 4.58 (d, 1H); 5.04 (m, 1H); 6.37 (d, 1H); 7.06 (t, 1H); 7.21 (dd, 1H); 7.51 (dd, 1H); 8.66 (d, 1H).

EXAMPLE 75

3-(4-(4-Acetylpiperazin-1-yl)-3-fluorophenyl)-5(R)-(isoxazol-3-yloxy-methyl)oxazolidin-2-one The title compound was prepared using essentially the method of Example 73, starting from 3-(4-(piperazin-1-yl)-3-fluorophenyl)-5(R)-(isoxazol-3-yloxymethyl)oxazolidin-2-one dihydrochloride (0.59 g, 1.35 mmol) and acetyl chloride. Purification by chromatography, eluting with a gradient increasing in polarity from 0 to 2.5% MeOH in dichloromethane gave the desired product (142 mg).

MS (ESP): 405 (MH$^+$) for $C_{19}H_{21}FN_4O_5$; NMR (DMSO-$d_6$) δ: 2.02 (s, 3H): 2.93 (br d, 4H); 3.55 (br, 4H); 3.87 (dd, 1H); 4.16 (t, 1H); 4.45 (m, 2H); 5.04 (m, 1H); 6.36 (d, 1H); 7.06 (t, 1H); 7.20 (dd, 1H); 7.51 (dd, 1H); 8.66 (d, 1H).

EXAMPLE 76

3-(4-(4-((3R)-3-Hydroxy-4-trimethylammoniobutanoyl)piperazin-1-yl)-3-fluorophenyl)-5(R)-(isoxazol-3-yloxymethyl)oxazolidin-2-one chloride 3-(4-(4-((3R)-3-Acetoxy-4-trimethylarnmoniobutanoyl)piperazin-1-yl)-3-fluorophenyl)-5(R)-(isoxazol-3-yloxymethyl)oxazolidin-2-one chloride (200 mg, 0.33 mmol) and potassium carbonate (67 mg, 0.49 mmol) were stirred at ambient temperature under nitrogen in MeOH (20 ml) for 5 hours. The mixture was evaporated to dryness, the solid triturated with water, filtered and washed with water (20 ml) to give the desired product (137 mg). MS (ESP): 506 (M$^+$) for $C_{24}H_{33}FN_5O_6$;

NMR(DMSO-$d_6$) δ: 2.51 (dd, 1H); 2.65 (dd, 11H); 2.93 (br d, 4H); 3.14 (s, 9H); 3.61 (br s, 4H); 3.87 (dd, 4H); 4.17 (t, 1H); 4.47 (m, 3H); 5.05 (m, 1H); 5.74 (br, 1H); 6.38 (d, 1H); 7.07 (t, 1H); 7.23 (dd, 1H); 7.52 (dd, 1H); 8.69 (d, 1H).

The intermediate for this compound was prepared as follows:
3-(4-(4-((3R)-3-Acetoxy-4-trimethylammoniobutanoyl)piperazin-1-yl)-3-fluoronhenyl)-5(R)-(isoxazol-3-yloxymethyl)oxazolidin-2-one chloride (3R)-3-Acetoxy-4-trimethylamrnoniobutanoic acid (527 mg, 2.2 mmol, see J. Org. Chem., 1967, 32, 3989) was stirred in thionyl chloride (3 ml) at ambient temperature for 3 hours, giving a solution. Excess thionyl chloride was evaporated, and the residue azeotroped with toluene, before dissolving in anhydrous dichloromethane (10 ml). This solution was added dropwise to a solution of 3-(4-(piperazin-1-yl)-3-fluorophenyl)-5(R)-(isoxazol-3-yloxymethyl)oxazolidin-2-one dihydrochloride (0.87 g, 2 mmol) and triethylamine (404 mg, 4 mmol) in anhydrous dichloromethane (10 ml) at 4°. The mixture was stirred for 18 hours at ambient temperature, then evaporated to dryness. The residue was dissolved in brine (20 ml) and purified by chromatography on an HP20SS resin column, eluting with a gradient increasing in polarity from 0 to 10% in acetonitrile in water. Relevant fractions were combined, evaporated to dryness, dissolved in de-ionised water (50 ml), and freeze-dried to give the required product (0.39 g). MS (ESP): 548 (M$^+$) for $C_{26}H_{35}FN_5O_7$;

NMR (DMSO-$d_6$) δ: 2.05 (s, 3H); 2.82 (d, 2H); 2.94 (br m, 4H); 3.12 (s, 9H); 3.55 (br m, 4H); 3.58–3.78 (overlapping m, 2H); 3.87 (dd, 1H); 4.17 (t, 1H); 4.46 (m, 2H); 5.04 (m, 1H); 5.49 (m, 1H); 6.38 (d, 1H); 7.06 (t, 1H); 7.21 (dd, 1H); 7.51 (dd, 1H); 8.68 (d, 1H).

EXAMPLE 77

3-(4-(4-Methoxycarbonyl-piperazin-1-yl)-3-fluorophenyl)-5(R)-(isoxazol-3-yloxymethyl)oxazolidin-2-one 3-(4-(piperazin-1-yl)-3-fluorophenyl)-5(R)-(isoxazol-3-yloxymethyl)oxazolidin-2-one dihydrochloride (866 mg, 2 mmol) was suspended in dichloromethane (40 ml) under nitrogen at ambient temperature. Triethylamine (707 mg, 7 mmol) was added, followed by methyl chloroforrnate (190 mg, 2 mmol). The mixture was stirred for 2 hours at ambient temperature, washed with water (2×50 ml), saturated brine (50 ml), and dried (magnesium sulfate). After filtration and evaporation, the residue was triturated with diethyl ether to give the desired product (689 mg).

MS (ESP): 421 (MH$^+$) for $C_{19}H_{21}FN_4O_6$; NMR (DMSO-$d_6$) δ: 2.93 (t, 4H); 3.52 (t d, 4H); 3.62 (s, 3H); 3.89 (dd, 1H); 4.16 (t, 1H); 4.46 (m, 2H); 5.04 (m, 1H); 6.37 (d, 1H); 7.08 (t, 1H); 7.20 (dd, 1H); 7.52 (dd, 1H); 8.67 (d, 1H).

EXAMPLE 78

3-(4-(4-(3-(4-Imidazolyl)acryloyl)piperazin-1-yl)-3-fluorophenyl)-5(R)-(isoxazol-3-yioxymethyl)oxazolidin-2-one 3-(4-Imidazolyl)acrylic acid (690 mg, 5 mmol) was suspended in anhydrous dichloromethane (5 ml) under nitrogen, and thionyl chloride (10 ml) and one drop of DMF added. The mixture was stirred at ambient temperature for 18 hours, excess thionyl chloride was evaporated, and the residue azeotroped with dichloromethane (2×50 ml). The acid chloride was suspended in dichloromethane (30 ml), cooled to 4°, and a solution of 3-(4-(piperazin-1-yl)-3-fluorophenyl)-5(R)-(isoxazol-3-yloxymethyl)oxazolidin-2-one dihydrochloride (866 mg, 2 mmol) and triethylamine (2.02 g, 20 mmol) in anhydrous dichloromethane (25 ml) added dropwise. The mixture was stirred for 18 hours at ambient temperature, and insoluble material filtered. The organic layer was treated with water (50 ml), further insoluble material removed, then washed with brine and dried over magnesium sulfate. After evaporation to dryness, the residue was dissolved in ethanol (5 ml) and treated with an excess of ethanol saturated with hydrogen chloride, to precipitate the desired product as a hydrochloride salt (122 mg).

Microanalysis: Found: C, 48.2, H, 5.0, N, 14.4%; $C_{23}H_{23}FN_6O_5.2HCl.H_2O$ requires C, 48.1, H, 4.7, N, 14.4%. MS (ESP): 483 (MH$^+$) for $C_{23}H_{23}FN_6O_5$; NMR (DMSO-$d_6$) δ: 3.01 (br, 4H); 3.86 (complex, overlapped by H$_2$O, ~5H); 4.16 (t, 1H); 4.45 (m, 2H); 5.04 (m, 1H); 6.36 (d, 1H); 7.08 (t, 1H); 7.21 (dd, 1H); 42 (d, 1H); 7.51 (dd, 1H); 7.71 (d, 1H); 7.97 (s, 1H); 8.66 (d, 1H); 9.20 (s, 1H).

EXAMPLE 79

3-(4-(4-(4-Imidazolylacetyl)-piperazin-1-yl)-3-fluorophenyl)-5(R)-(isoxazol-3-yloxymethyl)oxazolidin-2-one Using the procedure of Example 78, but starting with 4-imidazolylacetic acid hydrochloride salt (810 mg, 5 mmol), the acid chloride was prepared and reacted with the piperazine. After 18 hours reaction, the mixture was diluted with saturated sodium carbonate solution (20 ml). The organic layer was washed with water (2×50 ml), then brine (30 ml) and dried over magnesium sulfate. The residue was purified by chromatography on a 40 g silica Mega Bond Elut® column, eluting with 10% MeOH in dichloromethane. Relevant fractions were combined and evaporated. the residue dissolved in ethanol (5 ml) and treated with an excess of ethanol saturated with hydrogen chloride, then excess of diethyl ether to precipitate the desired product as a hydrochloride salt (124 mg).

Microanalysis: Found: C, 47.3, H, 5.1, N, 14.8%; $C_{22}H_{23}FN_6O_5.2HCl.H_2O$ requires C, 47.0, H, 4.8, N, 15.0%. MS (ESP): 471 (MH$^+$) for $C_{22}H_{23}FN_6O_5$; NMR (DMSO-d$_6$) δ: 2.95 (br m, 2H); 3.03 (br m, 2H); 3.63 (br m, 2H); 3.68 (br m, 2H); 3.95 (s+m, overlapped by H$_2$O, ~3H); 4.17 (t, 1H); 4.45 (m, 2H); 5.04 (m, 1H); 6.36 (d, 1H); 7.08 (t, 1H); 7.22 (dd, 1H); 7.44 (s, 1H); 7.52 (dd, 1H); 8.67 (d, 1H); 9.01 (s, 1H); 14.38 (br 2H).

EXAMPLE 80

3-(4-(4-(3-(4-Imidazolyl)propanoyl)piperazin-1-yl)-3-fluorophenyl)-5(R)-(isoxazol-3-yloxymethyl)oxazolidin-2-one 3-(4-(4-(3-(1-Triphenylmethyl-4-imidazolyl)propanoyl)-piperazin-1-yl)-3-fluorophenyl)-5(R)-(isoxazol-3-yloxymethyl)oxazolidin-2-one (460 mg, 0.63 mmol), was dissolved in a mixture of ethanol (20 ml) and MeOH (10 ml), cooled to 0° and treated with a solution of hydrogen chloride in ethanol (3.8 M, 5 ml). After stirring 48 hours at ambient temperature, the pH was adjusted to 8 with triethylamine, and the mixture evaporated to dryness. The residue was purified by chromatography on a 10 g silica Mega Bond Elut® column, eluting with a gradient from 0 to 20% MeOH in dichloromethane. Relevant fractions were combined and evaporated to give the desired product (60 mg). MS (ESP): 485 (MH$^+$) for $C_{23}H_{25}FN_6O_5$;

NMR (DMSO-d6) δ: 2.59 (t, 2H); 2.74 (t, 2H); 2.92 (br, 4H); 3.60 (br, 4H); 3.90 (dd, 1H); 4.16 (t, 1H); 4.46 (m, 2H); 5.06 (m, 1H); 6.38 (d, 1H); 6.76 (s, 1H); 7.06 (t, 1H); 7.22 (dd, 1H); 7.59 (s, 1H); 7.63 (dd 1H); 8.67 (d, 1H); 11.72 (br 1H).

The intermediates for this compound were prepared as follows:

3-(4-(4-(3-(1-Triphenylmethyl-4-imidazolyl)propanoyl)-piperazin-1-yl)-3-fluorophenyl)-5(R)-(isoxazol-3-yloxymethyl)oxazolidin-2-one 3-(1-Triphenylmethyl-4-imidazolyl)propionic acid (420 mg, 1.1 mmol) was suspended in dichloromethane (10 ml) under nitrogen, and treated successively with dicyclohexylcarbodiimide (227 mg, 1.1 mmol) and 1-hydroxybenzotriazole (149 mg, 1.1 mmol), then stirred at ambient temperature for 30 minutes. To it was added a solution of 3-(4-(piperazin-1-yl)-3-fluorophenyl)-5(R)-(isoxazol-3-yloxymethyl)oxazolidin-2-one dihydrochloride (435 mg, 1 mmol) and N,N-diisopropylethylamine (258 mg, 2 mmol) in dichloromethane (5 ml). The mixture was stirred for 18 hours at the same temperature, solid filtered off, and the organic phase purified by chromatography on a 20 g silica Mega Bond Elut® column, eluting with a gradient increasing in polarity from 0 to 15% MeOH in dichloromethane. Relevant fractions were combined and evaporated to give the desired product (460 mg).

MS (ESP): 727 (MH$^+$) for $C_{42}H_{39}FN_6O_5$; NMR (DMSO-d$_6$) δ: 2.61 (t, 2H); 2.70 (t, 2H); 2.87 (br, 4H); 3.54 (br, 4H); 3.88 (dd, 1H); 4.17 (t, 1H); 4.45 (m, 2H); 5.06 (m, 1H); 6.37 (d, 1H); 6.66 (d, 1H); 7.03 (t, 1H); 7.06 (d, 6H); 7.21 (dd, 1H); 7.25 (s, 1H); 7.36 (m, 9H); 7.52 (dd, 1H); 8.67 (d, 1H).

3-(1-Triphenylmethyl-4-imidazolyl)propionic Acid 3-(4-Imidazolyl)propionic acid (1.0 g, 7.1 mmol) was suspended in a mixture of dichloromethane (5 ml) and acetonitrile (25 ml). Trimethylsilyl chloride (781 mg, 7.2 nmmol) was added and the mixture refluxed for 4 hours. Triethylamine (1 ml) was added, and refluxing continued for 15 minutes. Cooled, triethylamine (1 ml) added followed by chlorotriphenylmethane (1.99 g, 7.1 mmol) in dichloromethane (10 ml), and the mixture stirred at ambient temperature for 2 hours. MeOH (20 ml) was added, the mixture stirred for 30 minutes, then evaporated to dryness. Water (50 ml) was added to the residue, and the pH adjusted to 8–8.5 with triethylamine. The precipitate was filtered off, washed with diethyl ether, and dried to give the desired product (2.25 g). MS (ESP): 383 (MH$^+$) for $C_{25}H_{22}N_2O_2$;

NMR (DMSO-d$_6$) δ: 2.48 (t, 2H); 2.77 (t, 2H); 6.65 (s, 1H); 7.08 (d, 6H); 7.29 (s, 1H); 7.36 (m, 9H); 12.10 (br, 1H).

EXAMPLE 81

3-(4-(4-Methanesulfonyl-piperazin-1-yl)-3-fluorophenyl)-5(R)-(isoxazol-3-yloxymethyl)oxazolidin-2-one 3-(4-(piperazin-1-yl)-3-fluorophenyl)-5(R)-(isoxazol-3-yloxymethyl)oxazolidin-2-one dihydrochloride (433 mg, 1 mmol) in pyridine (15 ml) and dichloromethane (15 ml) was treated with triethylarnine (353 mg, 3.5 mmol) and stirred for 30 minutes at ambient temperature. Methanesulfonyl chloride (138 mg, 1.2 mmol) was added and the mixture stirred for 18 hours. The mixture was diluted with dichloromethane (50 ml), washed with water (2×25 ml), saturated brine (25 ml), and dried (magnesium sulfate). After evaporation to dryness and azeotroping with toluene (10 ml), the residue was triturated with diethyl ether to give the desired product (365 mg).

MS (ESP): 441 (MH$^+$) for $C_{18}H_{21}FN_4O_6S$; NMR (DMSO-d$_6$) δ: 2.91 (s, 3H); 3.05 (br m, 4H); 3.26 (br m, 4H); 3.87 (dd, 1H); 4.15 (t, 1H); 4.42 (dd, 1H); 4.48 (dd, 1H); 5.05 (m, 1H); 6.36 (d, 1H); 7.10 (t, 1H); 7.21 (dd, 1H); 7.48 (dd, 1H); 8.66 (d, 1H).

EXAMPLE 82

3-(4-(4-Chloroacetyl-piperazin-1-yl)-3-fluorophenyl)-5(R)-(isoxazol-3-yloxymethyl)oxazolidin-2-one Chloroacetyl chloride (114 mg, 1 mmol) was added to a stirred solution of 3-(4-(piperazin-1-yl)-3-fluorophenyl)-5(R)-(isoxazol-3-yloxymethyl)oxazolidin-2-one dihydrochloride (435 mg, 1 mmol) and triethylamine (302 mg, 3 mmol) in dichloromethane (10 ml) at ambient temperature. After 10 minutes the reaction was purified by direct chromatography on a 10 g silica Mega Bond Elut® column, eluting with dichloromethane. Relevant fractions were combined and evaporated to give the desired product (390 mg). MS (ESP): 439 (MH$^+$) for $C_{19}H_{20}ClFN_4O_5$;

NMR (DMSO-d$_6$) δ: 2.93 (br m, 2H); 2.99 (br m, 2H); 3.59 (br m, 4H); 3.87 (dd, 1H); 4.16 (t, 1H); 4.40 (s, 2H); 4.46 (m, 2H); 5.04 (m, 1H); 6.36 (d, 1H); 7.07 (t, 1H); 7.21 (dd, 1H); 7.51 (dd, 1H); 8.66 (d, 1H).

EXAMPLE 83

3-(4-(4-Morpholinoacetyl-piperazin-1-yl)-3-fluorophenyl)-5(R)-(isoxazol-3-yloxymethyl)oxazolidin-2-one The preparation of Example 82 was repeated up to the stage of forming the chloroacetylamide. The mixture was then cooled to 0° and treated with morpholine (0.262 mg, 3 mmol), then stirred 48 hours allowing the temperature to rise to ambient. The reaction was evaporated to dryness, and purified by chromatography on a 10 g silica Mega Bond Elut® column, eluting with a gradient from 0 to 10% MeOH in dichloromethane. Relevant fractions were combined and evaporated to give the desired product after trituration with diethyl ether (420 mg).

MS (ESP): 490 (MH$^+$) for $C_{23}H_{28}FN_5O_6$; NMR (CDCl$_3$) δ: 2.52 (br m, 4H); 3.03 (m, 4H); 3.23 (s, 2H); 3.71 (m, 4H); 3.77 (m, 4H); 3.93 (dd, 1H); 4.14 (t, 1H); 4.50 (dd, 1H); 4.57 (dd, 1H); 5.01 (m, 1H); 6.00 (d, 1H); 6.92 (t, 1H); 7.26 (dd, 1H); 7.47 (dd, 1H); 8.16 (d, 1H).

EXAMPLE 84

3-(4-(4-((2S,4R)-1-Acetyl-4-hydroxy-2-pyrrolidinylcarbonyl)-piperazin-1-yl)-3-fluorophenyl)-5(R)-(isoxazol-3-yloxymethyl) oxazolidin-2-one A suspension of (2S,4R)-1-acetyl-4-hydroxy-2-pyrrolidinecarboxylic acid (173 mg, 1 mmol) in dichloromethane (10 ml) and DMF (2 ml) under nitrogen was treated successively with dicyclohexylcarbodiimide (227 mg, 1.1 mmol) and 1-hydroxybenzotriazole (149 mg, 1.1 mmol), then stirred at ambient temperature for 1 hour. A solution of 3-(4-(piperazin-1-yl)-3-fluorophenyl)-5(R)-(isoxazol-3-yloxymethyl)oxazolidin-2-one dihydrochloride (435 mg, 1 mmol) and N,N-diisopropylethylamine (258 mg, 2 mmol) in dichloromethane (5 ml) was added, and the mixture stirred for 18 hours. Solid was filtered off, the organic solution evaporated to dryness, and the residue purified by chromatography on a 10 g silica Mega Bond Elut® column, eluting with a gradient increasing in polarity from 0 to 15% MeOH in dichloromethane. Relevant fractions were combined and evaporated to give the desired product after trituration with diethyl ether (210 mg).

MS (ESP): 518 (MH$^+$) for $C_{24}H_{28}FN_5O_7$; NMR (CDCl$_3$) δ: 2.08 (s, 3H); 2.16 (m, 3H); 2.45 (m, 1H); 3.05 (m, 3H); 3.19 (m, 1H); 3.62 (overlapping m, 2H); 3.91 (dd overlapping m, 4H); 4.13 (t, 1H); 4.49 (dd, 1H); 4.56 (dd, 1H); 4.66 (m, 1H); 5.01 (overlapping m, 2H); 5.99 (d, 1H); 6.92 (t, 1H); 7.27 (dd, 1H); 7.48 (dd, 1H); 8.15 (d, 1H).

EXAMPLE 85

3-(4-(4-((2S,4R)-1-Methyl-4-hydroxy-2-nyrrolidinylcarbonyl)-piperazin-1-yl)-3-fluorophenyl)-5(R)-(isoxazol-3-yloxymethyl) oxazolidin-2-one A solution of 3-(4-(piperazin-1-yl)-3-fluorophenyl)-5(R)-(isoxazol-3-yloxymethyl)oxazolidin-2-one dihydrochloride (435 mg, 1 mmol) and N,N-diisopropylethylamine (258 mg, 2 mmol) in DMF (2 ml) was added to a stirred solution of (2S, 4R)-1-methyl-4-hydroxy-2-pyrrolidinecarboxylic acid (145 mg, 1 mmol ; see Angewandte Chemie, 1995, 9, 1095) and O-(7-azabenzotriazol-1-yl)-1,1,3,3-tetramethyluronium hexafluorophosphate (380 mg, 1 mmol) in DMF (5 ml) under nitrogen at ambient temperature. N,N-Diisopropylethylamine (387 mg, 3 mmol) was added, and the mixture stirred at ambient temperature for 18 hours. After evaporation to dryness, the residue was partitioned between water (5 ml) and dichloromethane (10 ml). The separated organic layer was evaporated, and the residue purified by chromatography on a 10 g silica Mega Bond Elut® column, eluting with a gradient increasing in polarity from 0 to 10% MeOH in dichloromethane. Relevant fractions were combined and evaporated to give the desired product (256 mg). MS (ESP): 490 (MH$^+$) for $C_{23}H_{28}FN_5O_6$.

NMR (CDCl$_3$) δ: 1.96 (m, 1H); 2.07 (m, 1H); 2.36 (m, 1H); 2.38 (s, 3H); 3.02 (m, 4H); 3.33 (dd, 1H); 3.71 (overlapping m, 5H); 3.89 (dd, 1H); 4.18 (t, 1H); 4.30 (m, 1H); 4.46 (m, 1H); 4.53 (dd, 1H): 4.59 (m, 1H); 5.03 (m, 1H); 6.28 (d, 1H); 7.08 (t, 1H); 7.20 (dd, 1H); 7.46 (dd, 1H); 8.57 (d, 1H).

EXAMPLE 86

3-(4-((3R)-3-Amino-1-pyrrolidinyl)-3-fluorophenyl)-5(R)-(isoxazol-3-yloxymethyloxazolidin-2-one 3-(4-((3R)-3-t-Butoxycarbonylamino-1-pyrrolidinyl)-3-fluorophenyl)-5(R)-(isoxazol-3-yloxymethyl)oxazolidin-2-one (108 mg, 0.23 mmol) was dissolved in dichloromethane (7 ml) under nitrogen and treated with TFA (3 ml) at ambient temperature. The mixture was stirred 48 hours, evaporated to dryness, and azeotroped with toluene (2×10 ml). The resulting gum was taken up in ethanol (5 ml), and a solution of hydrogen chloride in ethanol (3.8M, 2 ml). Excess diethyl ether was added to precipitate the title compound as its hydrochloride (80 mg).

MS (ESP): 363 (MH$^+$) for $C_{17}H_{19}FN_4O_4$; NMR (DMSO-d$_6$) δ: 1.99 (m, 1H); 2.23 (m, 1H); 3.25 (m, 1H); 3.41 (m, 1H); 3.52 (m, 2H); 3.84 (dd, 1H); 4.14 (t, 1H); 4.42 (m overlapping H$_2$O, ~3H); 5.02 (m, 1H); 6.37 (d, 1H); 6.79 (t, 1H); 7.15 (dd, 1H); 7.44 (dd, 1H); 8.34 (br, 2H); 8.68 (d, 1H).

The intermediates for this compound were prepared as follows

3-Fluoro-4-((3R)-3-t-butoxycarbonylamino-1-pyrrolidinyl) nitrobenzene 3,4-Difluoronitrobenzene (16.03 g, 0.101 M) was dissolved in acetonitrile (300 ml), and treated with N,N-diisopropylethylamine (32.63 g, 0.253 M) and (3R)-3-t-butoxycarbonylaminopyrrolidine (20.65 g, 0.111 M). The mixture was stirred and heated to reflux for 18 hours. Solvent was evaporated, and the residue treated with EtOAc (300 ml) and water (200 ml). The organic layer was washed with water (1 50 ml). citric acid solution (10% in water, 2×150 ml), and dried (magnesium sulfate). Evaporation gave the desired product as a yellow solid (32.7 g), of sufficient quality for use without purification. MS (ESP): 326 (MH$^+$) for $C_{15}H_{20}FN_3O_4$.

NMR(CDCl$_3$) δ: 1.43 (s, 9H); 1.85 (m, 1H); 2.25 (m, 1H); 3.44 (dt, 1H); 3.65 (overlapping m, 2H); 3.84 (dm, 1H); 4.34 (br m, 1H); 4.69 (br, 1H); 6.53 (t, 1H); 7.87 (dd, 1H); 7.92 (dd, 1H).

5-Amino-2-((3R)-3-t-butoxycarbonylamino-1-pyrrolidinyl) fluorobenzene

3-Fluoro-4-((3R)-3-t-butoxycarbonylamino-1-pyrrolidinyl)nitrobenzene (32.7 g, 0.101 M) was dissolved in EtOAc (500 ml) treated with palladium catalyst (10% on carbon, 7.5 g) and hydrogenated at atmospheric pressure until the theoretical uptake of gas. After filtration through celite and evaporation. the required product was obtained as a red gum of sufficient quality for use without purification (29.85 g).

MS (ESP): 296 (MH$^+$) for $C_{15}H_{22}FN_3O_2$; NMR (CDCl$_3$) δ: 1.44 (s, 9H); 1.82 (m, 1H); 2.27 (m, 1H); 3.11 (m, 2H); 3.37 (m, 2H); 3.43 (br, 2H); 4.27 (br m, 1H); 4.82 (br, 1H); 6.38 (dd, 1H); 6.44 (dd, 1H); 6.57 (t, 1H).

5-Ethoxycarbonylamino-2-((3R)-3-t-butoxycarbonylamino-1-pyrrolidinyl)fluorobenzene 5-Amino-2-((3R)-3-t-butoxycarbonylamino-1-pyrrolidinyl)fluorobenzene (27.33 g, 0.093 M) was dissolved in dry pyridine (150 ml) and cooled under nitrogen with stirring to 0°. Ethyl chloroformate (11.01, 0.102 M) was added dropwise, and the mixture stirred 30 minutes at the same temperature. Ice-water (250 ml) was added, and stirring continued for 1 hour. The resulting precipitate was collected, washed thoroughly with water, and dried, to give the desired product of sufficient quality for use without purification (33.6 g). MS (ESP): 368 (MH$^+$) for $C_{18}H_{26}FN_3O_4$.

NMR (DMSO-d$_6$) δ: 1.21 (t, 3H); 1.36 (s, 9H); 1.90 (m, 1H); 2.05 (m, 1H); 3.04 (m, 1H); 3.20 (m, 1H); 3.32 (m, 1H); 3.40 (m, 1H); 4.02 (br, 1H); 4.05 (q, 2H); 6.62 (t, 1H); 7.02 (d, 1H); 7.08 (d, 1H); 7.22 (d, 1H); 9.38 (br, 1H).

3-(3-Fluoro-4-((3R)-3-t-butoxycarbonylamino-1-pyrrolidinyl)phenyl)-5(R)-hydroxymethyloxazolidin-2-one 5-Ethoxycarbonylamino-2-((3R)-3-t-butoxycarbonylamino-1-pyrrolidinyl)fluorobenzene (33.6 g, 0.092 M) was dissolved in dry tetrahydrofuran (300 ml) under nitrogen. cooled to −70°, and treated dropwise over 30 minutes with a solution of lithiun t-butoxide (1 M in tetrahydrofuran, 100.7 ml), keeping the temperature below −65°. After stirring for 5 minutes, (R)-glycidylbutyrate (14.52 g, 0.101 M) was added, and stirring continued at −65° for 1 hour, before allowing the temperature to rise to ambient over 16 hours. The mixture was treated with MeOH (50 ml), stirred at ambient temperature for 1 hour, and the precipitate collected and washed well with tetrahydrofuran to give the desired product (21.8 g).

MS (ESP): 396 (MH$^+$) for $C_{19}H_{26}FN_3O_5$; NMR (DMSO-d$_6$) δ: 1.36 (s, 9H); 1.80 (m, 1H); 2.07 (m, 1H); 3.09 (m, 1H); 3.26 (t, 1H); 3.35 (m, 1H); 3.49 (m, 2H); 3.62 (m, 1H); 3.73 (dd, 1H); 3.98 (t, 1H); 4.04 (m, 1H); 4.63 (m, 1H); 5.15 (t, 1H); 6.70 (t, 1H); 7.09 (dd overlapping br, 2H); 7.39 (dd, 1H).

3-(4-((3R)-3-t-Butoxycarbonylamino-1-pyrrolidinyl)-3-fluorophenyl)-5(R)-(isoxazol-3-yloxymethyl)oxazolidin-2-one 3-(3-Fluoro-4-((3R)-3-t-butoxycarbonylamino-1-pyrrolidinyl)phenyl)-5(R)-hydroxymethyloxazolidin-2-one (5 g, 12.7 mmol), 3-hydroxyisoxazole (2.15 g, 25.3 mmol), and 1,1'-(azodicarbonyl)dipiperidine (6.39 g, 25.3 mmol) were suspended by stirring in dry tetrahydrofuran (100 ml) under nitrogen and cooled to 5° in an ice-bath. Tributylphosphine (5.12 g, 25.3 mmol) was added dropwise over 20 minutes, and the solution stirred 18 hours, allowing the temperature to rise to ambient. Reduced azo compound was filtered off, and the solution evaporated to dryness and the residue triturated with ether. The residue was purified by chromatography on a 90 g Biotage silica column, eluting with a gradient from 50 to 75% EtOAc in isohexane. Relevant fractions were combined and evaporated to give the product (3.92 g).

MS (ESP): 463 (MH$^+$) for $C_{22}H_{27}FN_4O_6$; NMR (DMSO-d$_6$) δ: 1.38 (s, 9H); 1.81 (m, 1H); 2.08 (m, 1H); 3.10 (m, 1H); 3.25 (t, 1H); 3.36 (m, 1H); 3.48 (m, 1H); 3.84 (dd, 1H); 4.05 (m, 1H); 4.12 (t, 1H); 4.44 (m, 2H); 5.02 (m, 1H); 6.36 (d, 1H); 6.71 (t, 1H); 7.11 (dd overlapping br, 2H); 7.38 (dd, 1H); 8.66 (d, 1H).

EXAMPLE 87

3-(4-(1,4-Dioxa-8-azaspiro[4,5]decan-8-yl)-3-fluorophenyl)-5(R)-(isoxazol-3-yloxymethyl)oxazolidin-2-one 3-(4-(1,4-Dioxa-8-azaspiro[4,5]decan-8-yl)-3-fluorophenyl)-5(R)-hydroxymethyloxazolidin-2-one (3.52 g, 10 mmol), 3-hydroxyisoxazole (893 mg, 10.05 mmol), and triphenylphosphine (3.03 g, 12 mmol) were dissolved by stirring in dry tetrahydrofuran (75 ml) under nitrogen. The mixture was cooled in an ice-bath, and diisopropylazodicarboxylate (2.33 g, 12 mmol) added dropwise over 10 minutes. The solution was stirred 18 hours, allowing the temperature to rise to ambient. The mixture was diluted with EtOAc (750 ml). the organic layer washed with water (3×500 ml), dried (magnesium sulfate) and evaporated. The residue was purified by MPLC on silica, eluting with a gradient between 0.25% and 1% MeOH in dichloromethane. Relevant fractions were combined and evaporated to give product (3.58 g).

MS (ESP): 420 (MH$^+$) for $C_{20}H_{22}FN_3O_6$; NMR (DMSO-d$_6$) δ: 1.73 (t, 4H); 3.03 (t, 4H); 3.86 (dd, 1H); 3.90 (s, 4H); 4.14 (t, 1H); 4.42 (dd, 1H); 4.47 (dd, 1H); 5.03 (m, 1H); 6.35 (d, 1H); 7.08 (t, 1H); 7.17 (dd, 1H); 7.47 (dd, 1H); 8.65 (d, 1H).

The intermediates for this compound were prepared as follows:

4-(1,4-Dioxa-8-azaspiro[4.5]decan-8-yl)-3-fluoronitrobenzene 3,4-Difluoronitrobenzene (15.53 g, 0.098 M) was dissolved in acetonitrile (150 ml), and treated with N,N-diisopropylethylamine (31.5 g, 0.244 M) and 1,4-dioxa-8-azaspiro[4,5]decane (15.36 g, 0.107 M). The mixture was stirred and heated to reflux for 18 hours. After cooling, product precipitated as a yellow solid, and was filtered off (16.1 g); further product could be obtained by concentrating the residues (8.43 g).

MS (ESP): 283 (MH$^+$) for $C_{13}H_{15}FN_2O_4$; NMR (CDCl$_3$) δ: 1.86 (t, 4H); 3.41 (t, 4H); 4.00 (s, 4H); 6.91 (t, 1H); 7.89 (dd, 1H); 7.96 (dd, 1H).

5-Amino-2-(1,4-dioxa-8-azaspiro[4,5]decan-8-yl)fluoroberzene

Starting from 4-(1,4-dioxa-8-azaspiro[4,5]decan-8-yl)-3-fluoronitrobenzene (24.48 g, 0.087 M). the title compound was prepared by essentially the samc technique as the corresponding intermediate of Example 86 (19.3 g).

MS (ESP): 253 (MH$^+$) for $C_{13}H_{17}FN_2O_2$; NMR (DMSO-d$_6$) δ: 1.69 (t, 4H); 2.84 (t, 4H); 3.86 (s, 4H); 4.91 (s, 2H); 6.28 (m, 2H); 6.75 (t, 1H).

5-Ethoxycarbonylanino-2-(1,4-dioxa-8-azaspiro[4,5decan-8-yl)fluorobenzene

Starting from 5-amino-2-(1,4-dioxa-8-azaspiro[4,5]decan-8-yl)fluorobenzene (19.26 g, 0.076 M), the title compound was prepared by essentially thc same technique as the corresponding intermediate of Example 86 (20.5 g).

MS (ESP): 325 (MH$^+$) for $C_{16}H_{21}FN_2O_4$; NMR (DMSO-d$_6$) δ: 1.21 (t, 3H); 1.71 (t, 4H); 2.96 (t, 4H); 3.88 (s, 4H); 4.09 (q, 2H); 6.95 (t, 1H); 7.09 (dd, 1H); 7.27 (dd, 1H); 9.54 (s, 1H).

3-(4-(1,4-Dioxa-8-azaspiro[4,5]decan-8-yl)-3-fluorophenvi)-5(R)-hydroxymethyloxazoldin-2-one Starting from 5-ethoxycarbonylarnino-2-(1,4-dioxa-8-azaspiro[4,5]decan-8-yl)fluorobenzene (22.9 g, 0.071 M)), the title compound was prepared by essentially the same technique as the corresponding intermediate of Example 86 (17.8 g).

MS (ESP): 353 (MH$^+$) for $C_{17}H_{21}FN_2O_5$; NMR (DMSO-d$_6$) δ: 1.83 (t, 4H); 3.09 (t, 4H); 3.69 (dd, 1H), 3.82 (dd, 1H), 3.88 (dd, 1H); 3.96 (s, 4H); 4.07 (t, 1H); 4.72 (m, 1H); 4.92 (s, 1H); 7.05 (t, 1H); 7.08 (dd, 1H); 7.46 (dd, 1H).

EXAMPLE 88

3-(4-(4-Oxopiperidin-1-yl)-3-fluorophenyl)-5(R)-(isoxazol-3-yloxymethyl)oxazolidin-2-one 3-(4-(1,4-Dioxa-8-azaspiro[4,5]decan-8-yl)-3-fluorophenyl)-5(R)-(isoxazol-3-yloxymethyl)oxazolidin-2- one (3.58 g, 8.52 mmol) was dissolved in a mixture of glacial acetic acid (50 ml) and water (50 ml), and heated at 50° for 12 hours. Solvent was evaporated, the residue azeotroped with toluene (50 ml), then partitioned between EtOAc (150 ml) and water (100 ml). The organic layer was washed with saturated aqueous sodium bicarbonate solution (2×100 ml), water (100 ml), dried (magnesium sulfate) and evaporated. The residue was purified by chromatography on a 90 g silica Biotage column eluting with a gradient from 5:1 EtOAc to isohexane to EtOAc. Relevant fractions were combined to give the desired product (2.84 g).

MS (ESP): 376 (MH$^+$) for $C_{18}H_{18}FN_3O_5$; NMR (CDCl$_3$) δ: 2.61 (t, 4H); 3.37 (t, 4H); 3.93 (dd, 1H); 4.14 (t, 1H); 4.50 (dd, 1H); 4.57 (dd, 1H); 5.02 (m, 1H); 6.00 (d, 1H); 6.98 (t, 1H); 7.14 (dd, 1H); 7.49 (dd, 1H); 8.15 (d, 1H).

EXAMPLE 89

3-(4-(4-Hydroxypiperidin-1-yl)-3-fluorophenyl)-5 (R)-(isoxazol-3-yloxymethyl)oxazolidin-2-one 3-(4-(4-Oxopiperidin-1-yl)-3-fluorophenyl)-5(R)-(isoxazol-3-yloxymethyl)oxazolidin-2-one (173 mg, 0.46 mmol) was dissolved in ethanol (5 ml), treated with sodium borohydride (18 mg, 0.48 mmol) and refluxed 1 hour. Solvent was evaporated, the residue treated with water (5 ml), neutralised with 1 N hydrochloric acid, extracted with dichloromethane (3×10 ml), and dried (magnesium sulfate). Evaporation gave the desired product (76 mg). MS (ESP): 378 (MH$^+$) for $C_{18}H_{20}FN_3O_5$.

NMR (CDCl$_3$) δ: 1.60 (br, ~1H); 1.76 (m, 2H); 2.05 (m, 2H); 2.85 (m, 2H); 3.32 (m, 2H); 3.85 (m, 1H); 3.91 (dd, 1H); 4.12 (t, 1H); 4.48 (dd, 1H); 4.55 (dd, 1H); 4.98 (m, 1H); 6.00 (d, 1H); 6.98 (br, 1H); 7.11 (dd, 1H); 7.42 (dd, 1H); 8.12 (d, 1H).

EXAMPLE 90

3-(4-(4-Aminopiridin-1-yl)-3-fluorophenyl)-5(R)-(isoxazol-3-yloxymethyl)oxazolidin-2-one 3-(4-(4-Oxopiperidin-1-yl)-3-fluorophenyl)-5(R)-(isoxazol-3-yloxymethyl)oxazolidin-2-one (375 mg, 1 mmol) was dissolved in MeOH (10 ml), treated with ammonium acetate (771 mg, 10 mmol) and sodium cyanoborohydride (440 mg, 7 mmol) and refluxed 4 hours. The mixture was neutralised with 1 N hydrochloric acid, water (15 ml) added, and extracted with dichloromethane (3×15 ml), and dried (magnesium sulfate). Evaporation gave the desired product (334 mg).

MS (ESP): 377 (MH$^+$) for $C_{18}H_{21}FN_4O_4$; NMR (CDCl$_3$) δ: 1.53 (br, 4H); 1.94 (m, 2H); 2.77 (overlapping m, 3H); 3.38 (m, 2H); 3.92 (dd, 1H); 4.13 (t, 1H); 4.47 (dd, 1H); 4.55 (dd, 1H); 4.99 (m, 1H); 6.00 (d, 1H); 6.94 (t, 1H); 7.12 (dd, 1H); 7.40 (dd, 1H); 8.15 (d, 1H).

EXAMPLE 91

3-(4-(4-Hydroxyiminopiperindin-1-yl)-3-fluorophenyl)-5(R)-(isoxazol-3-yloxymethyl) oxazolidin-2-one 3-(4-(4-Oxopiperidin-1-yl)-3-fluorophenyl)-5(R)-(isoxazol-3-yloxymethyl)oxazolidin-2-one (125 mg, 0.33 mmol) was dissolved in MeOH (5 ml) and dichloromethane (5 ml), and stirred at ambient temperature under nitrogen. The mixture was treated with hydroxylamine hydrochloride (27 mg, 0.39 mmol) and sodium acetate (65 mg, 0.79 mmol) and stirring continued for 4 hours. The mixture was filtered, evaporated, and the residue partitioned between water (10 ml), and dichloromethane (10 ml). The organic layer was washed with saturated sodium bicarbonate (10 ml), water (10 ml), dried (magnesium sulfate) and evaporated to dryness. The residue was purified by chromatography on a 5 g silica Mega Bond Elut® column, eluting with 1% MeOH in dichloromethane. Relevant fractions were combined to give the desired product (74 mg). MS (ESP): 391 (MH$^+$) for $C_{18}H_{19}FN_4O_5$.

NMR (DMSO-d$_6$) δ: 2.36 (t, 2H); 2.62 (t, 2H); 3.02 (t, 2H); 3.08 (t, 2H); 3.87 (dd, 1H); 4.16 (t, 1H); 4.42 (dd, 1H); 4.49 (dd, 1H); 5.04 (m, 1H); 6.37 (d, 1H); 7.08 (t, 1H); 7.21 (dd, 1H); 7.50 (dd, 1H); 8.67 (d, 1H); 10.38 (s, 1H).

EXAMPLE 92

3-(4-(4-Methoxycarbonylaminoiminopiperidin-1-yl)-3-fluorophenyl)-5(R)-(isoxazol-3-yloxymethyl) oxazolidin-2-one 3-(4-(4-Oxopiperidin-1-yl)-3-fluorophenyl)-5(R)-(isoxazol-3-yloxymethyl)oxazolidin-2-one (125 mg, 0.33 mmol) was dissolved in MeOH (5 ml) and dichloromethane (5 ml), methyl carbazate (34 mg, 0.37 mmol) added, and the mixture stirred at ambient temperature under nitrogen for 18 hours. The mixture was evaporated, and the residue purified by chromatography on a 5 g silica Mega Bond Elut® column, eluting with a gradient increasing in polarity from 0 to 1% MeOH in dichloromethane. Relevant fractions were combined to give the desired product (98 mg).

MS (ESP): 448 (MH$^+$) for $C_{20}H_{22}FN_5O_6$; NMR (CDCl$_3$) δ: 2.53 (t, 2H); 2.67 (t, 2H); 3.18 (t, 2H); 3.22 (t, 2H); 3.83 (s, 3H); 3.92 (dd, 1H); 4.14 (t, 1H); 4.49 (dd, 1H); 4.57 (dd, 1H); 5.01 (m, 1H); 6.01 (d, 1H); 6.96 (t, 1H); 7.13 (dd, 1H); 7.47 (dd, 1H); 7.79 (s, 1H); 8.16 (d, 1H).

EXAMPLE 93

3-(4-(4-(2-Hydroxyethyl)aminoiminopiperidin-1-yl)-3-fluorophenyl)-5(R)-(isoxazol-3-yloxymethyl) oxazolidin-2-one 3-(4-(4-Oxopiperidin-1-yl)-3-fluorophenyl)-5(R)-(isoxazol-3-yloxymethyl)oxazolidin-2-one (125 mg, 0.33 mmol) was dissolved in MeOH (5 ml) and dichloromethane (5 ml), 2-hydroxyethylhydrazine (29 mg, 0.37 mmol) added, and the mixture stirred at ambient temperature under nitrogen for 18 hours. The mixture was evaporated, and the residue purified by chromatography on a 5 g silica Mega Bond Elut® column, eluting with a gradient increasing in polarity from 0 to 1.5% MeOH in dichloromethane. Relevant fractions were combined to give the desired product (98 mg). MS (ESP): 434 (MH$^+$) for $C_{20}H_{24}FN_5O_5$.

NMR (DMSO-d$_6$) δ: 2.34 (t, 2H); 2.43 (t, 2H); 3.04 (m, 4H); 3.47 (q, 2H); 3.76 (q, 1H); 3.87 (dd, 1H); 4.16 (t, 1H); 4.43 (overlapping m, 4H); 5.04 (m, 1H); 5.73 (br, 1H); 6.37 (d, 1H); 7.07 (t, 1H); 7.18 (dd, 1H); 7.50 (dd, 1H); 8.67 (d, 1H).

EXAMPLE 94

3-(4-(4-Methanesulfonaminolpiperidin-1-yl)-3-fluorophenyl)-5(R)-(isoxazol-3-yloxymethyl) oxazolidin-2-one 3-(4-(4-Aminopiperidin-1-yl)-3-fluorophenyl)-5(R)-(isoxazol-3-yloxymethyl)oxazolidin-2-one (249 mg, 0.66 mmol) in dichloromethane (20 ml) was cooled in an ice-bath, treated with triethylamine (140 mg, 1.4 mmol) and methanesulfonyl choride (160 mg, 1.4 mmol), and stirred 18 hours, allowing the temperature to rise to ambient. The solution was washed with water (3×5 ml), and the residue after evaporation purified by chromatography on a 10 g silica Mega Bond Elut® column. eluting with a gradient increasing in polarity from 0 to 5% MeOH in dichloromethane. Relevant fractions were combined to give the desired product (38 mg).

MS (ESP): 455 (MH$^+$) for $C_{19}H_{23}FN_4O_6S$; NMR (CDCl$_3$) δ: 1.74 (m, 2H); 2.12 (m, 2H); 2.78 (t, 2H); 3.01 (s, 3H); 3.34 (d, 2H); 3.47 (m, 1H); 3.91 (dd, 1H); 4.12 (t, 1H); 4.34 (d, 1H); 4.48 (dd, 1H); 4.56 (dd, 1H); 4.99 (m, 1H); 5.99 (d, 1H); 6.92 (t, 1H); 7.11 (dd, 1H); 7.43 (dd, 1H); 8.14 (d, 1H).

EXAMPLE 95

3-(4-(4-Methoxycarbonylaminopiperidin-1-yl)-3-fluorophenyl)-5(R)-(isoxazol-3-yloxymethyl)oxazolidin-2-one Using essentially the technique of Example 94, starting with 3-(4-(4-aminopiperidin-1-yl)-3-fluorophenyl)-5(R)-(isoxazol-3-yloxymethyl)oxazolidin-2-one (249 mg, 0.66 mmol) and methyl chloroformate (70 mg, 0.74 mmol) in place of methanesulfonyl choride, gave the desired product (125 mg) after chromatography.

MS (ESP): 435 (MH$^+$) for $C_{20}H_{23}FN_4O_6$; NMR (CDCl$_3$) δ: 1.65 (m, 2H); 2.06 (m, 2H); 2.78 (td, 2H); 3.34 (dm, 2H); 3.67 (s overlapping br, 4H); 3.92 (dd, 1H); 4.11 (t, 1H); 4.48 (dd, 1H); 4.55 (dd, 1H); 4.63 (m, 1H); 4.99 (m, 1H); 5.99 (d, 1H); 6.93 (t, 1H); 7.11 (dd, 1H); 7.43 (dd, 1H); 8.15 (d, 1H).

EXAMPLE 96

3-(4-((3R)-3-Methoxycarbonylamino-1-pyrrolidinyl)-3-fluorophenyl)-5(R)-(isoxazol-3-yloxymethyl)oxazolidin-2-one Using essentially the technique of Example 94, starting with 3-(4-((3R)-3-amino-1-pyrrolidinyl)-3-fluorophenyl)-5(R)-(isoxazol-3-yloxymethyl)oxazolidin-2-one hydrochloride (249 mg, 0.62 mmol), the title compound (189 mg) was obtained without need of chromatography. MS (ESP): 441 (MH$^+$) for $C_{18}H_{21}FN_4O_6S$; NMR (DMSO-d$_6$) δ: 1.94 (m, 1H); 2.25 (m, 1H); 3.02 (s, 3H); 3.27 (m, 1H); 3.38 (t, 1H); 3.45 (t, 1H); 3.61 (m, 1H); 3.92 (dd, 1H); 4.05 (m, 1H); 4.19 (t, 1H); 4.48 (dd, 1H); 4.54 (dd, 1H); 5.08 (m, 1H); 6.37 (d, 1H); 6.83 (t, 1H); 7.19 (dd, 1H); 7.45, 7.48 (dd overlapping br, 2H); 8.76 (d, 1H).

EXAMPLE 97

3-(4-((3R)-3-Methanesulfonamino-1-pyrrolidinyl)-3-fluorophenyl)-5(R)-(isoxazol-3-yloxymethyl)oxazolidin-2-one Using essentially the technique of Example 94, starting with 3-(4-((3R)-3-amino-1-pyrrolidinyl)-3-fluorophenyl)-5(R)-(isoxazol-3-yloxymethyl)oxazolidin-2-one hydrochloride (232 mg, 0.58 mmol), and methyl chloroformate (66 mg, 0.7 mmol) in place of methanesulfonyl choride, gave the desired product (182 mg) without need of chromatography.

MS (ESP): 421 (MH$^+$) for $C_{19}H_{21}FN_4O_6$; NMR (DMSO-d$_6$) δ: 1.89 (m, 1H); 2.18 (m, 1H); 3.21 (m, 1H); 3.36 (m, 1H); 3.43 (m, 1H); 3.56 (m, 1H); 3.59 (s, 3H); 3.92 (dd, 1H); 4.19 (t overlapping m, 2H); 4.48 (dd, 1H); 4.55 (dd, 1H) 5.08 (m, 1H); 6.46 (d, 1H); 6.80 (t, 1H); 7.17 (dd, 1H); 7.48 (dd, 1H); 7.53 (d, 1H); 8.77 (d, 1H).

EXAMPLE 98

3-(3-Fluoro-4-(imidazol-1-yl)phenyl)-5(R)-(isoxazol-3-yloxymethyl)-oxazolidin-2-one 3-(3-Fluoro-4-(imidazol-1-yl)phenyl)-5(R)-hydroxymethyloxazolidin-2-one (WO 96/23788; 280 mg, 1 mmol), 3-hydroxyisoxazole (94 mg, 1.1 mmol), and triphenylphosphine (330 mg, 1.25 mmol) were suspended by stirring in dry tetrahydrofuran (10 ml) under nitrogen at ambient temperature. Diisopropylazodicarboxylate (308 mg, 1.5 mmol) was added dropwise over 10 minutes. The suspension dissolved, and stirring was continued at the same temperature for 2 hours. The mixture was evaporated to dryness, and the residue purified by chromatography on a 20 g silica Mega Bond Elut® columns, eluting with a gradient increasing in polarity from 50 to 100% EtOAc in isohexane. Relevant fractions were combined and evaporated to give the desired product (206 mg). MS (ESP): 345 (MH$^+$) for $C_{16}H_{13}FN_4O_4$.

NMR (DMSO-d$_6$) δ: 3.97 (dd, 1H); 4.24 (dd, 1H); 4.48 (m, 2H); 5.11 (m, 1H); 6.37 (d, 1H); 7.11 (d, 1H); 7.47 (dd, 1H); 7.52 (d, 1H); 7.66 (t, 1H); 7.74 (dd, 1H); 7.99 (s, 1H); 8.66 (d, 1H).

EXAMPLE 99–103

In a multiple parallel synthesis, using the conditions of the intermediate in Example 65, the same ratios of reagents, the appropriate hydroxymethyl starting material, and purifying as before on 10 g Mega Bond Elut® columns the following compounds were prepared.

| Example | Starting Material | Moles Used | Product | Weight of Product | Foot notes |
|---|---|---|---|---|---|
| 99 |  | 0.3 mmol |  | 20 mg | 1, 6 |

| Example | Starting Material | Moles Used | Product | Weight of Product | Foot notes |
|---|---|---|---|---|---|
| 100 | [structure] | 0.7 mmol | [structure] | 70 mg | 2, 6 |
| 101 | [structure] | 0.5 mmol | [structure] | 50 mg | 3, 7 |
| 102 | [structure] | 0.6 mmol | [structure] | 110 mg | 4, 8 |
| 103 | [structure] | 0.2 mmol | [structure] | 70 mg | 5, 9 |

Footnotes:
1. MS (ESP): 346 (MH$^+$) for $C_{15}H_{12}FN_5O_4$
2. MS (ESP): 346 (MH$^+$) for $C_{15}H_{12}FN_5O_4$ NMR (DMSO-d$_6$) δ: 3.97(dd, 1H); 4.26(dd, 1H); 4.48(m, 2H); 5.11(m, 1H); 6.37(d, 1H); 7.53(dd, 1H); 7.74 (dd, 1H); 7.83(t, 1H); 8.13(s, 2H); 8.69(d, 1H).
3. MS (ESP): 326 (MH$^+$) for $C_{17}H_{15}N_3O_4$ NMR (DMSO-d$_6$) δ: 3.93(dd, 1H); 4.22(t, 1H); 4.47(m, 2H); 5.06(m 1H); 6.22(m, 2H); 6.37(d, 1H); 7.31(m, 2H); 7.60(dd, 4H); 8.68(d, 1H).
4. MS (ESP): 369 (MH$^+$) for $C_{18}H_{13}FN_4O_4$ NMR (DMSO-d$_6$) δ: 3.96(dd, 1H); 4.23(t, 1H); 4.47(m, 2H); 5.10(m, 1H); 6.37(d, 1H); 6.70(m, 1H); 7.28 (m, 1H); 7.47(dd, 1H); 7.64(t, 1H); 7.74(dd, 1H); 7.99(m, 1H); 8.67(d, 1H).
5. MS (ESP): 405 (MH$^+$) for $C_{19}H_{21}FN_4O_5$ NMR (DMSO-d$_6$) δ: 1.04(t, 3H); 3.35(t + m, 6H); 3.59(s, 2H); 3.87(dd, 1H); 4.16(t, 1H); 4.45(m, 2H); 5.03 (m, 1H); 6.36(d, 1H); 7.05(t, 1H); 7.21(dd, 1H); 7.53(dd, 1H); 8.68(d, 1H).
6. Starting material described in WO 96/23788.
7. The intermediate for this compound was prepared as follows:

1-(4-Ethoxycarbonylaminophenyl)pyrrole

Ethyl chloroformate (0.38 ml) was added dropwise to a stirred solution of 1-(4-aminophenyl)pyrrole (0.56 g, 3.54 mmol , Corelli et al., Farmaco. Ed. Sci., 1983, 38, 219) in pyridine (5 ml) at 5–10° C. for 15 minutes. The cooling bath was removed and stirring continued for 1.5 hours. The mixture was evaporated and the residue was purified by flash column chromatography on silica gel, eluting with a gradient of 1–4% MeOH in dichloromethane to give the title product (0.43 g) as a solid.

MS (ESP): (MH$^+$) 231 for $C_{13}H_{14}N_2O_2$; NMR (CDCl$_3$) δ: 1.33 (t, 3H); 4.25 (q, 2H); 6.32 (t, 2H); 6.60 (s, 1H); 7.02 (t, 2H); 7.32–7.42 (m, 4H).

(5S)-3-(4-(1-Pyrrolyl)phenyl)-5(R)-hydroxymethyloxazolidin-2-one

To a solution of 1-(4-ethoxycarbonylaminophenyl)pyrrole (0.45 g, 2.14 mmol) in dry tetrahydrofuran (30 ml) at –60° C. under nitrogen, was added dropwise a solution of n-butyl lithium in (1.6 M in isohexane, 1.3 ml). The mixture was stirred for 20 minutes before (R)-glycidylbutyrate (0.3 g, 2.1 mmol) in tetrahydrofuran (2 ml) was added dropwise. The mixture was allowed to warm to room temperature, stirred for 16 hours and partitioned between EtOAc and saturated ammonium chloride solution. The organic layer was washed with brine, dried (magnesium sulfate) and evaporated. The residue was recrystallised from ethanol to give the title product (0.21 g), mp 179–181° C. MS (ESP): 259 (MH$^+$) for $C_{14}H_{14}N_2O_3$;

NMR (DMSO-d$_6$) δ: 3.5–3.75 (m, 2H); 3.87 (m, 1H); 4.12 (t, 1H); 4.70 (m, 1H); 5.18 (t, 1H); 6.24 (t, 2H); 7.31 (t, 2H); 7.5–7.7 (m, 4H). $C_{14}H_{14}N_2O_3$ requires C: 65.1, H: 5.46, N: 10.8%; found: C: 64.5, H: 5.5, N: 10.6%.

8. The intermediate for this compound was prepared as follows:

3-Fluoro-4-(3-cyano-1-pyrrolyl)nitrobenzene

3-Cyanopyrrole (3.6 g, 39.1 mmol , CE Loader et al, Can. J. Chem., 1981, 59, 2673) and 3,4-difluoronitrobenzene (6.5 g, 40.9 mmol) were dissolved in DMF (50 ml) and cooled in an ice-bath. The mixture was stirred and sodium hydride (60% in oil, 1.6 g, 40 mmol) added over 20 minutes. After allowing the mixture to come to ambient temperature, it was heated to 650 for 1 hour. Solvent was evaporated, the residue triturated with water, and filtered. The crude solide was purified by flash chromatography on silica, eluting with dichloromethane. Relevant fractions were combined to give the title product (3.75 g), mp 117–119°.

MS (ESP): 230 (MH$^-$) for $C_{11}H_6FN_3O_2$; NMR (CDCl$_3$) δ: 6.68 (s, 1H); 7.09 (m, 1H); 7.61 (overlapping m, 2H); 8.20 (overlapping m, 2H).

5-Amino-2-(3-cyano-1-pyrrolyl)fluorobenzene

3-Fluoro-4-(3-cyano-1-pyrrolyl)nitrobenzene (5.3 g, 22.9 mmnol) was dissolved in hot MeOH (250 ml) and palladium catalyst (10% on charcoal, 700 mg) added under a nitrogen atmosphere. The mixture was cooled and hydrogenated at atmospheric pressure for 3.5 hours. After filtration through celite, the solution was evaporated to dryness to give title product in sufficent purity for the next stage (4.6 g).

MS (ESP): 202 (MH$^+$) for $C_{11}H_8FN_3$; NMR (CDCl$_3$) δ: 3.93 (br s, 2H); 6.50 (m, 3H); 6.82 (s, 1H); 7.10 (t, 1H); 7.31 (s, 1H).

5-Ethoxycarbonylamino-2-(3-cyano-1-pyrrolyl) fluorobenzene

5-Amino-2-(3-cyano-1-pyrrolyl)fluorobenzene (4.6 g, 22.9 mmol) was stirred in dry pyridine (50 ml) 0°. Ethyl chloroformate (2.66 g, 24.5 mmol) was added, and stirring continued for 20 minutes at the same temperature before allowing the temperature to rise to ambient over 2 hours. Solvent was evaporated, the residue treated with iced water (50 ml), filtered off, and dried. Crystallisation of the crude product from ethanol (200 ml) gave the title product (4.9 g) mp 188–190°.

MS (ESP): 274 (MH$^-$) for $C_{14}H_{12}FN_3O_2$; NMR (DMSO-d$_6$) δ: 1.26 (t, 3H); 4.16 (q, 2); 6.69 (m, 1H); 7.23 (m, 1H); 7.33 (dd, 1H); 7.53 (t, 1H); 7.59 (dd, 1H); 7.92 (m, 1H); 10.04 (br s, 1H).

(5S)-3-(3-Fluoro-4-(3-cyano-1-pyrrolyl)phenyl)-5(R)-hydroxymethyloxazolidin-2-one 5-Ethoxycarbonylamino-2-(3-cyano-1-pyrrolyl) fluorobenzene (4.8 g, 17.6 mmol) was dissolved in dry tetrahydrofuran (200 ml) under nitrogen, cooled to –70°, and treated with a solution of n-butyllithium (1.6 M in isohexane, 11.0 ml). After stirring for 45 minutes at –70°, (R)-glycidylbutyrate (2.8 g, 19.4 mmol) dissolved in tetrahydrofuran (5 ml) was added at –70°. Stirring was continued for 18 hours allowing the temperature to rise to ambient. Saturated ammonium chloride solution (50 ml) was added and the mixture extracted with EtOAc (250 ml, then 2×100 ml). The combined extracts were washed with brine (60 ml), dried (magnesium sulfate) and evaporated, and the residue purified by crystallisation from ethanol to give the desired product (3.9 g), mp 157–159°, MS (ESP): 302 (MH$^+$) for $C_{15}H_{12}FN_3O_3$.

NMR (DMSO-d$_6$) δ: 3.58 (dd, 1H); 3.71 (dd, 1H); 3.88 (dd, 1H); 4.14 (t, 1H); 4.75 (m, 1H); 5.21 (t, 1H); 6.72 (m, 1H); 7.28 (m, 1H); 7.49 (dd, 1H); 7.65 (t, 1H); 7.76 (dd, 1H); 7.79 (m, 1H).

9. Starting material described in WO 97/27188.

EXAMPLE 104

3-(4-(4-Hydroxymethylimidazol-1-yl)-3-fluorophenyl)-5(R)-(isoxazol-3-yloxymethyl) oxazolidin-2-one 3-(4-(4-t-Butyldimethylsilyloxymethylimidazol-1-yl)-3-fluorophenyl)-5(R)-(isoxazol-3-yloxymethyl)oxazolidin-2-one (0.59 g, 1.2 mmol) in anhydrous tetrahydrofuran (15 ml) was cooled to 0°. A solution of tetra-n-butylarnmonium fluoride (1 M, 5 ml, 5 mmol) was added and the mixture stirred 3 hours as the temperature rose to ambient. The mixture was evaporated to drvness, redissolved in dichloromethane (50 ml), washed with water (3×25 ml), and dried over magnesium sulfate. After filtration and evaporation the residue was purified by chromatography on a 10 g silica Mega Bond Elut® column. cluting with a gradient increasing in polarity from 0 to 10% MeOH in dichloromethane. Relevant fractions were combined and evaporated to give the desired product (245 mg). MS (ESP): 375 (MH$^+$) for $C_{17}H_{15}FN_4O_5$.

NMR (DMSO-d$_6$) δ: 3.96 (dd, 1H); 4.26 (t, 1H); 4.40 (d, 2H); 4.48 (m, 2H); 4.99 (t, 1H); 5.11 (m, 1H); 6.39 (d, 1H); 7.35 (s, 1H); 7.47 (dd, 1H); 7.66 (t, 1H); 7.75 (dd, 1H); 7.93 (s, 1H); 8.70 (d, 1H).

The intermediate for this compound was prepared as follows.

3-(4-(4-t-Butyldimethylsilyloxymethylimidazol-1-yl)-3-fluorophenyl)-5(R)-hydroxy-methyloxazolidin-2-one (WO 99/10343, 1.57 g, 3.72 mmol), 3-hydroxyisoxazole (350 mg, 4.1 mmol), and tributylphosphine (934 mg, 4.6 mmol) were dissolved by stirring in dry tetrahydrofuran (100 ml) under nitrogen. The mixture was cooled in an ice-bath, and 1,1'-(azodicarbonyl)dipiperidine (1.16 g, 4.6 mmol) added dropwise over 10 minutes. The solution was stirred 18 hours, allowing the temperature to rise to ambient. Reduced azo compound was filtered off, and the solution evaporated to dryness and the residue triturated with ether. The ether layer was evaporated, dissolved in dichloromethane and purified by chromatography on a 40 g silica Mega Bond Elut® column, eluting with a dichloromethane, then 1% MeOH in dichloromethane. Relevant fractions were combined and evaporated to give (5S)-3-(4-(4-t-butyldimethylsilyloxymethylimidazol-1-yl)-3-fluorophenyl)-5(R)-(isoxazol-3-yloxymethyl)oxazolidin-2-one as an oil (0.59 g).

MS (ESP): 489 (MH$^+$) for $C_{23}H_{29}FN_4O_5Si$; NMR (CDCl$_3$) δ: 0.00 (s, 6H); 0.79 (s, 9H); 3.90 (dd, 1H); 4.07 (t, 1H); 4.38 (dd, 1H); 4.48 (dd, 1H); 4.63 (s, 2H); 4.92 (m, 1H); 5.88 (d, 1H); 6.98 (s, 1H); 7.21 (dd, 1H); 7.27 (t, 1H); 7.57 (dd, 1H); 7.61 (s, 1H); 8.03 (d, 1H).

EXAMPLE 105

3-(3-Fluoro-4-(2-methyl-imidazol-1-yl)phenyl)-5 (R)-(isoxazol-3-yl-oxymethyl)oxazolidin-2-one Using essentially the same procedure as for the intermediate of Example 65, but starting with 3-(3-fluoro-4-(2-methyl-imidazol-1-yl)phenyl)-5(R)-hydroxymethyloxazolidin-2-one (202 mg, 0.69 mmol), and purifying by chromatography on a 10 g silica Mega Bond Elut® column, eluting with a gradient increasing in polarity from 0 to 2.5% MeOH in dichloromethane, the title compound was prepared (137 mg).

MS (ESP): 359 (MH$^+$) for $C_{17}H_{15}FN_4O_4$; NMR (DMSO-d$_6$) δ: 2.16 (s, 3H); 4.00 (dd, 1H); 4.27 (t, 1H); 4.49 (m, 2H); 5.12 (m, 1H); 6.40 (d, 1H); 6.94 (d, 1H); 7.23 (d, 1H); 7.50 (dd, 1H); 7.57 (t, 1H); 7.77 (dd, 1H); 8.71 (d, 1H).

The intermediates for this compound were prepared as follows:

3-Fluoro-4-(2-methyl-imidazol-1-yl)nitrobenzene

2-Methylimidazole (9.02 g, 0.11 M) and N,N-diisopropylethylamine (32.2 g, 0.25 M) were dissolved in acetonitrile (160 ml), and 3.4-difluoronitrobenzene (15.9 g, 0.1 M) added. The mixture was stirred and heated to reflux under nitrogen for 24 hours. Solvent was evaporated, the residue dissolved in EtOAc (300 ml), washed with water (150 ml), brine (150 ml), and dried (magnesium sulfate). The residue was recrystallised from a mixture of EtOAc (25 ml) and cyclohexane (150 ml) with the addition of charcoal to give the title compound (11.5 g), mp 106–107°.

MS (ESP): 222 (MH$^+$) for $C_{10}H_8FN_3O_2$; NMR (DMSO-d$_6$) δ: 2.25 (s, 3H); 7.00 (d, 1H); 7.35 (t, 1H); 7.87 (t, 1H); 8.23 (dd, 1H); 8.43 (dd, 1H).

5-Amino-2-(2-methyl-imidazol-1-yl)fluorobenzene

3-Fluoro4-(2-methyl-imidazol-1-yl)nitrobenzene (40 g, 0.181 M) was dissolved in a mixture of MeOH (200 ml) and tetrahydrofuran (800 ml), cooled to 0° under nitrogen, and treated with ammonium formate (57 g, 0.905 M) followed by palladium on charcoal (10%, 2 g). The mixture was stirred at ambient temperature for 18 hours, filtered through celite, celite washed with MeOH (100 ml), and filtrate evaporated to dryness. The residue was partitioned between EtOAc (800 ml) and 10% aqueous sodium bicarbonate (250 ml). The organic layer was separated, washed with brine (250 ml), dried (magnesium sulfate) and evaporated to give title compound (34.6 g).

MS (ESP): 192 (MH$^+$) for $C_{10}H_{10}FN_3$; NMR (DMSO-d$_6$) δ: 2.08 (s, 3H); 5.68 (s, 2H); 6.45 (overlapping m, 2H); 6.84 (d, 1H); 7.03 (overlapping m, 2H).

5-Benzyloxycarbonylamino-2-(2-methyl-imidazol-1-yl)fluorobenzene

5-Amino-2-(2-methyl-imidazol-1-yl)fluorobenzene (34.25 g, 0.179 M) was dissolved in dry dichloromethane (600 ml) under nitrogen, and cooled to −5°. Pyridine (17.7 g, 0.224 M) was added, followed by benzyl chloroformate (33.7 g, 0.197 M) over 20 minutes. The mixture was stirred and the temperature allowed to rise to ambient over 16 hours. Aqueous sodium bicarbonate (5%, 250 ml) was added, the organic layer separated, the aqueous layer re-extracted with dichloromethane (2×300 ml), and combined extracts dried (magnesium sulfate). After filtration and evaporation, the residue was recrystallised from toluene (400 ml) to give title product (54.5 g).

MS (ESP): 326 (MH$^-$) for $C_{18}H_{16}FN_3O_2$; NMR (DMSO-d$_6$) δ: 2.13 (s, 3H); 5.18 (s, 2H); 6.89 (s, 1H); 7.17 (s, 1H); 7.41 (overlapping m, 7H); 7.73 (dd, 1H); 10.21 (br, 1H).

(5S)-3-(3-Fluoro-4-(2-methyl-imidazol-1-yl)phenyl)-5(R)-hydroxymethyloxazolidin-2-one 5-Benzyloxycarbonylamino-2-(2-methyl-imidazol-1-yl)fluorobenzene (54 g, 0.166 M) was dissolved in a mixture of dry tetrahydrofuran (600 ml) and 1,3-dimethyl-2,4,5,6-tetrahydro-2(1H)-pyrimidinonc (100 ml) under nitrogen, cooled to −70°, and treated with a solution of n-butyllithium (1.6 M in isohexane, 114 ml), over 30 minutes. After stirring for 30 minutes at −70°, a solution of (R)-glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and EtOAc (800 ml), the organic layer separated, and the aqueous extracted with further EtOAc (3×750 ml). The combined extracts were dried (magnesium sulfate) and evaporated, and the resulting oil triturated with diethyl ether. The resulting solid was recrystallisd from isopropanol to give the title compound (21.5 g). MS (ESP): 292 (MH$^+$) for $C_{14}H_{14}FN_3O_3$.

NMR (DMSO-d$_6$) δ: 2.16 (s, 3H); 3.56 (dt, 1H); 3.69 (dt, 1H); 3.88 (dd, 1H); 4.15 (t, 1H); 4.74 (m, 1H); 5.24 (t, 1H); 6.92 (s, 1H); 7.20 (s, 1H); 7.48 (dd, 1H); 7.53 (t, 1H); 7.74 (dd, 1H).

EXAMPLE 106

3-(3-Fluoro-4-(4-methyl-imidazol-1-yl)phenyl)-5(R)-(isoxazol-3-yl-oxymethyl)oxazolidin-2-one Using essentially the same procedure as for the intermediate of Example 65, but starting with 3-(3-fluoro-4-(4-methyl-imidazol-1-yl)phenyl)-5(R)-hydroxymethyloxazolidin-2-one (see Example 141; 81 mg, 0.29 mmol), and purifying by chromatography on a 5 g silica Mega Bond Elut® column, eluting with a gradient increasing in polarity from 0 to 2.5% MeOH in dichloromethane, gave the title compound (80 mg). MS (ESP): 359 (MH$^+$) for $C_{17}H_{15}FN_4O_4$.

NMR (CDCl$_3$) δ: 2.30 (s, 3H); 4.02 (dd, 1H); 4.23 (t, 1H); 4.52 (dd, 1H); 4.60 (dd, 1H); 5.07 (m, 1H); 6.00 (d, 1H); 6.94 (s, 1H); 7.50 (overlapping m, 2H); 7.69 (dd, 1H); 7.77 (s, 1H); 8.16 (d, 1H).

EXAMPLE 107

3-(3-Fluoro-4-(4-cyano-imidazol-1-yl)phenyl)-5(R)-(isoxazol-3-yloxymethyl)oxazolidin-2-one 3-(3-Fluoro-4-(4-hydroximinomethyl-imidazol-1-yl)phenyl)-5(R)-(isoxazol-3-yloxymethyl)-oxazolidin-2-one (360 mg, 0.93 mmol) and acetic anhydride (3 ml) were heated under nitrogen at reflux for 2 hours. After cooling and pouring onto ice, the mixture was extracted into dichloromethane (3×15 ml). dried (magnesium sulfate) and evaporated. The residue was purified by chromatography on a 10 g silica Mega Bond Elut® column, eluting with a gradient increasing in polarity from 0 to 2.5% MeOH in dichloromethane, to give the desired compound (135 mg).

MS (ESP): 370 (MH$^+$) for $C_{17}H_{12}FN_5O_4$; NMR (DMSO-d$_6$) δ: 3.99 (dd, 1H); 4.27 (t, 1H); 4.49 (m, 2H); 5.12 (m, 1H); 6.37 (d, 1H); 7.52 (dd, 1H); 7.74 (t, 1H); 7.82 (dd, 1H); 8.29 (d, 1H); 8.56 (t, 1H); 8.69 (d, 1H).

The intermediate for this compound was prepared as follows:

3-(3-Fluoro-4-(4-aldehydo-imidazol-1-yl)phenyl)-5(R)-(isoxazol-3-yloxymethyl)oxazolidin-2-one (WO 99/10343; 460 mg, 1.24 mmol), was dissolved in a mixture of ethanol (10 ml) and water (2 ml), and treated with hydroxylamine hydrochloride (86 mg, 1.24 mmol) and triethylamine (176 mg, 1.74 mmol). After stirring for 18 hours at ambient temperature the precipitated solid was filtered off, and the residue evaporated to dryness. Residue and precipitate were combined, washed with water (2×25 ml) and dried at 70° to give 3-(3-fluoro-4-(4-hydroximinomethyl-imidazol-1-yl)phenyl)-5(R)-(isoxazol-3-yloxymethyl)-oxazolidin-2-one (361 mg) as a 3:1 mixture of E and Z isomers. MS (ESP): 388 (MH$^+$) for $C_{17}H_{14}FN_5O_5$.

NMR (DMSO-d$_6$) δ: 3.97 (dd, 1H); 4.26 (t, 1H); 4.45 (dd, 2H); 5.11 (m, 1H); 6.39 (d, 1H); 7.44 (s, 0.25H); 7.49 (dd, 1H); 7.73 (t, 1H); 7.77 (dd+s, 1.75H); 8.00 (s, 0.75H); 8.06 (s, 0.75H); 8.10 (s, 0.25H); 8.13 (s, 0.25H); 8.70 (d, 1H); 10.91 (s, 0.75H); 11.60 (s, 0.25H).

EXAMPLE 108

3-(4-(Imidazol-1-yl)-3-fluorophenyl)-5(R)-(3-(1,2,5-thiadiazolyl)-oxymethyl)oxazolidin-2-one 3-(4-(imidazol-1-yl)-3-fluorophenyl)-5(R)-hydroxymethyloxazolidin-2-one (WO 96/23788; 500 mg, 1.8 mmol), 3-hydroxy-1,2,5-thiadiazole (221 mg, 2.17 mmol), and triphenylphosphine (707 mg, 2.7 mmol) were suspended in dry tetrahydrofuran (15 ml) under nitrogen by stirring. The mixture was cooled in an ice-bath and diisopropylazodicarboxylate (545 mg, 2.7 mmol) added dropwise over 10 minutes. The solution was stirred 18 hours, allowing the temperature to rise to ambient. The mixture was diluted with dichloromethane (200 ml), and extracted with hydrochloric acid (1 M, 200 ml). The aqueous layer was washed with dichloromethane (2×100 ml), and the aqueous layer made basic with the minimum of concentrated arnmonia solution. Organic material was extracted into dichloromethane (200 then 100 ml), dried (magnesium sulfate), and purified by chromatography on a 20 g silica Mega Bond Elut® column, eluting with a gradient increasing in polarity from 0 to 10% MeOH in dichloromethane. Relevant fractions were combined and evaporated to give the product (520 mg).

MS (ESP): 362 (MH$^+$) for $C_{15}H_{12}FN_5O_3S$; NMR (DMSO-d$_6$) δ: 4.02 (dd, 1H); 4.26 (t, 1H); 4.66 (d, 1H); 4.71 (d, 1H); 5.15 (m, 1H); 7.11 (t, 1H); 7.48 (dd, 1H); 7.52 (m, 1H); 7.66 (t, 1H); 7.74 (dd, 1H); 7.98 (m, 1H); 8.43 (s, 1H).

EXAMPLE 109

3-(4-((3R)-3-Hydroxy-1-pyrrolidinyl)-3-fluorophenyl)-5(R)-(isoxazol-3-yloxymethyl)oxazolidin-2-one 3-(4-((3R)-3-t-Butyldimethylsilyloxy-1-pyrrolidinyl)-3-fluorophenyl)-5(R)-(isoxazol-3-yloxymethyl)oxazolidin-2-one (1.8 g, 3.77 mmol) was stirred in a mixture of acetic acid, water, and tetrahydroftiran (3:1:1, 40 ml) at 90° for four hours. Solvent was evaporated, and the residue purified by chromatography on a 10 g silica Mega Bond Elut® column, eluting with a gradient increasing in polarity from 0 to 10% MeOH in dichloromethane. Relevant fractions were combined and evaporated to give the desired product (420 mg) as a foam. MS (ESP): 364 (MH$^+$) for $C_{17}H_{18}FN_3O_5$.

NMR (DMSO-d$_6$) δ: 1.82 (m, 1H); 1.97 (m, 1H); 3.10 (d, 1H); 3.25 (t, 1H); 3.40 (dd, 1H); 3.50 (m, 1H); 3.84 (dd, 1H); 4.12 (t, 1H); 4.32 (br, 1H); 4.43 (m, 2H); 4.87 (d, 1H); 5.02 (m, 1H); 6.36 (d, 1H); 6.70 (t, 1H); 7.10 (dd, 1H); 7.38 (dd, 1H); 8.67 (d, 1H).

The intermnediates for this compound were prepared as follows:

3-Fluoro-4-((3R)-3-hydroxy-1-pyrrolidinyl)nitrobenzene (3R)-3-Hydroxypyrrolidine hydrochloride (20 g, 0.163 M) was suspended by stirring in acetonitrile (200 ml) under nitrogen at 50°, and treated with N,N-diisopropylethylarnine (52.5 g, 0.41 M) and 3,4-difluoronitrobenzene (25.9 g, 0.153 M). The mixture was heated at 90° for 17 hours, then the solvent evaporated. The residue was dissolved in dichloromethane (500 ml) and washed with 5% aqueous sodium dihydrogen phosphate (300 ml), which caused partial precipitation. The precipitate was filtered, washed, and the combined aqueous layers re-extracted with dichloromethane (200 ml). The organic layers were evaporated, and the residue combined with the previously filtered material, and dried by azeotroping with toluene to give the desired product (35 g), of sufficient quality for use without purification.

MS (ESP): 227 (MH$^+$) for $C_{10}H_{11}FN_2O_3$; NMR (CDCl$_3$) δ: 1.89 (m, 1H); 1.97 (m, 1H); 3.47 (d, 1H); 3.61 (overlapping m, 3H); 4.35 (br m, 1H); 5.03 (d, 1H); 6.73 (t, 1H); 7.89 (overlapping m, 2H).

3-Fluoro-4-((3R)-3-t-butyldimethylsilyloxy-1-pyrrolidinyl)nitrobenzene

3-Fluoro-4-((3R)-3-hydroxy-1-pyrrolidinyl)nitrobenzene (35.8 g, 0.158 M) was dissolved in DMF (200 ml), and treated with imidazole (21.6 g, 0.318 M) and t-butyldimethylsilyl chloride (35.7 g, 0.239 M) and stirred for 18 hours at ambient temperature under nitrogen. Solvent was evaporated, and the residue treated with EtOAc (300 ml) and water (200 ml). The organic layer was washed with water (150 ml) and dried (magnesium sulfate). Evaporation gave the desired product (54 g), of sufficient quality for use without purification.

MS (ESP): 341 (MH$^+$) for $C_{16}H_{25}FN_2O_3Si$; NMR (CDCl$_3$) δ: 0.02 (2×s, 6H); 0.74 (s, 9H); 1.79 (br m, 1H); 1.97 (m, 1H); 3.27 (d, 1H); 3.53 (m, 2H); 3.68 (dt, 1H); 4.48 (br m, 1H); 6.69 (t, 1H); 7.83 (overlapping m, 2H).

5-Amino-2-((3R)-3-t-butyldimethylsilyloxy-1-nyrrolidinyl)fluorobenzene

3-Fluoro-4-((3R)-3-t-butyldimethylsilyloxy-1-pyrrolidinyl)nitrobenzene (54 g, 0.158 M) was treated in essentially the same way as the appropriate intermediate of Example 86, to give desired product required product of sufficient quality for use without purification (49 g). MS (ESP): 311 (MH$^+$) for $C_{16}H_{27}FN_2OSi$.

NMR (DMSO-d$_6$) δ: 0.00 (2×s, 6H); 0.79 (s, 9H); 1.66 (m, 1H); 2.01 (m, 1H); 2.84 (d, 1H); 3.02 (dd, 1H); 3.12 (dd, 1H), 3.32 (m, 1H); 4.41 (m, 1H); 4.63 (s, 2H); 6.22 (dd, 1H); 6.29 (dd, 1H); 6.49 (t, 1H).

5-Ethoxycarbonylamino-2-((3R)-3-t-butyldimethylsilyloxy-1-pyrrolidinyl)fluorobenzenc 5-Amino-2-((3R)-3-t-butyldimethylsilyloxy-1-pyrrolidinyl)fluorobenzene (49 g, 0.158 M) was treated in essentially the same way as the appropriate intermediate of Example 86, except that the product was isolated by extraction into dichloromethane, azeotroping with toluene, and crude product purified by dry column chromatography on silica, eluting with a gradient from 0–20% EtOAc in dichloromethane. Appropriate fractions were combined to give the desired product (29.6 g)

MS (ESP): 383 (MH$^+$) for $C_{19}H_{31}FN_2O_3Si$; MR (DMSO-d$_6$) δ: –0.02 (s, 3H); 0.01 (s, 3H); 0.78 (s, 9H); 1.16 (t, 3H); 1.72 (m, 1H); 1.98 (m, 1H); 2.97 (d, 1H); 3.18 (m, 1H); 3.27 (dd, 1H); 3.48 (m, 1H); 4.02 (q, 2H); 4.43 (m, 1H); 6.59 (t, 1H); 6.96 (dd, 1H); 7.17 (dd, 1H); 9.31 (s, 1H).

3-(4-((3R)-3-t-Butyldimethylsilyloxy-1-pyrrolidinyl)-3-fluorophenyl)-5(R)-hydroxymethyloxazolidin-2-one 5-Ethoxycarbonylamino-2-((3R)-3-t-butyldimethylsilyloxy-1-pyrrolidinyl)fluorobenzene (29.4 g, 0.077 M) was treated in essentially the same way as the appropriate intermediate of Example 86, except that the product was isolated by extraction into EtOAc, and crude product purified by dry column chromatography on silica, eluting with a gradient from 0–20% MeOH in dichloromethane. Appropriate fractions were combined to give the desired product (29.6 g).

MS (ESP): 411 (MH$^+$) for $C_{20}H_{31}FN_2O_4Si$; NMR (DMSO-d$_6$) δ: –0.01 (s, 3H); 0.02 (s, 3H); 0.79 (s, 9H); 1.73 (m, 1H); 2.00 (m, 1H); 3.02 (d, 1H); 3.23 (m overlapped by H$_2$O, 1H); 3.32 (dd, 1H); 3.50 (m, 2H); 3.57 (m, 1H); 3.69 (dd, 1H); 3.94 (t, 1H); 4.44 (m, 1H); 4.58 (m, 1H); 5.09 (t, 1H); 6.67 (t, 1H); 7.03 (dd, 1H); 7.34 (dd, 1H).

3-(4-((3R)-3-t-Butyldimethylsilyloxy-1-pyrrolidinyl)-3-fluorophenyl )-5(R)-(isoxazol-3-yloxymethyl)oxazolidin-2-one 3-(4-((3R)-3-t-Butyldimethylsilyloxy-1-pyrrolidinyl)-3-fluorophenyl)-5(R)-hydroxymethyloxazolidin-2-one (4.1 g, 10 mmol) was treated essentially as in Example 67, then purified by flash chromatography on silica, eluting with a gradient from 0–50% EtOAc in dichloromethanc, to give the desired product (2.0 g).

MS (ESP): 478 (MH$^+$) for $C_{23}H_{32}FN_3O_5Si$; NMR (DMSO-d$_6$) δ: 0.10 (s, 3H); 0.12 (s, 3H); 0.87 (s, 9H); 1.84 (m, 1H); 2.09 (m, 1H); 3.13 (d, 1H); 3.33 (m overlapped by H$_2$O, 1H); 3.43 (dd, 1H); 3.61 (m, 1H); 3.89 (dd, 1H); 4.18 (t, 1H), 4.49 (m, 2H); 4.55 (m, 1H); 5.07 (m, 1H); 6.44 (d, 1H); 6.78 (t, 1H); 7.15 (dd, 1H); 7.44 (dd, 1H); 8.72 (d, 1H).

EXAMPLE 110

3-(4-(3-Oxo-1-pyrrolidinyl)-3-fluorophenyl)-5(R)-(isoxazol-3-yloxymethyl)oxazolidin-2-one 3-(4-((3R)-3-Hydroxy-1-pyrrolidinyl)-3-fluorophenyl)-5(R)-(isoxazol-3-yloxymethyl)-oxazolidin-2-one (700 mg, 1.9 mmol) was dissolved in DMSO(5 ml) under nitrogen and triethylamine (2.03 g, 20 mmol) added. A solution of sulfur trioxide pyridine complex (0.95 g, 6 mmol) in DMSO(5 ml) was added dropwise over 20 minutes. After stirring 1 hour at ambient temperature, the mixture was diluted with water (100 ml) and extracted into EtOAc (150 ml). The organics were washed with water (2×50 ml), brine (50 ml) and dried (magnesium sulfate). After evaporation, the residue was purified by chromatography on a 20 g silica Mega Bond Elut® column, eluting with a gradient increasing in polarity from 0 to 3% MeOH in dichloromethane. Relevant fractions were combined and evaporated, and the residue crystallised from ethanol (35 ml) to give product (176 mg). MS (ESP): 362 (MH$^+$) for $C_{17}H_{16}FN_3O_5$.

NMR (DMSO-d$_6$) δ: 2.58 (t, 2H); 3.60 (t, 2H); 3.66 (d, 2H); 3.87 (dd, 1H); 4.15 (t, 1H); 4.45 (m, 2H); 5.03 (m, 1H); 6.36 (d, 1H); 6.94 (t, 1H); 7.20 (dd, 1H); 7.47 (dd, 1H); 8.67 (d, 1H).

EXAMPLE 111

3-(4-(3-Oximino-1-pyrrolidinyl)-3-fluorophenyl)-5(R)-(isoxazol-3-yloxymethyl)oxazolidin-2-one 3-(4-(3-Oxo-1-pyrrolidinyl)-3-fluorophenyl)-5(R)-(isoxazol-3-yloxymethyl)oxazolidin-2-one (124 mg, 0.34 mmol) was dissolved in a mixture of dichloromethane (10 ml) and MeOH (10 ml), and treated with a solution of hydroxylamine hydrochloride (220 mg, 3.17 mmol) and sodium acetate (500 mg) in water (2 ml). After stirring at ambient temperature for 4 hours, solvents were evaporated, and the residue triturated with water (10 ml), solid filtered and dried to give the desired product (118 mg) as a single isomer of unknown geometry. MS (ESP): 377 (MH$^+$) for $C_{17}H_{17}FN_4O_5$.

NMR (DMSO-d$_6$) δ: 2.67 (t, 2H); 3.41 (dd, 2H); 3.88 (dd, 1H); 3.96 (s, 2H); 4.16 (t, 1H); 4.46 (m, 2H); 5.04 (m, 1H); 6.38 (d, 1H); 6.91 (m, 1H); 7.18 (dd, 1H); 7.48 (dd, 1H); 8.69 (d, 1H); 10.72 (s, 1H).

EXAMPLE 112

3-(4-((3S)-3-Amino-1-pyrrolidinyl)-3-fluorophenyl)-5(R)-(isoxazol-3-yloxymethyl)oxazolidin-2-one 3-(4-((3S)-3-t-Butoxycarbonylamino-1-pyrrolidinyl)-3-fluorophenyl)-5(R)-(isoxazol-3-yloxymethyl)oxazolidin-2-one (2.1 g, 4.54 mmol) was suspended by stirring in dichloromethane (10 ml) under nitrogen and treated with a solution of hydrogen chloride in ethanol (4M, 50 ml) at ambient temperature. The mixture was stirred 1 hour, evaporated to a small volume, and treated with a mixture of dichloromethane (30 ml) and diethyl ether (30 ml). The precipitate was filtered and washed with diethyl ether to give the title compound as its hydrochloride (2.0 g).

MS (ESP): 363 (MH$^+$) for $C_{17}H_{19}FN_4O_4$; NMR (DMSO-d$_6$) δ: 2.03 (m, 1H); 2.25 (m, 1H); 3.26 (dd, 1H); 3.42 (m, 1H); 3.52 (m, 2H); 3.83 (dd overlapping m, 2H); 4.13 (t, 1H); 4.42 (m, 2H); 5.02 (m, 1H); 6.37 (d, 1H); 6.79 (t, 1H); 7.14 (dd, 1H); 7.44 (dd, 1H); 8.43 (br, 3H); 8.68 (d, 1H).

The intermediates for this compound were prepared as follows:

3-Fluoro-4-((3S)-3-t-butoxycarbonylamino-1-pyrrolidinyl) nitrobenzene

Using essentially the technique for the equivalent intermediate in Example 86, but starting from (3S)-3-t-butoxycarbonylaminopyrrolidine (20 g, 0.108 M), gave the desired product as a yellow solid (33.5 g), of sufficient quality for use without purification. MS (ESP): 326 (MH$^+$) for $C_{15}H_{20}FN_3O_4$.

NMR (DMSO-d$_6$) δ: 1.36 (s, 9H); 1.87 (m, 1H); 2.08 (m, 1H); 3.36 (m, 1H); 3.54 (m, 1H); 3.62 (tm, 1H); 3.73 (m, 1H); 4.09 (m, 1H); 6.72 (t, 1H); 7.19 (d, 1H); 7.88 (overlapping m, 2H).

5-Amino-2-((3S)-3-t-butoxycarbonylamino-1-pyrrolidinyl) fluorobenzene

Using essentially the technique for the equivalent intermediate in Example 86, but starting from 3-fluoro-4-((3S)-3-t-butoxycarbonylamino-1-pyrrolidinyl)nitrobenzene (33.5 g, 0.103 M), gave the desired product as an oil of sufficient quality for use without purification (~30 g). MS (ESP): 296 (MH$^+$) for $C_{15}H_{22}FN_3O_2$.

NMR (DMSO-d$_6$) δ: 1.35 (s, 9H); 1.71 (m, 1H); 2.06 (m, 1H); 2.87 (dd, 1H); 3.05 (m, 1H); 3.11 (m, 1H); 3.26 (m overlapping H$_2$O, ~1H); 3.97 (m, 1H); 4.68 (s, 2H); 6.25 (dd, 1H); 6.31 (dd, 1H); 6.51 (t, 1H); 7.03 (d, 1H).

5-Ethoxycarbonylamino-2-((3S)-3-t-butoxycarbonylamino-1-pyrrolidinyl)fluorobenzene Using essentially the technique for the equivalent intermediate in Example 86, but starting from 5-amino-2-((3S)-3-t-butoxycarbonylamino-1-pyrrolidinyl)fluorobenzene (30.4 g, 0.103 M), gave crude product after precipitation. This was purified by dissolving in toluene (500 ml), azeotroping until product began to precipitate, then cooling and adding isohexane (500 ml) to complete precipitation. Filtration gave the desired product (35.3 g). MS (ESP): 368 (MH$^+$) for $C_{18}H_{26}FN_3O_4$.

NMR (DMSO-d$_6$) δ: 1.21 (t, 3H); 1.37 (s, 9H); 1.77 (m, 1H); 2.06 (m, 1H); 3.04 (m, 1H); 3.20 (dd, 1H); 3.30 (m overlapping H$_2$O, 1H); 3.42 (tm, 1H); 4.02 (br, 1H); 4.08 (q, 2H); 6.63 (t, 1H); 7.02 (d, 1H) 7.08 (br, 1H); 7.22 (d, 1H); 9.38 (s, 1H).

3-(3-Fluoro-4-((3S)-3-t-butoxycarbonylamino-1-pyrrolidinyl)-5(R)-hydroxymethyloxazolidin-2-one 5-Ethoxycarbonylamino-2-((3S)-3-t-butoxycarbonylamino-1-pyrrolidinyl)fluorobenzene (35.2 g, 0.096 M) was dissolved in dry tetrahydrofuran (400 ml) under nitrogen, cooled to −70°, and treated dropwise over 20 minutes with a solution of lithium t-butoxide, prepared from t-butanol (9.3 g, 123 mmol) in dry tetrahydrofuran (70 ml) and n-butyl lithium (66 ml, 1.6 M in isohexane). After stirring for 20 minutes, (R)-glycidylbutyrate (15.2 g, 0.102 M) in tetrahydrofuran (20 ml) was added over 10 minutes, and the temperature allowed to rise to ambient over 16 hours. The mixture was treated with MeOH (10 ml), stirred at ambient temperature for 10 minutes. then treated with a mixture of 5% aqueous sodium bicarbonate (250 ml) and EtOAc (500 ml). The precipitate was collected and washed well with EtOAc and water to give the desired product (19.5 g). The filtrate was separated into an organic layer, which was dried (magnesium sulfate) and evaporated. The residue was refluxed briefly with EtOAc (100 ml), cooled, and filtered to give further product (16.6 g).

MS (ESP): 396 (MH$^+$) for $C_{19}H_{26}FN_3O_5$; NMR (DMSO-d$_6$) δ: 1.37 (s, 9H); 1.79 (m, 1H); 2.07 (m, 1H); 3.08 (m, 1H); 3.24 (m overlapping H$_2$O, ~1H); 3.36 (m, 1H); 3.48 (tm, 1H); 3.53 (d, 1H); 3.63 (d, 1H); 3.74 (dd, 1H); 3.99 (t, 1H); 4.04 (m, 1H); 4.63 (m, 1H); 5.15 (s, 1H); 6.71 (t, 1H); 7.08 (dd overlapping br, 2H); 7.39 (dd, 1H).

3-(4-((3S)-3-t-Butoxycarbonylamino-1-pyrrolidinyl)-3-fluorophenyl)-5(R)-(isoxazol-3-yloxymethyl)oxazolidin-2-one The title compound was prepared using essentially the method of Example 67, starting from 3-(4-((3S)-3-t-butoxycarbonylamino-1-pyrrolidinyl)-3-fluorophenyl)-5(R)-hydroxymethyl)oxazolidin-2-one (3.95 g, 10 mmol), and purifying by flash chromatography on silica, eluting with a gradient increasing in polarity from 0 to 20% EtOAc in dichloromethane. Relevant fractions were combined, evaporated, and the residue recrystallised from toluene (100 ml) to give the desired product (2.34 g).

MS (ESP): 463 (MH$^+$) for $C_{22}H_{27}FN_4O_6$; NMR (DMSO-$d_6$) δ: 1.37 (s, 9H); 1.81 (m, 1H); 2.08 (m, 1H); 3.10 (m, 1H); 3.24 (t, 1H); 3.35 (dd, 1H); 3.47 (dd, 1H); 3.83 (dd, 1H); 4.05 (m, 1H); 4.12 (t, 1H); 4.42 (dd, 1H); 4.48 (dd, 1H); 5.02 (m, 1H); 6.36 (d, 1H); 6.71 (t, 1H); 7.10 (dd overlapping br, 2H); 7.38 (dd, 1H); 8.66 (d, 1H).

EXAMPLE 113

3-(4-((3S)-3-Acetamido-1-pyrrolidinyl)-3-fluorophenyl)-5(R)-(isoxazol-3-yloxymethyl)oxazolidin-2-one 3-(4-((3S)-3-Amino-1-pyrrolidinyl)-3-fluorophenyl)-5(R)-(isoxazol-3-yloxymethyl)-oxazolidin-2-one hydrochloride salt (170 mg, 0.43 mmol) was stirred in a mixture of saturated sodium bicarbonate solution (5 ml) and dichloromethane (5 ml) in an ice-bath. Acetic anhydride (2 mmol) was added dropwise, and the mixture stirred 18 hours, allowing the temperature to rise to ambient. Dichloromethane (10 ml) was added, and the mixture filtered through phase separating paper, the organic layer evaporated, and crystallised from ethanol to give the desired product (108 mg).

MS (ESP): 405 (MH$^+$) for $C_{19}H_{21}FN_4O_5$; NMR (DMSO-$d_6$) δ: 1.79 (s overlapping m, 4H); 2.11 (hextet, 1H); 3.11 (dt, 1H); 3.24 (t, 1H); 3.42 (dd, 1H); 3.50 (m, 1H); 3.84 (dd, 1H); 4.12 (t, 1H); 4.28 (m, 1H); 4.42 (dd, 1H); 4.47 (dd, 1H); 5.02 (m, 1H); 6.37 (d, 1H); 6.73 (t, 1H); 7.11 (dd, 1H); 7.39 (dd, 1H); 8.08 (d, 1H); 8.67 (d, 1H).

EXAMPLE 114

3-(4-((3S)-3-Methylsulfonamino-1-pyrrolidinyl)-3-fluorophenyl)-5(R)-(isoxazol-3-yloxymethyl)oxazolidin-2-one Using essentially the technique of Example 113, starting from 3-(4-((3S)-3-amino-1-pyrrolidinyl)-3-fluorophenyl)-5(R)-(isoxazol-3-yloxymethyl)oxazolidin-2-one hydrochloride salt (170 mg, 0.43 mmol) and methanesulfonyl chloride gave the desired product (114 mg) after trituration with diethyl ether and isohexane.

MS (ESP): 441 (MH$^+$) for $C_{18}H_{21}FN_4O_6S$; NMR (DMSO-$d_6$) δ: 1.88 (hextet, 1H); 2.18 (hextet, 1H); 2.94 (s, 3H); 3.20 (m, 1H); 3.31 (t, 1H); 3.36 (m overlapped by $H_2O$, ~1H); 3.56 (m, 1H); 3.84 (dd, 1H); 3.98 (hextet, 1H); 4.12 (t, 1H); 4.42 (dd, 1H); 4.47 (dd, 1H); 5.02 (m, 1H); 6.37 (d, 1H); 6.74 (t, 1H); 7.12 (dd, 1H); 7.36 (d, 1H); 7.40 (dd, 1H); 8.68 (d, 1H).

EXAMPLE 115

3-(4-((3S)-3-Methoxycarbonylamino-1-pyrrolidinyl)-3-fluorophenyl)-5(R)-(isoxazol-3-yloxymethyl)oxazolidin-2-one Using essentially the technique of Example 113, starting from 3-(4-((3S)-3-amino-1-pyrrolidinyl)-3-fluorophenyl)-5(R)-(isoxazol-3-yloxymethyl)oxazolidin-2-one hydrochloride salt (170 mg, 0.43 mmol) and methyl chloroformate gave the desired product (114 mg) after trituration with diethyl ether and isohexane.

MS (ESP): 421 (MH$^+$) for $C_{19}H_{21}FN_4O_6$; NMR (DMSO-$d_6$) δ: 1.82 (hextet, 1H); 2.11 (hextet, 1H); 3.14 (m, 1H); 3.27 (m overlapped by $H_2O$, ~1H); 3.39 (dd, 1H); 3.49 (m, 1H); 3.53 (s, 3H); 3.84 (dd, 1H); 4.11 (t overlapping m, 2H); 4.42 (dd, 1H); 4.45 (dd, 1H); 5.02 (m, 1H); 6.37 (d, 1H); 6.72 (t, 1H); 7.11 (dd, 1H); 7.39 (dd, 1H); 7.42 (d, 1H); 8.67 (d, 1H).

EXAMPLE 116

3-(4(3S)-3-Acetoxyacetylamino-1-pyrrolidinyl)-3-fliuorophenyl)-5(R)-(isoxazol-3-yloxymethyl)oxazolidin-2-one Using essentially the technique of Example 73, starting from 3-(4-((3S)-3-amino-1-pyrrolidinyl)-3-fluorophenyl)-5(R)-(isoxazol-3-yloxymethyl)oxazolidin-2-one hydrochloride salt (300 mg, 0.75 mmol) and acetoxyacetyl chloride gave the desired product (240 mg) after trituration with diethyl ether and isohexane.

MS (ESP): 463 (MH$^+$) for $C_{21}H_{23}FN_4O_7$; NMR (DMSO-$d_6$) δ: 1.83 (hextet, 1H); 2.06 (s, 3H); 2.13 (hextet, 1H); 3.15 (m, 1H); 3.26 (m overlapped by $H_2O$, ~1H); 3.41 (dd, 1H); 3.50 (m, 1H); 3.84 (dd, 1H); 4.12 (t, 1H); 4.33 (dd, 1H); 4.43 (s, 2H); 4.45 (m, 2H); 5.03 (m, 1H); 6.36 (d, 1H); 6.74 (t, 1H); 7.11 (dd, 1H); 7.41 (dd, 1H); 8.24 (d, 1H); 8.66 (d, 1H).

EXAMPLE 117

3-(4-((3S)-3-Hydroxyacetylamino-1-pyrrolidinyl)-3-fluorophenyl)-5(R)-(isoxazol-3-yloxymethyl)oxazolidin-2-one Using essentially the technique of Example 74, starting from 3-(4-((3S)-3-acetoxyacetylamino-1-pyrrolidinyl)-3-fluorophenyl)-5(R)-(isoxazol-3-yloxymethyl)-oxazolidin-2-one (140 mg, 0.3 mmol) gave the desired product (125 mg) after trituration with water, diethyl ether and drying.

MS (ESP): 421 (MH$^+$) for $C_{19}H_{21}FN_4O_6$; NMR (DMSO-$d_6$) δ: 1.91 (hextet, 1H); 2.13 (hextet, 1H); 3.18 (m, 1H); 3.29 (m overlapped by $H_2O$, ~1H); 3.40 (dd, 1H); 3.49 (m, 1H); 3.79 (s, 2H); 3.84 (dd, 1H); 4.13 (t, 1H); 4.37 (dd, 1H); 4.46 (m, 2H); 5.02 (m, 1H); 5.36 (s, 1H); 6.36 (d, 1H); 6.74 (t, 1H); 7.11 (dd, 1H); 7.40 (dd, 1H); 7.84 (d, 1H); 8.67 (d, 1H).

EXAMPLE 118

3-(4-((3S)-3-(2,2-Dimethyl-1,3-dioxolan4(S)-ylcarbonamido)-1-pyrrolidinyl)-3-fluorophenyl)-5(R)-(isoxazol-3-yloxymethyl)oxazolidin-2-one 3-(4-((3S)-3-Amino-1-pyrrolidinyl)-3-fluorophenyl)-5(R)-(isoxazol-3-yloxymethyl)-oxazolidin-2-one hydrochloride salt (270 mg, 0.67 mmol) was stirred in pyridine (5 ml) at ambient temperature. A solution of 2,2-dimethyl-1,3-dioxolane-4(S)-carbonyl chloride (~50% strength, 270 mg, 0.85 mmol) in dichloromethane (2 ml) was added dropwise, and the mixture stirred 18 hours. Solvent was evaporated, and the residue partitioned between EtOAc (20 ml) and water (20 ml). The organic layer was washed with 5% aqueous sodium bicarbonate, brine, then dried (magnesium sulfate) and evaporated. The residue was azeotroped with toluene (15 ml), and purified by chromatography on a 10 g silica Mega Bond Elut® column, eluting with a gradient increasing in polarity from 0 to 100% EtOAc in dichloromethane. Relevant fractions were combined and evaporated to give the desired product (205 mg).

MS (ESP): 491 (MH$^+$) for $C_{23}H_{27}FN_4O_7$; NMR (DMSO-$d_6$) δ: 1.32 (s, 1H); 1.37 (s, 3H); 1.91 (hextet, 1H); 2.13 (hextet, 1H); 3.23 (m, 1H); 3.29 (m overlapped by $H_2O$, ~1H); 3.38 (m, 1H); 3.49 (m, 1H); 3.86 (dd, 1H); 3.94 (dd, 1H); 4.14 (t overlapping m, 2H); 4.37 (m, 1H); 4.43

(overlapping m, 3H); 5.04 (m, 1H); 6.40 (d, 1H); 6.76 (t, 1H); 7.14 (dd, 1H); 7.42 (dd, 1H); 8.00 (d, 1H); 8.69 (d, 1H).

EXAMPLE 119

3-(4-((3S)-3-(2(S),3-Dihydroxypropanoylamino)-1-pyrrolidinyl)-3-fluorophenyl)-5(R)-(isoxazol-3-yloxymethyl)oxazolidin-2-one 3-(4-((3S)-3-(2,2-Dimethyl-1,3-dioxolane-4(S)-carbonamido)-1-pyrrolidinyl)-3-fluorophenyl)-5(R)-(isoxazol-3-yloxymethyl)oxazolidin-2-one (170 mg, 0.35 mmol) was dissolved in tetrahydrofuran (6 ml), treated with 2 M aqueous hydrochloric acid (1 ml), and stirred at ambient temperature for 17 hours. After dilution with MeOH (10 ml), MP-Carbonate scavenger resin (Argonaut Technologies, 2 g) was added. and the mixture stirred 1 hour. Resin was filtered off, the filtrate evaporated, and the residue evaporated with MeOH/water (1:1, 10 ml, 3 times). and triturated with diethyl ether to give the desired product (125 mg). MS (ESP): 451 (MH$^+$) for $C_{20}H_{23}FN_4O_7$.

NMR (DMSO-d$_6$) δ: 1.91 (hextet, 1H); 2.12 (hextet, 1H); 3.19 (m, 1H); 3.28 (m overlapped by H$_2$O, ~1H); 3.46 (overlapping m, 3H); 3.56 (m, 1H); 3.84 (overlapping m, 2H); 4.13 (t, 1H); 4.33 (dd, 1H); 4.44 (m, 2H); 4.68 (t, 1H); 5.02 (m, 1H); 5.49 (d, 1H); 6.39 (d, 1H); 6.76 (t, 1H); 7.12 (dd, 1H); 7.43 (dd, 1H); 7.84 (d, 1H); 8.69 (d, 1H).

EXAMPLE 120

3-(4-((3S)-3-Amino-1-pyrrolidinyl)-3-fluorophenyl)-5(R)-(3-(1,2,5-thiadiazolyl)oxymethyl)oxazolidin-2-one Using essentially the technique of Example 113, starting from 3-(4-((3S)-3-t-butoxycarbonylamino-1-pyrrolidinyl)-3-fluorophenyl)-5(R)-(3-(1,2,5-thiadiazolyl)oxymethyl) oxazolidin-2-one (1 g, 2.09 mmol) gave the title product as its hydrochloride (850 mg). MS (ESP): 380 (MH$^+$) for $C_{16}H_{18}FN_5O_3S$.

NMR (DMSO-d$_6$) δ: 2.06 (m, 1H); 2.26 (m, 1H); 3.27 (dd, 1H); 3.42 (m overlapped by solvent, 1H); 3.54 (m, 2H); 3.82 (m, 1H); 3.89 (dd, 1H); 4.16 (t, 1H); 4.65 (m, 2H); 5.06 (m, 1H); 6.79 (t, 1H); 7.16 (dd, 1H); 7.45 (dd, 1H); 8.42 (s, 1H); 8.49 (br, 3H).

The intermediate for this compound was prepared as follows:

3-(4-((3S)-3-t-Butoxycarbonylamino-1-pyrrolidinyl)-3-fluorophenyl)-5(R)-(3-(1,2,5-thiadiazolyl)oxymethyl)oxazolidin-2-one The title compound was prepared using essentially the method of Example 67, starting from 3-(4-((3S)-3-t-butoxycarbonylamino-1-pyrrolidinyl)-3-fluorophenyl)-5(R)-hydroxymethyl)oxazolidin-2-one (2.0 g, 5.06 mmol), and purifying by chromatography on a 90 g Biotage silica column, eluting with a gradient increasing in polarity from 0 to 5% EtOAc in dichloromethane. Relevant fractions were combined, evaporated, and the residue recrystallised from toluene (20 ml) to give the desired product (1.67 g).

MS (ESP): 480 (MH$^+$) for $C_{21}H_{26}FN_5O_5S$; NMR (DMSO-d$_6$) δ: 1.37 (s, 9H); 1.81 (hextet, 1H); 2.08 (hextet, 1H); 3.11 (m, 1H); 3.26 (m overlapped by H$_2$O, ~1H); 3.37 (dd, 1H); 3.48 (t, 1H); 3.88 (dd, 1H); 4.05 (m, 1H); 4.14 (t, 1H); 4.64 (m, 2H); 5.06 (m, 1H); 6.71 (t, 1H); 7.11 (dd overlapping br, 2H); 7.48 (dd, 1H); 8.42 (s, 1H).

EXAMPLE 121

3-(4-((3S)-3-Acetamido-1-pyrrolidinyl)-3-fluorophenyl)-5(R)-(3-(1,2,5-thiadiazolyl)oxymethyl)oxazolidin-2-one The title compound was prepared using essentially the method of Example 115, starting from 3-(4-((3S)-3-amino-1-pyrrolidinyl)-3-fluorophenyl)-5(R)-(3-(1,2,5-thiadiazolyl)oxymethyl)oxazolidin-2-one hydrochloride salt (250 mg, 0.60 mmol). Work-up involved separating the organic layer, washing with aqueous sodium dihydrogen phosphate (2%), brine, and drying (magnesium sulfate). Evaporation gave the desired product (170 mg). MS (ESP): 422 (MH$^+$) for $C_{18}H_{20}FN_5O_4S$.

NMR (DMSO-d$_6$) δ: 1.79 (s overlapping m, 4H); 2.11 (hextet, 1H); 3.11 (m, 1H); 3.26 (m overlapped by H$_2$O, ~1H); 3.41 (dd, 1H); 3.49 (m, 1H); 3.88 (dd, 1H); 4.14 (t, 1H); 4.28 (dd, 1H); 4.65 (m, 2H); 5.07 (m, 1H); 6.74 (t, 1H); 7.11 (dd, 1H); 7.42 (dd, 1H); 8.08 (d, 1H); 8.42 (s, 1H).

EXAMPLE 122

3-(4-((3S)-3-Methanesulfonamino-1-pyrrolidinyl)-3-fluorophenyl)-5(R)-(3-(1,2,5-thiadiazolyl)oxymethyl)oxazolidin-2-one The title compound was prepared using essentially the method of Example 115, starting from 3-(4-((3S)-3-amino-1-pyrrolidinyl)-3-fluorophenyl)-5(R)-(3-(1,2,5-thiadiazolyl)oxymethyl)oxazolidin-2-one hydrochloride salt (250 mg, 0.60 mmol) and methanesulfonyl chloride. The same work-up gave the desired product (183 mg).

MS (ESP): 458 (MH$^+$) for $C_{17}H_{20}FN_5O_5S_2$; NMR (DMSO-d$_6$) δ: 1.87 (hextet, 1H); 2.20 (hextet, 1H); 2.94 (s, 3H) 3.21 (m, 1H); 3.31 (t, 1H); 3.38 (m overlapped by H$_2$O, ~1H); 3.56 (m, 1H); 3.89 (dd, 1H); 3.98 (dd, 1H); 4.15 (t, 1H); 4.65 (m, 2H); 5.07 (m, 1H); 6.74 (t, 1H); 7.13 (dd, 1H); 7.36 (d, 1H); 7.40 (dd, 1H); 8.42 (s, 1H).

EXAMPLE 123

3-(4-((3S)-3-Acetoxyacetylamino-1-pyrrolidinyl)-3-fluorophenyl)-5(R)-(3-(1,2,5-thiadiazolyl)oxymethyl)oxazolidin-2-one The title compound was prepared using essentially the method of Example 73, starting from 3-(4-((3S)-3-amino-1-pyrrolidinyl)-3-fluorophenyl)-5(R)-(3-(1,2,5-thiadiazolyl)oxymethyl)oxazolidin-2-one hydrochloride salt (350 mg, 0.84 mmol) and acetoxy,acetyl chloride. Work-up involved separating the organic layer, washing with aqueous sodium dihydrogen phosphate (10%), aqueous sodium bicarbonate (5%), and drying (magnesium sulfate). Evaporation and trituration with diethyl ether/isohexane (1:1, 10 ml) gave the desired product (187 mg).

MS (ESP): 480 (MH$^+$) for $C_{20}H_{22}FN_5O_8$; NMR (DMSO-d$_6$) δ: 1.86 (hextet, 1H); 2.07 (s, 3H); 2.14 (hextet, 1H); 3.16 (m, 1H); 3.26 (m overlapped by H$_2$O, ~1H); 3.42 (m, 1H); 3.51 (dd, 1H); 3.89 (dd, 1H); 4.14 (t, 1H); 4.33 (hextet, 1H); 4.43 (s, 2H); 4.67 (m, 2H); 5.07 (m, 1H); 6.76 (t, 1H); 7.14 (dd, 1H); 7.43 (dd, 1H); 8.26 (d, 1H); 8.45 (s, 1H).

EXAMPLE 124

3-(4-((3S)-3-Hydroxyacetylamino-1-pyrrolidinyl)-3-fluorophenyl)-5(R)-(isoxazol-3-yloxymethyl)oxazolidin-2-one The title compound was prepared using essentially the method of Example 74, starting from 3-(4-((3S)-3-acetoxyacetylamino-1-pyrrolidinyl)-3-fluorophenyl)-5(R)-(3-(1,2,5-thiadiazolyl)oxymethyl)oxazolidin-2-one (136 mg, 0.28 mmol). Evaporation of the reaction mixture and trituration of the residue with water gave the desired product (0.27 g). MS (ESP): 438 (MH$^+$) for $C_{18}H_{20}FN_5O_5S$.

NMR (DMSO-d$_6$) δ: 1.92 (hextet, 1H); 2.16 (hextet, 1H); ~3.20 (m, overlapped by H$_2$O, ~3H); 3.51 (m, overlapped by H$_2$O, ~1H); 3.81 (s, 2H); 3.91 (dd, 1H); 4.15 (t, 1H); 4.38 (hextet, 1H); 4.67 (m, 2H); 5.08 (m, 1H); 6.75 (t, 1H); 7.12 (dd, 1H); 7.41 (dd, 1H); 7.87 (d, 1H); 8.45 (s, 1H).

EXAMPLE 125

3-(4-((3S)-3-Methoxycarbonylamino-1-pyrrolidinyl)-3-fluorophenyl)-5(R)-(3-(1,2,5-thiadiazolyl)oxymethyl)oxazolidin-2-one The title compound was prepared using essentially the method of Example 115, starting from 3-(4-((3S)-3-amino-1-pyrrolidinyl)-3-fluorophenyl)-5(R)-(3-(1,2,5-thiadiazolyl)oxymethyl)oxazolidin-2-one hydrochloride salt (152 mg, 0.37 mmol) and methyl chloroformate. Work-up and trituration with diethyl ether gave the desired product (53 mg). MS (ESP): 438 (MH$^+$) for C$_{18}$H$_{20}$FN$_5$O$_5$S.

NMR (DMSO-d$_6$) δ: 1.83 (hextet, 1H); 2.12 (hextet, 1H); 3.16 (m, 1H); 3.28 (m overlapped by H$_2$O, ~1H); 3.41 (dd, 1H); 3.53 (s overlapping m, 4H); 3.89 (dd, 1H); 4.08 (m, 1H); 4.14 (t, 1H); 4.64 (m, 2H); 5.06 (m, 1H); 6.74 (t, 1H); 7.12 (dd, 1H); 7.40 (dd, 1H); 7.43 (s, 1H); 8.45 (s, 1H).

EXAMPLE 126

3-(4-((3S)-3-(2,2-Dimethyl-1,3-dioxolan-4(S)-ylcarbonamido)-1-pyrrolidinyl)-3-fuorophenyl)-5(R)-(3-(1,2,5-thiadiazolyloxymethyl)oxazolidin-2-one The title compound was prepared using essentially the method of Example 115, starting from 3-(4-((3S)-3-amino-1-pyrrolidinyl)-3-fluorophenyl)-5(R)-(3-(1,2,5-thiadiazolyl)oxymethyl)oxazolidin-2-one hydrochloride salt (336 mg, 0.81 mmol). Work-up and chromatography gave the desired product (210 mg).

MS (ESP): 508 (MH$^+$) for C$_{22}$H$_{26}$FN$_5$O$_6$S; NMR (DMSO-d$_6$) δ: 1.32 (s, 3H); 1.38 (s, 3H); 1.89 (hextet, 1H); 2.13 (hextet, 1H); 3.21 (m overlapped by H$_2$O, ~2H); 3.38 (t, 1H); 3.48 (m, 1H); 3.90 (dd, 1H); 3.92 (dd, 1H); 4.12 (dd, 1H); 4.14 (t, 1H); 4.37 (dd, 1H); 4.42 (t, 1H); 4.64 (m, 2H); 5.06 (m, 1H); 6.74 (t, 1H); 7.11 (dd, 1H); 7.40 (dd, 1H); 7.94 (d, 1H); 8.42 (d, 1H).

EXAMPLE 127

3-(4-((3S)-3-(2(S),3-Dihydroxypropanoylamino)-1-pyrrolidinyl)-3-fluorophenyl)-5(R)-(3-(1,2,5-thiadiazolyl)oxymethyl)oxazolidin-2-one The title compound was prepared using essentially the method of Example 119, starting from 3-(4-((3S)-3-((4S)-2,2-dimethyl-1,3-dioxoiane-4-carbonamido)-1-pyrrolidinyl)-3-fluorophenyl)-5(R)-(3-(1,2,5-thiadiazolyl)oxymethyl)oxazolidin-2-one (165 mg, 0.33 mmol). For work-up the aqueous organics were treated with solid potassium carbonate, filtered and evaporated to dryness and the residue triturated with diethyl ether to give the desired product (90 mg).

MS (ESP): 468 (MH$^+$) for C$_{19}$H$_{22}$FN$_5$O$_6$S; NMR (DMSO-d$_6$) δ: 1.92 (hextet, 1H); 2.13 (hextet, 1H); 3.17 (m, 1H); 3.30 (m overlapped by H$_2$O, ~1H); 3.48 (overlapping m, 3H); 3.56 (m, 1H); 3.87 (m, 1H); 3.90 (dd, 1H); 4.14 (t, 1H); 4.34 (hextet, 1H); 4.66 (overlapping m, 3H); 5.07 (m, 1H); 5.48 (br, 1H); 6.76 (t, 1H); 7.13 (dd, 1H); 7.43 (dd, 1H); 7.85 (d, 1H), 8.46 (s, 1H).

EXAMPLE 128

3-(4-(4-(6-Cyano-3-pyridazinyl)piperazin-1-yl)-3-fluorophenyl)-5(R)-(isoxazol-3-yl)oxymethyloxazolidin-2-one 3-(4-(4-(6-Cyano-3-pyridazinyl)piperazin-1-yl)-3-fluorophenyl)-5(R)-hydroxy methyloxazolidin-2-one (398 mg, 1 mmol), 3-hydroxyisoxazole (93.5 mg, 1.1 mmol) and triphenylphosphine (328 mg, 1.25 mmol), were suspended with stirring in dry tetrahydrofiran (10 ml). Diisopropylazodicarboxylate (242 mg, 1.2 mmol) was added dropwise by syringe, and the mixture stirred at ambient temperature for 30 minutes. The reaction mixture was filtered, evaporated to dryness, dissolved in EtOAc/isohexane (1:1), and applied to a 10 g silica Mega Bond Elut® column, eluting with a gradient from 75 to 100% EtOAc in isohexane. Relevant fractions were combined and evaporated to give the title compound (120 mg).

MS (ESP): 466 (MH$^+$) for C$_{22}$H$_{20}$FN$_7$O$_4$; NMR (DMSO-d$_6$) δ: 3.08 (t, 4H); 3.89 (overlapping m, 5H); 4.16 (t, 1H); 4.45 (m, 2H); 5.05 (m, 1H); 6.37 (d, 1H); 7.10 (t, 1H); 7.21 (dd, 1H); 7.40 (d, 1H); 7.53 (dd, 1H); 7.88 (d, 1H); 8.67 (d, 1H).

The intermediates for this compound were prepared as follows:

3-(3-Fluoro-4-(piperazin-1-yl)phenyl)-5(R)-hydroxymethyloxazolidin-2-one hydrochloride 3-(3-Fluoro-4-(4-t-butoxycarbonylpiperazin-1-yl)phenyl)-5(R)-hydroxymethyloxazolidin-2-one (WO 93/23384; 43.1 g, 0.11 M) was suspended by stirring in ethanol (1000 ml) under nitrogen. An ethanol solution of hydrogen chloride (3.8 M, 400 ml) was added slowly, to give a solution. The mixture was stirred at ambient temperature for 18 hours. The resulting precipitate was filtered, washed with diethyl ether (3×250 ml), and dried, to give the title product. A further crop was obtained by evaporation of the mother liquors. Total yield: 38.7 g.

MS (ESP): 296 (MH$^+$) for C$_{14}$H$_{18}$FN$_3$O$_3$; NMR (DMSO-d$_6$) δ: 3.17 (m, 8H); 3.53 (dd, 1H); 3.64 (dd, 1H); 3.79 (dd, 1H); 4.03 (t, 1H); 4.66 (m, 1H); 7.10 (t, 1H); 7.21 (dd, 1H); 7.52 (dd, 1H); 9.39 (br s, 2H).

3-(4-(4-(6-cyano-3-pyridazinyl)piperazin-1-yl)-3-fluorophenyl)-5(R)-hydroxymethyloxazolidin-2-one 3-(3-Fluoro4-(piperazin-1-yl)phenyl)-5(R)-hydroxymethyloxazolidin-2-one hydrochloride (6.63 g, 20 mmol) was suspended by stirring in acetonitrile (200 ml) under nitrogen, and triethylamine (4.44 g, 44 mmol) added. The mixture was stirred for 10 minutes 3-chloro-6-cyanopyridazine (2.79 g, 20 mmol) added, and the mixture heated under reflux for 18 hours. After cooling, solid was filtered, washed with water (3×150 ml) and diethyl ether (2×150 ml) to give the title product (6.3 g).

MS (ESP): 398 (MH$^+$) for C$_{20}$H$_{20}$FN5O$_3$; NMR (DMSO-d$_6$) δ: 3.03 (t, 4H); 3.54 (m, 1H); 3.63 (m, 1H); 3.78 (t overlapping m, 5H); 4.03 (t, 1H); 4.66 (m, 1H); 5.18 (t, 1H); 6.97 (d, 1H); 7.07 (t, 1H); 7.20 (dd, 1H); 7.53 (dd, 1H); 7.85 (dd, 1H); 8.49 (d, 1H).

EXAMPLE 129

3-(3-Fluoro4-(2-methyl-imidazol-1-yl)phenyl)-5(R)-(3-(1,2,5-thiadiazolyl)oxymethyl)oxazolidin-2-one Using essentially the same procedure as for the intermediate of Example 65, but starting with 3-(3-fluoro-4-(2-methyl-imidazol-1-yl)phenyl)-5(R)-hydroxymethyloxazolidin-2-one (582 mg, 2.0 mmol) and 3-hydroxy-1,2,5-thiadiazole (224 mg, 2.2 mmol), and purifying by chromatography on a 10 g silica Mega Bond Elut® column, eluting with a gradient increasing in polarity from 0 to 10% MeOH in dichloro-methane, the title compound was prepared (160 mg).

MS (ESP): 376 (MH$^+$) for C$_{16}$H$_{14}$FN$_5$O$_3$S; NMR (DMSO-d$_6$) δ: 2.15 (s, 3H); 4.02 (dd, 1H); 4.27 (t, 1H); 4.66

(dd, 1H); 4.72 (dd, 1H); 5.18 (m, 1H); 6.92 (d, 1H); 7.20 (d, 1H); 7.48 (dd, 1H); 7.55 (t, 1H); 7.74 (dd, 1H); 8.42 (s, 1H).

EXAMPLE 130

3-(4-(4-Hydroxymethylimidazol-1-yl)-3-fluorophenyl)-5(R)-(3—(1,2,5-thiadiazolyl)methyl)oxazolidin-2-one Essentially the same procedure as for the intermediate of Example 65 was used, but starting with 3-(4-(4-t-butyldimethylsilyloxymethylimidazol-1-yl)-3-fluorophenyl)-5(R)-hydroxymethyloxazolidin-2-one (842 mg, 2.0 mmol) and 3-hydroxy-1,2,5-thiadiazole (224 mg, 2.2 mmol). After filtration of reduced azo compound, the solution was treated with 10% TFA in acetonitrile (10 ml), evaporated to dryness and purified by chromatography on a 10 g silica Mega Bond Elut® column, eluting with a gradient increasing in polarity from 0 to 20% MeOH in dichloromethane, to give the title compound (65 mg). MS (ESP): 392 (MH$^+$) for $C_{16}H_{14}FN_5O_4S$.

NMR (DMSO-d$_6$) δ: 4.02 (dd, 1H); 4.27 (t, 1H); 4.50 (s, 2H); 4.60 (br, 1H); 4.66 (dd, 1H); 4.72 (dd, 1H); 5.18 (m, 1H); 7.53 (dd, 1H); 7.69 (s, 1H); 7.74 (t, 1H); 7.80 (dd, 1H); 8.42 (s, 1H); 8.81 (s, 1H).

EXAMPLE 131

3-(4-(1-(2,2-Dimethyl-1,3-dioxolan-4(S)-ylmethoxycarbonyl)-1,2,5,6-tetrahydro-4-pyridinyl)-3-fluorophenyl)-5(R)-(isoxazol-3-yloxymethyl)oxazolidin-2-one 3-(4-(1,2,5,6-Tetrahydro4-pyridinyl)-3-fluorophenyl)-5(R)-(isoxazol-3-yloxymethyl)-oxazolidin-2-one hydrochloride (144 mg, 0.36 mmol) was stirred in dichloromethane (5 ml) at ambient temperature, and treated with diisopropylethylamine (67 mg, 0.52 mmol) to give a solution. A solution of (4S)-2,2-dimethyl4-(1,3-dioxolane)methyl 4-nitrophenyl carbonate (202 mg, 0.68 mmol) in dichloromethane (2.5 ml) was added dropwise, and the mixture stirred 18 hours. The mixture was diluted with dichloromethane (10 ml), and washed with water (4×15 ml). After drying (magnesium sulfate), the residue after evaporation was purified by chromatography on a 10 g silica Mega Bond Elut® column, eluting with a gradient increasing in polarity from 0 to 5% MeOH in dichloromethane. Relevant fractions were combined and evaporated to give the desired product (152 mg). MS (ESP): 518 (MH$^+$) for $C_{25}H_{28}FN_3O_8$.

NMR (DMSO-d$_6$) δ: 1.26 (s, 3H); 1.31 (s, 3H); 2.43 (m, 2H); 3.56 (m, 2H); 3.69 (dd, 1H); 3.92 (dd, 1H); 4.02 (overlapping m, 4H); 4.11 (dd, 1H); 4.20 (t, 1H); 4.25 (m, 1H); 4.44 (dd, 1H); 4.49 (dd, 1H); 5.06 (m, 1H); 5.98 (br s, 1H); 6.36 (d, 1H); 7.31 (dd, 1H); 7.37 (t, 1H); 7.49 (dd, 1H); 8.66 (d, 1H).

EXAMPLE 132

3-(4-(1-(2(S),3-Dihydroxypropyloxycarbonyl)-1,2,5,6-tetrahydro-4-pyridinyl)-3-fluorophenyl)-5(R)-(isoxazol-3-yloxymethyl)oxazolidin-2-one 3-(4-(1-(2,2-Dimethyl-1,3-dioxolan-4(S)-ylmethoxycarbonyl)-1,2,5,6-tetrahydro-4-pyridinyl)-3-fluorophenyl)-5(R)-(isoxazol-3-yloxymethyl)oxazolidin-2-one (130 mg, 0.25 mmol) was dissolved in tetrahydrofuran (5 ml), treated with 2 M aqueous hydrochloric acid (2 ml), and stirred at ambient temperature for 72 hours. Excess potassium carbonate was added to remove acid and water, and the solution filtered. The filtrate was evaporated, and the residue purified by chromatography on a 10 g silica Biotage column, eluting with a gradient increasing in polarity from 0 to 10% MeOH in dichloromethane. Relevant fractions were combined and evaporated to give the desired product (103 mg). MS (ESP): 478 (MH$^+$) for $C_{22}H_{24}FN_3O_8$.

NMR (DMSO-d6) δ: 2.42 (m, 2H); 3.37 (t, 2H); 3.57 (m, 2H); 3.65 (dd, 1H); 3.93 (overlapping m, 2H); 4.06 (overlapping m, 3H); 4.19 (t, 1H); 4.47 (m, 2H); 4.59 (t, 1H); 4.84 (d, 1H); 5.07 (m, 1H); 5.99 (br s, 1H); 6.37 (d, 1H); 7.32 (dd, 1H); 7.39 (t, 1H); 7.51 (dd, 1H); 8.78 (d, 1H).

EXAMPLE 133

3-(4-(1-(2,2-Dimethyl-1,3-dioxolan-4(S)-ylmethoxycarbonyl)-1,2,5,6-tetrahydro-4-pyridinyl)-3,5-difluorophenyl)-5(R)-(isoxazol-3-yloxymethyl)oxazolidin-2-one Using essentially the same procedure as for Example 131, but starting with 3-(4-(1,2,5,6-tetrahydro-4-pyridinyl)-3,5-difluorophenyl)-5(R)-(isoxazol-3-yloxymethyl)oxazolidin-2-one hydrochloride (151 mg, 0.36 mmol), gave the title compound (170 mg).

MS (ESP): 536 (MH$^+$) for $C_{25}H_{27}F_2N_3O_8$; NMR (DMSO-d$_6$) δ: 1.26 (s, 3H); 1.32 (s, 3H); 2.31 (m, 2H); 3.58 (m, 2H); 3.69 (dd, 1H); 3.91 (dd, 11H); 4.03 (overlapping m, 4H); 4.12 (dd, 1H); 4.18 (t, 1H); 4.26 (m, 1H); 4.43 (m, 2H); 5.08 (m, 1H); 5.85 (br s, 1H); 6.37 (d, 1H); 7.34 (d, 2H); 8.67 (d, 1H).

EXAMPLE 134

3-(4-(1-(2(S),3-Dihydroxypronyloxycarbonyl)-1,2,5,6-tetrahydro-4-pyridinyl)-3,5-difluorophenyl)-5(R)-(isoxazol-3-yloxymethyl)oxazolidin-2-one Using essentially the same procedure as for Example 132, but starting with 3-(4-(1-(2,2-dimethyl-1,3-dioxolan-4(S)-ylmethoxycarbonyl)-1,2,5,6-tetrahydro-4-pyridinyl)-3,5-difluorophenyl)-5(R)-(isoxazol-3-yloxymethyl)oxazolidin-2-one (140 mg, 0.26 mmol), gave the title compound (116 mg). MS (ESP): 496 (MH$^+$) for $C_{22}H_{23}F_2N_3O_8$.

NMR (DMSO-d$_6$) δ: 2.32 (m, 2H); 3.36 (t, 2H); 3.59 (m, 2H); 3.66 (dd, 1H); 3.94 (overlapping m, 2H); 4.06 (overlapping m, 3H); 4.19 (t, 1H); 4.49 (m, 2H); 4.57 (t, 1H); 4.85 (d, 1H); 5.10 (m, 1H); 5.87 (br s, 1H); 6.37 (d, 1H); 7.34 (d, 2H); 8.78 (d, 1H).

EXAMPLE 135

3-(4-(1-(2-Hydroxyethoxycarbonyl)-1,2,5,6-tetrahydro-4-pyridinyl)-3-fluorophenyl)-5(R)-(isoxazol-3-yloxymethyl)oxazolidin-2-one Resin bound 3-(4-(1-(2-hydroxyethoxycarbonyl)-1,2,5,6-tetrahydro-4-pyridinyl)-3-fluorophenyl)-5(R)-(isoxazol-3-yloxymethyl)oxazolidin-2-one (200 mg, 0.118 mmol) was swelled in dichloromethane (2 ml) over 1 hour. Solvent was drained, and the resin treated with TFA (1% in dichloromethane, 2 ml), to develop a red colour from bound trityl cation. The resin was washed with dichloromethane (6×1 ml), and the combined washings evaporated to dryness, then azeotroped with 3 portions of isohexane/dichloromethane to give the title compound (46 mg) as a white powder.

MS (ESP): 448 (MH$^+$) for $C_{21}H_{22}FN_3O_7$. NMR (DMSO-d$_6$) δ: 2.42 (m, 2H); 3.56 (m, 4H); 3.92 dd, 1H); 4.02 (m, 4H); 4.19 (t, 1H); 4.45 (m, 2H); 5.07 (m, 1H); 5.98 (s, 1H); 6.36 (d, 1H); 7.32 (dd, 1H); 7.39 (t, 1H); 7.48 (dd, 1H); 8.66 (d, 1H).

The intermediate for this compound was prepared as follows:
Resin bound 2-hydroxyethyl 4-nitrophenyl carbonate Ethylene glycol 2-chlorotrityl resin (Novabiochem, polystyrene backbone, 0.59 mmol /g, 400 mg, 0.236 mmol) was swelled in based washed dichloromethane (2 ml) over 30 minutes. Solvent was drained, and a premixed solution of 4-nitrophenyl chloroformate (237 mg, 1.18 mmol) and triethylamine (357 mg, 3.54 mmol) in base washed dichloromethane (2 ml) was added, and the mixture shaken for 18 hours. Solvent and reagents were drained, and the resin washed with dichloromethane (6×1 ml), then diethyl ether (2×2 ml) to give title product. IR (single bead) v: 1767 $cm^{-1}$
Resin bound 3-(4-(1-(2-hydroxyethoxycarbonyl)-1,2,5,6-tetrahydro-4-pyridinyl)-3-fluorophenyl)-5(R)-(isoxazol-3-yloxymethyl)oxazolidin-2-one Resin bound 2-hydroxyethyl 4-nitrophenyl carbonate (200 mg, 0.118 mmol) was swelled in based washed dichloromethane (2 ml) over 30 minutes. Solvent was drained, and a premixed solution of 1,2,5,6-tetrahydro-4-pyridinyl)-3-fluorophenyi)-5(R)-(isoxazol-3-yloxymethyl)-oxazolidin-2-one hydrochloride (233 mg, 0.59 mmol) and diisopropyl-ethylamine (227 mg, 1.77 mmol) in base washed dichloromethane (3 ml) was added, and the mixture shaken for 6 hours. Solvent and reagents were drained, and the resin washed with dichloromethane (6×1 ml), then diethyl ether (2×2 ml) to give title product. IR (single bead) v: 1761, 1695 $cm^{-1}$

EXAMPLE 136

3-(4-(1-(2-Hydroxyethoxycarbonyl)-1,2,5,6-tetrahydro-4-pyridinyl)-3,5-difluorophenyl)-5(R)-(isoxazol-3-yloxymethyl)oxazolidin-2-one Using the same technique as in Example 135 but starting from resin bound 3-(4-(1-(2-hydroxyethoxycarbonyl)-1,2,5,6-tetrahydro-4-pyridinyl)-3,5-difluorophenyl)-5(R)-(isoxazol-3-yloxymethyl)oxazolidin-2-one (200 mg, 0.118 mmol), gave the title compound (44 mg) as a gum. MS (ESP): 466 (MH$^+$) for $C_{21}H_{21}F_2N_3O_7$.

NMR (DMSO-d$_6$) δ: 2.30 (m, 2H); 3.54 (m, 4H); 3.90 dd, 1H); 4.03 (m, 4H); 4.18 (t, 1H); 4.45 (m, 2H); 5.08 (m, 1H); 5.85 (s, 1H); 6.35 (d, 1H); 7.32 (d, 2H); 8.66 (d, 1H).

The intermediate for this compound was prepared as follows:
Resin bound 3-(4-(1-(2-hydroxyethoxycarbonyl)-1,2,5,6-tetrahydro-4-pyridinyl)-3,5-difluorophenyl)-5(R)-(isoxazol-3-yloxymethyl)oxazolidin-2-one
Using the same technique as in Example 72 but using from 3-(4-(1-(2-hydroxyethoxycarbonyl)-1,2,5,6-tetrahydro-4-pyridinyl)-3,5-difluorophenyl)-5(R)-(isoxazol-3-yloxymethyl)oxazolidin-2-one hydrochloride (244 mg, 0.118 mmol), gave the title product. IR (single bead) v: 1764, 1696 $cm^{-1}$

EXAMPLE 137

3-(4-(1-Benzyl-1,2,5,6-tetrahydro-4-pyridinyl)-3,5-difluorophenyl)-5-(3-methyl-5(R)-isoxazolyloxymethyl)oxazolidin-2-one 3-(4-(1-Benzyl-1,2,5,6-tetrahydro-4-pyridinyl)-3,5-difluorophenyl)-5(R)-hydroxymethyloxazolidin-2-one (1.28 g, 3.2 mmol), 3-methyl-5-hydroxyisoxazole (291 mg, 3.5 mmol), and tributylphosphine (0.97 g, 4.8 mmol) were dissolved by stirring in dry tetrahydrofuran (20 ml) under nitrogen. The mixture was cooled in an ice-bath, and 1,1'-(azodicarbonyl)dipiperidine (1.21 g, 4.8 mmol) added dropwise over 10 minutes. The solution was stirred 18 hours. allowing the temperature to rise to ambient. Reduced azo compound was filtered off, and the solution evaporated to dryness. The residue was purified by chromatography on a 90 g Biotage silica column, eluting with 1:1 diethyl ether/dichloromethane. Relevant fractions were combined and evaporated to give the title product (0.58 g). Starting isoxazole described in Bull. Soc. Chim. France, 1970, 2690.

MS (ESP): 482 (MH$^+$) for $C_{26}H_{25}F_2N_3O_4$; NMR (500 MHz, DMSO-d$_6$) δ: 2.20 (s, 3H); 2.43 (br s, 2H); 2.70 (t, 2H); 3.18 (m, 2H); 3.65 (s, 2H); 3.95 (dd, 2H); 4.13 (t, 1H); 4.40 (dd, 1H); 4.50 (dd, 1H); 4.97 (m, 1H); 5.15 (s, 1H); 5.81 (s, 1H); 7.13 (d, 2H); 7.26 (t, 1H); 7.33 (m, 2H); 7.37 (m, 1H).

EXAMPLE 138

3-(3-Fluoro-4-(4-methyl-imidazol-1-yl)phenyl)-5(R)-(5-(1 2,3-triazolyl)-thiomethyl)oxazolidin-2-one 3-(3-fluoro-4-(4-methyl-imidazol-1-yl)phenyl)-5(R)-methanesulfonyloxymethyloxazolidin-2-one (see Example 141; 369 mg, 1 mmol) and 5-mercapto-1,2,3-tnrazole sodium salt (186 mg, 1.5 mmol), were dissolved in DMF (7 ml), then heated at 75° for 1 hour. The mixture was diluted with sodium bicarbonate solution (5%, 25 ml), extracted with EtOAc (50 ml), washed with water (2×15 ml), brine (15 ml), dried (magnesium sulfate) and purified by chromatography on a 10 g silica Mega Bond Elut® column, eluting with a gradient increasing in polarity from 0 to 10% MeOH in dichloromethane. to give the title compound (110 mg).

MS (ESP): 375 (MH$^+$) for $C_{16}H_{15}FN_6O_2S$; NMR (DMSO-d$_6$) δ: 2.14 (s, 3H); 3.31 (m, 2H); 3.91 (dd, 1H); 4.26 (t, 1H); 4.89 (m, 1H); 7.22 (s, 1H); 7.42 (dd, 1H); 7.61 (t, 1H); 7.73 (dd, 1H); 7.87 (s, 1H); 8.02 (s, 1H); 15.23 (br, 1H).

EXAMPLE 139

3-(3-Fluoro-4-(4-methyl-imidazol-1-yl)phenyl)-5(R)-(5-(1-methyltetrazolyl)thiomethyl)oxazolidin-2-one Using the same technique as in Example 138 but starting from 1-methyl-5-mercapto-tetrazole (174 mg, 1.5 mmol), gave the title compound (220 mg).

MS (ESP): 390 (MH$^+$) for $C_{16}H_{16}FN_7O_2S$; NMR (DMSO-d$_6$) δ: 2.16 (s, 3H); 3.73 (d, 2H); 3.96 (s overlapping dd, 4H); 4.28 (t, 1H); 5.04 (m, 1H); 7.22 (s, 1H); 7.45 (dd, 1H); 7.64 (t, 1H); 7.72 (dd, 1H); 7.87 (s, 1H).

EXAMPLE 140

3-(4-(4-Methylimidazol-1-yl)-3-fluorophenyl)-5(R)-(3-(1,2,5-thiadiazolyl)methyl)oxazolidin-2-one Sodium hydride (50% in oil, 72 mg, 1.5 mmol) was stirred in suspension in DMF (7 ml) under nitrogen at ambient temperature. 3-Hydroxy-1,2,5-thiadiazole (153 mg, 1.5 mmol) was added and stirring continued for 10 minutes. then 3-(3-fluoro-4-(4-methyl-imidazol-1-yl)phenyl)-5(R)-methanesulfonyloxymethyloxazolidin-2-one (369 mg, 1 mmol) was added and the mixture heated at 750 for 2 hours. The mixture was diluted with sodium bicarbonate solution (5%, 25 ml), extracted with EtOAc (50 ml), washed with water (2×15 ml), brine (15 ml), dried (magnesium sulfate) and purified by chromatography on a 10 g silica Mega Bond Elut® column, eluting with a gradient increasing in polarity from 0 to 10% MeOH in dichloromethane, to give the title compound (330 mg). MS (ESP): 376 (MH$^+$) for $C_{16}H_{14}FN_5O_3S$.

NMR (DMSO-d$_6$) δ: 2.17 (s, 3H); 4.02 (dd, 1H); 4.26 (t, 1H); 4.80 (m, 2H); 5.16 (m, 1H); 7.22 (s, 1H); 7.48 (dd, 1H); 7.63 (t, 1H); 7.77 (dd, 1H); 7.88 (s, 1H); 8.47 (s, 1H).

EXAMPLE 141

3-(4-5-Methylimidazol-1-yl)-3-fluorophenyl)-5(R)-(3-(1,2,5-thiadiazolyl)methyl)oxazolidin-2-one Sodium hydride (60% in oil, 110 mg, 2.75 mmol) was added to a solution 3-hydroxyisoxazole (229 mg, 2.7 mmol) in DMF (15 ml) under nitrogen at 0°, and the mixture stirred 15 minutes. A solution of 3-(3-fluoro-4-(5-methyl-imidazol-1-yl)phenyl)-5(R)-methanesulfonyloxymethyloxazolidin-2-one (680 mg, 1.8 mmol) in DMF (7 ml) was added, and the mixture stirred 18 hours at ambient temperature. Solvent was evaporated, the residue dissolved in EtOAc (50 ml), washed with water (2×30 ml), brine (15 ml), dried (magnesium sulfate) and purified by chromatography on a 10 g silica Mega Bond Elut® column, eluting with a gradient increasing in polarity from 0 to 3% MeOH in dichloromethane, to give the title compound (149 mg).

MS (ESP): 359 (MH$^+$) for $C_{17}H_{15}FN_4O_4$; NMR (CDCl$_3$) δ: 2.12 (s, 3H); 4.03 (dd, 1H); 4.21 (t, 1H); 4.53 (dd, 1H); 4.61 (dd, 1H); 5.08 (m, 1H); 6.01 (d, 1H); 6.91 (d, 1H); 7.29 (dd, 1H); 7.36 (t, 1H); 7.48 (d, 1H); 7.71 (dd, 1H) 8.16 (d, 1H).

The intermediates for Examples 106, 140 & 141 were prepared as follows:
3-Fluoro-4-(4-methyl-imidazol-1-yl)nitrobenzene and 3-fluoro-4-(5-methyl-imidazol-1-yl)nitrobenzene 4-Methylimidazole (45.1 g, 0.55 M) and N,N-diisopropylethylamine (161 g, 1.25 M) were dissolved in acetonitrile (800 ml), and 3,4-difluoronitrobenzene (79.5 g, 0.5 M) added. The mixture was stirred and heated to reflux under nitrogen for 24 hours. Solvent was evaporated, the residue dissolved in EtOAc (800 ml), washed with water (400 ml), brine (200 ml), and dried (magnesium sulfate). The residue was dissolved in toluene (250 ml), treated with charcoal, filtered, and diluted with hot cyclohexane (75 ml) to crystallise 3-fluoro-4-(4-methyl-imidazol-1-yl)nitrobenzene (64.7 g).

MS (ESP): 222 (MH$^+$) for $C_{10}H_8FN_3O_2$; NMR (DMSO-d$_6$) δ: 2.18 (s, 3H); 7.29 (s, 1H); 7.92 (t, 1H); 8.07 (s, 1H); 8.18 (dd, 1H); 8.38 (dd, 1H).

The mother liquors were evaporated, and chromatographed on a 90 g Biotage silica column, eluting with a gradient from dichloromethane to 1:1 dichloromethane/acetonitrile. Relevant fractions were combined and evaporated to give a 2:1 mixture of the 5-methyl:4-methyl isomers (8 g). This was then subjected to HPLC on Merck Lichro Prep silica eluting with EtOAc/MeOH (95:5) at 400 ml/min to separate 3-fluoro-4-(5-methyl-imidazol-1-yl) nitrobenzene (5.2 g).

NMR (DMSO-d$_6$) δ: 2.09 (s, 3H); 6.87 (d, 1H); 7.81 (d, 1H); 7.87 (t, 1H); 8.23 (dd 1H); 8.42 (dd, 1H). MS (ESP): 222 (MH$^+$) for $C_{10}H_8FN_3O_2$.
5-Amino-2-(4-methyl-imidazol-1-yl)fluorobenzene 3-Fluoro4-(4-methyl-imidazol-1-yl)nitrobenzene (64.7 g, 0.293 M) was dissolved in a mixture of MeOH (200 ml) and tetrahydrofuran (800 ml), cooled to 0° under nitrogen, and treated with ammonium formate (99.3 g, 1.46 M) followed by palladium on charcoal (10%. 2.5 g). The mixture was stirred at ambient temperature for 48 hours, filtered through celite, celite washed with MeOH (200 ml), and filtrate evaporated to dryness. The residue was partitioned between EtOAc (800 ml) and 10% aqueous sodium bicarbonate (250 ml). The organic layer was separated, washed with brine (250 ml), dried (magnesium sulfate) and evaporated to give title compound (50.6 g).

MS (ESP): 192 (MH$^+$) for $C_{10}H_{10}FN_3$; NMR (DMSO-d$_6$) δ: 2.12 (s, 3H); 5.60 (br s, 2H); 6.42 (dd, 1H); 6.47 (dd, 1H); 6.98 (s, 1H); 7.11 (t, 1H) 7.60 (s, 1H).
5-Amino-2-(5-methyl-imidazol-1-yl)fluorobenzene Using essentially the same procedure as for the 4-methyl isomer, but starting from 3-fluoro-4-(5-methyl-imidazol-1-yl)nitrobenzene (5.2 g, 23.5 mmol) gave the title product (3.45 g). MS (ESP): 192 (MH$^+$) for $C_{10}H_{10}FN_3$;
5-Benzyloxycarbonylamino-2-(4-methyl-imidazol-1-yl) fluorobenzene 5-Amino-2-(4-methyl-imidazol-1-yl)fluorobenzene (50.6 g, 0.265 M) was dissolved in dry dichloromethane (800 ml) under nitrogen, and cooled to −5°. Pyridine (26.1 g, 0.33 M) was added, followed by benzyl chloroformate (49.9 g, 0.292 M) over 30 minutes. The mixture was stirred and the temperature allowed to rise to ambient over 16 hours. Aqueous sodium bicarbonate (5%, 350 ml) was added, the organic layer separated, and the aqueous layer re-extracted with dichloromethane (2×200 ml), and combined organics dried (magnesium sulfate). After filtration and evaporation, the residue was recrystallised from toluene (300 ml) to give title product (80 g).

MS (ESP): 326 (MH$^+$) for $C_{18}H_{16}FN_3O_2$; NMR (DMSO-d$_6$) δ: 2.15 (s, 3H); 5.16 (s, 2H); 7.13 (s, 1H); 7.31 (dd, 1H); 7.41 (m, 51H); 7.48 (t, 1H); 7.57 (dd, 1H); 7.78 (s, 1H); 10.15 (br s, 1H).
5-Benzyloxycarbonylamino-2-(5-methyl-imidazol-1-yl) fluorobenzene Using essentially the same procedure as for the 4-methyl isomer, but starting from 5-amino-2-(5-methyl-imidazol-1-yl)fluorobenzene (3.45 g, 18.1 mmol) gave the title product (3.35 g), after trituration of the crude with a mixture of diethyl ether/isohexane (1:1). MS (ESP): 326 (MH$^+$) for $C_{18}H_{16}FN_3O_2$; NMR (DMSO-d$_6$) δ: 2.00 (s, 3H); 5.17 (s 2H); 6.78 (s, 1H); 7.37 (overlapping m, 7H); 7.61 (dd, 1H); 7.63 (s, 1H); 10.21 (br s, 1H).
3-(3-Fluoro-4-(4-methyl-imidazol-1-yl)phenyl)-5(R)-hydroxymethyloxazolidin-2-one 5-Benzyloxycarbonylamino-2-(4-methyl-imidazol-1-yl) fluorobenzene (54 g, 0.166 M) was dissolved in a mixture of dry tetrahydrofuran (600 ml) and 1,3-dimethyl-2,4,5,6-tetrahydro-2(1H)-pyrimidinone (100 ml) under nitrogen, cooled to −70°, and treated with a solution of n-butyllithium (1.6 M in isohexane, 114 ml), over 30 minutes. After stirring for 30 minutes at −70°, a solution of (R)-glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and EtOAc (800 ml), and undissolved solid was removed and washed well with diethyl ether to give title product (16.3 g). The aqueous layer was further extracted with EtOAc (2×750 ml), the combined extracts dried (magnesium sulfate) and evaporated, and the residue triturated with diethyl ether. The resulting solid was recrystallisd from ethanol to give more product (10.9 g). MS (ESP): 292 (MH$^+$) for $C_{14}H_{14}FN_3O_3$.

NMR (DMSO-d$_6$) δ: 2.13 (s, 3H); 3.56 (dd, 1H); 3.68 (dd, 1H); 3.86 (dd, 1H); 4.11 (t, 1H); 4.73 (m, 1H); 5.21 (br, 1H); 7.18 (s, 1H); 7.45 (dd, 1H); 7.60 (t, 1H); 7.73 (dd, 1H); 7.83 (s, 1H).

3-(3-Fluoro-4-(5-methyl-imidazol-1-yl)phenyl)-5(R)-hydroxymethyloxazolidin-2-one 5-Benzyloxycarbonylamino-2-(5-methyl-imidazol-1-yl) fluorobenzene (3.2 g, 9.85 mmol) was dissolved in dry tetrahydrofuran (40 ml) under nitrogen, cooled to −70°, and treated with a solution of n-butyllithium (1.6 M in isohexane, 6.81 ml). After stirring for 20 minutes at −70°, (R)-glycidylbutyrate (1.57 g, 10.09 mmol) was added at −70°. Stirring was continued for 16 hours allowing the temperature to rise to ambient. The mixture was treated MeOH (10 ml), stirred 15 minutes, then poured into aqueous sodium bicarbonate (5%, 100 ml) and extracted with EtOAc (3×40 ml). The combined extracts were washed with brine (20 ml), dried (magnesium sulfate) and evaporated. and the residue purified by chromatography on a 20 g silica Mega Bond Elut® column, eluting with a gradient increasing in polarity from 5 to 10% MeOH in dichloromethane. Relevant fractions were combined and evaporated, to give the desired product (0.86 g). MS (ESP): 292 (MH$^+$) for $C_{14}H_{14}FN_3O_3$.

NMR (DMSO-d$_6$) δ: 2.03 (s, 3H); 3.57 (dt, 1H); 3.69 (dt, 1H); 3.87 (dd, 1H); 4.14 (t, 1H); 4.74 (m, 1H); 5.22 (t, 1H); 6.81 (s, 1H); 7.50 (overlapping m, 2H); 7.66 (s, 1H); 7.75 (t, 1H).

3-(3-fluoro-4-(4-methyl-imidazol-1-yl)phenyl)-5(R)-methanesulfonyloxymethyloxazolidin-2-one 3-(3-Fluoro-4-(4-methyl-imidazol-1-yl)phenyl)-5(R)-hydroxymethyloxazolidin-2-one (11.8 g, 40.5 mmol) was stirred in a mixture of pyridine (200 ml) and triethylamine (4.86 g, 48.2 mmol) under nitrogen in an ice-bath. Methanesulfonyl chloride (5.16 g, 45 mmol) was added dropwise, and the mixture stirrd for 2 hours, allowing the temperature to rise to ambient. Solvent was evaporated, and the residue stirred vigorously with a mixture of aqueous sodium bicarbonate (5%, 200 ml) and isohexane (200 ml). The precipitate was filtered, washed with water then isohexane, and dried. The residue was recrystallised from hot acetone (200 ml) by dilution with isohexane (300 ml) to give the title product (11.7 g), mp 151–153°. MS (EI): 369 (M$^+$) for $C_{15}H_{16}FN_3O_5S$.

NMR (DMSO-d$_6$) δ: 2.16 (s, 3H); 3.27 (s, 3H); 3.88 (dd, 1H); 4.24 (t, 1H); 4.47 (dd, 1H); 4.54 (dd, 1H); 5.04 (m, 1H); 7.20 (d, 1H); 7.45 (dd, 1H); 7.63 (t, 1H); 7.73 (dd, 1H); 7.85 (t, 1H).

3-(3-fluoro-4-(5-methyl-imidazol-1-yl)phenyl)-5(R)-methanesulfonyloxymethyloxazolidin-2-one 3-(3-Fluoro-4-(5-methyl-imidazol-1-yl)phenyl)-5(R)-hydroxymethyloxazolidin-2-one (0.86 g, 2.96 mmol) was stirred in a mixture of pyridine (30 ml) and triethylamine (0.36 g, 3.55 mmol) under nitrogen in an ice-bath. Methanesulfonyl chloride (0.37 g, 3.26 mmol) was added dropwise, and the mixture stirrd for 18 hours, allowing the temperature to rise to ambient. Solvent was evaporated. and the residue dissolved in dichloromethane (50 ml), and washed with aqueous sodium bicarbonate (5%, 25 ml), water (2×25 ml), brine (20 ml), and dried (magnesium sulfate). The residue after evaporation was triturated with diethyl ether to give the title product (0.68 g).

MS (ESP): 370 (MH$^+$) for $C_{15}H_{16}FN_3O_5S$;

EXAMPLE 142

5(R)-1,2,5-Thiadiazol-3-yloxymethyl-3-(4-[3,6-dihydro-(2H)-pyran4-yl]-3-fluorophenyl)oxazolidin-2-one Diisopropylazodicarboxylate (0.22 g, 1.1 mmol) was added dropwise at ambient temperature to a stirred solution of 5(R)-hydroxymethyl-3-(4-[3,6-dihydro-(2H)-pyran-4-yl]-3-fluorophenyl)oxazolidin-2-one (WO97/09328; 0.275 g, 0.93 mmol), 3-hydroxy1,2,5-thiadiazole (Weinstock et al. Journal of Organic Chemistry 32, 2823 [1967]; 0.1 12 g, 1.1 mmol) and triphenylphosphine (0.288 g, 1.1 mmol) in dry THF (7 ml). The solution was kept for 1.5 hours. Solvent was evaporated and the residue was purified by flash column chromatography, eluting with EtOAc/isohexane (1:1) to give the title product (0.256 g , 73%) as a solid (mp 146–148 ° C.). MS: 378 (MH$^+$); NMR: 2.4 (1H, bs); 3.78 (3H, t); 3.96 (1H, m); 4.2 (3H, m); 4.66 (2H, m); 5.1 (1H, m); 6.05 (1H, s); 7.27–7.5 (3H, m); 8.41 (1H, s).

EXAMPLE 143

5(R)-(3-Methyl-1,2,5-oxadiazol-5-oxide-4-yl)oxymethyl-3-(4-[3,6-dihydro-(2H)-pyran-4-yl]-3-fluorophenyl)oxazolidin-2-one Sodium hydride (28 mg of a 60% suspension in mineral oil, 0.69 mmol) was added portionwise to a solution of 5(R)-hydroxymethyl-3-(4-[3,6-dihydro-(2H)-pyran-4-yl]-3-fluorophenyl)oxazolidin-2-one (0.2 g, 0.69 mmol) in dry dimethoxyethane (3 ml) and the mixture was stirred for 40 minutes. 3-Methyl-4-nitro-1,2,5-oxadiazole-5-oxide [Nikolaeva et al. Izv. Akad. Nauk SSSR, Ser. Khim. 965 (1972)] (0.1 g, 0.69 mmol) was added portionwise over 5 minutes and the cloudy solution stirred for 40 minutes. Water (20 ml) was added and the mixture extracted three times with EtOAc. The combined extracts were dried by filtration through phase separation paper (Whatman 1 PS) and evaporated. The residue was purified by flash column chromatography, eluting with EtOAc/isohexane (7:3) to give the title product (0.112 g, 41%) as a solid mp 138–140° C. NMR(CDCl$_3$): 2.07 (3H, s); 2.5 (2H, bs); 3.91 (3H, t); 4.2 (1H, t); 4.31 (2H, m); 4.62 (2H, m); 5.06 (1H, m); 6.05 (1H, s); 7.2–7.42 (3H, m).

EXAMPLE 144

5(R)-(2-Methyl-1,3,4-oxadiazol-5-yl)oxymethyl-3-(4-[3,6-dihydro-(2H)-pyran-4-yl]-3-fluorophenyl)oxazolidin-2-one Sodium hydride (28 mg of a 60% suspension in mineral oil, 0.69 mmol) was added to a solution of 5(R)-hydroxymethyl-3-(4-[3,6-dihydro-(2H)-pyran-4-yl]-3-fluorophenyl)oxazolidin-2-one (0.2 g, 0.69 mmol) in DMSO (5 ml) and the mixture was stirred for 1 hour. 2-Methyl-5-sulfonylmethyl-1,3,4-oxadiazole (RB Woodward et al, (Journal of the American Chemical Society 105, 904 [1983]) (0.11 g, 0.69 mmol) was added and the solution heated at 110° C. for 9 hours. Water (40 ml) was added and the mixture extracted three times with EtOAc. The combined extracts were dried by filtration through phase separation paper (Whatman 1PS) and evaporated. The residue was purified by flash column chromatography, eluting first with EtOAc and then with EtOAc/MeOH (20:1) to give the title product (23 mg, 9%) as a solid (mp 146–147° C.). MS: 376 (MH+).

NMR (CDCl$_3$): 2.41 (3H, s); 2.49 (2H, bs); 3.91 (3H, t); 418 (1H, t); 4.31 (2H, m); 4.7 (2H, m); 5.05 (1H, m); 6.04 (1H, s); 7.23 (2H, m); 7.4 (1H, d).

EXAMPLE 145

5(R)-(5-Methoxycarbonylisoxazol-3-yl)oxymethyl-3-(4-[3,6-dihydro-(2H-pyran-4-yl]-3-fluorophenyl)oxazolidin-2-one Using the method of Example 142 but starting from 5-methoxycarbonyl-3-hydroxyisoxazole, the title compound was obtained in 65% yield as a solid (mp 145–147° C.). MS: 419 (MH$^+$).

NMR (CDCl$_3$): 2.5 (2H, bs); 3.93 (3H, s+3H, m); 4.18 (1H, t); 4.32 (2H, s); 4.59 (2H, m); 5.04 (1H, m); 6.06 (1H, s); 6.58 (1H, s) 7.24 (2H, m); 7.4 (1H, d).

EXAMPLE 146

5(R)-1,2,5-Thiadiazol-3-yloxymethyl-3-(4-iodophenyl)oxazolidin-2-one

Iodine (0.67 g, 2.64 mmol) was added portionwise to a stirred solution of 5(R)-1,2,5-thiadiazol-3-yloxymethyl-3-phenyloxazolidin-2-one (0.7 g, 2.53 mmol) and silver trifluoroacetate (0.727 g, 3.29 mmol) in acetonitrile (4 ml) and chloroforrn (6 ml). The mixture was stirred for 24 hours in the dark. The mixture was filtered and the filtrate evaporated. The residue was extracted with EtOAc and the extract washed with water, dilute ammonia (0.1 ml of 0.88SG ammonia in 25 ml water), water and brine, dried (Na$_2$SO$_4$) and evaporated to give the title product as a solid (0.749 g, 73%)

MS: 404 (MH$^+$); NMR: 3.94 (1H, m); 4.18 (1H, t); 4.67 (2H, m); 5.1 (1H, m); 7.38 (2H, d); 7.7 (2H, d); 8.41 (1H, s).

The necessary starting material, 5(R)-1,2,5-thiadiazol-3-yloxymethyl-3-phenyloxazolidin-2-one, was made by the method of Example 142, but starting from 5(R)-hydroxymethyl-3-phenyloxazolidin-2-one (Gregory, W A. et al, J. Med. Chem. (1989), 32, 1673–81), the title product being obtained as a solid in 83% yield. MS: 278 (MH$^+$);

NMR (CDCl$_3$): 4.0 (1H, m); 4.2 (1H, t); 4.68 (2H, m); 5.04 (1H, m); 7.18 (1H, t); 7.4 (2H, t); 7.55 (2H, d); 8.0 (1H, s).

EXAMPLE 147

5(R)-1,2,5-Thiadiazol-3-yloxymethyl-3-(-4-[2,5-dihydrothiophen-1,1-dioxo-3-yl]phenyl)oxazolidin-2-one A mixture of 5(R)-1,2,5-thiadiazol-3-yloxymethyl-3-(4-iodophenyl)oxazolidin-2-one (Example 146) (0.6 g, 1.49 mmol), 2,5-dihydrothiophen-1,1-dioxide (0.185 g, 1.57 mmol), triethylamine (0.26 ml, 01.87 mmol), tetrabutylammonium bromide (0.48 g, 1.49 mmol) and palladium acetate (17 mg, 0.0759 mmol) in DMF (4 ml) was heated at 60° C. for 19 hours under nitrogen. After cooling, the mixture was partitioned between water and EtOAc and the aqueous layer was twice further extracted with EtOAc. The combined extracts were washed with water and brine, dried (Na$_2$SO$_4$) and evaporated. The residue was triturated with acetonitrile to give the title product (71 mg, 12%) as a solid. MS: 394 (MH$^+$);

NMR (400 MHz): 4.0 (1H, m); 4.1 (21H, m); 4.25 (1H, t); 4.4 (2H, s); 4.7 (2H, m); 5.15 (1H, m); 6.57 (1H, s); 7.6 (4H, m); 8.45 (1H, s).

EXAMPLE 148

5(R)-1,2,5-Thiadiazol-3-yloxymethyl-3-(3-fluoro4-(1-(2(S),3-dihydroxypropanoyl)-1,2,5,6-tetrahydropyrid-4-yl)phenyl)oxazolidin-2-one 1N aqueous HCl (1 ml) was added to a solution of 5(R)-(1,2,5-thiadiazol-3-yloxymethyl)-3-(3-fluoro4-(1-(2,2-dimethyl-1,3-dioxolan-4(S)-ylcarbonyl)-1,2,5,6-tetrahydropyrid-4-yl)phenyl)oxazolidin-2-one (0.154 g, 0.32 mmol) in THF (3 ml) and the solution kept for two days. The solution was evaporated and the residue azeotroped twice with ethanol. The residue was purified by chromatography on a BondElut silica column, eluting first with dichloromethane and then 2% MeOH/dichloromethane to give the title product (37 mg, 26%) as a solid. MS: 465 (MH$^+$); NMR(400 MHz): 2.5 (2H+DMSO); 3.3 (1H, s)3.4 (1H, m); 3.5 (1H, m); 3.76 (1H, m); 4.0 (1H, t); 4.15 (1H, s); 4.26 (1H, t); 4.4 (1H, m); 4.8 (3H, m); 4.97 (1H, m); 5.18 (1H, m); 6.03 (1H, s); 7.32–7.46 (2H, m); 7.53 (1H, d); 8.47 (1H, s).

The necessary starting material was made by the method of Example 142, but starting from 5(R)-hydroxymethyl-3-(3-fluoro-4-(1-(2,2-dimethyl-1,3-dioxolan-4(S)-ylcarbonyl)-1,2,5,6-tetrahydropyrid-4-yl)phenyl) oxazolidin-2-one (prepared by analogy to Example 1H) to give the title product in 56% yield. MS: 505 (MH$^+$); NMR; 1.32 (6H, s); 2.41 (2H+DMSO); 3.58 (1H, m); 3.66 (2H, m); 3.82 (1H, t); 4.02–4.27 (5H, m); t); 4.69 (1H, m); 4.9 (1H, m); 5.19 (1H, t); 6.0 (1H, s); 7.32 (2H, m); 7.5 (1H, d); 8.47.

EXAMPLE 149

5(R)-1,2,5-Thiadiazol-3-yloxymethyl-3-(4-(1-(2(R), 3-dihydroxy propanoyl)-1,2,5,6-tetrahydropyrid-4-yl-3-fluorophenyl)oxazolidin-2-one Using the method described for Example 148, but starting from 5(R)-1,2,5-thiadiazol-3-yloxymethyl-3-(4-(1-(2,2-dimethyl-1,3-dioxolan-4(R)-ylcarbonyl)-1,2,5,6-tetrahydropyrid-4-yl)-3-fluorophenyl)oxazolidin-2-one, the title product was obtained in 50% as a solid. MS: 465 (MH$^+$); NMR(400 MHz): 2.42 (2H+DMSO); 3.5 (1H, m); 3.58 (1H, m); 3.71 (1H, m); 3.98 (1H, t); 4.1 (1H, s); 4.2 (1H, t); 4.35 (1H, m); 4.77 (3H, m); 4.93 (1H, m); 5.12 (1H, m); 6.02 (1H, s); 7.3–7.42 (2H, m); 7.5 (1H, d); 8.42 (1H, s).

The necessary starting material, 5(R)-1,2,5-Thiadiazol-3-yloxymethyl-3-(4-(1-(2,2-dimethyl-1,3-dioxolan-4(R)-ylcarbonyl)-1,2,5,6-tetrahydropyrid-4-yl)-3-fluoro phenyl) oxazolidin-2-one, was made as follows:

i) 5(R)-1,2,5-Thiadiazol-3-yloxymethyl-3-(3-fluoro-4-(1-benzyl-1,2,5,6-tetrahydropyrid-4-yl)phenyl) oxazolidin-2-one was made by the method of Example 142, but starting from 5(R)-hydroxymethyl-3-(4-(1-benzyl-1,2,5,6-tetrahydropyrid-4-yl)-3-fluorophenyl) oxazolidin-2-one (WO97/30995 & by analogy to reference Example 4) in 58% yield. MS: 467 (MH$^+$); NMR; 2.4 (2H+DMSO); 2.6 (2H, m); 3.02 (2H, m); 3.57 (2H, s); 3.92 (1H, m); 4.2 (1H, t); 4.62 (2H, m); 5.1 (1H, m); 5.91 (1H, s); 7.2–7.4 (7H, m); 7.48 (1H, d); 8.4 (1H, s).

ii) Diisopropylethylamine (0.39 ml, 2.24 mmol) was added dropwise to a stirred solution at 5° C. under nitrogen of 5(R)-1,2,5-thiadiazol-3-yloxymethyl-3-(4-(1-benzyl-1,2,5,6-tetrahydropyrid-4-yl)-3-fluorophenyl)oxazolidin-2-one (3.48 g, 7.47 mmol) in dichloromethane (60 ml), followed by 1-chloroethyl chloroforrnate (1.05 ml, 9.73 mmol). The mixture was stirred at 5° C. for 2 hours and the intermediate carbamate was freed from benzyl chloride by flash-column chromatography (silica gel. Merck 7736), eluting with a gradient of 10–30% EtOAc in isohexane. The carbamate was heated in refluxing MeOH (40 ml) for 1 hour. Solvent was evaporated and the residue triturated with ether to give 5(R)-1,2,5-thiadiazol-3-yloxymethyl-3-(3-fluoro-4-(1,2,5,6-tetrahydropyrid-4-yl)phenyl)oxazolidin-2-one hydrochloride as a solid in 82% yield MS: 376 (MH$^+$)(free base); NMR; 2.67 (2H, s); 3.3 (2H+DMSO); 3.75 (2H, s); 4.0 (1H, m); 4.25 (1H, t); 4.7 (2H, m); 5.14 (1H, m); 6.05 (1H, s); 7.4 (2H, m): 7.55 (1H, d); 8.42 (1H, s); 9.35 (1H, bs).

iii) A solution of (R)-2,2-dimethyl-1,3-dioxolan-4-ylcarbonyl chloride (S Handa et al, Synth. Commun. (1995), 25, 2837) [0.597 g, 3.63 mmol ] in dichloromethane (5 ml) was added dropwise to a stirred mixture of 5(R)-1,2,5-thiadiazol-3-yloxymethyl-3-(3-fluoro-4-(1,2,5,6-tetrahydropyrid-4-yl)phenyl) oxazolidin-2-one hydrochloride (1 g, 2.42 mmol) and pyridine (0.49 ml, 6.06 mmol) in dichloromethane (30 ml) under nitrogen at −10° C. After 10 minutes the cooling bath was removed and the mixture stirred for a further hour. Water (30 ml) was added and the organic layer washed with brine, dried ($Na_2SO_4$) and evaporated. The residue was triturated with ether and filtered to give 5(R)-1,2,5-thiadiazol-3-yloxymethyl-3-(4-(1-(2,2-dimethyl-1,3-dioxolan-4(R)-ylcarbonyl)-1,2,5,6-tetrahydropyrid-4-yl)-3-fluorophenyl)oxazolidin-2-one as a solid (1.13 g, 93%) MS: 504 ($MH^+$); NMR: 1.32 (6H, s); 2.42 (2H+DMSO); 3.7 (2H, m); 4.0 (1H, m); 4.11 (2H, m); 4.25 (2H, m); 4.8 (2H, m); 4.91 (1H, m); 5.12 (1H, m); 6.02 (1H, s); 7.29–7.43 (2H, m); 7.5 (1H, d); 8.42 (1H, s).

EXAMPLE 150

5(R)-1,2,5-Thiadiazol-3-yloxnmethyl-3-(3,5-difluoro-4-(1-(2(S),3-dihydroxypropanoyl)-1,2,5,6-tetrahydropyrid-4-yl)phenyl)oxazolidin-2-one Using the method described for Example 148, but starting from 5(R)-1,2,5-thiadiazol-3-yloxymethyl-3-(3,5-difluoro-4-(1-(2,2-dimethyl-1-3-dioxolan-4(S)-ylcarbonyl)-1,2,5,6-tetrahydropyrid-4-yl)phenyl)oxazolidin-2-one, the title compound was obtained in 51% yield as a solid. MS: 483 ($MH^+$); NMR: 2.48 (2H+DMSO); 3.48 (1H, m); 3.54 (1H, m); 3.97, (1H, t); 4.1 (1H, s); 4.17 (1H, t); 4.34 (1H, m); 4.67 (3H, m); 4.95 (1H, m); 5.12 (1H, m); 5.88 (1H, s); 7.33 (1H, s); 7.36 (1H, s); 8.42 (1H, s).

The necessary starting material was made as follows:

i) Using the method described for Example 149 step i), but starting from 5(R)-hydroxymethyl-3-(4-(1-benzyl-1,2,5,6-tetrahydropyrid-4-yl)-3,5-difluoro phenyl) oxazolidin-2-one, there was obtained in 58% yield, 5(R)-1,2,5-thiadiazol-3-yloxymethyl-3-(4-(1-benzyl-1,2,5,6-tetrahydropyrid-4-yl)-3.5-difluoro phenyl) oxazolidin-2-one as a solid. MS: 485 ($MH^+$); NMR; 2.3 (2H, bs); 2.6 (2H, t); 3.03 (2H, s); 3.39 (2H, s); 3.95 (1H, m); 4.2 (1H, t); 4.65 (2H, m); 5.12 (1H, s); 5.77 (1H, s); 7.2–7.38 (7H, m); 8.41 (1H, s).

ii) Using the method described for Example 149 step ii), but starting from 5(R)-1,2,5-thiadiazol-3-yloxymethyl-3-(4-(1-benzyl-1,2,5,6-tetrahydropyrid-4-yl)-3,5-difluorophenyl)oxazolidin-2-one, there was obtained in 84% vield, 5(R)-1,2,5-thiadiazol-3-yloxymethyl-3-(3,5-difluoro-4-(1,2,5,6-tetrahydropyrid-4-yl)phenyl) oxazolidin-2-one hydrochloride as a solid. MS: 395 ($MH^+$)(free base); NMR; 2.51 (2H, s); 3.28 (2H+DMSO); 3.71 (2H, s); 3.98 (1H, m); 4.2 (1H, t); 4.65 (2H, m); 5.1 (1H, m); 5.88 (1H, s); 7.33 (1H, s); 7.39 (1H, s); 8.41 (1H, s); 9.32 (1H, bs).

iii) Using the method described for Example 149 step iii), but starting from, 5(R)-1,2,5-thiadiazol-3-yloxymethyl-3-(3,5-difluoro-4-(1,2,5,6-tetrahydropyrid-4-yl)phenyl)oxazolidin-2-one hydrochloride and the appropriate (S)-dioxolan there was obtained in 86% yield, 5(R)-1,2,5-thiadiazol-3-yloxymnethyl-3-(4-(1-(2,2-dimethyl-1,3-dioxolan-4(S)-ylcarbonyl)-1,2,5,6-tetrahydropyrid-4-yl)-3,5-difluorophenyl)oxazolidin-2-one as a solid. MS: 523 ($MH^+$); NMR: 1.31 (6H, 2s); 2.4 (2H+DMSO); 3.6–3.8 (2H, m); 4.08–4.2 (5H, m); 4.9 (1H, m); 5.12 (1H, m); 5.89 (1H, s); 7.32–7.37 (2H, 2s); 8.41 (1H, s).

EXAMPLE 151

5(R)-1,2,5-Thiadiazol-3-yloxymethyl-3-(4-(1-hydroxyacetyl-1,2,5,6-tetrahydropyrid-4-yl)-3-fluorophenyl)oxazolidin-2-one A saturated solution of ammonia in MeOH (8 ml) was added to a stirred solution of 5(R)-1,2,5-thiadiazol-3-yloxymethyl-3-(4-(1-acetoxyacetyl-1,2,5,6-tetrahydropyrid-4-yl)-3-fluorophenyl)oxazolidin-2-one (0.275 g, 0.576 mmol) in MeOH (8 ml) and the solution kept for 20 hours. A small amount of insoluble material was filtered off and the filtrate concentrated. On keeping at 5° C., a solid was obtained which was filtered and washed with a little cold MeOH and then cold ether to give the title compound (0.161 g, 64%) as a solid. MS: 435 ($MH^+$); NMR: 2.42 (2H+DMSO); 3.52 (1H, m); 3.67 (1H, m); 3.94.(1H, m); 4.0–4.17(4H, m); 4.2 (1H, t); 4.5–4.73 (3H, m); 5.12 (1H, m); 6.0 (1H, m); 7.28–7.42 (2H, m); 7.5 (1H, dd); 8.42 (1H, s).

The necessary starting material, was made as follows:

Acetoxyacetyl chloride (0.21 ml, 1.95 mmol) was added to a stirred mixture of 5(R)-1,2,5-thiadiazol-3-yloxymethyl-3-(3-fluoro-4-(1,2,5,6-tetrahydropyrid-4-yl)phenyl) oxazolidin-2-one hydrochloride (product of step ii, Example 149) [0.412 g, 1 mmol] and sodium bicarbonate (0.42 g, 5 mmol) in acetone/water (15 ml, 2:1) at 5° C. The mixture was allowed to warm up to room temperature after 10 minutes and stirred for 18 hours. More acetoxyacetyl chloride (0.3 ml) and sodium bicarbonate (0.42 g,) were added and after a further 6 hours. water was added and the mixture extracted three times with EtOAc. The combined extracts were washed successively with water, 1N HCl and brine, dried ($Na_2SO_4$) and evaporated. The residue was triturated with ether and the solid filtered to give 5(R)-1,2,5-thiadiazol-3-yloxymethyl-3-(4-(1-acetoxyacetyl-1,2,5,6-tetrahydropyrid-4-yl)-3-fluorophenyl)oxazolidin-2-one (0.3 g, 63% yield). MS: 477 ($MH^+$); NMR: 2.08 (3H, s); 2.42 (2H+DMSO); 3.4 (2H, m); 3.98 (1H, m); 4.08 (2H, bs); 4.21 (1H, t); 4.65 (2H, m); 4.8 (2H, m); 5.12 (1H, m); 6.0 (1H, m); 7.31 (2H, m); 7.5 (1H, d); 8.4 (1H, s).

EXAMPLE 152

5(R)-1,2,5-Thiadiazol-3-yloxymethyl-3-(4-{1-hydroxyacetyl-1,2,5,6-tetrahydropyrid-4-yl]}-3,5-difluorophenyl)oxazolidin-2-one Using the method described for Example 151, but starting from 5(R)-1,2,5-thiadiazol-3-yloxymethyl-3-(4-(1-acetoxyacetyl-1,2,5,6-tetrahydropyrid-4-yl)-3,5-difluorophenyl)oxazolidin-2-one, the title compound was obtained in 80% yield as a solid.

MS: 453 ($MH^+$); NMR: 2.34 (2H, m); 3.54 (1H, m); 3.71 (1H, m); 4.1 (1H, m); 4.05–4.28 (5H, m); 4.2 (1H, t); 4.54–4.72 (3H, m); 5.15 (1H, m); 5.89 (1H, m); 7.39 (2H, d); 8.45 (1H, s).

The necessary starting material was made by the method used to make the starting material for Example 151, but starting from 5(R)-1,2,5-thiadiazol-3-yloxymethyl-3-(3,5- difluoro-4-(1,2,5,6-tetrahydropyrid-4-yl)phenyl)oxazolidin-2-one hydrochloride (see Example 150 product (ii)) to give the product in 78% yield. MS: 477 (MH+); NMR: 2.08 (3H, s); 2.42 (2H+DMSO); 3.4 (2H, m); 3.98 (1H, m); 4.08 (2H, bs); 4.21 (1H, t) 4.65 (2H, m); 4.8 (2H, m); 5.12 (1H, m); 6.0 (1H, m); 7.31 (2H, m); 7.5 (1H, d); 8.4 (1H, s).

EXAMPLE 153

5(R)-Imidazol-2-ylthiomethyl-3-(4-[3,6-dihydro-(2H)-pyran-4-yl]-3-fluorophenyl)oxazolidin-2-one 1,8-Diazabicyclo[5,4,0]undec-7-ene (0.1 ml, 0.674 mmol) was added to a stirred suspension of 5(R)-methanesulfonyloxymethyl 3-(4-[3,6-dihydro-(2H)-pyran-4-yl]-3-fluorophenyl)oxazolidin-2-one (prepared from the 5(R)-hydroxymethyl compound (WO97/09328) by reaction with methylsulfonyl chloride) (0.25 g, 0.674 mmol) and 2-mercaptoimidazole (0.067 g, 0.674 mmol) in dioxan (2 ml) under nitrogen. The mixture was heated at 60° C. for 4 hours and evaporated. The residue was purified by column chromatography, eluting first with 2% MeOH/EtOAc and then with 4% MeOH/EtOAc to give the title product as a solid (0.077 g, 30%); mp 178–179° C. (dec.) MS: 476 (MH+); NMR: 2.39 (2H, bs); 3.42 (2H, m); 3.79 (2H, t); 3.86 (1H, m); 4.19 (3H, m); 4.89 (1H, m); 6.07 (1H, s); 7.04 (2H, s); 7.26 (1H, dd); 7.38 (1H, t); 7.46 (1H, d).

EXAMPLE 154

5(R)-1,2,5-Thiadiazol-3-yloxymethyl-3-(4-((1 S)(4S)-2-benzyl-2,5-diazabicyclo{2,2,1}hentan-5-yl)-3-fluorophenyl)oxazolidin-2-one

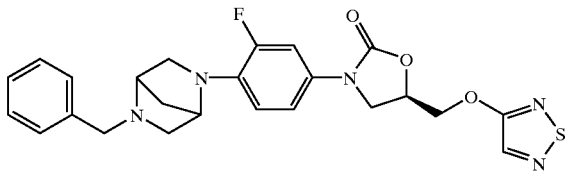

A mixture of 1-amino-4-[(1S)(4S)-2-benzyl-2,5-diazabicyclo{2,2,1}heptan-5-yl]-3-fluorobenzene (0.13 g, 0.43 8 mmol) and 3(S)-oxiranylmethoxy-1,2,5-thiadiazole (0.069 g, 0.483 mmol) in MeOH (2 ml) was stirred and heated at 60° C. for 20 hours. Solvent was evaporated and the residue partially purified by flash column chromatography, eluting with 4/96/0.8 MeOH/dichloromethane/0.88SG ammonia. The resulting crude ethanolamine (0.144 g), with diethyl carbonate (0.2 ml), sodium methoxide (9 mg) and MeOH (0.05 ml) was stirred and heated at 110° C. for 5 hours. The reaction mixture was purified by flash column chromatography, eluting with EtOAc/0.1% 0.88SG ammonia to give an oil which was triturated with ether to give the title product as a solid (mp 97–98° C.) (0.049 g, 23% over two stages). MS: 482 (MH+); NMR(CDCl₃); 1.83–2.0 (2H, dd); 2.72–2.96 (2H, dd); 3.41 (1H, m); 3.5 (2H, s); 3.91 (1H, m); 4.13 (1H, t); 4.3 (1H, s); 4.67 (2H, m); 5.0 (1H, m); 6.6 (1H, t); 7.05 (1H, dd); 7.2–7.38 (6H, m); 8.02 (1H, s).

The necessary starting materials were made as follows:
1-Amino-4-[(1S)(4S)-2-benzyl-2,5-diazabicyclo{2,2,1}heptan-5-yl]-3-fluorobenzene:

i) A mixture of (1S)(4S)-2-benzyl-2,5-diazabicyclo{2,2,1}heptane dihydrobromide [Henry et al. J. Med. Chem. (1974), 17, 481] (1.05 g, 3 mmol), 3,4-difluoronitrobenzene (0.48 g, 3 mmol) and 1,8-diazabicyclo[5,4,0]undec-7-ene (1.38 g, 9 mmol) in acetonitrile (10 ml) was stirred and heated at reflux for 2 hours. Solvent was evaporated and the residue was partitioned between EtOAc and water. The organic layer was filtered (1PS paper) and the filtrate evaporated to give 4-[(1S)(4S)-2-benzyl-2,5-diazabicyclo{2,2,1}heptan-5-yl]-3-fluoro-1-nitrobenzene (0.95 g, 97%) as a solid. MS: 328 (M+); NMR(CDCl₃); 1.82–2.07 (2H, dd); 2.77–2.98 (2H, dd); 3.59 (2H+1H, s); 3.72 (2H, s); 3.91 (1H, m); 4.58 (1H, s); 6.6 (1H, t); 7.2–7.34 (5H+CHCl₃);

ii) Hydrazine hydrate (0.57 ml) was added to a suspension of 4-[(1S)(4S)-2-benzyl-2,5-diazabicyclo{2,2,1}heptan-5-yl]-3-fluoro-1-nitrobenzene (1.63 g, 5 mmol) in ethanol (35 ml) with stirring, followed by Raney nickel (~1 g). The mixture was heated at 60° C. for 1.5 hours. More hydrazine hydrate (0.2 ml) and Raney nickel (~0.5 g) were added and heating continued for a further 3 hours. The mixture was cooled and stirred with charcoal (0.5 g) for 1 hour and filtered. The filtrate was evaporated to give 1-amino-4-[(1S)(4S)-2-benzyl-2,5-diazabicyclo{2.2.1}heptan-5-yl]-3-fluorobenzene (1.28 g, 86%) as an oil. MS: 287 (MH+); NMR(CDCl₃); 1.8–1.95 (2H, dd); 2.73–2.9 (2H, dd); 3.17–3.5 (5H, m); 3.71 (2H, s); 4.12 (1H, s); 6.32–6.52 (3H, m); 7.18–7.35 (5H+CHCl₃).

3(S)-oxiranylmethoxy-1,2,5-thiadiazole:

Diisopropylazodicarboxylate (4.2 g, mmol) was added dropwise at ambient temperature to a stirred solution of(S)-glycidol (1.54 g), 3-hydroxy-1,2,5-thiadiazole (2.12 g, 20.8 mmol) and triphenylphosphine (5.45 g, 20.8 mmol) in dry THF (25 ml). The solution was kept for 21 hours. Solvent was evaporated and the residue was extracted twice with isohexane (2×50 ml). The combined extracts were evaporated and the residue purified by flash column chromatography, eluting with EtOAc/isohexane (1:3) to give the title product (0.41 g ) as an oil NMR(CDCl₃); 2.75 (1H, m); 2.9(1H, m); 3.38 (1H, m); 4.28 (1H, m); 4.7 (1H, m); 8.0 (1H, s).

EXAMPLE 155

5(R)-1,2,5-Thiadiazol-3-yloxymethyl-3-(4-[(1S)(4S)-2,5-diazabicyclo{2,2,1}heptan-5-yl]-3-fluorophenyl)oxazolidin-2-one hydrochloride

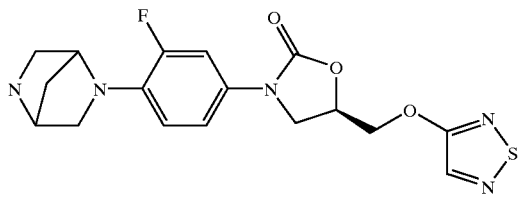

Diisopropylethylamine (52 mg, 0.4 mmol) was added dropwise to a stirred solution at 5° C. under nitrogen of 5(R)-1,2,5-Thiadiazol-3-yloxymethyl-3-(4-[(1S)(4S)-2-benzyl-2,5-diazabicyclo{2,2,1}heptan-5-yl]-3-fluorophenyl)oxazolidin-2-one (0.65 g, 1.35 mmol) in dichloromethane (10 ml), followed by 1-chloroethyl chlorofornate (0.19 ml, 1.76 mmol). The mixture was stirred at 5° C. for 2 hours and the interrnediate carbamate was freed from benzyl chloride by trituration with three portions of isohexane (3×15 ml). The carbarnate was heated in refluxing MeOH (10 ml) for 1 hour. Solvent was evaporated and the residue triturated with acetone to give the title product as a solid (0.366 g, 63% yield). MS: 391 (MH⁺); NMR(CDCl₃); 2.0 (2H, dd); 3.2–3.34 (2H+DMSO); 3.56 (2H, dd); 3.9 (1H, m); 4.18 (1H, t); 4.34 (1H, s); 4.5 (1H, s); 5.07 (1H, m); 6.86 (1H, t); 7.15 (1H, d); 7.45 (1H, d); 8.42 (1H, s); 9.04 (1H, bs); 9.57 (1H, bs).

EXAMPLE 156

5(R)-1,2,5-Thiadiazol-3-yloxymethyl-3-(4-[(1S)(4S)-2-acetoxyacetyl-2,5-diazabicyelo{2,2,1}heptan-5-yl]-3-fluorophenyl)oxazolidin-2-one

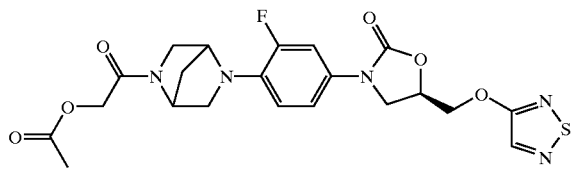

Using the method to make the starting material for Example 151 but starting from the title product of Example 155, the title product was obtained as an amorphous solid in 46% yield. MS: 491 (MH⁺); NMR(CDCl₃); 1.85–2.02 (2H, dd); 2.03 (3H, s); 3.28 (1H, d); 3.57 (1H, s); 3.63–3.83 (2H, m); 3.91 (1H, m); 4.1 (1H, t); 4.42–4.73 (5H, m); 5.0 (2H, m); 6.6 (1H, m); 7.07 (1H, m); 7.4 (1H, d); 8.01 (1H, s).

EXAMPLE 157

5(R)-1,2,5-Thiadiazol-3-yloxymethyl-3-(4-[(1S)(4S)-2-hydroxy acetyl-2,5-diazabicyclo{2,2,1}heptan-5-yl]-3-fluorophenyl)oxazolidin-2-one

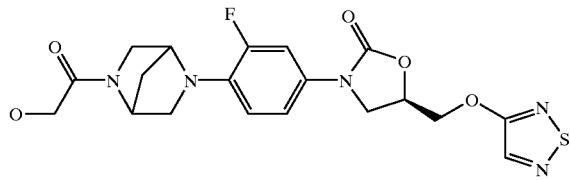

A solution of the title product of Example 156 (91 mg, 0.185 mmol) in MeOH saturated with ammonia (2.5 ml) was kept for 22 hours. Solvent was evaporated and the residue was redissolved in dichloromethane (5 ml) and the solution washed with water. The organic layer was dried by filtration through phase separation paper (Whatman 1PS) and evaporated to give the title product as a foam (57 mg, 69%). MS; 450 (MH⁺); NMR(CDCl₃); 1.85–2.17 (2H, m); 3.14–3.84 (5H, m); 3.88–4.29 (4H, m); 4.6–4.74 (3H, m); 5.0 (2H, m); 6.6 (1H, m); 7.08 (1H, m); 7.38 (1H d); 8.02 (1H, s).

EXAMPLE 158

5(R)-1,2,5-Thiadiazol-3-yloxymethyl-3-(4-[(1S)(4S)-2-(2(S),3-dihydroxypropanoyl)-2,5-diazabicyclo{2,2,1}heptan-5-yl]-3-fluorophenyl)oxazolidin-2-one

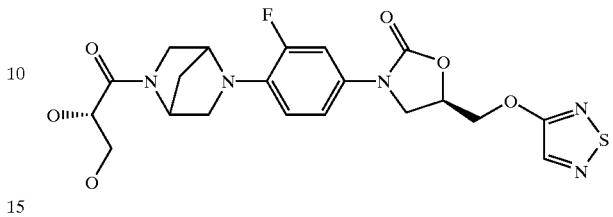

Using the method to make the starting material for Example 148 but starting from 5(R)-1,2,5-thiadiazol-3-yloxymethyl-3-(3-fluoro-4-(2-(2,2-dimethyl-1,3-dioxolan-4(S)-ylcarbonyl)-2,5-diazabicyclo{2,2,1}heptan-5-yl) phenyl)oxazolidin-2-one, the title product was obtained as an amorphous solid in 79% yield MS: 480 (MH⁺); NMR (400 MHz, DMSO-d6+acetic acid-d4); 1.87–2.0 (2H, m); 3.12 (1H, m); 3.31 (1H, d); 3.48 (2H, m); 3.65 (2H, m); 3.86 (1H, m); 4.11 (1H, m); 4.45 (1H, m); 4.62 (1H, m); 4.78 (1H, m); 5.02 (1H, m); 6.78 (1H, m); 7.12 (1H, m); 7.4 (1H, dd); 8.33 (1H, s).

The necessary starting material was made as a solid in 63% yield (MS: 520 (MH⁺)) by the method used to make the starting material for Example 149 step iii), but starting from the title product of Example 155 and the appropriate (S)-dioxolan.

EXAMPLE 159

5(R)-Isoxazol-3-yloxymethyl-3-(4-{8-acetoxyacetyl-8-azabicyclo[3.2.1]oct-2-ene-3-yl}-3-nluorophenyl)oxazolidin-2-one

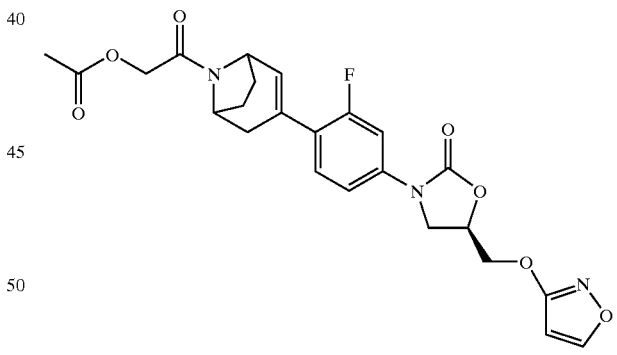

Acetoxyacetyl chloride (0.3 ml, 2.72 mmol) was added dropwise to a stirred mixture of 5(R)-isoxazol-3-yyloxymethyl-3-(4-{8-azabicyclo[3.2.1]oct-2-ene-3-yl}-3-fluorophenyl)oxazolidin-2-one (0.35 g, 0.91 mmol), acetone (7 ml), sodium bicarbonate (0.35 g, 4.17 mmol) and water (3.5 ml) and the mixture was stirred for 2 hours. More sodium bicarbonate (0.7 g) and acetoxyacetyl chloride (0.15 ml) were added and after 2.5 hours a further portion of sodium bicarbonate (0.7 g) was added and the mixture stirred for 20 hours. Solvent was evaporated and the residue partitioned between water and EtOAc. The organic layer was washed with sodium bicarbonate solution, dried (Na₂SO₄) and evaporated. The residue was purified by chromatography on a MegaBondElut column, eluting with a gradient of dichloromethane-6% MeOH/dichloromethane to give the title product as an oil (0.16 g, 36%). MS: 486 (MH⁺).

NMR(400 MHz): 1.79 (2H, m); 1.88–2.1 (5H, s+m); 2.25 (2H, d); 3.56 (1H, t); 3.62 (1H, m); 3.9 (1H, m); 4.19 (1H, t); 4.48 (3H, m); 4.62 (1H, m); 4.78 (2H, m); 5.06 (1H, m); 6.32 (1H, t); 6.35 (1H, s); 7.3 (2H, m); 7.48 (1H, dd); 8.66 (1H, s).

The necessary starting material was made as follows:
i) Tris(dibenzylideneacetone) dipalladium(0) (0.19 g, 0.208 mmol), triphenylarsine (0.13 g, 0.425 mmol) and lithium chloride (0.265 g, 6.31 mmol) were added to a stirred solution of 5(R)-isoxazol-3-yloxymethyl-3-(3-fluoro-4-iodophenyl)oxazolidin-2-one (prepared by analogy to reference Example 28) (0.85 g, 2.1 mmol) in degassed DMF (35 ml) under nitrogen. After 5 minutes, a solution of 8-tert-butyloxycarbonyl-3-trimethylstannyl-8-azabicyclo[3.2.1]oct-2-ene (GB 2298647; 0.78 g, 2.1 mmol) in DMF (4 ml) was added and the mixture was heated at 60° C. for 18 hours. A solution of 2M potassium fluoride (30 ml) was added and the mixture stirred for 40 minutes. Solvent was evaporated and the residue partitioned between water and EtOAc. The aqueous layer was extracted twice with EtOAc and the combined extracts dried (Na₂SO₄) and evaporated. The residue was purified by column chromatography, eluting with a gradient of dichloromethane-5% MeOH/dichloromethane to give 5(R)-isoxazol-3-yloxymethyl-3-(4-{8-tert-butyloxycarbonyl-8-azabicyclo[3.2.1]oct-2-ene-3-yl}-3-fluorophenyl)oxazolidin-2-one as an oil of 85% purity [hplc](0.97 g, 81%). MS: 486 (MH⁺).
ii) Saturated methanolic HCl (1 ml) was added to a solution of the product of step i) (0.07 g, 0.144 mmol) in MeOH (1 ml) and the mixture kept for 20 hours. Solvent was evaporated and the residue partitioned between water and EtOAc. The organic layer was washed with brine dried (Na₂SO₄) and evaporated to give 5(R)-isoxazol-3-yloxymethyl-3-(3-fluoro-4-iodophenyl)oxazolidin-2-one as an oil (0.03 g, 54% yield). MS: 386 (MH⁺).

EXAMPLE 160

5(R)-Isoxazol-3-yloxymethyl-3-(4-{8-hydroxyacetyl-8-azabicyclo[3.2.1]oct-2-ene-3-yl}-3-fluorophenyl)oxazolidin-2-one

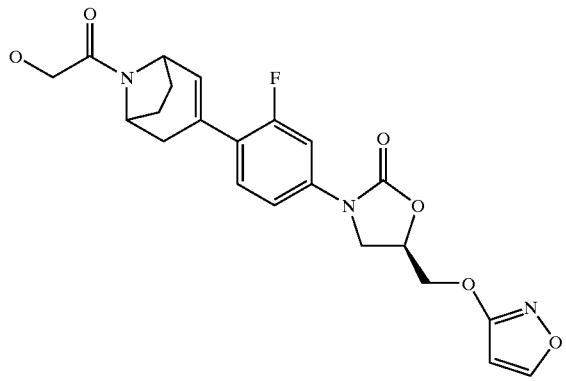

Saturated methanolic ammonia (2 ml) was added to a solution of the title product of Example 159 (0.21 g) in MeOH/dichloromethane (1/1, 1 ml) and the mixture kept for 44 hours. Solvent was evaporated and the residue purified by chromatography on a MegaBondElut column, euting with a gradient of 10% EtOAc/dichloromethane-50% EtOAc/dichloromethane-5% MeOHidichloromethane-10% MeOH/dichloromethane to give the title product as an oil (0.03 g, 27%). MS: 444 (MH⁺); NMR 1.75 (2H, m); 1.98 (2H, m); 2.24 (2H, m); 2.82 (1H, bd); 3.9(1H, m); 4.10 (1H, t); 4.19 (1H, t); 4.46 (3H, m); 4.66 (14H, t); 5.08 (1H, m); 6.32 (1H, d); 6.36 (1H, s); 7.29 (1H, m); 7.34 (1H, m) 7.48 (1H, dd); 8.68 (1H, s).

N.B: The stereochemistry of the azabicyclo rings in Examples 159 and 160 is a mixture of (1S),(5R) and (1R),(5S), with the numbering ordered to give the lowest number to the double bond.

EXAMPLE 161

3-(4-Methylthio)phenyl-5(R)-(2-thiazoyloxymethyl) oxazolidin-2-one

Sodium hydride (60% w/w in oil, 387 mg, 10 mmol) was washed with isohexane and suspended in DMF (2 ml) under nitrogen. 5(R)-hydroxymethyl-3-(4-methylthiophenyl)oxazolidin-2-one (1.39 g, 5.8 mmol) was dissolved in DMF and added dropwise to the hydride suspension. Gas was evolved and stirnring at ambient temperature was continued for 2 hours, 2-Bromothiazole (0.52 ml, 5.8 mmol) in DMF (10 ml) was added slowly, an exotherm from 22 to 29° C. was observed. The reaction mixture was then stirred at ambient temperature for 4 hours and poured into water. The product was extracted into dichloromethane, dried (MgSO₄) and concentrated to leave a dark brown gum. The residue was purified by flash chromatography on silica gel, eluting with EtOAc: isohexane, 2:1. The relevant fractions were combined and evaporated to give the product as a white powder (740 mg, mp 83–86° C.).

MS: 322 (M⁺), 323 (MH⁺) for C₁₄H₁₄N₂O₃S₂; NMR (CDCl₃) 7.5 (m, 2H); 7.3 (m, 2H); 7.11 (d, 1H); 6.75 (d, 1H); 5.05 (M, 1H); 4.7 (dd, 2H); 4.15 (t, 1H); 4.00 (dd, 1H); 2.5 (s, 3H).

EXAMPLE 162

3-(4-Methylsulfonylphenyl)-5(R)-(2-thiazoyloxymethyl)-oxazolidin-2-one 3-(4-methylthiophenyl)-5(R)-(2-thiazoyloxymethyl) oxazolidin-2-one (600 mg, 2.0 mmol) was dissolved in dichloromethane (20 ml). 3-Chloroperoxybenzoic acid (50% w/w, 1.42 g, 4.13 mmol) was added portionwise maintaining the temperature at <20° C. with external cooling. A white suspension formed and this was stirred at ambient temperature for 2 hours. The reaction mixture was concentrated under reduced pressure yielding a white solid. This was triturated twice, initially using diethyl ether and then using dichloromethane leaving the oxidised product as a white powder (285 mg, mp 136° C.). MS: 354 (M⁺), 355 (MH⁺) for C₁₄H₁₄N₂O₅S₂.

NMR (DMSO-d₆) 7.95 (m, 2H); 7.82 (m, 2H); 7.12 (d, 1H); 6.82 (d, 1H); 5.15 (M, 1H); 4.74 (m, 2H); 4.32 (t, 1H); 4.08 (dd, 1H); 3.09 (s, 3H).

EXAMPLE 163

3-(4-Methylsulfonylphenyl)-5(R)-(isoxazol-3-yloxymethyl)oxazolidin-2-one

5(R)-hydroxymethyl-3-(4-methylthiophenyl)oxazolidin-2-one (see Example 42; 1.0 g, 4.18 mmol), 3-hydroxyisoxazole (0.43 g, 5.05 mmol) and tributylphosphine (1.4 g, 5.34 mmol) were suspended in tetrahydrofuran (10 ml) under nitrogen. Diethylazodicarboxylate (0.79 ml, 5.02 mmol) was added dropwise. an exotherm from 19 to 33° C. was observed. The resulting yellow solution was stirred at ambient temperature for 2 hours. The complete reaction mixture was then passed down a flash chromatography column using silica gel, eluting with EtOAc:isohexane, 7:3. The relevant fractions were combined and evaporated to give impure product as a white powder (1.4 g). A portion of this crude material (388 mg,) was dissolved in dichloromethane (20 ml). 3-Chloroperoxybenzoic acid (50% w/w, 0.872 g, 2.5 mmol) was added portionwise, maintaining the temperature at <20° C. with external cooling, the reaction was then stirred at ambient temperature for 4 hours. The reaction mixture was concentrated under reduced pressure yielding a white solid. This was triturated with diethyl ether and filtered leaving the oxidised product as a white powder (300 mg, mp 180° C.). MS (ESP): 339 (MH$^+$) for $C_{14}H_{14}N_2O_6S$.

NMR (CDCl$_3$) 8.18 (d, 1H); 7.98 (m, 2H); 7.8 (m, 2H); 6.0 (d, 1H); 5.1 (M, 1H); 4.5 (m, 2H); 4.25 (t, 1H); 4.08 (dd, 1H); 3.09 (s, 3H).

EXAMPLE 164

5(R)-Isoxazol-3-yloxymethyl-3-(4-bromo-pyrid-2-yl)-oxazolidin-2-one

To a stirred solution of 5(R)-hydroxymethyl-3-(4-bromo-pyrid-2-yl)oxazolidin-2-one (EP 694543; 3.75 g, 13.7 mmol), 3-hydroxyisoxazole (1.28 g, 15.1 mmol) and triphenylphosphine(4.31 g, 16.4 mmol) in anhydrous THF (83 ml), was added dropwise diisopropyl azodicarboxylate (3.20 g, 3.11 ml, 15.8 mmol) and stirred at room temperature for 5h. The solvent was then removed by rotary evaporation and purification by MPLC (Merck 9385 silica, eluting with CH$_2$Cl$_2$) and trituration with diethyl ether gave the title compound as a white solid (2.93 g, 63%)

NMR (300 MHz, DMSO-d$_6$) δ/ppm: 3.98 (dd, 1H), 4.28 (t, 1H), 4.50 (m, 2H), 5.08 (m, 1H), 6.38 (d, 1H), 8.07 (br s, 2H), 8.50 (d, 1H), 8.69 (d, 1H). MS: (M+H)$^+$=340-Br isotopes.

EXAMPLE 165

5(R)-Isoxazol-3-yloxymethyl-3-(4-(1-tert-butoxycarbonyl-1,2,5,6-tetrahydropyrid-4-yl)pyrid-2-yl)oxazolidin-2-one To a stirred solution of Example 164 (340 mg, 1.0 mmol) in anhydrous deoxygenated DMF (8 ml), under N$_2$, was added lithium chloride (113.6 mg, 3.0 mmol), bis (dibenzylideneacetone)palladium (91.6 mg, 0.10 mmol), triphenylarsine (124 mg, 0.40 mmol) and the vinyl stannane (CAS[162046-38-0]; 502 mg, 1.5 mmol) and the reaction mixture heated to 55° C. and stirred for 64 hours. The solvent was removed by high-vac. rotary evaporation giving an oil which was taken into CH$_2$Cl$_2$, filtered and purified by MPLC (Merck 9385 silica, eluted with 40% EtOAc/isohexane), to give the title compound as a white powder (202 mg, 46%) upon trituration with diethyl ether. MS: (M+H)$^+$=443.

NMR (300 MHz, DMSO-d$_6$) δ/ppm: 1.35 (s, 9H), 2.40 (m, partially obscured, 2H), 3.51 (t, 2H), 3.95 (m, 3H), 4.27 (t, 1H), 4.44 (m, 2H), 5.03 (m, 1H), 6.13 (br s, 1H), 6.28 (d, 1H), 7.85 (dd, 1H), 8.02 (dd, 1H), 8.38 (d, 1H), 8.54 (d, 1H).

REFERENCE EXAMPLE 38

5(R)-Isoxazol-3-yloxymethyl-3-(4-(1,2,5,6-tetrahydropyrid-4-yl)pyrid-2-yl)oxazolidin-2-one To Example 165 (185 mg, 0.42 mmol) was added TFA (0.45 ml), with stirring and heating in a water bath at 60° C., for 1 minute, to produce an orange/yellow solution which was triturated with diethyl ether to give the title compound as a yellow powder (180 mg, 94%). MS: (M+H)$^+$=343.

EXAMPLE 166

5(R)-Isoxazol-3-yloxymethyl-3-(4-(1-formyl-1,2,5,6-tetrahydropyrid-4-yl)pyrid-2-yl)oxazolidin-2-one Reference Example 38 (58 mg, 0.13 mmol) and triethylamine(71 μl, 0.51 mmol) were dissolved in ethyl formate (1.0 ml) and heated to reflux for 5 days, followed by removal of the solvent by high-vac rotary evaporation to give a gum which was redissolved in CH$_2$Cl$_2$, washed with water, concentrated and triturated with diethyl ether to give the title compound as a pale yellow powder (38 mg, 81%). MS: (M+H)$^+$=371.

NMR (300 MHz, DMSO-d$_6$) δ/ppm: 2.55 (m, partially obscured, 2H), 3.59 (m, 2H), 4.02 (m, 3H), 4.27 (m, 1H), 4.47 (m, 2H), 5.05 (m, 1H), 6.18 (br s, 1H), 6.31 (d, 1H), 7.86 (dd, 1H), 8.02 (m, 1H), 8.09 (m, 1H)8.40 (d, 1H), 8.61 (d, 1H).

EXAMPLE 167

5(R)-(3-Methyl-1,2,4-oxadiazol-5-yloxymethyl)-3-(4-(1-benzyl-1,2,5,6-tetrahydropyrid-4-yl)-3,5-difluorophenyl)oxazolidin-2-one Prepared by the general method of Example 1 using Reference Example 4 (3.57 g, 8.93 mmol), 3-methyl-1,2,4-oxadiazol-5-one (1.00 g, 0.01M), diisopropylazodicarboxylate (2.02 g, 0.01M) and triphenylphosphine (2.81 g, 0.011M) in dry THF (70 ml). The resultant product was purified by MPLC (Merck 9385 silica, 20–30% EtOAc in tert-butyl methyl ether plus 0.5% MeOH) to give the title compound as a yellow oil (0.340 g, 8%). MS: ESP$^{30}$ (M+H)$^+$=483.

$^1$H-NMR (300 MHz, CDCl$_3$): δ=2.27 (s, 3H), 2.44 (m, 2H), 2.60 (t, 2H), 3.17 (m, 2H), 3.64 (s, 2H), 3.89 (dd, 1H), 4.12 (m, 1H), 4.62 (m, 2H), 5.02 (m, 1H), 5.83 (s, 1H), 7.12 (m, 2H), 7.23–7.41 (m, 5H).

REFERENCE EXAMPLE 39

5(R)-(3-Methyl-1,2,4-oxadiazol-5-yloxymethyl)-3-(4-(1,2,5,6-tetrahydroyyrid-4-yl)-3,5-dinluorophenyl)oxazolidin-2-one Prepared by the general method of Reference Example 6, using Example 167 (0.33 g, 0.68 mmol), diisopropylamine (0.03 g, 0.21 mmol) and 1-chloroethyl chloroformate (0.13 g, 0.89 mmol) in dichloromethane (8 ml), to give the title compound as a yellow solid (0.21 g, 72%). MS: ESP$^+$ (M+H)$^+$=393.

$^1$H-NMR (300 MHz, DMSO-d$_6$): δ=2.22 (s, 3H), 2.54 (partially obscured by DMSO, 2H), 3.25 (partially obscured by water, 2H), 3.74 (m, 2H), 3.95, 4.20 (dd×2,2H), 4.66 (m, 2H), 5.14 (m, 1H), 5.88 (broad s, 1H), 7.35 (m, 2H), 9.25 (broad s, 2H).

EXAMPLE 168

5(R)-(3-Methyl-1,2,4-oxadiazol-5-yloxymethyl)-3-(4-(1-acetoxyacetyl-1,2,5,6-tetrahydropyrid-4-yl)-3,5-difluorophenylsoxazolidin-2-one Reference Example 39 (198 mg, 0.46 mmol), and sodium hydrogen carbonate (0.39 g, 4.62 mmol) were stirred in acetone/water (2:1, 9 ml) at 0° C. Acetoxyacetyl chloride (0.13 g, 0.92 mmol) was added dropwise and the reaction mixture was stirred at 0° C. for 30min. Additional acetoxy-acetyl chloride (0.03 g, 0.23 mmol), was added and the mixture was stirred for a further 30 min. The reaction mixture was diluted with water and extracted with EtOAc. The combined organic layers were washed with saturated sodium chloride solution, dried (MgSO$_4$) and the solvent evaporated to give the title compound as a yellow solid after trituration with diethyl ether (170 mg, 75%).

$^1$H-NMR (300 MHz, DMSO-d$_6$): δ=2.09 (s, 3H), 2.23 (s, 3H), 2.31, 2.43 (2×m, 2H), 3.57, 3.66 (2×t, 2H), 3.97, 4.22 (2×dd, 2H), 4.10 (broad d, 2H), 4.78 (m, 2H), 4.86 (d, 2H), 5.14 (m, 1H), 5.88 (m, 1H), 7.34 (m, 2H), MS: ESP$^+$ (M+H)$^+$=493.

EXAMPLE 169

The following illustrate representative pharmaceutical dosage forms containing a compound of the formula (I), an in-vivo hydrolysable ester or a pharmaceutically-acceptable salt thereof, including a pharrnaceutically-acceptable salt of an in-vivo hydrolysable ester, (hereafter compound X), for therapeutic or prophylactic use in humans:

| Tablet I | mg/tablet |
|---|---|
| Compound X | 500 |
| Lactose Ph.Eur | 430 |
| Croscarmellose sodium | 40 |
| Polyvinylpyrrolidone | 20 |
| Magnesium stearate | 10 |
| Tablet II | mg/tablet |
| Compound X | 100 |
| Lactose Ph.Eur | 179 |
| Croscarmellose sodium | 12 |
| Polyvinylpyrrolidone | 6 |
| Magnesium stearate | 3 |
| Tablet III | mg/tablet |
| Compound X | 50 |
| Lactose Ph.Eur | 229 |
| Croscarmellose sodium | 12 |
| Polyvinylpyrrolidone | 6 |
| Magnesium stearate | 3 |
| Tablet IV | mg/tablet |
| Compound X | 1 |
| Lactose Ph.Eur | 92 |
| Croscarmellose sodium | 4 |
| Polyvinylpyrrolidone | 2 |
| Magnesium stearate | 1 |
| Capsule | mg/capsule |
| Compound X | 10 |
| Lactose Ph.Eur | 389 |
| Croscarmellose sodium | 100 |
| Magnesium stearate | 1 |
| Injection I | |
| Compound X | 50% w/v |
| Isotonic aqueous solution | to 100% |
| Injection II (e.g. bolus) | |
| Compound X | 10% w/v |
| Isotonic aqueous solution | to 100% |
| Injection III | |
| Compound X | 5% w/v |
| Isotonic aqueous solution | to 100% |
| Injection IV (e.g. infusion) | |
| Compound X | 1% w/v |
| Isotonic aqueous solution | to 100% |

Buffers, pharmaceutically-acceptable surfactants, oils or cosolvents such as polyethylene glycol, polypropylene glycol, glycerol or ethanol, glidants (such as silicon dioxide) or complexing agents such as a cyclodextrin (for example, hydroxy-propyl β-cyclodextrin or sulfo-butyl-ether β-cyclodextrin) may be used to aid formulation. Also, improvements in aqueous solubility, if desired, may be achieved. for example, by conjugation of a compound of formula (I) with a phospholipid (such as a (phospho)choline derivative) to form a micellar emulsion.

Note: The above formulations may be obtained by conventional procedures well known in the pharmaceutical art, for example as described in "Remington: The Science & Practice of Pharmacy" Vols. I & II (Ed. A. R.Gennaro (Chairman) et al; Publisher: Mack Publishing Company, Easton. Pa.; 19th Edition—1995) and "Pharmaceutics—The Science of Dosage Form Design" (Ed. M. E. Aulton; Publisher: Churchill Livingstone: first published 1988). The tablets (a)-(d) may be (polymer) coated by conventional means, for example to provide an enteric coating of cellulose acetate phthalate.

What is claimed is:

1. 5(R)-Isoxazol-3-yloxymethyl-3-(4-(1-(2(S),3-dihydroxypropanoyl)-1,2,5,6-tetrahydropyrid-4-yl)-3,5-difluorophenyl)-oxazolidin-2-one, or a pharmaceutically-acceptable salt or in vivo-hydrolyzable ester thereof.

2. 5(R)-Isoxazol-3-yloxymethyl-3-(4-(1-(2(S)-hydroxy-3-phosphoryl-propanoyl)-1,2,5,6-tetrah dropyrid-4-yl)-3,5-difluorophenyl)oxazolidin-2-one, or a pharmnaceutically-acceptable salt thereof.

3. The disodium salt of 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one.

4. A pharmaceutical composition comprising a pharmaceutically-acceptable diluent or carrier and 5(R)-isoxazol-3-yloxymethyl-3-(4-(1-(2(S),3-dihydroxypropanoyl)-1,2,5,6-tetrahydropyrid-4-yl)-3,5-difluorophenyl)-oxazolidin-2-one, or a pharmaceutically-acceptable salt, or in-vivo hydrolysable ester thereof.

5. A pharmaceutical composition comprising a pharmaceutically-acceptable diluent or carrier and 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one or a pharmaceutically-acceptable salt thereof.

6. A pharmaceutical composition comprising a pharmaceutically-acceptable diluent or carrier and the disodium salt of 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one.

7. A method for producing an antibacterial effect in a warm blooded animal, comprising administering to the said animal in need thereof an effective amount of the compound 5(R)-isoxazol-3-yloxymethyl-3-(4-(1-(2(S),3-dihydroxypropanoyl)-1,2,5,6-tetrahydropyrid-4-yl)-3,5-difluorophenyl)-oxazolidin-2-one or a pharmaceutically-acceptable salt or in vivo-hydrolyzable ester thereof.

8. A method for producing an antibacterial effect in a warm blooded animal, comprising administering to said animal in need thereof an effective amount of the compound 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one, or a pharmaceutically-acceptable salt thereof.

9. A method for producing an antibacterial effect in a warm blooded animal, comprising administering to said animal in need thereof an effective amount of the disodium salt of 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one.

10. A method for producing an antibacterial effect in a warm blooded animal, comprising administering to said animal in need thereof an effective amount of a pharmaceutical composition comprising the compound 5(R)-isoxazol-3-yloxymethyl-3-(4-(1-(2(S),3-dihydroxypropanoyl)-1,2,5,6-tetrahydropyrid-4-yl)-3,5-difluorophenyl)-oxazolidin-2-one, or a pharmaceutically-acceptable salt, or in vivo-hydrolyzable ester thereof; and a pharmaceutically-acceptable diluent or carrier.

11. A method for producing an antibacterial effect in a warm blooded animal, comprising administering to said animal in need thereof an effective amount of a pharmaceutical composition comprising the compound 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one or a pharmaceutically-acceptable salt thereof; and a pharmaceutically-acceptable diluent or carrier.

12. A method for producing an antibacterial effect in a warm blooded animal, comprising administering to said animal in need thereof an effective amount of a pharmaceutical composition comprising the disodium salt of 5(R)-isoxazol-3-yloxymethyl-3-(4-(1-(2(S)-hydroxy-3-phosphoryl-propanoyl)-1,2,5,6-tetrahydropyrid-4-yl)-3,5-difluorophenyl)oxazolidin-2-one; and a pharmaceutically-acceptable diluent or carrier.

* * * * *